US007220583B2

(12) United States Patent
Alfano et al.

(10) Patent No.: US 7,220,583 B2
(45) Date of Patent: May 22, 2007

(54) *PSEUDOMONAS* AVR AND HOP PROTEINS, THEIR ENCODING NUCLEIC ACIDS, AND USE THEREOF

(75) Inventors: James R. Alfano, Lincoln, NE (US); Alan Collmer, Ithaca, NY (US); Samuel W. Cartinhour, Ithaca, NY (US); David J. Schneider, Trumansburg, NY (US)

(73) Assignees: Cornell Research Foundation, Inc., Ithaca, NY (US); The Board of Regents of the University of Nebraska, Lincoln, NE (US); The United States of America, as Represented by the Secretary of Agriculture, Washington, DC (US)

( * ) Notice: Subject to any disclaimer, the term of this patent is extended or adjusted under 35 U.S.C. 154(b) by 12 days.

(21) Appl. No.: 10/365,742

(22) Filed: Feb. 12, 2003

(65) Prior Publication Data

US 2003/0204868 A1    Oct. 30, 2003

Related U.S. Application Data

(60) Provisional application No. 60/356,408, filed on Feb. 12, 2002, provisional application No. 60/380,185, filed on May 10, 2002.

(51) Int. Cl.
| | |
|---|---|
| *C12N 9/12* | (2006.01) |
| *C12N 15/00* | (2006.01) |
| *C12N 15/82* | (2006.01) |
| *C12P 21/06* | (2006.01) |
| *C07H 21/04* | (2006.01) |
| *C12Q 1/48* | (2006.01) |
| *A61K 38/52* | (2006.01) |

(52) U.S. Cl. .................. 435/375; 435/15; 435/69.1; 435/320.1; 435/194; 424/94.5; 800/279; 800/280; 800/292; 800/293; 536/23.2

(58) Field of Classification Search ................ 424/94.1, 424/94.5; 435/252.3, 254.2, 325, 419, 320.1, 435/468, 471, 375, 194, 69.1, 15; 536/23.1; 800/3, 4, 278
See application file for complete search history.

(56) References Cited

U.S. PATENT DOCUMENTS 6,342,654 B1    1/2002  Li et al.

FOREIGN PATENT DOCUMENTS

WO    WO 99/07207    2/1999

OTHER PUBLICATIONS

Seffernick et al., Melamine deaminase and atrazine chlorohydrolase: 98 percent identical but functionally different. J Bacteriol. 183(8): 2405-2410, 2001.*
Houslay et al., Cell-type specific integration of cross-talk between extracellular signal-regulated kinase and cAMP signaling. Mol Pharmacol. 58(4): 659-668, 2000.*
Whisstock et al., Prediction of protein function from protein sequence and structure. Q Rev Biophys. 36(3): 307-340, 2003.*
Collmer et al., "*Pseudomonas syringae* Hrp Type III Secretion System and Effector Proteins," *PNAS* 97(16):8770-8777 (2000).
Alfano et al., "The *Pseudomonas syringae* Hrp Pathogenicity Island has a Tripartite Mosaic Structure Composed of a Cluster of Type III Secretion Genes Bounded by Exchangeable Effector and Conserved Effector Loci That Contribute to Parasitic Fitness and Pathogenicity in Plants," *PNAS* 97(9):4856-4861 (2000).
Fouts et al., "Genomewide Identification of *Pseudomonas syringae* pv. Tomato DC3000 Promoters Controlled by the HrpL Alternative Sigma Factor," *PNAS* 99(4):2275-2280 (2002), with supplemental material available online at www.pnas.org.
Petnicki-Ocwieja et al., "Genomewide Identification of Proteins Secreted by the Hrp Type III Protein Secretion System of *Pseudomonas syringae* pv. Tomato DC3000," *PNAS* 99(11):7652-7657 (2002), with supplemental material available online at www.pnas.org.
Zwiesler-Vollick et al., "Identification of Novel *hrp*-regulated Genes through Functional Genomic Analysis of the *Pseudomonas syringae* pv. Tomato DC3000 Genome," *Molecular Microbiology* 45(5):1207-1218 (2002).
Guttman et al., "A Functional Screen for the Type III (hrp) Secretome of the Plant Pathogen *Pseudomonas syringae*," *Science*, 295(5560):1722-1726 (2002).
Vinatzer et al., GenBank Accession No. AF458398, (2002).

* cited by examiner

*Primary Examiner*—Rebecca E. Prouty
*Assistant Examiner*—Ganapathirama Raghu
(74) *Attorney, Agent, or Firm*—Nixon Peabody LLP

(57) ABSTRACT

One aspect of the present invention relates to isolated nucleic acid molecules encoding avirulence proteins or polypeptides of *Pseudomonas syringae* pv. *syringae* DC 3000, or nucleic acid molecules which are complementary thereto. Expression vectors, host cells, and transgenic plants which include the DNA molecules of the present invention are also disclosed. Another aspect relates to the isolated proteins or polypeptides and compositions containing the same. The various nucleic acid molecules and proteins of the present invention can be used to impart disease resistance to a plant, make a plant hypersusceptible to colonization by nonpathogenic bacteria, modify a metabolic pathway in a cell, cause eukaryotic cell death and treat a cancerous condition, as well as inhibit programmed cell death.

5 Claims, 7 Drawing Sheets

A
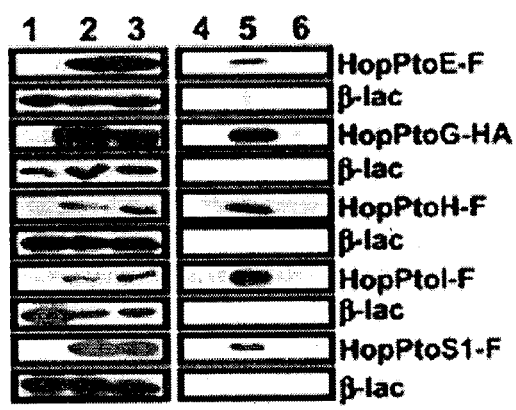
B
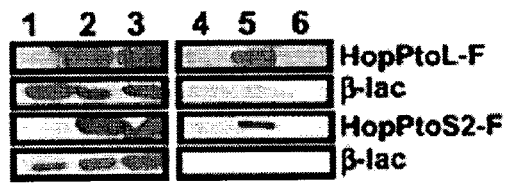
C
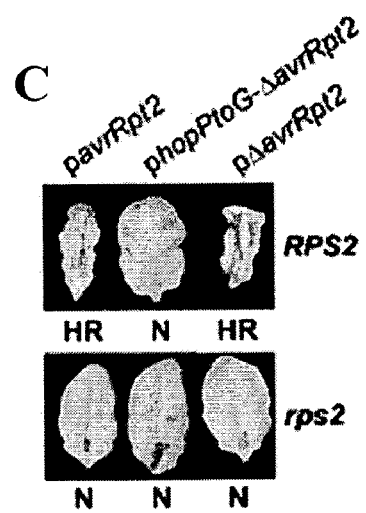
Figures 1A-C

| Effector | AvrPphE$_{Pto}$ | AvrPpiB1$_{Pto}$ | AvrPto | AvrPtoB | HopPtoB | HopPtoC | HopPtoD1 | HopPtoD2 | HopPtoE | HopPtoF | HopPtoG | HopPtoH | HopPtoI | HopPtoJ | HopPtoK | HopPtoL | HopPtoS1 | HopPtoS2 | HopPtoT |
|---|---|---|---|---|---|---|---|---|---|---|---|---|---|---|---|---|---|---|---|
| Suppression | y | y | n | y | n | n | y* | n | y | y | n | n | n | n | y* | n | n | n | n |
Figure 4A
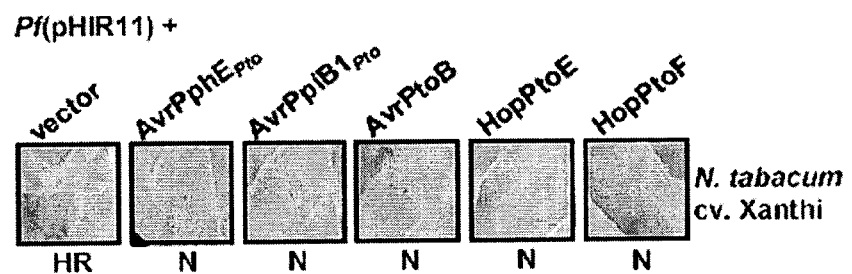
Figure 4B
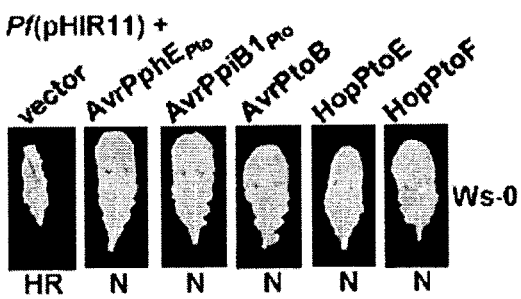
Figure 4C

SEQUENCE LISTING

```
<160> NUMBER OF SEQ ID NOS: 209

<210> SEQ ID NO 1
<211> LENGTH: 1899
<212> TYPE: DNA
<213> ORGANISM: Pseudomonas syringae pv. tomato DC3000

<400> SEQUENCE: 1
atgcttatcg ggcacagctt gcatcacatg cgacccactg ctgtggattc tagcctacca      60
acttccgcaa ctagccagac tatcagcaat accaaaagtc ggctggatcc gcatcgtgtc     120
cgtgaactta cattcatcgg agtgggtagt agtgttgcct acctactcaa tgagcttaat     180
```

```
ggtcgctttg ccgatagcgg ggtaacaacg ccgtttttag gaaaagtcag tattgtaggc      240
aaggacgact cttgggccga gaatgttcgt gggaaaggtt atattaacca ccagactgaa      300
attataagcc aatgggacca acaggttcca aaatatgatc ctaactatgc tgctcgtgcc      360
gaattttctg cgagtaaccg aagacagttg acgcgaacag tggagttagg cgcagaacat      420
ttgaaagcac agtaacagg catttcgcga ttggatgacg gttgttttcg aataaatctg       480
gacaatggcc agattttgca aagccgacag attgtactgg ggactggtgc cggaccccat      540
accagtatct ggaacagcgt tacatcacac actcaagcag aaaaacgact ggacaacatc      600
aaattgcatg agcagaaagc cttgcgtggc aaggtgctgg acctggatga gtttatgcga      660
gcgagtgatg cctctcccca gacgtttgct ggaaaaacgg tggtgataca tggaccaaat      720
gcaggcattg atgcagctga acgtgccggg gagcttgggg caaatgcggt ttggtttacc      780
cgcagtacga atccggtatt gctggatggc aatcaactaa aattcgcgcc agagctggcc      840
aaaagcgcta acataaagt tgacaaatta gatattcgcc caacaaaact agagaatggt       900
ttcgcattgc gactacatta cagttcgcta ggacaagact cacgggagcc aaagaaggtg      960
ctagatgcgg actattatgt gtacgccatg ggtcaagata ttcataagcc gggtagcgca     1020
gcggccatac taggcagtct tcttgaccac ctagaaccta tatgactac cgatcaagtc     1080 tatagcgacc agcctttcaa gacagtaata ggcttgcaaa gtcgcggctc caatagcgat     1140
aatggtttaa ttattgtcgg ggcggcagtt gctcagctgg ccactaatgt tcagcatagc     1200
tataaggacc acgcgttgga tcgtatactt gaggaaatga ccaggctccc cgaaaagcaa     1260
acagaaaagc tatcacaaat gctgttagaa ggtgcgccat cagtacagat ccagacatat     1320
ctaaaaacct ggcagttaga tagcggtcaa ccgccagata acaggtact gcagaatcaa      1380 gtagaaaact atctggcggc ccgagactac ttccagcggc aaaccaacga acaaaagggc     1440
aacctggacg gggttgccgc agaggtaaaa aatcaaacct taaccgaggt tgcatcggtc     1500
atcgtgtcac cacagttagg cacgatcaag gcctccgctg cagcattgtc gggacttatg     1560
ccagcatatg tggctaacgg cgaaaataac tttaccaccg ataatcgaac tatgctccgt     1620
gccggcattg cagcaagata tccgaatata ggtaacgctg aagccagtgc atttatcgat     1680
gaagtagtaa ctttgcgtca ccttaatagt cagcgtttta ttgagaaggt agcaggcgaa     1740
atgatggaca aaggagctca accactggtg tcgttacgcc ccccggtcct aggtgtcccg     1800
gcgtcggtca ggactgctta tgaggcttac ttgcacgcgc tgaattctgg agcgcacgat     1860
ggtacgccgt taagtcagcg ctggctgccc aaaaaatag                             1899
```

<210> SEQ ID NO 2
<211> LENGTH: 632
<212> TYPE: PRT
<213> ORGANISM: Pseudomonas syringae pv. tomato DC3000

<400> SEQUENCE: 2

```
Met Leu Ile Gly His Ser Leu His His Met Arg Pro Thr Ala Val Asp
  1               5                  10                  15

Ser Ser Leu Pro Thr Ser Ala Thr Ser Gln Thr Ile Ser Asn Thr Lys
             20                  25                  30

Ser Arg Leu Asp Pro His Arg Val Arg Glu Leu Thr Phe Ile Gly Val
         35                  40                  45

Gly Ser Ser Val Ala Tyr Leu Leu Asn Glu Leu Asn Gly Arg Phe Ala
     50                  55                  60
```

-continued

```
Asp Ser Gly Val Thr Thr Pro Phe Leu Gly Lys Val Ser Ile Val Gly
 65                  70                  75                  80

Lys Asp Asp Ser Trp Ala Glu Asn Val Arg Gly Lys Gly Tyr Ile Asn
                 85                  90                  95

His Gln Thr Glu Ile Ile Ser Gln Trp Asp Gln Gln Val Pro Lys Tyr
            100                 105                 110

Asp Pro Asn Tyr Ala Ala Arg Ala Glu Phe Ser Ala Ser Asn Arg Arg
        115                 120                 125

Gln Leu Thr Arg Thr Val Glu Leu Gly Ala Glu His Leu Lys Ala Gln
    130                 135                 140

Val Thr Gly Ile Ser Arg Leu Asp Asp Gly Cys Phe Arg Ile Asn Leu
145                 150                 155                 160

Asp Asn Gly Gln Ile Leu Gln Ser Arg Gln Ile Val Leu Gly Thr Gly
                165                 170                 175

Ala Gly Pro His Thr Ser Ile Trp Asn Ser Val Thr Ser His Thr Gln
            180                 185                 190

Ala Glu Lys Arg Leu Asp Asn Ile Lys Leu His Glu Gln Lys Ala Leu
        195                 200                 205

Arg Gly Lys Val Leu Asp Leu Asp Glu Phe Met Arg Ala Ser Asp Ala
    210                 215                 220

Ser Pro Gln Thr Phe Ala Gly Lys Thr Val Val Ile His Gly Pro Asn
225                 230                 235                 240

Ala Gly Ile Asp Ala Ala Glu Arg Ala Gly Glu Leu Gly Ala Asn Ala
                245                 250                 255

Val Trp Phe Thr Arg Ser Thr Asn Pro Val Leu Leu Asp Gly Asn Gln
            260                 265                 270

Leu Lys Phe Ala Pro Glu Leu Ala Lys Ser Ala Ile His Lys Val Asp
        275                 280                 285

Lys Leu Asp Ile Arg Pro Thr Lys Leu Glu Asn Gly Phe Ala Leu Arg
    290                 295                 300

Leu His Tyr Ser Ser Leu Gly Gln Asp Ser Arg Glu Pro Lys Lys Val
305                 310                 315                 320

Leu Asp Ala Asp Tyr Tyr Val Tyr Ala Met Gly Gln Asp Ile His Lys
                325                 330                 335

Pro Gly Ser Ala Ala Ala Ile Leu Gly Ser Leu Leu Asp His Leu Glu
            340                 345                 350

Pro Ile Tyr Asp Tyr Asp Gln Val Tyr Ser Asp Gln Pro Phe Lys Thr
        355                 360                 365

Val Ile Gly Leu Gln Ser Arg Gly Ser Asn Ser Asp Asn Gly Leu Ile
    370                 375                 380

Ile Val Gly Ala Ala Val Ala Gln Leu Ala Thr Asn Val Gln His Ser
385                 390                 395                 400

Tyr Lys Asp His Ala Leu Asp Arg Ile Leu Glu Glu Met Thr Arg Leu
                405                 410                 415

Pro Glu Lys Gln Thr Glu Lys Leu Ser Gln Met Leu Leu Glu Gly Ala
            420                 425                 430

Pro Ser Val Gln Ile Gln Thr Tyr Leu Lys Thr Trp Gln Leu Asp Ser
        435                 440                 445

Gly Gln Pro Pro Asp Lys Gln Val Leu Gln Asn Gln Val Glu Asn Tyr
    450                 455                 460

Leu Ala Ala Arg Asp Tyr Phe Gln Arg Gln Thr Asn Glu Gln Lys Gly
465                 470                 475                 480
```

-continued

```
Asn Leu Asp Gly Val Ala Ala Glu Val Lys Asn Gln Thr Leu Thr Glu
                485                 490                 495

Val Ala Ser Val Ile Val Ser Pro Gln Leu Gly Thr Ile Lys Ala Ser
            500                 505                 510

Ala Ala Ala Leu Ser Gly Leu Met Pro Ala Tyr Val Ala Asn Gly Glu
            515                 520                 525

Asn Asn Phe Thr Thr Asp Asn Arg Thr Met Leu Arg Ala Gly Ile Ala
            530                 535                 540

Ala Arg Tyr Pro Asn Ile Gly Asn Ala Glu Ala Ser Ala Phe Ile Asp
545                 550                 555                 560

Glu Val Val Thr Leu Arg His Leu Asn Ser Gln Arg Phe Ile Glu Lys
                565                 570                 575

Val Ala Gly Glu Met Met Asp Lys Gly Ala Gln Pro Leu Val Ser Leu
            580                 585                 590

Arg Pro Pro Val Leu Gly Val Pro Ala Ser Val Arg Thr Ala Tyr Glu
            595                 600                 605

Ala Tyr Leu His Ala Leu Asn Ser Gly Ala His Asp Gly Thr Pro Leu
            610                 615                 620

Ser Gln Arg Trp Leu Pro Lys Lys
625                 630
```

<210> SEQ ID NO 3
<211> LENGTH: 657
<212> TYPE: DNA
<213> ORGANISM: Pseudomonas syringae pv. tomato DC3000

<400> SEQUENCE: 3

```
atgatcactc cgtctcgata tccaggcatc tatatcgccc ccctcagtaa cgaaccgaca      60
gcagctcaca catttaaaga acaagcagag gaagcacttg accatatcag cgccgcaccc     120
tctggcgata gctattgcg aaaaatatcc actcttgcca gtcaaaaaga tagaaaagtc      180
acgctaaaag agattgaaat aaataaccag tgttataccg aagctgttct gagcagragg     240
caactggaaa agtacgaacc agaaaacttt aacgagaacc ggcacattgc atcacagcta     300
tcacgaaagg ggacctttac caaaggtgaa ggaagcaacg cgattattgg ctggtcacca     360
gacaaagcaa gcatacgctt aaatcagaat ggctcaccgt tacaccttgg aatggataac     420
gacgacaaaa tcacgaccct agctcatgag ctcgttcatg ctcgacatgt gttaggtggc     480
agctccttag cggatggcgg agatcgctat aatccacgta cgggatctgg caaagaggaa     540
cttagggccg ttggattaga taagtaccgc tattcactta caaaaaaacc gtcagagaac     600
tccatccgag ctgaacacgg cctgcctctg cgcatgaagt acagggcaca tcaatag        657
```

<210> SEQ ID NO 4
<211> LENGTH: 218
<212> TYPE: PRT
<213> ORGANISM: Pseudomonas syringae pv. tomato DC3000

<400> SEQUENCE: 4

```
Met Ile Thr Pro Ser Arg Tyr Pro Gly Ile Tyr Ile Ala Pro Leu Ser
1               5                   10                  15

Asn Glu Pro Thr Ala Ala His Thr Phe Lys Glu Gln Ala Glu Glu Ala
                20                  25                  30

Leu Asp His Ile Ser Ala Ala Pro Ser Gly Asp Lys Leu Leu Arg Lys
            35                  40                  45

Ile Ser Thr Leu Ala Ser Gln Lys Asp Arg Lys Val Thr Leu Lys Glu
        50                  55                  60
```

-continued

```
Ile Glu Ile Asn Asn Gln Cys Tyr Thr Glu Ala Val Leu Ser Arg Arg
 65                  70                  75                  80

Gln Leu Glu Lys Tyr Glu Pro Glu Asn Phe Asn Glu Asn Arg His Ile
             85                  90                  95

Ala Ser Gln Leu Ser Arg Lys Gly Thr Phe Thr Lys Gly Glu Gly Ser
            100                 105                 110

Asn Ala Ile Ile Gly Trp Ser Pro Asp Lys Ala Ser Ile Arg Leu Asn
        115                 120                 125

Gln Asn Gly Ser Pro Leu His Leu Gly Met Asp Asn Asp Lys Ile
    130                 135                 140

Thr Thr Leu Ala His Glu Leu Val His Ala Arg His Val Leu Gly Gly
145                 150                 155                 160

Ser Ser Leu Ala Asp Gly Gly Asp Arg Tyr Asn Pro Arg Thr Gly Ser
                165                 170                 175

Gly Lys Glu Glu Leu Arg Ala Val Gly Leu Asp Lys Tyr Arg Tyr Ser
            180                 185                 190

Leu Thr Lys Lys Pro Ser Glu Asn Ser Ile Arg Ala Glu His Gly Leu
        195                 200                 205

Pro Leu Arg Met Lys Tyr Arg Ala His Gln
    210                 215

<210> SEQ ID NO 5
<211> LENGTH: 636
<212> TYPE: DNA
<213> ORGANISM: Pseudomonas syringae pv. tomato DC3000

<400> SEQUENCE: 5
atgaatagag tttccggtag ctcgtcagcg acttggcagg cagtcaacga tcttgtggag      60
caagtaagcg agagaaccac gttgtctacg acaggttatc agacggcaat gggccgcttg     120
aacaaaccgg aaaaatcaga tgcggatgcg ctgatgacta tgaggagggc gcaacagtac     180
acggatagcg cgaagcgaac ttatatttcg gaaacgctga tgaatctggc agatttgcag     240
caaaggaaaa tctatcgcac caacagcggg aacttgcgtg gcgcgattga gatgacgcct     300
acgcaactca cagattgcgt acagaagtgc cgcgaagagg ggttctccaa ttgtgacata     360
caggcgctgg aaatcggctt gcaccttcga cataagttag aatctcagat tttcaccatc     420
tacagcaacc gtaagttaag ccataactat gtggtcatcc accccagcaa tgcatttccg     480
aaaggagcga ttgtagactc ttggacggga cagggcgtgg tggagctgga cttcaagacc     540
cgattgaaat tcaagcaccg ggaagagaac tacgcagtga acgccaatat gcacgagtgg     600
atcgagagat acggccaagc gcatgtgatt gactga                                636

<210> SEQ ID NO 6
<211> LENGTH: 211
<212> TYPE: PRT
<213> ORGANISM: Pseudomonas syringae pv. tomato DC3000

<400> SEQUENCE: 6

Met Asn Arg Val Ser Gly Ser Ser Ser Ala Thr Trp Gln Ala Val Asn
  1               5                  10                  15

Asp Leu Val Glu Gln Val Ser Glu Arg Thr Thr Leu Ser Thr Thr Gly
             20                  25                  30

Tyr Gln Thr Ala Met Gly Arg Leu Asn Lys Pro Glu Lys Ser Asp Ala
         35                  40                  45

Asp Ala Leu Met Thr Met Arg Arg Ala Gln Gln Tyr Thr Asp Ser Ala
     50                  55                  60
```

-continued

| | | | | | | | | | | | | | | | |
|---|---|---|---|---|---|---|---|---|---|---|---|---|---|---|---|
|Lys|Arg|Thr|Tyr|Ile|Ser|Glu|Thr|Leu|Met|Asn|Leu|Ala|Asp|Leu|Gln|
|65| | | |70| | | |75| | | |80| | | |

| | | | | | | | | | | | | | | | |
|---|---|---|---|---|---|---|---|---|---|---|---|---|---|---|---|
|Gln|Arg|Lys|Ile|Tyr|Arg|Thr|Asn|Ser|Gly|Asn|Leu|Arg|Gly|Ala|Ile|
| | | | |85| | | |90| | | |95| | | |

| | | | | | | | | | | | | | | | |
|---|---|---|---|---|---|---|---|---|---|---|---|---|---|---|---|
|Glu|Met|Thr|Pro|Thr|Gln|Leu|Thr|Asp|Cys|Val|Gln|Lys|Cys|Arg|Glu|
| | | |100| | | |105| | | |110| | | | |

| | | | | | | | | | | | | | | | |
|---|---|---|---|---|---|---|---|---|---|---|---|---|---|---|---|
|Glu|Gly|Phe|Ser|Asn|Cys|Asp|Ile|Gln|Ala|Leu|Glu|Ile|Gly|Leu|His|
| | |115| | | |120| | | |125| | | | | |

| | | | | | | | | | | | | | | | |
|---|---|---|---|---|---|---|---|---|---|---|---|---|---|---|---|
|Leu|Arg|His|Lys|Leu|Gly|Ile|Ser|Asp|Phe|Thr|Ile|Tyr|Ser|Asn|Arg|
|130| | | |135| | | |140| | | | | | | |

| | | | | | | | | | | | | | | | |
|---|---|---|---|---|---|---|---|---|---|---|---|---|---|---|---|
|Lys|Leu|Ser|His|Asn|Tyr|Val|Val|Ile|His|Pro|Ser|Asn|Ala|Phe|Pro|
|145| | | |150| | | |155| | | |160| | | |

| | | | | | | | | | | | | | | | |
|---|---|---|---|---|---|---|---|---|---|---|---|---|---|---|---|
|Lys|Gly|Ala|Ile|Val|Asp|Ser|Trp|Thr|Gly|Gln|Gly|Val|Val|Glu|Leu|
| | | |165| | | |170| | | |175| | | | |

| | | | | | | | | | | | | | | | |
|---|---|---|---|---|---|---|---|---|---|---|---|---|---|---|---|
|Asp|Phe|Lys|Thr|Arg|Leu|Lys|Phe|Lys|His|Arg|Glu|Glu|Asn|Tyr|Ala|
| | |180| | | |185| | | |190| | | | | |

| | | | | | | | | | | | | | | | |
|---|---|---|---|---|---|---|---|---|---|---|---|---|---|---|---|
|Val|Asn|Ala|Asn|Met|His|Glu|Trp|Ile|Glu|Arg|Tyr|Gly|Gln|Ala|His|
| |195| | | |200| | | |205| | | | | | |

| | | |
|---|---|---|
|Val|Ile|Asp|
|210| | |

```
<210> SEQ ID NO 7
<211> LENGTH: 1482
<212> TYPE: DNA
<213> ORGANISM: Pseudomonas syringae pv. tomato DC3000

<400> SEQUENCE: 7
atgcaaataa agaacagtca tctctattca gcttcaagaa tggtgcagaa tacttttaat      60
gcctcgccta agatggaagt aactaatgca atagcaaaaa ataatgaacc tgctgcgctg     120
agcgctacgc aaactgcaaa gacacacgaa ggcgattcaa aaggccaatc cagcaataac     180
tctaaattgc ccttccgcgc catgaggtac gctgcatacc ttgcaggcag cgcctacctc     240
tacgataaaa ctgccaataa ttttttttctt ctaccactt ctctgcatga tggcaaaggt     300
ggttttacca gcgatgccag gcttaacgat gcacaagata aagcgcgaaa gcgctaccaa     360
aacaaccata gcagcactct tgaaaataaa aactcgcttt taagcccgct taggctttgc     420
ggagagaatc agttcttaac gatgattgat tatcgtgcag caactaagat ttacctctcc     480
gacctagttg acacggagca agcgcacaca tcaattctga agaatattat gtgcctgaaa     540
ggtgagctta ccaatgaaga ggcaataaaa aaactcaacc cggaaaaaac accaaaagac     600
tatgacctta caaatagcga agcctatata agcaagaaca atattctttt gaccggcgtt     660
aaaaatgagg agacgggatc tactggttat acatctcgtt ctatcacaaa gccatttgtg     720
gaaaaaggcc tgaaacactt tataaaagcg actcatggcg aaaaagctct cacgcccaag     780
cagtgtatgg aaactcttga taacttactt cgaaaaagta tcacgctcaa cagtgattcc     840
caattcgcag caggccaggc acttttggtt ttcagacagg tctatgcggg tgaagacgct     900
tgggggatg cggaacgggt catattgaaa agccattata tcggggcac tgtactccaa     960
gatgaagctg ataaaataga actaagtagg ccgttctcag agcaagattt agcaaagaac    1020
atgtttaaga ggaataccag cattgcaggg ccagtgctct accacgcata tatttatata    1080
caagaaaaaa tcttcaagct accccccgac aaaatagaag atttgaaaca taaatcaatg    1140
gcagacttga aaaccctgcc tttgactcat gttaagctta gcaattccgg tgtgggattt    1200
gaagacgcct cagggttagg agactcgttt acagctctca acgcgacgtc ctgtgttaat    1260
```

```
cacgcaagaa taatgagtgg tgagcctccc ttgtcaaaag atgatgttgt gattctgata    1320
ggttgcctca acgccgtata cgacaattcg agcggaataa ggcattctct ccgcgaaatt    1380
gcacgagggt gctttgtggg tgctggtttt acggtccagg acggtgacga cttctacaaa    1440
cagatctgca aaaacgcctc taagcagttt tacaacggct aa                       1482
```

<210> SEQ ID NO 8
<211> LENGTH: 493
<212> TYPE: PRT
<213> ORGANISM: Pseudomonas syringae pv. tomato DC3000

<400> SEQUENCE: 8

```
Met Gln Ile Lys Asn Ser His Leu Tyr Ser Ala Ser Arg Met Val Gln
 1               5                  10                  15

Asn Thr Phe Asn Ala Ser Pro Lys Met Glu Val Thr Asn Ala Ile Ala
            20                  25                  30

Lys Asn Asn Glu Pro Ala Ala Leu Ser Ala Thr Gln Thr Ala Lys Thr
        35                  40                  45

His Glu Gly Asp Ser Lys Gly Gln Ser Ser Asn Asn Ser Lys Leu Pro
    50                  55                  60

Phe Arg Ala Met Arg Tyr Ala Ala Tyr Leu Ala Gly Ser Ala Tyr Leu
65                  70                  75                  80

Tyr Asp Lys Thr Ala Asn Asn Phe Phe Leu Ser Thr Thr Ser Leu His
                85                  90                  95

Asp Gly Lys Gly Gly Phe Thr Ser Asp Ala Arg Leu Asn Asp Ala Gln
            100                 105                 110

Asp Lys Ala Arg Lys Arg Tyr Gln Asn Asn His Ser Ser Thr Leu Glu
        115                 120                 125

Asn Lys Asn Ser Leu Leu Ser Pro Leu Arg Leu Cys Gly Glu Asn Gln
    130                 135                 140

Phe Leu Thr Met Ile Asp Tyr Arg Ala Ala Thr Lys Ile Tyr Leu Ser
145                 150                 155                 160

Asp Leu Val Asp Thr Glu Gln Ala His Thr Ser Ile Leu Lys Asn Ile
                165                 170                 175

Met Cys Leu Lys Gly Glu Leu Thr Asn Glu Ala Ile Lys Lys Leu
            180                 185                 190

Asn Pro Glu Lys Thr Pro Lys Asp Tyr Asp Leu Thr Asn Ser Glu Ala
        195                 200                 205

Tyr Ile Ser Lys Asn Lys Tyr Ser Leu Thr Gly Val Lys Asn Glu Glu
    210                 215                 220

Thr Gly Ser Thr Gly Tyr Thr Ser Arg Ser Ile Thr Lys Pro Phe Val
225                 230                 235                 240

Glu Lys Gly Leu Lys His Phe Ile Lys Ala Thr His Gly Glu Lys Ala
                245                 250                 255

Leu Thr Pro Lys Gln Cys Met Glu Thr Leu Asp Asn Leu Leu Arg Lys
            260                 265                 270

Ser Ile Thr Leu Asn Ser Asp Ser Gln Phe Ala Ala Gly Gln Ala Leu
        275                 280                 285

Leu Val Phe Arg Gln Val Tyr Ala Gly Glu Asp Ala Trp Gly Asp Ala
    290                 295                 300

Glu Arg Val Ile Leu Lys Ser His Tyr Asn Arg Gly Thr Val Leu Gln
305                 310                 315                 320

Asp Glu Ala Asp Lys Ile Glu Leu Ser Arg Pro Phe Ser Glu Gln Asp
                325                 330                 335
```

```
Leu Ala Lys Asn Met Phe Lys Arg Asn Thr Ser Ile Ala Gly Pro Val
            340                 345                 350

Leu Tyr His Ala Tyr Ile Tyr Ile Gln Glu Lys Ile Phe Lys Leu Pro
            355                 360                 365

Pro Asp Lys Ile Glu Asp Leu Lys His Lys Ser Met Ala Asp Leu Lys
            370                 375                 380

Asn Leu Pro Leu Thr His Val Lys Leu Ser Asn Ser Gly Val Gly Phe
385                 390                 395                 400

Glu Asp Ala Ser Gly Leu Gly Asp Ser Phe Thr Ala Leu Asn Ala Thr
                405                 410                 415

Ser Cys Val Asn His Ala Arg Ile Met Ser Gly Glu Pro Pro Leu Ser
                420                 425                 430

Lys Asp Asp Val Val Ile Leu Ile Gly Cys Leu Asn Ala Val Tyr Asp
            435                 440                 445

Asn Ser Ser Gly Ile Arg His Ser Leu Arg Glu Ile Ala Arg Gly Cys
            450                 455                 460

Phe Val Gly Ala Gly Phe Thr Val Gln Asp Gly Asp Asp Phe Tyr Lys
465                 470                 475                 480

Gln Ile Cys Lys Asn Ala Ser Lys Gln Phe Tyr Asn Gly
                485                 490

<210> SEQ ID NO 9
<211> LENGTH: 852
<212> TYPE: DNA
<213> ORGANISM: Pseudomonas syringae pv. tomato DC3000

<400> SEQUENCE: 9
atgggtaata tttgtggtac ttctggctcc aatcatgtgt atagtccgcc tattagccct      60
caacatgcat ctggttcgtc cacaccagtg cccagtgctt ctgggacgat gctttctctc     120
agtcatgaac aaatattaag ccagaactat gctagcaata taagggggaa atatcgcacg     180 aaccccgaa aggaccatc tcctaggctt tctgatacgc tgatgaagca ggcgctgtct       240
tcagtgatca cacaagagaa aaagcgactt aaaagtcaac caaagtcaat agcccaagat     300
attcagcctc caaacagcat gatcaaaaat gcacttgatg aaaaagacag ccacccttt      360 ggtgattgct tttcagacga tgaatttctt gcgatccatc tctatacgag ttgtctttac     420
agaccgatca accatcatct gcggtatgcc ccgaaaaatg atgtcgcgcc tgttgtcgag     480
gcaatgaata gcggtttggc caaacttgct caatacccctg attatcaggt gtctggtcag     540
ctgcatagag gcatcaagca aaagatggat gatggtgaag ttatgagtcg cttcaagccg     600
ggtaatactt atcgtgatga cgcgttcatg agcacatcga ctagaatgga tgttacagaa     660
gaatttactt ccgatgtcac gttacatctg cagtcctcat cagccgtcaa tataggtccc     720
ttttcaaaaa acccatacga ggacgaagcg ctcatcccgc ccctgacgcc tttcaaagta     780
accggtctgc acaagcagga cgataggtgg cacgtccact tgaacgagat cgcagagagc     840
tctgacgagt ga                                                        852

<210> SEQ ID NO 10
<211> LENGTH: 283
<212> TYPE: PRT
<213> ORGANISM: Pseudomonas syringae pv. tomato DC3000
```

```
<400> SEQUENCE: 10

Met Gly Asn Ile Cys Gly Thr Ser Gly Ser Asn His Val Tyr Ser Pro
 1               5                  10                  15

Pro Ile Ser Pro Gln His Ala Ser Gly Ser Ser Thr Pro Val Pro Ser
            20                  25                  30

Ala Ser Gly Thr Met Leu Ser Leu Ser His Glu Gln Ile Leu Ser Gln
        35                  40                  45

Asn Tyr Ala Ser Asn Ile Lys Gly Lys Tyr Arg Thr Asn Pro Arg Lys
    50                  55                  60

Gly Pro Ser Pro Arg Leu Ser Asp Thr Leu Met Lys Gln Ala Leu Ser
65                  70                  75                  80

Ser Val Ile Thr Gln Glu Lys Lys Arg Leu Lys Ser Gln Pro Lys Ser
                85                  90                  95

Ile Ala Gln Asp Ile Gln Pro Pro Asn Ser Met Ile Lys Asn Ala Leu
            100                 105                 110

Asp Glu Lys Asp Ser His Pro Phe Gly Asp Cys Phe Ser Asp Asp Glu
        115                 120                 125

Phe Leu Ala Ile His Leu Tyr Thr Ser Cys Leu Tyr Arg Pro Ile Asn
130                 135                 140

His His Leu Arg Tyr Ala Pro Lys Asn Asp Val Ala Pro Val Val Glu
145                 150                 155                 160

Ala Met Asn Ser Gly Leu Ala Lys Leu Ala Gln Tyr Pro Asp Tyr Gln
                165                 170                 175

Val Ser Gly Gln Leu His Arg Gly Ile Lys Gln Lys Met Asp Asp Gly
            180                 185                 190

Glu Val Met Ser Arg Phe Lys Pro Gly Asn Thr Tyr Arg Asp Asp Ala
        195                 200                 205

Phe Met Ser Thr Ser Thr Arg Met Asp Val Thr Glu Glu Phe Thr Ser
210                 215                 220

Asp Val Thr Leu His Leu Gln Ser Ser Ser Ala Val Asn Ile Gly Pro
225                 230                 235                 240

Phe Ser Lys Asn Pro Tyr Glu Asp Glu Ala Leu Ile Pro Pro Leu Thr
                245                 250                 255

Pro Phe Lys Val Thr Gly Leu His Lys Gln Asp Asp Arg Trp His Val
            260                 265                 270

His Leu Asn Glu Ile Ala Glu Ser Ser Asp Glu
        275                 280

<210> SEQ ID NO 11
<211> LENGTH: 393
<212> TYPE: DNA
<213> ORGANISM: Pseudomonas syringae pv. tomato DC3000

<400> SEQUENCE: 11
atgagcttat cgccgacgct gcaaaagcta actaatatat tgggcccgac aaaaaatgcc      60
aagcctgtca cagaggctat ccagtggcag gaaggcatgg atataacgct gcatgtcagc     120
ggcgacagcc ttaccttact agctaaaatc atagaactgc gtacagaccc taaagacgac     180
attttattgc gcaagctgct tacccatacg tttccgggcc tgcgtctgcg ccgtggcgcg     240
cttaccatca accctgatga agtgccctg gttttctctt atgaacacga ttttcacctt     300
ctggacaaag cccgttttga gagcctgctg gccaactttg ctgaaacggc gcaggagctt     360
cgagacacag cgacacattt tcgtttaac tga                                    393
```

<210> SEQ ID NO 12
<211> LENGTH: 130
<212> TYPE: PRT
<213> ORGANISM: Pseudomonas syringae pv. tomato DC3000

<400> SEQUENCE: 12

```
Met Ser Leu Ser Pro Thr Leu Gln Lys Leu Thr Asn Ile Leu Gly Pro
  1               5                  10                  15

Thr Lys Asn Ala Lys Pro Val Thr Glu Ala Ile Gln Trp Gln Glu Gly
             20                  25                  30

Met Asp Ile Thr Leu His Val Ser Gly Asp Ser Leu Thr Leu Leu Ala
         35                  40                  45

Lys Ile Ile Glu Leu Arg Thr Asp Pro Lys Asp Asp Ile Leu Leu Arg
 50                  55                  60

Lys Leu Leu Thr His Thr Phe Pro Gly Leu Arg Leu Arg Arg Gly Ala
 65                  70                  75                  80

Leu Thr Ile Asn Pro Asp Glu Ser Ala Leu Val Phe Ser Tyr Glu His
                 85                  90                  95

Asp Phe His Leu Leu Asp Lys Ala Arg Phe Glu Ser Leu Leu Ala Asn
            100                 105                 110

Phe Ala Glu Thr Ala Gln Glu Leu Arg Asp Thr Ala Thr His Phe Arg
        115                 120                 125

Phe Asn
    130
```

<210> SEQ ID NO 13
<211> LENGTH: 387
<212> TYPE: DNA
<213> ORGANISM: Pseudomonas syringae pv. tomato DC3000

<400> SEQUENCE: 13

```
atgaaacaac gagcgacagt catctgcaaa cgtgacggcc aggtgcttta cgtacgcaaa    60
ccaaaatccc gctgggcttt gccaggtggc aagattgaag ccggggaaac gcctttccag   120
gctgccgtgc gcgagctttg cgaagaaacc ggtctggaaa atctcgatct gttgtacctg   180
gcggtgtacg agaaaggtga ggtcacgcac tacgtgttca ccactcaggt tcctgcctac   240
agcgagcctt cgccccagaa cgagatttct gcctgcaaat ggcttgcgcc caaaatcttt   300
ggcgacctta aggccagcag cgcgaccaag gctatcgtca gtcgtatgg ccgccaggct   360 gaagacggtt tactcagcgc taactag                                       387
```

<210> SEQ ID NO 14
<211> LENGTH: 128
<212> TYPE: PRT
<213> ORGANISM: Pseudomonas syringae pv. tomato DC3000

<400> SEQUENCE: 14

```
Met Lys Gln Arg Ala Thr Val Ile Cys Lys Arg Asp Gly Gln Val Leu
  1               5                  10                  15

Tyr Val Arg Lys Pro Lys Ser Arg Trp Ala Leu Pro Gly Gly Lys Ile
             20                  25                  30

Glu Ala Gly Glu Thr Pro Phe Gln Ala Ala Val Arg Glu Leu Cys Glu
         35                  40                  45

Glu Thr Gly Leu Glu Asn Leu Asp Leu Leu Tyr Leu Ala Val Tyr Glu
 50                  55                  60

Lys Gly Glu Val Thr His Tyr Val Phe Thr Thr Gln Val Pro Ala Tyr
 65                  70                  75                  80
```

-continued

Ser Glu Pro Ser Pro Gln Asn Glu Ile Ser Ala Cys Lys Trp Leu Ala
                85                  90                  95

Pro Lys Asn Leu Gly Asp Leu Lys Ala Ser Ser Ala Thr Lys Ala Ile
            100                 105                 110

Val Lys Ser Tyr Gly Arg Gln Ala Glu Asp Gly Leu Leu Ser Ala Asn
        115                 120                 125

<210> SEQ ID NO 15
<211> LENGTH: 1014
<212> TYPE: DNA
<213> ORGANISM: Pseudomonas syringae pv. tomato DC3000

<400> SEQUENCE: 15
gtgctcgctt tgcatacgt cagcctgatt agagagcaga aattggacat caaaaaacgt      60
tggccttcca gtgagcagga gttggtagaa gtccgacggt ttaacaaaac cctcgcccgg    120
ctgccgcgtt tccaggttcg caatcgcctc acgcccgct tgattcaggc gctgctgcgg    180
gcggctcaga ttggtcgcgc gttgaaaccg gtcaaacatg acctgcggat tgaaacaacc    240
atcgtcagca ccgtaacgt ccctgtttca gtgcgaatca taggcccaa aggcaaaccc    300
aaaggcgtgg tgtttgatat tcacggcggc ggttgggtga tcggcaacgc ccagatgaac    360
gatgacctca atatcggtat cgttaacgcg tgcaacgtgg cggtcgtgtc cgttgattac    420
agattggctt tatcgacccc cgtcgaaggg ctgatggatg actgcttttc tgccgcatgc    480
tggctgctgg gtagcgactg taaggagttt gccggcctgc cggttattgt cgtcggtgag    540
tccgcgggcg ggcatcttgc cgcagccact ttgctcaaat tgaaagccag gcccgacttg    600
ctcaagcgcg tagtcggcac ggttctgtat tacggcgtgt acgacctgac cgggacaaaa    660
agcgttcgta ccgcaggccc ggaaacgctg gtgctcgacg gcccgggcat ggtcggcgca    720
atgcgcttgc tcgccccgga cagaaccgac gagaagcgcc gcgagccgcc gttatcgccc    780
ttgtatggcg acctcacgga tctgccgccc gccctgatgt ttgtcggcga actcgacccg    840
ctgctggacg acacgctgga aatggccgag cgatggaaaa actcggcaga cgttgaaatg    900
catcttctgc ccgagtctcc acatgggttc atccacttcc cgactgcctt ggcgcgcaag    960
gtacttgcgc gcagccacga gtggataaac gcgaggatgg aagaacggcc ttaa         1014

<210> SEQ ID NO 16
<211> LENGTH: 337
<212> TYPE: PRT
<213> ORGANISM: Pseudomonas syringae pv. tomato DC3000

<400> SEQUENCE: 16

Val Leu Ala Phe Ala Tyr Val Ser Leu Ile Arg Glu Gln Lys Leu Asp
 1               5                  10                  15

Ile Lys Lys Arg Trp Pro Ser Ser Glu Gln Glu Leu Val Glu Val Arg
            20                  25                  30

Arg Phe Asn Lys Thr Leu Ala Arg Leu Pro Arg Phe Gln Val Arg Asn
        35                  40                  45

Arg Leu Thr Pro Arg Leu Ile Gln Ala Leu Leu Arg Ala Ala Gln Ile
    50                  55                  60

Gly Arg Ala Leu Lys Pro Val Lys His Asp Leu Arg Ile Glu Thr Thr
65                  70                  75                  80

Ile Val Ser Thr Gly Asn Val Pro Val Ser Val Arg Ile Ile Arg Pro
                85                  90                  95

Lys Gly Lys Pro Lys Gly Val Val Phe Asp Ile His Gly Gly Gly Trp
            100                 105                 110

-continued

```
Val Ile Gly Asn Ala Gln Met Asn Asp Asp Leu Asn Ile Gly Ile Val
        115                 120                 125

Asn Ala Cys Asn Val Ala Val Val Ser Val Asp Tyr Arg Leu Ala Leu
    130                 135                 140

Ser Thr Pro Val Glu Gly Leu Met Asp Asp Cys Phe Ser Ala Ala Cys
145                 150                 155                 160

Trp Leu Leu Gly Ser Asp Cys Lys Glu Phe Ala Gly Leu Pro Val Ile
                165                 170                 175

Val Val Gly Glu Ser Ala Gly Gly His Leu Ala Ala Thr Leu Leu
            180                 185                 190

Lys Leu Lys Ala Arg Pro Asp Leu Leu Lys Arg Val Val Gly Thr Val
        195                 200                 205

Leu Tyr Tyr Gly Val Tyr Asp Leu Thr Gly Thr Lys Ser Val Arg Thr
        210                 215                 220

Ala Gly Pro Glu Thr Leu Val Leu Asp Gly Pro Gly Met Val Gly Ala
225                 230                 235                 240

Met Arg Leu Leu Ala Pro Asp Arg Thr Asp Glu Lys Arg Arg Glu Pro
                245                 250                 255

Pro Leu Ser Pro Leu Tyr Gly Asp Leu Thr Asp Leu Pro Pro Ala Leu
                260                 265                 270

Met Phe Val Gly Glu Leu Asp Pro Leu Leu Asp Asp Thr Leu Glu Met
            275                 280                 285

Ala Glu Arg Trp Lys Asn Ser Ala Asp Val Glu Met His Leu Leu Pro
        290                 295                 300

Glu Ser Pro His Gly Phe Ile His Phe Pro Thr Ala Leu Ala Arg Lys
305                 310                 315                 320

Val Leu Ala Arg Ser His Glu Trp Ile Asn Ala Arg Met Glu Gly Arg
                325                 330                 335
Pro
```

<210> SEQ ID NO 17
<211> LENGTH: 483
<212> TYPE: DNA
<213> ORGANISM: Pseudomonas syringae pv. tomato DC3000

<400> SEQUENCE: 17

```
atgcaaacct atataccta tccaaaaaac cctcccaccg ttggtacagt tctgctgact      60
tcctatggct cattcgccca tgaaaacgag atacctaaat cttgtgctgc cgacgcttta     120
agagtaggca aagagctcgc tgatggtttc gatggcgagg ttcatcatct aggcgctctg    180
atgctgatga tttccgactt tccagcagag ccgctgctga agcatctgc tgctaagaaa     240
ggttctttgc taggaattac ttcgcttggc tacctattat cctatggatc tactggtgaa    300
aaagcgaagc gaatcatcga agcaggttgt ggtattttc tcgtcagagt gagtggtgat    360
attgaaaacc ctaaagcaaa aattgaagtt tatagctctt ggtctgaata ccagaagttc    420
cttgaaccca ttttgaagac aggtgactt tatccagtga aaacgtcgtc gttttccgaa     480
taa                                                                  483
```

<210> SEQ ID NO 18
<211> LENGTH: 160
<212> TYPE: PRT
<213> ORGANISM: Pseudomonas syringae pv. tomato DC3000

-continued

```
<400> SEQUENCE: 18

Met Gln Thr Tyr Ile Pro Tyr Pro Lys Asn Pro Pro Thr Val Gly Thr
 1               5                  10                 15

Val Leu Leu Thr Ser Tyr Gly Ser Phe Ala His Glu Asn Glu Ile Pro
             20                  25                 30

Lys Ser Cys Ala Ala Asp Ala Leu Arg Val Gly Lys Glu Leu Ala Asp
         35                  40                 45

Gly Phe Asp Gly Glu Val His His Leu Gly Ala Leu Met Leu Met Ile
     50                  55                 60

Ser Asp Phe Pro Ala Glu Pro Leu Leu Lys Ala Ser Ala Ala Lys Lys
 65                 70                  75                 80

Gly Ser Leu Leu Gly Ile Thr Ser Leu Gly Tyr Leu Leu Ser Tyr Gly
                 85                  90                 95

Ser Thr Gly Glu Lys Ala Lys Arg Ile Ile Glu Ala Gly Cys Gly Ile
            100                 105                110

Phe Leu Val Arg Val Ser Gly Asp Ile Glu Asn Pro Lys Ala Lys Ile
        115                 120                 125

Glu Val Tyr Ser Ser Trp Ser Glu Tyr Gln Lys Phe Leu Glu Pro Ile
    130                 135                 140

Leu Lys Thr Gly Asp Phe Tyr Pro Val Lys Thr Ser Ser Phe Ser Glu
145                 150                 155                 160

<210> SEQ ID NO 19
<211> LENGTH: 1467
<212> TYPE: DNA
<213> ORGANISM: Pseudomonas syringae pv. tomato DC3000

<400> SEQUENCE: 19
atgatcaacc tcacccacat tgcgtcttca ttggcgcggg cagcgctcag cgattcgaca      60
aagccgaaga tggagcgcgc gataaacgtc gcgagccaca tcgctggcaa agtcgcgttg     120
caggtcacca gctcattact ggagcagaaa ggtctgctta cgagcgtca gcagaaaggg      180 ctctcgatga ttctgaaggc cttgagcggc aaggagccgg tgaacaatgt cgagacgcac     240 gaaggggag gccgattcaa tctggcgcga gccgccttcg acgtggccag cgttgtctgg      300
gagcgcgaca gtcgatgca taacgtgatg agctttctgg gcgtcagcga cagcaagggc      360
aagatgttgt tctctctggg caagaagctg gcggatgcaa tggccaagcc tgagcctggc     420
aaggacaaca gtgaggccac aaatgcgcgc catgcctatt tctccagcaa cttgaaactg     480
aacaagttga tgaacgacct cactgaccag gttttcaaca agattcgcca gtcgaacggt     540
gatcgcgtgc gacgacccat gccagaacca ttctggagac cttacggcgc ccaacagcaa     600
gcgcgcccgc aaacgcctcc cggcactcgc ccacaagcca cagcgcccc gccaccgccg      660 ccgaaagcag agccacgacc tgcgtcgggc cggcctgacg gcgcccaaca gcaggcgcgc     720
ccggaaacgc gcctcgtac tcgaccgcag gccaatagca ctccgccacc gccgccgaaa      780
gcagagccac gacctgcgtc gggccggcct gacggcgccc agcagcaagc acgcccggaa     840
acgccgccgc gcactcgccc gcaggcgaac agcacgccgc caccgccgcc caaggcagag     900
ccacgacctg cgtccggccg gcctgacggc gcccaacagc aagcacgccc ggaaacgcca     960
cctcgcactc gccccaagc gaacagcgcg ccgcctccgc cgcccaaagc agagccacga    1020
cctgcgtccg gccggcctga cggcacccaa cagcaagcac gcccggaaac gccacctcgc   1080
actcgccccc aagcgaacag cgcgccgcct ccgccgccca agcagaaacc cagcgcaggc   1140
ggcgaacggc cttcaacggc gcggcccaat aacacatcgg ctgctgacgc atctgccagg   1200
```

```
gtgggcgatt ccgcacctgc caagccgccc gtcaagccgt tgtacgagca cttgggcctc    1260
actgacatgt cggtagactt atccgccgtt aaaaaggctt acagagatgc cgcgatgaag    1320
aaccaccctg ataaaaaccg cggcaacgag gccgaggcgg ccgagcgctt caaagtcatt    1380
tcaaatgcgt acaagatttt gtccgacccg gagttgcgca agcatacga caacggccgt     1440 atcaatgagg ctggtaatag ggcatga                                        1467
```

<210> SEQ ID NO 20
<211> LENGTH: 488
<212> TYPE: PRT
<213> ORGANISM: Pseudomonas syringae pv. tomato DC3000

<400> SEQUENCE: 20

```
Met Ile Asn Leu Thr His Ile Ala Ser Ser Leu Ala Arg Ala Ala Leu
  1               5                  10                  15

Ser Asp Ser Thr Lys Pro Lys Met Glu Arg Ala Ile Asn Val Ala Ser
             20                  25                  30

His Ile Ala Gly Lys Val Ala Leu Gln Val Thr Ser Ser Leu Leu Glu
         35                  40                  45

Gln Lys Gly Leu Leu Asn Glu Arg Gln Gln Lys Gly Leu Ser Met Ile
     50                  55                  60

Leu Lys Ala Leu Ser Gly Lys Glu Pro Val Asn Asn Val Glu Thr His
 65                  70                  75                  80

Glu Gly Gly Gly Arg Phe Asn Leu Ala Arg Ala Ala Phe Asp Val Ala
                 85                  90                  95

Ser Val Val Trp Glu Arg Asp Lys Ser Met His Asn Val Met Ser Phe
            100                 105                 110

Leu Gly Val Ser Asp Ser Lys Gly Lys Met Leu Phe Ser Leu Gly Lys
        115                 120                 125

Lys Leu Ala Asp Ala Met Ala Lys Pro Glu Pro Gly Lys Asp Asn Ser
    130                 135                 140

Glu Ala Thr Asn Ala Arg His Ala Tyr Phe Ser Ser Asn Leu Lys Leu
145                 150                 155                 160

Asn Lys Leu Met Asn Asp Leu Thr Asp Gln Val Phe Asn Lys Ile Arg
                165                 170                 175

Gln Ser Asn Gly Asp Arg Val Arg Arg Pro Met Pro Glu Pro Phe Trp
            180                 185                 190

Arg Pro Tyr Gly Ala Gln Gln Gln Ala Arg Pro Gln Thr Pro Pro Gly
        195                 200                 205

Thr Arg Pro Gln Ala Asn Ser Ala Pro Pro Pro Pro Lys Ala Glu
    210                 215                 220

Pro Arg Pro Ala Ser Gly Arg Pro Asp Gly Ala Gln Gln Gln Ala Arg
225                 230                 235                 240

Pro Glu Thr Pro Pro Arg Thr Arg Pro Gln Ala Asn Ser Thr Pro Pro
                245                 250                 255

Pro Pro Pro Lys Ala Glu Pro Arg Pro Ala Ser Gly Arg Pro Asp Gly
            260                 265                 270

Ala Gln Gln Gln Ala Arg Pro Glu Thr Pro Pro Arg Thr Arg Pro Gln
        275                 280                 285

Ala Asn Ser Thr Pro Pro Pro Pro Lys Ala Glu Pro Arg Pro Ala
    290                 295                 300

Ser Gly Arg Pro Asp Gly Ala Gln Gln Gln Ala Arg Pro Glu Thr Pro
305                 310                 315                 320
```

```
Pro Arg Thr Arg Pro Gln Ala Asn Ser Ala Pro Pro Pro Lys
            325                 330                 335

Ala Glu Pro Arg Pro Ala Ser Gly Arg Pro Asp Gly Thr Gln Gln Gln
            340                 345                 350

Ala Arg Pro Glu Thr Pro Pro Arg Thr Arg Pro Gln Ala Asn Ser Ala
            355                 360                 365

Pro Pro Pro Pro Lys Ala Glu Pro Ser Ala Gly Gly Glu Arg Pro
            370                 375                 380

Ser Thr Ala Arg Pro Asn Asn Thr Ser Ala Ala Asp Ala Ser Ala Arg
385                 390                 395                 400

Val Gly Asp Ser Ala Pro Ala Lys Pro Pro Val Lys Pro Leu Tyr Glu
            405                 410                 415

His Leu Gly Leu Thr Asp Met Ser Val Asp Leu Ser Ala Val Lys Lys
            420                 425                 430

Ala Tyr Arg Asp Ala Ala Met Lys Asn His Pro Asp Lys Asn Arg Gly
            435                 440                 445

Asn Glu Ala Glu Ala Ala Glu Arg Phe Lys Val Ile Ser Asn Ala Tyr
            450                 455                 460

Lys Ile Leu Ser Asp Pro Glu Leu Arg Lys Ala Tyr Asp Asn Gly Arg
465                 470                 475                 480

Ile Asn Glu Ala Gly Asn Arg Ala
            485
```

<210> SEQ ID NO 21
<211> LENGTH: 864
<212> TYPE: DNA
<213> ORGANISM: Pseudomonas syringae pv. tomato DC3000

<400> SEQUENCE: 21

```
atgaacatta cgccgctcac gtcagccgcg ggcaagggct cgtccgcaca aggcacagac      60
aaaatttcca ttcccaactc cacgcgcatg atcaatgccg cttcaatcaa gtggttgaat     120
aaggtgcgta cgccatcag tgaccacatc cgcaccagca tcgagaaagg gaaactgttc     180
gagctcgcct ccttgggcag caacatgttc ggtgtcccgg ctctttcagc cgcccctcg     240
acgctccaac ctgtgttggc gtttgaggct gaccccaatc acgacctgaa ccttgtcagg     300
gtctatatgc aggacagcgc cggcaagctc actccctggg acccgacgcc caacgcggtc     360
acgacgacgt cgaatccatc agagcctgat gcgcagagcg atacggcttc gtcatcatta     420
cctcggcggc tccccgcagg ctcggtgctg agtttgctgg cattgcgct ggatcacgcg      480
caacgccaca gtcctcgcgc ggacaggtct gccaagggac gacctggccg agaggagagg     540
aacgggcaa ggttcaatgc caagcaaaca aagccgacag aggctgaagc ctacggtgat      600
catcagacac ccaatcctga tttgcacagg caaaaagaga cagctcaacg cgttgctgaa     660
agcatcaaca gcatgcgaga gcagcaaaat ggaatgcaac gcgccgaagg gcttctcaga    720
gccaaagaag cgttgcaagc tcgggaagcc gcgcgcaagc agcttctgga cgtgctcgag    780
gccatccagg ctggccgtga agactccacc gacaagaaga tcagcgccac tgaaaagaac    840
gccacgggca tcaactacca gtga                                            864
```

<210> SEQ ID NO 22
<211> LENGTH: 287
<212> TYPE: PRT
<213> ORGANISM: Pseudomonas syringae pv. tomato DC3000

<400> SEQUENCE: 22

```
Met Asn Ile Thr Pro Leu Thr Ser Ala Ala Gly Lys Gly Ser Ser Ala
  1               5                  10                  15
Gln Gly Thr Asp Lys Ile Ser Ile Pro Asn Ser Thr Arg Met Ile Asn
             20                  25                  30
Ala Ala Ser Ile Lys Trp Leu Asn Lys Val Arg Ser Ala Ile Ser Asp
         35                  40                  45
His Ile Arg Thr Ser Ile Glu Lys Gly Lys Leu Phe Glu Leu Ala Ser
     50                  55                  60
Leu Gly Ser Asn Met Phe Gly Val Pro Ala Leu Ser Ala Arg Pro Ser
 65                  70                  75                  80
Thr Leu Gln Pro Val Leu Ala Phe Glu Ala Asp Pro Asn His Asp Leu
                 85                  90                  95
Asn Leu Val Arg Val Tyr Met Gln Asp Ser Ala Gly Lys Leu Thr Pro
             100                 105                 110
Trp Asp Pro Thr Pro Asn Ala Val Thr Thr Ser Asn Pro Ser Glu
         115                 120                 125
Pro Asp Ala Gln Ser Asp Thr Ala Ser Ser Ser Leu Pro Arg Arg Pro
    130                 135                 140
Pro Ala Gly Ser Val Leu Ser Leu Leu Gly Ile Ala Leu Asp His Ala
145                 150                 155                 160
Gln Arg His Ser Pro Arg Ala Asp Arg Ser Ala Lys Gly Arg Pro Gly
                165                 170                 175
Arg Glu Glu Arg Asn Gly Ala Arg Phe Asn Ala Lys Gln Thr Lys Pro
            180                 185                 190
Thr Glu Ala Glu Ala Tyr Gly Asp His Gln Thr Pro Asn Pro Asp Leu
        195                 200                 205
His Arg Gln Lys Glu Thr Ala Gln Arg Val Ala Glu Ser Ile Asn Ser
    210                 215                 220
Met Arg Glu Gln Gln Asn Gly Met Gln Arg Ala Glu Gly Leu Leu Arg
225                 230                 235                 240
Ala Lys Glu Ala Leu Gln Ala Arg Glu Ala Arg Lys Gln Leu Leu
                245                 250                 255
Asp Val Leu Glu Ala Ile Gln Ala Gly Arg Glu Asp Ser Thr Asp Lys
            260                 265                 270
Lys Ile Ser Ala Thr Glu Lys Asn Ala Thr Gly Ile Asn Tyr Gln
        275                 280                 285
```

<210> SEQ ID NO 23
<211> LENGTH: 429
<212> TYPE: DNA
<213> ORGANISM: Pseudomonas syringae pv. tomato DC3000

<400> SEQUENCE: 23

```
atgcgcacat ccgttaatgg tctgcttgag cacagcctga agaccctggg ctttgatact    60
tcggcattgc aggccttgcg cgacgacggt tatttactgt ggcaaggcaa ggataagcaa   120
gccagtcttc tggttccctc tactgacggc gacgcgcttt tcgctatctg taccttgagc   180
cgtgtcgatc ccgagcacga cggacgtctg ctggcgcttg cattgcacct gaacctgtct   240
cctgtccaca cgatgagcgc atgtatagca cttgatgtcg agcaaaacac gttgtgtctt   300
cgctacaccc atgaccttgg cgggaacggg gcagataccc tgttgcttgc gctcgaaaac   360
gcccaagcgc ttgctgaaca gatcaagcag gtaatcgaaa actttaggca cgatcaggga   420
cgccgatag                                                           429
```

<210> SEQ ID NO 24
<211> LENGTH: 142
<212> TYPE: PRT
<213> ORGANISM: Pseudomonas syringae pv. tomato DC3000

<400> SEQUENCE: 24

```
Met Arg Thr Ser Val Asn Gly Leu Leu Glu His Ser Leu Lys Thr Leu
 1               5                  10                  15

Gly Phe Asp Thr Ser Ala Leu Gln Ala Leu Arg Asp Asp Gly Tyr Leu
            20                  25                  30

Leu Trp Gln Gly Lys Asp Lys Gln Ala Ser Leu Leu Val Pro Ser Thr
        35                  40                  45

Asp Gly Asp Ala Leu Phe Ala Ile Cys Thr Leu Ser Arg Val Asp Pro
 50                  55                  60

Glu His Asp Gly Arg Leu Ala Leu Ala Leu His Leu Asn Leu Ser
 65                  70                  75                  80

Pro Val His Thr Met Ser Ala Cys Ile Ala Leu Asp Val Glu Gln Asn
                85                  90                  95

Thr Leu Cys Leu Arg Tyr Thr His Asp Leu Gly Gly Asn Gly Ala Asp
            100                 105                 110

Thr Leu Leu Leu Ala Leu Glu Asn Ala Gln Ala Leu Ala Glu Gln Ile
        115                 120                 125

Lys Gln Val Ile Glu Asn Phe Arg His Asp Gln Gly Arg Arg
    130                 135                 140
```

<210> SEQ ID NO 25
<211> LENGTH: 474
<212> TYPE: DNA
<213> ORGANISM: Pseudomonas syringae pv. tomato DC3000

<400> SEQUENCE: 25

```
atgatcgcgt tcgcaaccgg actgctagaa cacagcctga acggcttggg atacgacgcc    60
gcagatttgc aatcccttcg ggatgaaggg tatttgctgt ggcacgggaa aaacggtcac   120
accagcctgt tggtgcccgc tgctggcggg gatgcgcttt ttgtcatcag caccctgagc   180
tacatcgatc ctgaacagga cgggcggctg ctggcgcttg cgctgcattt gaacttgtcg   240
ccagcccaca ctctgggcgc cagtatcgcg ctggatatcg agcaaaatac cttgtgcctg   300
cgttacacgc acgacctcac tgggcacggc acagacaatt tgtcccgcgc gcttgaaagc   360
actcaggcac ttgccgagca gatcaagcag gtcatcgaaa ccttccgcag tgaattcgga   420
cgcccgccaa tgcccgccca cacagcccga cggccagatg ccgtggcgct ttag         474
```

<210> SEQ ID NO 26
<211> LENGTH: 157
<212> TYPE: PRT
<213> ORGANISM: Pseudomonas syringae pv. tomato DC3000

<400> SEQUENCE: 26

```
Met Ile Ala Phe Ala Thr Gly Leu Leu Glu His Ser Leu Lys Arg Leu
 1               5                  10                  15

Gly Tyr Asp Ala Ala Asp Leu Gln Ser Leu Arg Asp Glu Gly Tyr Leu
            20                  25                  30

Leu Trp His Gly Lys Asn Gly His Thr Ser Leu Leu Val Pro Ala Ala
        35                  40                  45

Gly Gly Asp Ala Leu Phe Val Ile Ser Thr Leu Ser Tyr Ile Asp Pro
 50                  55                  60
```

-continued

```
Glu Gln Asp Gly Arg Leu Leu Ala Leu Ala Leu His Leu Asn Leu Ser
 65                  70                  75                  80

Pro Ala His Thr Leu Gly Ala Ser Ile Ala Leu Asp Ile Glu Gln Asn
                 85                  90                  95

Thr Leu Cys Leu Arg Tyr Thr His Asp Leu Thr Gly His Gly Thr Asp
            100                 105                 110

Asn Leu Ser Arg Ala Leu Glu Ser Thr Gln Ala Leu Ala Glu Gln Ile
        115                 120                 125

Lys Gln Val Ile Glu Thr Phe Arg Ser Glu Phe Gly Arg Pro Pro Met
    130                 135                 140

Pro Ala His Thr Ala Arg Arg Pro Asp Ala Val Ala Leu
145                 150                 155
```

<210> SEQ ID NO 27
<211> LENGTH: 534
<212> TYPE: DNA
<213> ORGANISM: Pseudomonas syringae pv. tomato DC3000

<400> SEQUENCE: 27

```
gtgaaaaagt ctggcgctgg aactcaagcc tatgcgttgt tcgcctctgc gacgggaagc     60
tcgtcgaagg gcgttctaag taccattgcc aggcacctga cgggatgttt tgcacccaac    120
aagactgcgc ttcattcagc aacagccgtt tcgtatgagc tattgccggg caattattct    180
gtcgccgcca gtgtgcatgg cttgtcggtt gatcaccgcc agccggcgct gacacgactg    240
agtaacgtgc tgttcaatca ggcactggcg ctggacctgg agcgttttga cgagggcgcg    300
ccagccgacg aaatgttcag gccttcactg aaacgcgaag gtgcccatcc ccgattggcc    360
gactcactgg gtggcgagca actggctgtg caaaccatgg agaagggcct taaacggctg    420
gcagaggatc ctgcgcagtc ctttgcgcga tgccattcat ttttttaccc gatcagtagt    480
gataccactt cacctcaagc atcacttcat tctgtggcga gctcatctgg ctga          534
```
<210> SEQ ID NO 28
<211> LENGTH: 177
<212> TYPE: PRT
<213> ORGANISM: Pseudomonas syringae pv. tomato DC3000

<400> SEQUENCE: 28

```
Val Lys Lys Ser Gly Ala Gly Thr Gln Ala Tyr Ala Leu Phe Ala Ser
  1               5                  10                  15

Ala Thr Gly Ser Ser Ser Lys Gly Val Leu Ser Thr Ile Ala Arg His
            20                  25                  30

Leu Thr Gly Cys Phe Ala Pro Asn Lys Thr Ala Leu His Ser Ala Thr
        35                  40                  45

Ala Val Ser Tyr Glu Leu Leu Pro Gly Asn Tyr Ser Val Ala Ala Ser
     50                  55                  60

Val His Gly Leu Ser Val Asp His Arg Gln Pro Ala Leu Thr Arg Leu
 65                  70                  75                  80

Ser Asn Val Leu Phe Asn Gln Ala Leu Ala Leu Asp Leu Glu Arg Phe
                 85                  90                  95

Asp Glu Gly Ala Pro Ala Asp Glu Met Phe Arg Pro Ser Leu Lys Arg
            100                 105                 110

Glu Gly Ala His Pro Arg Leu Ala Asp Ser Leu Gly Gly Glu Gln Leu
        115                 120                 125

Ala Val Gln Thr Met Glu Lys Gly Leu Lys Arg Leu Ala Glu Asp Pro
    130                 135                 140
```

```
Ala Gln Ser Phe Ala Arg Cys His Ser Phe Phe Tyr Pro Ile Ser Ser
145                 150                 155                 160

Asp Thr Thr Ser Pro Gln Ala Ser Leu His Ser Val Ala Ser Ser Ser
                165                 170                 175
Gly

<210> SEQ ID NO 29
<211> LENGTH: 1137
<212> TYPE: DNA
<213> ORGANISM: Pseudomonas syringae pv. tomato DC3000

<400> SEQUENCE: 29
atgaaaacag tcagcaatca ctcgataccc agtacaaatc tcgtcgtgga tgcgggaacg      60
gaaacttcgg cgcagaaatc ccagccggtt tgcagcgaaa tccagcgtaa cagcaagatc     120 gaaaagcag tcatcgaaca cattgccgac cacccggcag cgaaaatgac aataagcgcg     180
ctggttgaca cgttgacaga cgttttttgtc agggctcatg gggaggttaa ggggtggggcc     240 gaaatcgtcc aggcagtctc tcgccctcat gacagtaatc gacacggcag tggagtgctc     300
agcccgcgct ttgatgtaat ggggagtgtt ggttggaatg cggcagctat ccggccacc     360 agtcgcgtcg ggacgcttcg agagaaaggt acactgttca ctaaccttat gctcagtaac     420
aactttaaac atttgcttaa cgagtggtt aacgatccag ccttgcagca aaagctcgac     480
ggtgggttag acctcaacta tctgaaggct tgtgaaggcg atctttatgt catgtcaggg     540
tgggctgcac gggctagcga aagtcgtgaa caaattggca agcccggta tgaaacggca     600 tcaaatctta gccagacgct gatcagtgca cgtgagttgg cttttcatcg tcacaatccg     660
gttaatcatc cgtctgccca aacgaaagtg ggcttcgata agggttttgcc tgaggaatct     720 gatctgcagg ttctgagagg ccatggcagc agtgtatgga gtgtaaaacc gggcagcgat     780
ttcgcaaagc gtgctgaagt ttctggaaag cctattatcg ccggcccgtc cggtaccgct     840
tcgcgcatgg tcgctgttgc gcgttttctg gcaccggctt gtttgaaaag cctgggtatt     900
gagagtgagc agaacctgaa agagcttgtg cggtatgcct gctatgccta tttcggtcag     960
gacagccacc attcgatgct tgaagtgaat cttggtgtcg cttcccatgg aatgccggaa    1020
caatgggacg acacgcttta taacgagcct ttcagtaatt caattaaagg tcgcgggttt    1080
ggtatagaca atctcgcgca taggcaagtc gtcaggcagg cggctcaaaa gtcatga        1137

<210> SEQ ID NO 30
<211> LENGTH: 378
<212> TYPE: PRT
<213> ORGANISM: Pseudomonas syringae pv. tomato DC3000

<400> SEQUENCE: 30

Met Lys Thr Val Ser Asn His Ser Ile Pro Ser Thr Asn Leu Val Val
  1               5                  10                  15

Asp Ala Gly Thr Glu Thr Ser Ala Gln Lys Ser Gln Pro Val Cys Ser
                 20                  25                  30

Glu Ile Gln Arg Asn Ser Lys Ile Glu Lys Ala Val Ile Glu His Ile
             35                  40                  45

Ala Asp His Pro Ala Ala Lys Met Thr Ile Ser Ala Leu Val Asp Thr
         50                  55                  60

Leu Thr Asp Val Phe Val Arg Ala His Gly Glu Val Lys Gly Trp Ala
 65                  70                  75                  80

Glu Ile Val Gln Ala Val Ser Arg Pro His Asp Ser Asn Arg His Gly
                 85                  90                  95
```

```
Ser Gly Val Leu Ser Pro Arg Phe Asp Val Met Gly Ser Val Gly Trp
            100                 105                 110

Asn Ala Ala Ala Ile Arg Ala Thr Ser Arg Val Gly Thr Leu Arg Glu
            115                 120                 125

Lys Gly Thr Leu Phe Thr Asn Leu Met Leu Ser Asn Asn Phe Lys His
        130                 135                 140

Leu Leu Lys Arg Val Val Asn Asp Pro Ala Leu Gln Gln Lys Leu Asp
145                 150                 155                 160

Gly Gly Leu Asp Leu Asn Tyr Leu Lys Ala Cys Glu Gly Asp Leu Tyr
                165                 170                 175

Val Met Ser Gly Trp Ala Ala Arg Ala Ser Glu Ser Arg Glu Gln Ile
            180                 185                 190

Gly Lys Ala Arg Tyr Glu Thr Ala Ser Asn Leu Ser Gln Thr Leu Ile
        195                 200                 205

Ser Ala Arg Glu Leu Ala Phe His Arg His Asn Pro Val Asn His Pro
    210                 215                 220

Ser Ala Gln Thr Lys Val Gly Phe Asp Lys Gly Leu Pro Glu Glu Ser
225                 230                 235                 240

Asp Leu Gln Val Leu Arg Gly His Gly Ser Ser Val Trp Ser Val Lys
                245                 250                 255

Pro Gly Ser Asp Phe Ala Lys Arg Ala Glu Val Ser Gly Lys Pro Ile
            260                 265                 270

Ile Ala Gly Pro Ser Gly Thr Ala Ser Arg Met Val Ala Val Ala Arg
        275                 280                 285

Phe Leu Ala Pro Ala Cys Leu Lys Ser Leu Gly Ile Glu Ser Glu Gln
    290                 295                 300

Asn Leu Lys Glu Leu Val Arg Tyr Ala Cys Tyr Ala Tyr Phe Gly Gln
305                 310                 315                 320

Asp Ser His His Ser Met Leu Glu Val Asn Leu Gly Val Ala Ser His
                325                 330                 335

Gly Met Pro Glu Gln Trp Asp Asp Thr Leu Tyr Asn Glu Pro Phe Ser
            340                 345                 350

Asn Ser Ile Lys Gly Arg Gly Phe Gly Ile Asp Asn Leu Ala His Arg
        355                 360                 365

Gln Val Val Arg Gln Ala Ala Gln Lys Ser
        370                 375

<210> SEQ ID NO 31
<211> LENGTH: 1173
<212> TYPE: DNA
<213> ORGANISM: Pseudomonas syringae pv. tomato DC3000

<400> SEQUENCE: 31
atgcggtttg atgctgcccg aggccagaag cccaaagccc ctatggatgc accgtcatca     60
ttacgtttgc gagcgatagc aggtggcatg cccagtgaag aagcaggaac gactgcacct    120
gctgacgtga atcagcctcc acctgctgat gttcgtccag aaatgggtgt aggtcctgtg    180
agactcttcg ttaaactgat ggtaggaact ctggcgctgt cgacaggagt ccgttttgca    240
agatacccag gtgatttcgc gaaggatccg ggaggcagtg tatgggcagc aatcaatctg    300
cagcatcgct cgagcgtcac acatcttgaa caagcaata agacggttct tgagcgtttc    360
ggtgcacata ttccaaaaga cagtgcgtgt ttcaaagctc gcgctgacgt cacacacgat    420
gttccctcag gcgtggcagg gcagtggaac cacaaaaccc aacgggtaaa actgaaccct    480
aacattcatt tcgagagcca tccggcacag gtcgccggac atgagttcat acactgttac    540
```

-continued

```
acgcatcctg agtttgtcga acgccatata aaacatccgc actggaaagc cctgaacgaa      600
gggttgacga ctcgtttgac agagaaactg ccagaccctg agcgtctctt gcccattccc      660
ttggcaaagg atccctatca tggtttcaag ctgtccaccg gggactcctg gccggatgcg      720
gccaggcgaa tcgaagacga agttggcgaa gatgtgttgt tgaaagcgtt ctttggcggc      780
gatgaccagg ctattagtga agtagctaaa gccgctgctc agatctaccc caagattgcc      840
tcacgtatta ccgagaggga gttgtatcaa gcgggcagca tgcgtggagg acaacagctg      900
gccgagtgtt acgtaggtgc tttgctcaaa aacggtcaga aactgcctga cagttttacg      960
aattatctgc tacctgtatt tagctattca gatataagcc ctggtcacgc gaaaaaata     1020
caggcgcaag cggaaaaaag tcaaaagcgg atgggaattg tgttcgatac agcgtttttt     1080
tcacctgacc tgaagaccca gagactggca cttggcatgc tacgggagga cctgctgatg     1140
cactggaaaa aagttattcc ggatagaaag taa                                  1173
```

<210> SEQ ID NO 32
<211> LENGTH: 390
<212> TYPE: PRT
<213> ORGANISM: Pseudomonas syringae pv. tomato DC3000

<400> SEQUENCE: 32

```
Met Arg Phe Asp Ala Ala Arg Gly Gln Lys Pro Lys Ala Pro Met Asp
  1               5                  10                  15

Ala Pro Ser Ser Leu Arg Leu Arg Ala Ile Ala Gly Gly Met Pro Ser
             20                  25                  30

Glu Glu Ala Gly Thr Thr Ala Pro Ala Asp Val Asn Gln Pro Pro Pro
         35                  40                  45

Ala Asp Val Arg Pro Glu Met Gly Val Gly Pro Val Arg Leu Phe Val
     50                  55                  60

Lys Leu Met Val Gly Thr Leu Ala Leu Ser Thr Gly Val Arg Phe Ala
 65                  70                  75                  80

Arg Tyr Pro Gly Asp Phe Ala Lys Asp Pro Gly Gly Ser Val Trp Ala
                 85                  90                  95

Ala Ile Asn Leu Gln His Arg Ser Ser Val Thr His Leu Glu Gln Gly
            100                 105                 110

Asn Lys Thr Val Leu Glu Arg Phe Gly Ala His Ile Pro Lys Asp Ser
        115                 120                 125

Ala Cys Phe Lys Ala Arg Ala Asp Val Thr His Asp Val Pro Ser Gly
    130                 135                 140

Val Ala Gly Gln Trp Asn His Lys Thr Gln Arg Val Lys Leu Asn Pro
145                 150                 155                 160

Asn Ile His Phe Glu Ser His Pro Ala Gln Val Ala Gly His Glu Phe
                165                 170                 175

Ile His Cys Tyr Thr His Pro Glu Phe Val Glu Arg His Ile Lys His
            180                 185                 190

Pro His Trp Lys Ala Leu Asn Glu Gly Leu Thr Thr Arg Leu Thr Glu
        195                 200                 205

Lys Leu Pro Asp Pro Lys Arg Leu Leu Pro Ile Pro Leu Ala Lys Asp
    210                 215                 220

Pro Tyr His Gly Phe Lys Leu Ser Thr Gly Asp Ser Trp Pro Asp Ala
225                 230                 235                 240

Ala Arg Arg Ile Glu Asp Glu Val Gly Glu Asp Val Leu Leu Lys Ala
                245                 250                 255
```

-continued

```
Phe Phe Gly Gly Asp Asp Gln Ala Ile Ser Glu Val Ala Lys Ala Ala
            260                 265                 270

Ala Gln Ile Tyr Pro Lys Ile Ala Ser Arg Ile Thr Glu Arg Glu Leu
        275                 280                 285

Tyr Gln Ala Gly Ser Met Arg Gly Gln Gln Leu Ala Glu Cys Tyr
    290                 295                 300

Val Gly Ala Leu Leu Lys Asn Gly Gln Lys Leu Pro Asp Ser Phe Thr
305                 310                 315                 320

Asn Tyr Leu Leu Pro Val Phe Ser Tyr Ser Asp Ile Ser Pro Gly His
                325                 330                 335

Ala Lys Lys Ile Gln Ala Gln Ala Glu Lys Ser Gln Lys Arg Met Gly
            340                 345                 350

Ile Val Phe Asp Thr Ala Phe Phe Ser Pro Asp Leu Lys Thr Gln Arg
        355                 360                 365

Leu Ala Leu Gly Met Leu Arg Glu Asp Leu Leu Met His Trp Lys Lys
    370                 375                 380

Val Ile Pro Asp Arg Lys
385                 390
```

<210> SEQ ID NO 33
<211> LENGTH: 474
<212> TYPE: DNA
<213> ORGANISM: Pseudomonas syringae pv. tomato DC3000

<400> SEQUENCE: 33

```
atgaacaggc ttcacaagac cagtctgctg gcggctatat tgaccgcatc ccctgcatt    60
atggcagcta acgctcatgc tatgagttgt cctgtcccgc aaagcgtgaa gtacgttaat   120
ggtatctata tcgcgccgga aacgtttgct ggttgggagg ggaactgggt ttctcaacca   180
cacaagaaac actccattaa agagttttcc actgctttat atctttcagt ggataaagt    240
cagaagggag gaacattgac taactgtagt tattcactaa gcggagataa tggcgtaata   300
gatcttgagt atcgaaaatc aggaaatgag aatagactaa agacacttat cgtttccatt   360
gaaggtcagc acaattggat taaagagcgt ggcgcggttg gaattcaagg atatgaatgt   420
acaaagtcag catctgagtg tcagttcgtt ccgctgcggc taaacgagga ctga          474
```

<210> SEQ ID NO 34
<211> LENGTH: 157
<212> TYPE: PRT
<213> ORGANISM: Pseudomonas syringae pv. tomato DC3000

<400> SEQUENCE: 34

```
Met Asn Arg Leu His Lys Thr Ser Leu Leu Ala Ala Ile Leu Thr Ala
1               5                   10                  15

Ser Pro Cys Ile Met Ala Ala Asn Ala His Ala Met Ser Cys Pro Val
            20                  25                  30

Pro Gln Ser Val Lys Tyr Val Asn Gly Ile Tyr Ile Ala Pro Glu Thr
        35                  40                  45

Phe Ala Gly Trp Glu Gly Asn Trp Val Ser Gln Pro His Lys Lys His
    50                  55                  60

Ser Ile Lys Glu Phe Ser Thr Ala Leu Tyr Leu Ser Val Asp Lys Ser
65                  70                  75                  80

Gln Lys Gly Gly Thr Leu Thr Asn Cys Ser Tyr Ser Leu Ser Gly Asp
            85                  90                  95

Asn Gly Val Ile Asp Leu Glu Tyr Arg Lys Ser Gly Asn Glu Asn Arg
        100                 105                 110
```

Leu Lys Thr Leu Ile Val Ser Ile Glu Gly Gln His Asn Trp Ile Lys
        115                 120                 125

Glu Arg Gly Ala Val Gly Ile Gln Gly Tyr Glu Cys Thr Lys Ser Ala
    130                 135                 140

Ser Glu Cys Gln Phe Val Pro Leu Arg Leu Asn Glu Asp
145                 150                 155

<210> SEQ ID NO 35
<211> LENGTH: 1344
<212> TYPE: DNA
<213> ORGANISM: Pseudomonas syringae pv. tomato DC3000

<400> SEQUENCE: 35

| | | | | | | |
|---|---|---|---|---|---|---|
| atgcatcgtc | ctataccgc | aggccatacc | acctcacgtc | tcatcctaga | tcagtcaaaa | 60 |
| caaatatcac | gtaccccatc | ggaaagtagc | gcgcaatcag | cgctttctca | gcaagcaagc | 120 |
| atgagcagcc | cagttttgga | gcggtcgaaa | agtgcgccag | ctttattgac | tgcggcacag | 180 |
| cgcacgatgc | ttgcacaagt | gggagcctgt | aacgctcatc | tgacctcaga | tgaaaacatg | 240 |
| gccatcaacg | aactgagatc | acacaagccc | cttttaccta | aggatacgtg | gttttttcact | 300 |
| gatcctaaca | aggacccaga | tgatgtcgtg | acctacacct | tgggcaagca | attgcaggct | 360 |
| gagggctttg | tgcacatcac | ggatgtagtg | gcgacactgg | gtgatgctga | agttcgctct | 420 |
| caacgtgccg | agatggccaa | aggcgtgttc | aacaagcttg | agttgcatga | cgtgcatgtg | 480 |
| tcgcgtggtc | gggattacgc | aatgaattcg | cttcagtcga | aggaacatgc | caaattttta | 540 |
| ctggaaggtc | atgctttaag | ggctggacct | ggtgaaatac | accgcgacag | cttgcaggac | 600 |
| atgagcaggc | gcctggcccg | tgcgccacat | ggagtcggta | ttgtcgtaat | tgcaggcatg | 660 |
| agtgatatca | atgcgctcat | cactacctgc | ccggatatgg | tgcgcgaacg | ggttgatgac | 720 |
| atcaccatca | tgggcggcgt | cgagccttta | aaggacgcag | atggttttgt | acagcctgat | 780 |
| gcacgcgctt | acaacaatgc | gaccgacatg | gacgctgcgc | gcagtcttta | tcggaaagcg | 840 |
| caggagcttg | gcattccact | tcgtatagtg | acaaaggagg | cggcctataa | aacggcggtt | 900 |
| tcgccttcat | tttacgaagg | gatagcgggg | agcggacatc | cagtaggcca | ctacctgaga | 960 |
| gacgttcaga | agagtgcgtt | gaaaggcctc | tgggaaggta | ttcaagctgg | attgcttccc | 1020 |
| gggttggatg | actcatggtt | ctttcggacg | ttcatgccga | atgcacagat | tgaagcagca | 1080 |
| caactggata | aaaataaaga | gagttcgttt | gaagatatct | ggcctaaggt | gacgaagcta | 1140 |
| aacctgtatg | atcctctgac | attactggcc | tcagtgccag | gggcggcaaa | actgctattt | 1200 |
| aaaccaaaag | ctatacacac | agaaggattt | ggtgttgtag | agcaagtagg | tccagatgat | 1260 |
| gtgacgcatc | cagagaaagc | aaagttattg | atgtccgctt | tagccaaatc | tgcgcttgtc | 1320 |
| cagtcgacgg | tagccccaga | ttga | | | | 1344 |

<210> SEQ ID NO 36
<211> LENGTH: 447
<212> TYPE: PRT
<213> ORGANISM: Pseudomonas syringae pv. tomato DC3000

<400> SEQUENCE: 36

Met His Arg Pro Ile Thr Ala Gly His Thr Thr Ser Arg Leu Ile Leu
  1               5                  10                  15

Asp Gln Ser Lys Gln Ile Ser Arg Thr Pro Ser Glu Ser Ser Ala Gln
             20                  25                  30

Ser Ala Leu Ser Gln Gln Ala Ser Met Ser Ser Pro Val Leu Glu Arg
        35                  40                  45

```
Ser Lys Ser Ala Pro Ala Leu Leu Thr Ala Ala Gln Arg Thr Met Leu
     50                  55                  60

Ala Gln Val Gly Ala Cys Asn Ala His Leu Thr Ser Asp Glu Asn Met
 65                  70                  75                  80

Ala Ile Asn Glu Leu Arg Ser His Lys Pro Leu Leu Pro Lys Asp Thr
                 85                  90                  95

Trp Phe Phe Thr Asp Pro Asn Lys Asp Pro Asp Val Val Thr Tyr
                100                 105                 110

Thr Leu Gly Lys Gln Leu Gln Ala Glu Gly Phe Val His Ile Thr Asp
            115                 120                 125

Val Val Ala Thr Leu Gly Asp Ala Glu Val Arg Ser Gln Arg Ala Glu
130                 135                 140

Met Ala Lys Gly Val Phe Asn Lys Leu Glu Leu His Asp Val His Val
145                 150                 155                 160

Ser Arg Gly Arg Asp Tyr Ala Met Asn Ser Leu Gln Ser Lys Glu His
                165                 170                 175

Ala Lys Phe Leu Leu Glu Gly His Ala Leu Arg Ala Gly Pro Gly Glu
                180                 185                 190

Ile His Arg Asp Ser Leu Gln Asp Met Ser Arg Arg Leu Ala Arg Ala
                195                 200                 205

Pro His Gly Val Gly Ile Val Val Ile Ala Gly Met Ser Asp Ile Asn
                210                 215                 220

Ala Leu Ile Thr Thr Cys Pro Asp Met Val Arg Glu Arg Val Asp Asp
225                 230                 235                 240

Ile Thr Ile Met Gly Gly Val Glu Pro Leu Lys Asp Ala Asp Gly Phe
                245                 250                 255

Val Gln Pro Asp Ala Arg Ala Tyr Asn Asn Ala Thr Asp Met Asp Ala
                260                 265                 270

Ala Arg Ser Leu Tyr Arg Lys Ala Gln Glu Leu Gly Ile Pro Leu Arg
            275                 280                 285

Ile Val Thr Lys Glu Ala Ala Tyr Lys Thr Ala Val Ser Pro Ser Phe
            290                 295                 300

Tyr Glu Gly Ile Ala Gly Ser Gly His Pro Val Gly His Tyr Leu Arg
305                 310                 315                 320

Asp Val Gln Lys Ser Ala Leu Lys Gly Leu Trp Glu Gly Ile Gln Ala
                325                 330                 335

Gly Leu Leu Pro Gly Leu Asp Asp Ser Trp Phe Phe Arg Thr Phe Met
                340                 345                 350

Pro Asn Ala Gln Ile Glu Ala Ala Gln Leu Asp Lys Asn Lys Glu Ser
                355                 360                 365

Ser Phe Glu Asp Ile Trp Pro Lys Val Thr Lys Leu Asn Leu Tyr Asp
            370                 375                 380

Pro Leu Thr Leu Leu Ala Ser Val Pro Gly Ala Ala Lys Leu Leu Phe
385                 390                 395                 400

Lys Pro Lys Ala Ile His Thr Glu Gly Phe Gly Val Val Glu Gln Val
                405                 410                 415

Gly Pro Asp Asp Val Thr His Pro Glu Lys Ala Lys Leu Leu Met Ser
                420                 425                 430

Ala Leu Ala Lys Ser Ala Leu Val Gln Ser Thr Val Ala Pro Asp
            435                 440                 445
```

<210> SEQ ID NO 37
<211> LENGTH: 366
<212> TYPE: DNA
<213> ORGANISM: Pseudomonas syringae pv. tomato DC3000

<400> SEQUENCE: 37

```
gtgaaaatca atctccccgc gctcagaaca acgtcttcac gcgtgcagat ctgcttgacc      60
gcagtcctgc tgtgcacacc gctgctgttt tccgcgcatg cccaggcagc cggcacggct     120
tctgaacaag ccaatgtgga agtgatgatt cgtcagctca acgcgctcga ggccgtcgcc     180
cagcgcagtg tcgatcttcc acaagacccg gcccaacgct atcacctgga ctatccccgg     240
ttggtcagcg acatcgcgcg catccgccag ggcttgcaag actacctgtc gccgtcccgc     300
gcacagcccc gcgaccccgt ggagctatca ggccattaca acgtcagcgg tgatcacacg     360
ccatga                                                                366
```

<210> SEQ ID NO 38
<211> LENGTH: 121
<212> TYPE: PRT
<213> ORGANISM: Pseudomonas syringae pv. tomato DC3000

<400> SEQUENCE: 38

```
Val Lys Ile Asn Leu Pro Ala Leu Arg Thr Thr Ser Ser Arg Val Gln
 1               5                  10                  15

Ile Cys Leu Thr Ala Val Leu Leu Cys Thr Pro Leu Leu Phe Ser Ala
            20                  25                  30

His Ala Gln Ala Ala Gly Thr Ala Ser Glu Gln Ala Asn Val Glu Val
        35                  40                  45

Met Ile Arg Gln Leu Asn Ala Leu Glu Ala Val Ala Gln Arg Ser Val
    50                  55                  60

Asp Leu Pro Gln Asp Pro Ala Gln Arg Tyr His Leu Asp Tyr Pro Arg
65                  70                  75                  80

Leu Val Ser Asp Ile Ala Arg Ile Arg Gln Gly Leu Gln Asp Tyr Leu
                85                  90                  95

Ser Pro Ser Arg Ala Gln Pro Arg Asp Pro Val Glu Leu Ser Gly His
            100                 105                 110

Tyr Asn Val Ser Gly Asp His Thr Pro
        115                 120
```

<210> SEQ ID NO 39
<211> LENGTH: 1242
<212> TYPE: DNA
<213> ORGANISM: Pseudomonas syringae pv. tomato DC3000

<400> SEQUENCE: 39

```
atgcgttcca gggttataac tacatcgctg gtagtcatta tgctctcatg tgcatcagcc      60
gctccagctt gcttctccgc agacatgact cccagcgtgt cgaacgagag cacgtcggag     120
gcggatttc agcaatggct ggctactttc gcagcaatg caactactaa gggcatcgac      180
acagccacac tcgatcttgc tttccaaaac atcacgcttg acccgactgt gcaccagttg     240
gatatggcgc aaccgagtt cacgacggcc atctgggatt atttgtctga acgtctgact      300
ccgaagaata tccagcaagg gcaggagctt ctgcaaaaag agccagttct gaacgaggta     360
gagcgtcact acggtgtgga tgcgaagatt atcgcggcca tctggtgtat tgaaagcggc     420
tacggtaagg atattggtag tcgcgatgtg attcgttcct ggccacgct tgcttacaag     480
ggccggcgga tggattacgg ggctacacag ttgatggccg cccttcatat cgtgcaaaac     540
```

```
aaagacatcg cccgtgcgca attgattggc tcgtgggctg gcgcgatggg gcagacgcaa      600
ttcatcccga cgacctatct cgactatgca gttgatttta accacgacaa tcggcgcgac      660
gtttggagtt cccgggccga tgcgctggcc tccactgcct cttatttaca acgcagcgct      720
tggaactcgc gcgtctcttg gggacaggag gtgcagttgc ccgagaattt cgattacgct      780
caggctgaca tgtcgatcaa gaagcccgtt gccgaatggc aacggctcgg ggtgatggga      840
acgaagcaag cgattccggg cgagctcgca caggagcaag catcggtcct gctgcccgca      900
ggttatcgcg gccagcatt tatggtccta agtaatttcc gtagcatcct gcgctataac       960
aactccactg cctatgcgct aacgatcggg ctactagccg acagttatgc tggcgggacc     1020
ggcgtgtctc acccgtggcc aactgataat cctcccttgg gcagcattgc gcaggtaacc     1080
gatttgcaga aactgctgac tgctaagggc tactccctgg gtgctgctga cggtgttata     1140
ggggcgatga cccgggcggc catccgggct taccagaagg atcagcattt gccacccgac     1200
ggttacgcca gcactgtact actggagagc ctgcgccgat ag                        1242
```

<210> SEQ ID NO 40
<211> LENGTH: 413
<212> TYPE: PRT
<213> ORGANISM: Pseudomonas syringae pv. tomato DC3000

<400> SEQUENCE: 40

```
Met Arg Ser Arg Val Ile Thr Thr Ser Leu Val Val Ile Met Leu Ser
 1               5                  10                  15

Cys Ala Ser Ala Ala Pro Ala Cys Phe Ser Ala Asp Met Thr Pro Ser
            20                  25                  30

Val Ser Asn Glu Ser Thr Ser Glu Ala Asp Phe Gln Gln Trp Leu Ala
        35                  40                  45

Thr Phe Arg Ser Asn Ala Thr Thr Lys Gly Ile Asp Thr Ala Thr Leu
    50                  55                  60

Asp Leu Ala Phe Gln Asn Ile Thr Leu Asp Pro Thr Val His Gln Leu
 65                  70                  75                  80

Asp Met Ala Gln Pro Glu Phe Thr Thr Ala Ile Trp Asp Tyr Leu Ser
                85                  90                  95

Glu Arg Leu Thr Pro Lys Asn Ile Gln Gln Gly Gln Glu Leu Leu Gln
            100                 105                 110

Lys Glu Pro Val Leu Asn Glu Val Arg His Tyr Gly Val Asp Ala
        115                 120                 125

Lys Ile Ile Ala Ala Ile Trp Cys Ile Glu Ser Gly Tyr Gly Lys Asp
    130                 135                 140

Ile Gly Ser Arg Asp Val Ile Arg Ser Leu Ala Thr Leu Ala Tyr Lys
145                 150                 155                 160

Gly Arg Arg Met Asp Tyr Gly Ala Thr Gln Leu Met Ala Ala Leu His
                165                 170                 175

Ile Val Gln Asn Lys Asp Ile Ala Arg Ala Gln Leu Ile Gly Ser Trp
            180                 185                 190

Ala Gly Ala Met Gly Gln Thr Gln Phe Ile Pro Thr Thr Tyr Leu Asp
        195                 200                 205

Tyr Ala Val Asp Phe Asn His Asp Asn Arg Arg Asp Val Trp Ser Ser
    210                 215                 220

Arg Ala Asp Ala Leu Ala Ser Thr Ala Ser Tyr Leu Gln Arg Ser Ala
225                 230                 235                 240

Trp Asn Ser Arg Val Ser Trp Gly Gln Glu Val Gln Leu Pro Glu Asn
                245                 250                 255
```

-continued

```
Phe Asp Tyr Ala Gln Ala Asp Met Ser Ile Lys Lys Pro Val Ala Glu
            260                 265                 270
Trp Gln Arg Leu Gly Val Met Gly Thr Lys Gln Ala Ile Pro Gly Glu
        275                 280                 285
Leu Ala Gln Glu Gln Ala Ser Val Leu Leu Pro Ala Gly Tyr Arg Gly
    290                 295                 300
Pro Ala Phe Met Val Leu Ser Asn Phe Arg Ser Ile Leu Arg Tyr Asn
305                 310                 315                 320
Asn Ser Thr Ala Tyr Ala Leu Thr Ile Gly Leu Leu Ala Asp Ser Tyr
                325                 330                 335
Ala Gly Gly Thr Gly Val Ser His Pro Trp Pro Thr Asp Asn Pro Pro
            340                 345                 350
Leu Gly Ser Ile Ala Gln Val Thr Asp Leu Gln Lys Leu Leu Thr Ala
        355                 360                 365
Lys Gly Tyr Ser Leu Gly Ala Ala Asp Gly Val Ile Gly Ala Met Thr
    370                 375                 380
Arg Ala Ala Ile Arg Ala Tyr Gln Lys Asp Gln His Leu Pro Pro Asp
385                 390                 395                 400
Gly Tyr Ala Ser Thr Val Leu Leu Glu Ser Leu Arg Arg
                405                 410
```

<210> SEQ ID NO 41
<211> LENGTH: 960
<212> TYPE: DNA
<213> ORGANISM: Pseudomonas syringae pv. tomato DC3000

<400> SEQUENCE: 41

| | | |
|---|---|---|
| atgcttgctc ctgacggcgt agaaatcgat atcgtgctat caggtatatg cggaactgat | 60 |
| ctggcggtat tgtcgggccg tgaaggtgga gaggtgggca ttatacgcgg gcacgaagca | 120 |
| gttggcatta ttatcgatgt aggtaaggat gtagtacacc tacaaaaagg gatgcgggtg | 180 |
| gtggttgatc ccaacgaata ctgtggcgtt tgcgaacctt gccgtcttgc taaaacgcac | 240 |
| ctatgcaatg gggggtgaa cgctgggttg gatatcgcag gtgtcaacaa acatggaact | 300 |
| tttgccgagc gcttcgttac tcgtgagcgt tttgtgtatc aattgccaga cgatatgagc | 360 |
| tgggcagctg tgtgttggt tgagcctgtt gcctgcattc tgaataatat agaccaggcg | 420 |
| ttcattcgag cgggagagcg tgtgttgatc ctagggtctg gccctatgag tctgattgcg | 480 |
| cagatcgttc tgcgctcaat gggagttgac acgctcgcca ctgatcgaaa cacacatcgc | 540 |
| atacagttcg gccgctcaca aagtcttgat gttatacatg ccgatgatct tgagttgcag | 600 |
| atgcagcacc aagaaaagtt tgatgttgtt atcgatactg tcggtaatca gatcgataca | 660 |
| gcttcacgct acatcggtcg cggtgggaga attgtacttt ttggatttga tagtgactat | 720 |
| cactacatgc tgcctgtaaa gtacttcctg gttaacgcta tcagtattat ttctgctgga | 780 |
| gaatacaatc agcactttcc tagagcaatt cgtcttgtgc aaaaacttcc tgagctaggg | 840 |
| cggctggtaa cgcatcgcta cgtactagaa aatcactcgg aggttttcga tgcacttctg | 900 |
| aacgatgctt ccgcccccaa tataaaaagc gtattcacac caaatctcgc ttatctttaa | 960 |

<210> SEQ ID NO 42
<211> LENGTH: 319
<212> TYPE: PRT
<213> ORGANISM: Pseudomonas syringae pv. tomato DC3000

<400> SEQUENCE: 42

```
Met Leu Ala Pro Asp Gly Val Glu Ile Asp Ile Val Leu Ser Gly Ile
 1               5                  10                  15
Cys Gly Thr Asp Leu Ala Val Leu Ser Gly Arg Glu Gly Gly Glu Val
            20                  25                  30
Gly Ile Ile Arg Gly His Glu Ala Val Gly Ile Ile Asp Val Gly
        35                  40                  45
Lys Asp Val Val His Leu Gln Lys Gly Met Arg Val Val Asp Pro
 50                  55                  60
Asn Glu Tyr Cys Gly Val Cys Glu Pro Cys Arg Leu Ala Lys Thr His
 65                  70                  75                  80
Leu Cys Asn Gly Gly Val Asn Ala Gly Leu Asp Ile Ala Gly Val Asn
            85                  90                  95
Lys His Gly Thr Phe Ala Glu Arg Phe Val Thr Arg Glu Arg Phe Val
            100                 105                 110
Tyr Gln Leu Pro Asp Asp Met Ser Trp Ala Ala Gly Val Leu Val Glu
            115                 120                 125
Pro Val Ala Cys Ile Leu Asn Asn Ile Asp Gln Ala Phe Ile Arg Ala
130                 135                 140
Gly Glu Arg Val Leu Ile Leu Gly Ser Gly Pro Met Ser Leu Ile Ala
145                 150                 155                 160
Gln Ile Val Leu Arg Ser Met Gly Val Asp Thr Leu Ala Thr Asp Arg
            165                 170                 175
Asn Thr His Arg Ile Gln Phe Gly Arg Ser Gln Ser Leu Asp Val Ile
            180                 185                 190
His Ala Asp Asp Leu Glu Leu Gln Met Gln His Gln Glu Lys Phe Asp
            195                 200                 205
Val Val Ile Asp Thr Val Gly Asn Gln Ile Asp Thr Ala Ser Arg Tyr
210                 215                 220
Ile Gly Arg Gly Gly Arg Ile Val Leu Phe Gly Phe Asp Ser Asp Tyr
225                 230                 235                 240
His Tyr Met Leu Pro Val Lys Tyr Phe Leu Val Asn Ala Ile Ser Ile
            245                 250                 255
Ile Ser Ala Gly Glu Tyr Asn Gln His Phe Pro Arg Ala Ile Arg Leu
            260                 265                 270
Val Gln Lys Leu Pro Glu Leu Gly Arg Leu Val Thr His Arg Tyr Val
            275                 280                 285
Leu Glu Asn His Ser Glu Val Phe Asp Ala Leu Leu Asn Asp Ala Ser
            290                 295                 300
Ala Pro Asn Ile Lys Ser Val Phe Thr Pro Asn Leu Ala Tyr Leu
305                 310                 315
```

<210> SEQ ID NO 43
<211> LENGTH: 675
<212> TYPE: DNA
<213> ORGANISM: Pseudomonas syringae pv. tomato DC3000

<400> SEQUENCE: 43

```
atgaaagtta ctgtattcag tcagatatca attgatggca agttgacgat gggcaaaggc    60
gcatccagca agccgttgtt tcagaacttt gatgatgatg acatgcgttt tattcataag   120
ttccgcggcg aagtcgacgc aatcatggta gggcgcaata caattgttac tgacgatcca   180
caattgacca atcgctatga gtcgggtcgt aacccaatac gtatcattcc caccacctcc   240
ttagatctgc ctacttccgc cagtattttc aaatcaccag agaaaactat tatcgcaact   300
```

-continued

```
agcgaacagg ctcgtgatca tgaaatggtc aaacatatcc gtgcttgtgg aaaggaggtg      360
ctctttgccg gtgcaaagca tgtcgacttt acacgacttt ccctatgct ggaggcgcgc       420 ggaataaacc acatcatggt tgagggcggt ggccacctga actggcaggt attcaatctc      480
gatctggtag atgaaattat actcatgcag gtgcctatca tcataggtgg tgcggcaact      540
gcaacgcttg ctgacggggt ggggtatcgg gatatcaaca tggccaattc gtttacgctg      600
catgctttag aagcacgccc ccattacaat ctcatgcact tcaagcgcga atcgaacaat      660
cggagcccgt actga                                                       675
```

<210> SEQ ID NO 44
<211> LENGTH: 224
<212> TYPE: PRT
<213> ORGANISM: Pseudomonas syringae pv. tomato DC3000

<400> SEQUENCE: 44

```
Met Lys Val Thr Val Phe Ser Gln Ile Ser Ile Asp Gly Lys Leu Thr
  1               5                  10                  15

Met Gly Lys Gly Ala Ser Ser Lys Pro Leu Phe Gln Asn Phe Asp Asp
             20                  25                  30

Asp Asp Met Arg Phe Ile His Lys Phe Arg Gly Glu Val Asp Ala Ile
         35                  40                  45

Met Val Gly Arg Asn Thr Ile Val Thr Asp Asp Pro Gln Leu Thr Asn
     50                  55                  60

Arg Tyr Glu Ser Gly Arg Asn Pro Ile Arg Ile Ile Pro Thr Thr Ser
 65                  70                  75                  80

Leu Asp Leu Pro Thr Ser Ala Ser Ile Phe Lys Ser Pro Glu Lys Thr
                 85                  90                  95

Ile Ile Ala Thr Ser Glu Gln Ala Arg Asp His Glu Met Val Lys His
            100                 105                 110

Ile Arg Ala Cys Gly Lys Glu Val Leu Phe Ala Gly Ala Lys His Val
        115                 120                 125

Asp Phe Thr Arg Leu Phe Pro Met Leu Glu Ala Arg Gly Ile Asn His
    130                 135                 140

Ile Met Val Glu Gly Gly His Leu Asn Trp Gln Val Phe Asn Leu
145                 150                 155                 160

Asp Leu Val Asp Glu Ile Ile Leu Met Gln Val Pro Ile Ile Ile Gly
                165                 170                 175

Gly Ala Ala Thr Ala Thr Leu Ala Asp Gly Val Gly Tyr Arg Asp Ile
            180                 185                 190

Asn Met Ala Asn Ser Phe Thr Leu His Ala Leu Glu Ala Arg Pro His
        195                 200                 205

Tyr Asn Leu Met His Phe Lys Arg Glu Ser Asn Asn Arg Ser Pro Tyr
    210                 215                 220
```

<210> SEQ ID NO 45
<211> LENGTH: 588
<212> TYPE: DNA
<213> ORGANISM: Pseudomonas syringae pv. tomato DC3000

<400> SEQUENCE: 45

```
atggagcagg aaaagagttc ctgtttgcgc tacggcgtga cccttaatga aaaagatctg      60
tcacgttttt tgggaactac acagcactac atgtggagca cgattaaaaa tgagtacgcg     120
ctcactgaat ccatcgacca cttgatggca cagcatcaac agcaattaat gcgctcaatc     180
agttttgaat tgtttcaatc catgcctggc gtggaggcgc ttctcaattt actggagcat     240
```

-continued

| | | |
|---|---|---|
| accggagtgc cctgtgccgt agcctcttcg tctccacgta atttggtcga gcttatattg | 300 |
| aagaaaacga aattgcgtcg attttttcaaa gaggttattt gtggtactga tgttaaagag | 360 |
| agtaaaccga atccggagat ttttcttacg gcggccaagg gacttggagt gtcacctcgt | 420 |
| gcatgtctgg ttattgaaga ctcccatcac ggtgttaccg ctgcgaaggc cgcccatatg | 480 |
| ttttgtatag gtttgcgtca ttccagctca tttcagcagg atctgagcgc tgctgatctg | 540 |
| atcgccaata atcattatga catcaagcaa tggtttgcag aaaaatag | 588 |

<210> SEQ ID NO 46
<211> LENGTH: 195
<212> TYPE: PRT
<213> ORGANISM: Pseudomonas syringae pv. tomato DC3000

<400> SEQUENCE: 46

Met Glu Gln Glu Lys Ser Ser Cys Leu Arg Tyr Gly Val Thr Leu Asn
1               5                   10                  15

Glu Lys Asp Leu Ser Arg Phe Leu Gly Thr Thr Gln His Tyr Met Trp
            20                  25                  30

Ser Thr Ile Lys Asn Glu Tyr Ala Leu Thr Glu Ser Ile Asp His Leu
        35                  40                  45

Met Ala Gln His Gln Gln Leu Met Arg Ser Ile Ser Phe Glu Leu
    50                  55                  60

Phe Gln Ser Met Pro Gly Val Glu Ala Leu Leu Asn Leu Leu Glu His
65                  70                  75                  80

Thr Gly Val Pro Cys Ala Val Ala Ser Ser Pro Arg Asn Leu Val
                85                  90                  95

Glu Leu Ile Leu Lys Lys Thr Lys Leu Arg Arg Phe Phe Lys Glu Val
            100                 105                 110

Ile Cys Gly Thr Asp Val Lys Glu Ser Lys Pro Asn Pro Glu Ile Phe
        115                 120                 125

Leu Thr Ala Ala Lys Gly Leu Gly Val Ser Pro Arg Ala Cys Leu Val
    130                 135                 140

Ile Glu Asp Ser His His Gly Val Thr Ala Ala Lys Ala Ala His Met
145                 150                 155                 160

Phe Cys Ile Gly Leu Arg His Ser Ser Ser Phe Gln Gln Asp Leu Ser
                165                 170                 175

Ala Ala Asp Leu Ile Ala Asn Asn His Tyr Asp Ile Lys Gln Trp Phe
            180                 185                 190

Ala Glu Lys
        195

<210> SEQ ID NO 47
<211> LENGTH: 474
<212> TYPE: DNA
<213> ORGANISM: Pseudomonas syringae pv. tomato DC3000

<400> SEQUENCE: 47

| | | |
|---|---|---|
| atgaatgcgt tcgcaaccgg tcagcttgaa tacagcctga aaaagctggg atacgatgcc | 60 |
| gccgctttgc aggccctgcg cgaagaaggg tacttgctgt ggaaagggaa aaacgaccag | 120 |
| accagcttgc tggtgccctc ggccgatctg gatgcacttt tcgttatcaa cacgttgagc | 180 |
| tacatcgacc ccgagcatga cggacgtctg ctggcgcttg cattgcacct taacctgtcc | 240 |
| cctgtccata cgatgagcgc ctgcatagcc ctcgatgtcg agcaaaacac gttatgcctg | 300 |
| cgctacaccc atgaccttgg cgggagcggg gctgataccc tgttgcttgc gctcgaaaac | 360 |

-continued

```
gcccaggcgc tggccgaaca ggtcaggcag gtgatcgaaa ccttcaggcg tgaccaaggg    420
cgtccgtccg ggcaaacgtc tttgtcccgg caatccagtg ctctgatgcg ataa          474
```

<210> SEQ ID NO 48
<211> LENGTH: 157
<212> TYPE: PRT
<213> ORGANISM: Pseudomonas syringae pv. tomato DC3000

<400> SEQUENCE: 48

```
Met Asn Ala Phe Ala Thr Gly Gln Leu Glu Tyr Ser Leu Lys Lys Leu
  1               5                  10                  15

Gly Tyr Asp Ala Ala Leu Gln Ala Leu Arg Glu Gly Tyr Leu
             20                  25                  30

Leu Trp Lys Gly Lys Asn Asp Gln Thr Ser Leu Leu Val Pro Ser Ala
         35                  40                  45

Asp Leu Asp Ala Leu Phe Val Ile Asn Thr Leu Ser Tyr Ile Asp Pro
     50                  55                  60

Glu His Asp Gly Arg Leu Leu Ala Leu Ala Leu His Leu Asn Leu Ser
 65                  70                  75                  80

Pro Val His Thr Met Ser Ala Cys Ile Ala Leu Asp Val Glu Gln Asn
                 85                  90                  95

Thr Leu Cys Leu Arg Tyr Thr His Asp Leu Gly Gly Ser Gly Ala Asp
            100                 105                 110

Thr Leu Leu Ala Leu Glu Asn Ala Gln Ala Leu Ala Glu Gln Val
        115                 120                 125

Arg Gln Val Ile Glu Thr Phe Arg Arg Asp Gln Gly Arg Pro Ser Gly
    130                 135                 140

Gln Thr Ser Leu Ser Arg Gln Ser Ser Ala Leu Met Arg
145                 150                 155
```

<210> SEQ ID NO 49
<211> LENGTH: 357
<212> TYPE: DNA
<213> ORGANISM: Pseudomonas syringae pv. tomato DC3000

<400> SEQUENCE: 49

```
atgaaaatat ccggctccac atcgcctgca cacacttcaa cgaattccgc gcagaagtcc    60
tcttcaaaag gctgctgag tggtttggcc aagcatttca aggggatgct cgtttctggc     120
aacacttctg gtcattcggc gctcgggcat tacgcgtcat ccagcagcgg ctccaaggc    180 aaggcaccgg tacgggacga ttacagcaac ggaccgcaaa cacgccttaa caacacacct    240
ctgaaacgag cactggcccg agagcttgat cgctttggct acggttcatc ggcgaccgag    300
tcttttgacc gctcattgca gcgtaaggat aaaaatccag agcttgggaa ggtctga       357
```

<210> SEQ ID NO 50
<211> LENGTH: 118
<212> TYPE: PRT
<213> ORGANISM: Pseudomonas syringae pv. tomato DC3000

<400> SEQUENCE: 50

```
Met Lys Ile Ser Gly Ser Thr Ser Pro Ala His Thr Ser Thr Asn Ser
  1               5                  10                  15

Ala Gln Lys Ser Ser Ser Lys Gly Leu Leu Ser Gly Leu Ala Lys His
             20                  25                  30

Phe Lys Gly Met Leu Val Ser Gly Asn Thr Ser Gly His Ser Ala Leu
         35                  40                  45
```

```
Gly His Tyr Ala Ser Ser Ser Gly Ser Lys Gly Lys Ala Pro Val
 50                  55                  60

Arg Asp Asp Tyr Ser Asn Gly Pro Gln Thr Arg Leu Asn Asn Thr Pro
 65                  70                  75                  80

Leu Lys Arg Ala Leu Ala Arg Glu Leu Asp Arg Phe Gly Tyr Gly Ser
                 85                  90                  95

Ser Ala Thr Glu Ser Phe Asp Arg Ser Leu Gln Arg Lys Asp Lys Asn
            100                 105                 110

Pro Glu Leu Gly Lys Val
            115

<210> SEQ ID NO 51
<211> LENGTH: 1299
<212> TYPE: DNA
<213> ORGANISM: Pseudomonas syringae pv. tomato DC3000

<400> SEQUENCE: 51
```

| | | | | | |
|---|---|---|---|---|---|
| atgaaaaaat | gtattgctct | gctccttact | ctggtcgtct | gcgaaggtgc | attggcagga | 60 |
| acggcacgtg | atgaacagaa | catcacgtct | tacatcgaca | gtcacggcac | cgaacagatc | 120 |
| gcgttgcttg | agaagctggt | caacatcaac | agcgggacag | acaacgttga | gggtgtcgtc | 180 |
| aaggtcggta | acctgatcaa | gccggagctg | gaggcgttgg | gtttcgagac | cgcctggcac | 240 |
| gacctgccct | cggcaatgaa | ccatgccggc | agccttgtcg | ctgtgcatga | cggcagcaag | 300 |
| tctgcaaaac | gtattctgct | gataggccat | ctggatacgg | tctttcctca | aacaagccgc | 360 |
| tttcagacgt | tcgcttacct | ggacggcggc | aaaaaagcca | agggcccggg | cgtcattgat | 420 |
| gacaaaggcg | gcgtggtcac | gatgctttat | gcattgcagg | cgctcaagca | cagcggcgcg | 480 |
| ctggaaaaga | tgaacatctc | ggtagtcttg | ataggcgatg | aagagctggc | ggccaaaccg | 540 |
| accgagattt | ccagagagtg | gctgatcgcc | gaagccaaaa | gaagcgacat | tgcgctgggc | 600 |
| ttcgaattcg | ccttgtcgcc | caatcaactg | atcaccgagc | gaagagggct | gagcgaatgg | 660 |
| tttttgacca | gcaccggcat | cgacaaacat | tcagcgacga | tctttcagcc | tgagaccggt | 720 |
| tttggtgcga | tgtacgagtc | ggcccgagtg | cttgacgaga | ttcgtcagaa | actgtcgaac | 780 |
| gagcagggcc | tgaccatcaa | tccgggactc | attctgggcg | gctcaacggc | tgtggaagat | 840 |
| agcgccagtg | ggcaaggcac | ggcttctgga | agaaagacaa | cagttgcccg | gatcacgtcg | 900 |
| gtgcatggtg | atttgcgctt | cagcagtgaa | gaccagaggg | cctctgcgga | aacccgaatg | 960 |
| aaggacatag | ccagtcaccc | gctgccgcag | accaacagcg | acctgaaaat | aaaagccatc | 1020 |
| atgccggtca | tggcggatcg | cgaaagcaat | cgccaactac | tggcagccta | cagtcaggtc | 1080 |
| agccaggatc | tcgacggacc | tgctttggag | tcggcgccct | tcagcagaacg | aggcggcgca | 1140 |
| gatatttcct | atgtgaacaa | gtatgtgact | gcgagcctgg | acggtcttgg | tgcgtggggg | 1200 |
| gcaggtgcgc | acagtgaaaa | tgaaaccatc | gagttgggct | ccttgcccgt | ggtgacgaaa | 1260 |
| cgggcggcta | ttttcctgag | ccgctatggt | aaccagtga | | | 1299 |

```
<210> SEQ ID NO 52
<211> LENGTH: 432
<212> TYPE: PRT
<213> ORGANISM: Pseudomonas syringae pv. tomato DC3000

<400> SEQUENCE: 52

Met Lys Lys Cys Ile Ala Leu Leu Leu Thr Leu Val Val Cys Glu Gly
 1               5                  10                  15
```

```
Ala Leu Ala Gly Thr Ala Arg Asp Glu Gln Asn Ile Thr Ser Tyr Ile
            20                  25                  30

Asp Ser His Gly Thr Glu Gln Ile Ala Leu Leu Glu Lys Leu Val Asn
            35                  40                  45

Ile Asn Ser Gly Thr Asp Asn Val Glu Gly Val Lys Val Gly Asn
 50                  55                  60

Leu Ile Lys Pro Glu Leu Glu Ala Leu Gly Phe Glu Thr Ala Trp His
 65                  70                  75                  80

Asp Leu Pro Ser Ala Met Asn His Ala Gly Ser Leu Val Ala Val His
                85                  90                  95

Asp Gly Ser Lys Ser Ala Lys Arg Ile Leu Ile Gly His Leu Asp
                100                 105                 110

Thr Val Phe Pro Gln Thr Ser Arg Phe Gln Thr Phe Ala Tyr Leu Asp
            115                 120                 125

Gly Gly Lys Lys Ala Lys Gly Pro Gly Val Ile Asp Asp Lys Gly Gly
 130                 135                 140

Val Val Thr Met Leu Tyr Ala Leu Gln Ala Leu Lys His Ser Gly Ala
 145                 150                 155                 160

Leu Glu Lys Met Asn Ile Ser Val Val Leu Ile Gly Asp Glu Glu Leu
                165                 170                 175

Ala Ala Lys Pro Thr Glu Ile Ser Arg Glu Trp Leu Ile Ala Glu Ala
                180                 185                 190

Lys Arg Ser Asp Ile Ala Leu Gly Phe Glu Phe Ala Leu Ser Pro Asn
            195                 200                 205

Gln Leu Ile Thr Glu Arg Arg Gly Leu Ser Glu Trp Phe Leu Thr Ser
            210                 215                 220

Thr Gly Ile Asp Lys His Ser Ala Thr Ile Phe Gln Pro Glu Thr Gly
 225                 230                 235                 240

Phe Gly Ala Met Tyr Glu Ser Ala Arg Val Leu Asp Glu Ile Arg Gln
                245                 250                 255

Lys Leu Ser Asn Glu Gln Gly Leu Thr Ile Asn Pro Gly Leu Ile Leu
                260                 265                 270

Gly Gly Ser Thr Ala Val Glu Asp Ser Ala Ser Gly Gln Gly Thr Ala
            275                 280                 285

Ser Gly Arg Lys Thr Thr Val Ala Arg Ile Thr Ser Val His Gly Asp
 290                 295                 300

Leu Arg Phe Ser Ser Glu Asp Gln Arg Ala Ser Ala Glu Thr Arg Met
 305                 310                 315                 320

Lys Asp Ile Ala Ser His Pro Leu Pro Gln Thr Asn Ser Asp Leu Lys
                325                 330                 335

Ile Lys Ala Ile Met Pro Val Met Ala Asp Arg Glu Ser Asn Arg Gln
                340                 345                 350

Leu Leu Ala Ala Tyr Ser Gln Val Ser Gln Asp Leu Asp Gly Pro Ala
            355                 360                 365

Leu Glu Ser Ala Pro Ser Ala Glu Arg Gly Gly Ala Asp Ile Ser Tyr
            370                 375                 380

Val Asn Lys Tyr Val Thr Ala Ser Leu Asp Gly Leu Gly Ala Trp Gly
 385                 390                 395                 400

Ala Gly Ala His Ser Glu Asn Glu Thr Ile Glu Leu Gly Ser Leu Pro
                405                 410                 415

Val Val Thr Lys Arg Ala Ala Ile Phe Leu Ser Arg Tyr Gly Asn Gln
            420                 425                 430
```

<210> SEQ ID NO 53
<211> LENGTH: 459
<212> TYPE: DNA
<213> ORGANISM: Pseudomonas syringae pv. tomato DC3000

<400> SEQUENCE: 53

```
atgaaccecta taacacacag ctttagtcat cttgggtttt caaacgctca agtacgtca      60
gcgctggcgc ccggcggtaa taaagtgccg aactttgttt cgcgagggcg aggcaaagga     120
gtcccgcttg agcatttcaa caccgctgat gagtatcgtt tggcacgcca gcaggcggc     180
gtgctgaaat caatagacgg cagagagttc atgctactgc tgcagaagta cacggccgcc     240
gaaacaagcg acgaagaatt tgcggatttg agggccgcca taccgcgcta ttccattgac     300
ctggccgagc cgggtcaaac taaagtgctt tatcggggga tatcgctgcc ggagaagact     360
gcggcgcgat tactgaatat ctcttggggt tacgaaagtc gcgaaatagc ccatggtctt     420
atccatggct tgcgggtagt taaggaaggt ctgaagtag                           459
```

<210> SEQ ID NO 54
<211> LENGTH: 152
<212> TYPE: PRT
<213> ORGANISM: Pseudomonas syringae pv. tomato DC3000

<400> SEQUENCE: 54

```
Met Asn Pro Ile Thr His Ser Phe Ser His Leu Gly Phe Ser Asn Ala
 1               5                  10                  15

Gln Ser Thr Ser Ala Leu Ala Pro Gly Gly Asn Lys Val Pro Asn Phe
            20                  25                  30

Val Ser Arg Gly Arg Gly Lys Gly Val Pro Leu Glu His Phe Asn Thr
        35                  40                  45

Ala Asp Glu Tyr Arg Leu Ala Arg Gln Gln Gly Gly Val Leu Lys Ser
    50                  55                  60

Ile Asp Gly Arg Glu Phe Met Leu Leu Leu Gln Lys Tyr Thr Ala Ala
65                  70                  75                  80

Glu Thr Ser Asp Glu Glu Phe Ala Asp Leu Arg Ala Ala Ile Pro Arg
                85                  90                  95

Tyr Ser Ile Asp Leu Ala Glu Pro Gly Gln Thr Lys Val Leu Tyr Arg
            100                 105                 110

Gly Ile Ser Leu Pro Glu Lys Thr Ala Ala Arg Leu Leu Asn Ile Ser
        115                 120                 125

Trp Gly Tyr Glu Ser Arg Glu Ile Ala His Gly Leu Ile His Gly Leu
    130                 135                 140

Arg Val Val Lys Glu Gly Leu Lys
145                 150
```

<210> SEQ ID NO 55
<211> LENGTH: 2700
<212> TYPE: DNA
<213> ORGANISM: Pseudomonas syringae pv. tomato DC3000

<400> SEQUENCE: 55

```
atgactactc tgaccaccag acagatacaa ctcgcccacg cttggacatc cgttcataca      60
ggcgctggcc tggccctgga ctgggtcgcc gatgtggccg aaaaggtcga ggaaatcgcc     120
accaaggccg acgccctcag ccgtgacttg caccgcgcgc gcaacctgtc ccgcagcctt     180
gggcgggtct cgacgacacc catgggtatc ggtttcttcg gcttgtctca ggcaggcaag     240
agctacctga tttccgctct ggcggcggac gagaaaggcc agttgctgac ccggctgggt     300
```

-continued

```
actcagcaac tggacttcat caagcacgtg aacccggtgg gcggcggtaa ggaggccacc      360
ggtctggtca cgcggttcac ccgcaccgcc gcgccaagtc tggacccgca ctttccggtg      420
gagctgcgtc tgtttcgcga ggtcgagatc gccatcattt tggccaacgc ctggtttgag      480
gatttcgatc atcagcgctt gaacagccaa gtcaccgatg cgcagatcga tgccctttg      540 cagcgtttcg aggggcaatt ggcagccgct ccgacacctg gcgtcagcag tgacgacgtg      600
gtgctgctat gggattacct ggagcaccat tacgctaacg ccatgcgccc gctgaacgcc      660
cgttattggc cttgcgtggt caaactggcg ccgcgcttgt cggcacgcga gcgcgctcaa      720
ttgttcgagc cgctgtgggg cggcatcggc aaaatgaccg aaacctatga gcaactggcc      780
tcggccctgc accgcctggg gctggcagag acagttttg cgcccatcag cgcgctggtc      840
accgagcgcg atgggcaact ggtacaaagc aaaagcatca tcaacgtcga cattctcagc      900
cgtcttggcg gcagcgcgga ctcggccatc gaggtacgtc cggccagtga aggcactttg      960
cgccctgccg tgtcggtgaa tcgggccgaa ctggcggcgc tcaccaacga gttgattttt      1020
cgcctggata cgaaccggc caacgccatc gtcaatagcg tcgatctgct cgacttcccg       1080
ggctaccgca gccggcagaa gctgatgagc atcaacgagg ccagcgaagt cgacagcaat      1140
ggcaccgcca acaatccggt cgccaggctg ttgctgcgcg gcaaggtcgc ttacttgttt      1200
gagcgttaca ccaacgagca ggaaatgaac gcgctggtga tgtgcaccag caccttcaag      1260
cagagcgaag tggtgagcgt cggtccggta ctcaagagct ggatcgacaa gacccaaggc      1320
accagccccc agcagcgcga tggtcgggcc agcggtctga tctgggcgtt gaccatgtgt      1380 gacggctta tcggcggcgc gctcaacggc gaggttgtgc agtttcccga aggttgcgac       1440
aacatgctca aactgaccat gatcgagcga ttcggcaacg aagactggat gaaacaatgg      1500
ggcagcacgc ctttcaaaaa cacctatctg gtgcgcaagc cgcgcttcaa gaccagcttc      1560
atcgagttgg cggcggacgg tgaagaacgc gcttacaacg actcatcgca ctctgcgtta      1620
caggcattgc aacaagcgtt cagcaacagt gaactggtca agcgccatgt ggcagaaccg      1680
caggacgcct ggcaggcaat gctgacactg aacgacggcg gcatgactcg tttcagctcg      1740
gcgttcagcc cgattgccaa catcgacttc aagttacagc gtattgccga gcaactggac      1800
gagttgatgg tgcaattact gccgcgcctg gagcagtact acgaagccgg tggcgaagac      1860
gaacgggcca ggaagaaggt tatcgccaac ctgattgccc gcccgttcgc gaccacgccg      1920
cacggcaaac acgtgcttgg cgaactgctc ggttacatgt cgttgccgga acagcagttg      1980
cgcgaccttt acctgaacgg tgatttcgcc agccctgcca gcgacgccac tgcaccggtg      2040
caggccgtcg gcaagcctga agtggaatac gacatattcg gcgaggccat cgcagccact      2100
gccacggtgg aaatacccgc ggcaccggcc gtagcgccgc ataccagag ccacgaacac       2160 cgtttcgccc gagcggcctt cgacctgtgg gcaacgcacc tgcgcaacct cagccgtcgc      2220
cagcacctgc tggacctgtt ggagctgcct gccgaggcca tcgccctgct ggtcaaggaa      2280
ctggtggtct cgccgagcg cctggacttg ccattgcagc tcagcaacgc gctgctcaag       2340
cgcgcccaga gcgtgtgcg caaagaaaac ctggtgcagc gccaagtgct gaccgcgcaa       2400
ctgctgctca acgacttcgc cgcctggttc gggcacaccg cccagccggc gggtcagcgg      2460
ccaacgggcc tgctgggtgc caaacaaccg ctgtttgctt tttatcaaaa ggaaatgcca      2520
gggcgcttcc cgcacctcgc agcgcaagcc gacgaccaga gcgtgatttt cgccgatgac      2580
tggatttctg gcattgccat tcataccca aaaaacgtcg gccaccgcaa gggcaaagaa       2640
atcactcctg agcagaacga ggccatgggc cgcgtcatcc aggcgttcaa agcgagataa      2700
```

-continued

<210> SEQ ID NO 56
<211> LENGTH: 899
<212> TYPE: PRT
<213> ORGANISM: Pseudomonas syringae pv. tomato DC3000

<400> SEQUENCE: 56

```
Met Thr Thr Leu Thr Thr Arg Gln Ile Gln Leu Ala His Ala Trp Thr
 1               5                  10                  15

Ser Val His Thr Gly Ala Gly Leu Ala Leu Asp Trp Val Ala Asp Val
                20                  25                  30

Ala Glu Lys Val Glu Ile Ala Thr Lys Ala Asp Ala Leu Ser Arg
             35                  40                  45

Asp Leu His Arg Ala Arg Asn Leu Ser Arg Ser Leu Gly Arg Val Ser
     50                  55                  60

Thr Thr Pro Met Gly Ile Gly Phe Phe Gly Leu Ser Gln Ala Gly Lys
 65                  70                  75                  80

Ser Tyr Leu Ile Ser Ala Leu Ala Ala Asp Glu Lys Gly Gln Leu Leu
                85                  90                  95

Thr Arg Leu Gly Thr Gln Gln Leu Asp Phe Ile Lys His Val Asn Pro
            100                 105                 110

Val Gly Gly Gly Lys Glu Ala Thr Gly Leu Val Thr Arg Phe Thr Arg
        115                 120                 125

Thr Ala Ala Pro Ser Leu Asp Pro His Phe Pro Val Glu Leu Arg Leu
    130                 135                 140

Phe Arg Glu Val Glu Ile Ala Ile Ile Leu Ala Asn Ala Trp Phe Glu
145                 150                 155                 160

Asp Phe Asp His Gln Arg Leu Asn Ser Gln Val Thr Asp Ala Gln Ile
                165                 170                 175

Asp Ala Leu Leu Gln Arg Phe Glu Gly Gln Leu Ala Ala Pro Thr
            180                 185                 190

Pro Gly Val Ser Ser Asp Asp Val Val Leu Leu Trp Asp Tyr Leu Glu
        195                 200                 205

His His Tyr Ala Asn Ala Met Arg Pro Leu Asn Ala Arg Tyr Trp Pro
    210                 215                 220

Cys Val Val Lys Leu Ala Pro Arg Leu Ser Ala Arg Glu Arg Ala Gln
225                 230                 235                 240

Leu Phe Glu Pro Leu Trp Gly Gly Ile Gly Lys Met Thr Glu Thr Tyr
                245                 250                 255

Glu Gln Leu Ala Ser Ala Leu His Arg Leu Gly Leu Ala Glu Thr Val
            260                 265                 270

Phe Ala Pro Ile Ser Ala Leu Val Thr Glu Arg Asp Gly Gln Leu Val
        275                 280                 285

Gln Ser Lys Ser Ile Ile Asn Val Asp Ile Leu Ser Arg Leu Gly Gly
    290                 295                 300

Ser Ala Asp Ser Ala Ile Glu Val Arg Pro Ala Ser Glu Gly Thr Leu
305                 310                 315                 320

Arg Pro Ala Val Ser Val Asn Arg Ala Glu Leu Ala Ala Leu Thr Asn
                325                 330                 335

Glu Leu Ile Phe Arg Leu Asp Asn Glu Pro Ala Asn Ala Ile Val Asn
            340                 345                 350

Ser Val Asp Leu Leu Asp Phe Pro Gly Tyr Arg Ser Arg Gln Lys Leu
        355                 360                 365

Met Ser Ile Asn Glu Ala Ser Glu Val Asp Ser Asn Gly Thr Ala Asn
    370                 375                 380
```

```
Asn Pro Val Ala Arg Leu Leu Arg Gly Lys Val Ala Tyr Leu Phe
385                 390                 395                 400

Glu Arg Tyr Thr Asn Glu Gln Glu Met Asn Ala Leu Val Met Cys Thr
            405                 410                 415

Ser Thr Phe Lys Gln Ser Glu Val Val Ser Val Gly Pro Val Leu Lys
            420                 425                 430

Ser Trp Ile Asp Lys Thr Gln Gly Thr Ser Pro Gln Gln Arg Asp Gly
            435                 440                 445

Arg Ala Ser Gly Leu Ile Trp Ala Leu Thr Met Cys Asp Gly Phe Ile
    450                 455                 460

Gly Gly Ala Leu Asn Gly Glu Val Val Gln Phe Pro Glu Gly Cys Asp
465                 470                 475                 480

Asn Met Leu Lys Leu Thr Met Ile Glu Arg Phe Gly Asn Glu Asp Trp
                485                 490                 495

Met Lys Gln Trp Gly Ser Thr Pro Phe Lys Asn Thr Tyr Leu Val Arg
            500                 505                 510

Lys Pro Arg Phe Lys Thr Ser Phe Ile Glu Leu Ala Ala Asp Gly Glu
            515                 520                 525

Glu Arg Ala Tyr Asn Asp Ser Ser His Ser Ala Leu Gln Ala Leu Gln
    530                 535                 540

Gln Ala Phe Ser Asn Ser Glu Leu Val Lys Arg His Val Ala Glu Pro
545                 550                 555                 560

Gln Asp Ala Trp Gln Ala Met Leu Thr Leu Asn Asp Gly Met Thr
                565                 570                 575

Arg Phe Ser Ser Ala Phe Ser Pro Ile Ala Asn Ile Asp Phe Lys Leu
                580                 585                 590

Gln Arg Ile Ala Glu Gln Leu Asp Glu Leu Met Val Gln Leu Leu Pro
            595                 600                 605

Arg Leu Glu Gln Tyr Tyr Glu Ala Gly Gly Glu Asp Glu Arg Ala Arg
            610                 615                 620

Lys Lys Val Ile Ala Asn Leu Ile Ala Arg Pro Phe Ala Thr Thr Pro
625                 630                 635                 640

His Gly Lys His Val Leu Gly Glu Leu Gly Tyr Met Ser Leu Pro
                645                 650                 655

Glu Gln Gln Leu Arg Asp Leu Tyr Leu Asn Gly Asp Phe Ala Ser Pro
            660                 665                 670

Ala Ser Asp Ala Thr Ala Pro Val Gln Ala Val Gly Lys Pro Glu Val
            675                 680                 685

Glu Tyr Asp Ile Phe Gly Glu Ala Ile Ala Thr Ala Thr Val Glu
    690                 695                 700

Ile Pro Ala Ala Pro Ala Val Ala Pro Gln Tyr Gln Ser His Glu His
705                 710                 715                 720

Arg Phe Ala Arg Ala Ala Phe Asp Leu Trp Ala Thr His Leu Arg Asn
            725                 730                 735

Leu Ser Arg Arg Gln His Leu Leu Asp Leu Leu Glu Leu Pro Ala Glu
            740                 745                 750

Ala Ile Ala Leu Leu Val Lys Glu Leu Val Val Cys Ala Glu Arg Leu
            755                 760                 765

Asp Leu Pro Leu Gln Leu Ser Asn Ala Leu Leu Lys Arg Ala Gln Ser
    770                 775                 780

Gly Val Arg Lys Glu Asn Leu Val Gln Arg Gln Val Leu Thr Ala Gln
785                 790                 795                 800
```

-continued

```
Leu Leu Leu Asn Asp Phe Ala Ala Trp Phe Gly His Thr Ala Gln Pro
            805                 810                 815

Ala Gly Gln Arg Pro Thr Gly Leu Leu Gly Ala Lys Gln Pro Leu Phe
        820                 825                 830

Ala Phe Tyr Gln Lys Glu Met Pro Gly Arg Phe Pro His Leu Ala Ala
            835                 840                 845

Gln Ala Asp Asp Gln Ser Val Ile Phe Ala Asp Trp Ile Ser Gly
    850                 855                 860

Ile Ala Ile His Thr Gln Lys Asn Val Gly His Arg Lys Gly Lys Glu
865                 870                 875                 880

Ile Thr Pro Glu Gln Asn Glu Ala Met Gly Arg Val Ile Gln Ala Phe
                885                 890                 895
Lys Ala Arg
```

```
<210> SEQ ID NO 57
<211> LENGTH: 795
<212> TYPE: DNA
<213> ORGANISM: Pseudomonas syringae pv. tomato DC3000

<400> SEQUENCE: 57
```

| | | |
|---|---|---|
| atgaatataa atcgacaact gcctgtatca ggctcggagc gattgttgac tcccgacgtg | 60 |
| ggcgtatctc gccaggcttg ttccgaaagg cattattcta ctggacagga tcggcatgat | 120 |
| ttttaccgtt ttgctgccag gctacatgtg gatgcgcagt gttttggtct gtcaatagac | 180 |
| gatttgatgg ataagttttc tgacaagcac ttcagggctg agcatcctga atacagggat | 240 |
| gtctatccgg aggaatgttc tgccatttat atgcataccg ctcaagacta ttctagtcac | 300 |
| ctcgtaaggg gggaaatagg aacgccgctg taccgagagg tcaataatta tcttcgactt | 360 |
| caacatgaga attctgggcg agaagctgaa attgataatc acgacgaaaa gctatcgcct | 420 |
| cacataaaaa tgctttcatc tgcgcttaat cgtttaatgg atgtcgccgc ttttagagga | 480 |
| acggtttata gaggcattcg cggtgattta gataccattg ctcggctcta ccatctattc | 540 |
| gatacgggcg gccggtacgt agagcccgct ttcatgagta caactcgaat aaaggacagt | 600 |
| gcccaggtgt tgagccagg cacgccaaac aacatagctt tccagataag cctaaaaaga | 660 |
| ggcgccgaca tttcgggatc ttcccaagcg ccctcagagg aagaaatcat gctacccatg | 720 |
| atgagtgagt tcgtcattga acatgcatcc gctctttccg aaggaaagca tttatttgta | 780 |
| ttaagtcaga tttga | 795 |

```
<210> SEQ ID NO 58
<211> LENGTH: 264
<212> TYPE: PRT
<213> ORGANISM: Pseudomonas syringae pv. tomato DC3000

<400> SEQUENCE: 58
```

```
Met Asn Ile Asn Arg Gln Leu Pro Val Ser Gly Ser Glu Arg Leu Leu
1               5                   10                  15

Thr Pro Asp Val Gly Val Ser Arg Gln Ala Cys Ser Glu Arg His Tyr
            20                  25                  30

Ser Thr Gly Gln Asp Arg His Asp Phe Tyr Arg Phe Ala Ala Arg Leu
        35                  40                  45

His Val Asp Ala Gln Cys Phe Gly Leu Ser Ile Asp Asp Leu Met Asp
    50                  55                  60

Lys Phe Ser Asp Lys His Phe Arg Ala Glu His Pro Glu Tyr Arg Asp
65                  70                  75                  80
```

-continued

```
Val Tyr Pro Glu Glu Cys Ser Ala Ile Tyr Met His Thr Ala Gln Asp
                85                  90                  95

Tyr Ser Ser His Leu Val Arg Gly Glu Ile Gly Thr Pro Leu Tyr Arg
            100                 105                 110

Glu Val Asn Asn Tyr Leu Arg Leu Gln His Glu Asn Ser Gly Arg Glu
        115                 120                 125

Ala Glu Ile Asp Asn His Asp Glu Lys Leu Ser Pro His Ile Lys Met
    130                 135                 140

Leu Ser Ser Ala Leu Asn Arg Leu Met Asp Val Ala Ala Phe Arg Gly
145                 150                 155                 160

Thr Val Tyr Arg Gly Ile Arg Gly Asp Leu Asp Thr Ile Ala Arg Leu
                165                 170                 175

Tyr His Leu Phe Asp Thr Gly Gly Arg Tyr Val Glu Pro Ala Phe Met
            180                 185                 190

Ser Thr Thr Arg Ile Lys Asp Ser Ala Gln Val Phe Glu Pro Gly Thr
        195                 200                 205

Pro Asn Asn Ile Ala Phe Gln Ile Ser Leu Lys Arg Gly Ala Asp Ile
    210                 215                 220

Ser Gly Ser Ser Gln Ala Pro Ser Glu Glu Ile Met Leu Pro Met
225                 230                 235                 240

Met Ser Glu Phe Val Ile Glu His Ala Ser Ala Leu Ser Glu Gly Lys
                245                 250                 255

His Leu Phe Val Leu Ser Gln Ile
            260
```

<210> SEQ ID NO 59
<211> LENGTH: 897
<212> TYPE: DNA
<213> ORGANISM: Pseudomonas syringae pv. tomato DC3000

<400> SEQUENCE: 59

```
atgaatatca gtcctgtatc gggtgcccac ggtagcagct accccttcagc tcaatccaca      60
gcatcgacgg catcgaaagg tccctctgga tcctttctca acagctcgg cggctgtttt       120
tcaccctgcc tgggtagcag ctctactggg gccatacttt ctcccgctca tgagcaggta      180
ttgagccaca cctattccag caatattaaa ggaaagttgc gcacgacgcc cccaaaagga      240
ccgtcgccca ggttgtctga cacacctatg aagcaggcgc tttcttcaat gatcgtacag      300
gagcgaaaac ggcttaaaag tcaacccaag tcattggcct cggatataga acgtccagac      360
agtatgatca aaaagcgct tgatgaaaaa gacggccacc cgtttggcga gcgcttttca       420
gacgacgaat tcttgcgat tcatctctat acgagctgtc tttataggcc gatcaatcat       480
catctgcggt atgccccgaa caatgatgtt gcaccggttg tcgaggcact gaaaagtggt      540
ttggcaaagc ttgctcaaga ccctgattat caagtgtcta gccagcttca tagaggcatc      600
aagcaaaaga tgagtgatgg cgaggtcatg agtcgtttca aacccgggtaa gacctatcgt     660
gatgaagcgt tcatgagcac atcaactcat atgcaggttt cagaagagtt tacctccgac     720
gttacgttgc acctgcggtc ctcatcagct gtcaatatag gccccttttc gaaaatccca     780
tacgaggacg aagcgcttat ctcgcccctg acgcctttca agtaaccgg tctgcgcaag     840
caggacgata gtggcacgt cgatttgaac gagatagcag ataattcaga cgagtga         897
```

<210> SEQ ID NO 60
<211> LENGTH: 298
<212> TYPE: PRT
<213> ORGANISM: Pseudomonas syringae pv. tomato DC3000

-continued

```
<400> SEQUENCE: 60

Met Asn Ile Ser Pro Val Ser Gly Ala His Gly Ser Ser Tyr Pro Ser
 1               5                  10                  15

Ala Gln Ser Thr Ala Ser Thr Ala Ser Lys Gly Pro Ser Gly Ser Phe
             20                  25                  30

Leu Lys Gln Leu Gly Gly Cys Phe Ser Pro Cys Leu Gly Ser Ser Ser
         35                  40                  45

Thr Gly Ala Ile Leu Ser Pro Ala His Glu Gln Val Leu Ser His Thr
     50                  55                  60

Tyr Ser Ser Asn Ile Lys Gly Lys Leu Arg Thr Thr Pro Pro Lys Gly
 65                  70                  75                  80

Pro Ser Pro Arg Leu Ser Asp Thr Pro Met Lys Gln Ala Leu Ser Ser
                 85                  90                  95

Met Ile Val Gln Glu Arg Lys Arg Leu Lys Ser Gln Pro Lys Ser Leu
            100                 105                 110

Ala Ser Asp Ile Glu Arg Pro Asp Ser Met Ile Lys Lys Ala Leu Asp
        115                 120                 125

Glu Lys Asp Gly His Pro Phe Gly Glu Arg Phe Ser Asp Asp Glu Phe
130                 135                 140

Leu Ala Ile His Leu Tyr Thr Ser Cys Leu Tyr Arg Pro Ile Asn His
145                 150                 155                 160

His Leu Arg Tyr Ala Pro Asn Asn Asp Val Ala Pro Val Val Glu Ala
                165                 170                 175

Leu Lys Ser Gly Leu Ala Lys Leu Ala Gln Asp Pro Asp Tyr Gln Val
            180                 185                 190

Ser Ser Gln Leu His Arg Gly Ile Lys Gln Lys Met Ser Asp Gly Glu
        195                 200                 205

Val Met Ser Arg Phe Lys Pro Gly Lys Thr Tyr Arg Asp Glu Ala Phe
    210                 215                 220

Met Ser Thr Ser Thr His Met Gln Val Ser Glu Glu Phe Thr Ser Asp
225                 230                 235                 240

Val Thr Leu His Leu Arg Ser Ser Ser Ala Val Asn Ile Gly Pro Phe
                245                 250                 255

Ser Lys Asn Pro Tyr Glu Asp Glu Ala Leu Ile Ser Pro Leu Thr Pro
            260                 265                 270

Phe Lys Val Thr Gly Leu Arg Lys Gln Asp Asp Lys Trp His Val Asp
        275                 280                 285

Leu Asn Glu Ile Ala Asp Asn Ser Asp Glu
        290                 295

<210> SEQ ID NO 61
<211> LENGTH: 507
<212> TYPE: DNA
<213> ORGANISM: Pseudomonas syringae pv. tomato DC3000

<400> SEQUENCE: 61
atgaatatta accctttccct gggcgctcat ggcagcgcct actcgtcgcc tcaaagtgat      60
acttcgaagg ccactggaaa agcacctgcg ccttctttttt tcaaacagtt gggcggctgt    120
ttttcgccgt gccttggttc ccatgcgtca agcagccaac aactgtccgc cagtcatgcg    180
cagacgctca gtcagaatta ctccagcaac attcagggga cgagccgcac acgccagccg    240
agagcaccct cgccacgcct gtcagatacg cccatgaagc aggcgctttc ctcaatgatc    300
gaacgcgagc gtttgcggct tcaaggtctt tcgggaggaa tgttctcggg cattgactcc    360
```

| gccgatgcca tgattggtcg agcgctcacg aagaaggatt caaacccaaa ggctgcgcgt | 420 |
| tttagtgatg atgagtttct cgccgttcac ctctacacaa cttgcctcta cagacctatc | 480 |
| aatcatcatc ttcggtatca acactag | 507 |

<210> SEQ ID NO 62
<211> LENGTH: 168
<212> TYPE: PRT
<213> ORGANISM: Pseudomonas syringae pv. tomato DC3000

<400> SEQUENCE: 62

```
Met Asn Ile Asn Pro Ser Leu Gly Ala His Gly Ser Ala Tyr Ser Ser
 1               5                  10                  15

Pro Gln Ser Asp Thr Ser Lys Ala Thr Gly Lys Ala Pro Ala Pro Ser
            20                  25                  30

Phe Phe Lys Gln Leu Gly Gly Cys Phe Ser Pro Cys Leu Gly Ser His
        35                  40                  45

Ala Ser Ser Ser Gln Gln Leu Ser Ala Ser His Ala Gln Thr Leu Ser
    50                  55                  60

Gln Asn Tyr Ser Ser Asn Ile Gln Gly Thr Ser Arg Thr Arg Gln Pro
65                  70                  75                  80

Arg Ala Pro Ser Pro Arg Leu Ser Asp Thr Pro Met Lys Gln Ala Leu
                85                  90                  95

Ser Ser Met Ile Glu Arg Glu Arg Leu Arg Leu Gln Gly Leu Ser Gly
           100                 105                 110

Gly Met Phe Ser Gly Ile Asp Ser Ala Asp Ala Met Ile Gly Arg Ala
       115                 120                 125

Leu Thr Lys Lys Asp Ser Asn Pro Lys Ala Ala Arg Phe Ser Asp Asp
   130                 135                 140

Glu Phe Leu Ala Val His Leu Tyr Thr Thr Cys Leu Tyr Arg Pro Ile
145                 150                 155                 160

Asn His His Leu Arg Tyr Gln His
                165
```

<210> SEQ ID NO 63
<211> LENGTH: 2823
<212> TYPE: DNA
<213> ORGANISM: Pseudomonas syringae pv. tomato DC3000

<400> SEQUENCE: 63

| atgagctcga tcacgcacac caacacgccg caattggcgg tcagcgattc acggggtctg | 60 |
| ccggtacgca gtgtgcagtt ctatcgtggc gctgatggtc agcctgttga cgcgagggtg | 120 |
| acgcagcact atttcgacaa ggccgggcga ctgatcgcca gtcgcgatcc acgttttttcc | 180 |
| agtcgtttga aatacggtgt ctgtgcgcct gtgaacctga tgcaaatcgt cagcttgtcc | 240 |
| gggcttttgc tgttatcgaa aagtgtcgat tcaggttggc gggtgagcct gaacggcgaa | 300 |
| gcggggcagt tagtcgacag ctgtgacgga cgtgacaacc cgcgccagat cgaatacgac | 360 |
| gggctgttgc gccctttggc gatcaacgaa tcaggccgaa tgaccgagcg cttcacttat | 420 |
| ggcgggcctg ccactgctga gcataaccag tgcaatcaac tgattcgcca tgacgatacg | 480 |
| gcaggctcgc gcttgctgcg ggactatgga ctgtcgggta gggcgttgag cgaaaaaagg | 540 |
| tacttcctgc agtcgcccga cagcccggac tggccacttg ccgagcctga tcgtgatgca | 600 |
| ctgctcgagc cggtcggcct gcagacgcgc tgggctttca acgcgcaggg cgaggacctg | 660 |
| gcgcagactg acgcaaacgg taatgtccag cgtttcagtc acggtgtggc tgggcaactg | 720 |

```
cacgctgttg aactgaccct ggccaatacg gcacagcggc aaacgctggt cagtgcaatt      780
cactacgacg cgttcaatca ggccgagcag gagacggcag gaaatggtgt ggtcagtcgc      840
tatgtgtatg atcaacagga cggtcggctg actgagctca gtgcgctatc tgccgacggc      900
tcagtgttgc aaaaactgaa ctacagctat gacccggcag gtaacgttct actcatcaac      960
gatgcctcgc aaccagaccg gtattgcggc aatcagcgta tcgagccgat aaaccgttac     1020
tgttacgaca cgttgtatca gttgatcgaa gccacggggc gggaggtcag aaacggggcc     1080
agccatggtc cggcgctacc cggtctgcaa cctctgccga cgctcgatcc ttgccaggtc     1140
agcaactaca cacagcgtta cagctacgac gctgcgggta acctgctgca aatgcgccac     1200
gaaggcgcgc acaacttcac ccgcaacatg cacgttgatc ccgacagcaa tcgcagcctg     1260
cccgacaatg acaggtatgt ggatttcgcc acgagttttg atgccaacgg caatctgctg     1320
caactcgtgc gtgggcagac catgagctgg gatgtgcgta atcagttgcg gcaaatcact     1380
accgtgcaac gtgaagacgc accgaatgat gaagagcgct atgtatacga cggccagggc     1440
cagcgctgcc gcaagatcag caccgcgcag gcatcaggtc gcacactgac caatgaagtt     1500
cgctacctgc cgggactgga agttcggacc acggccgatg gagaaactct tcacgtcgtt     1560
acggctcagg cgggtcgcaa cagcgtgcgg gtgttgcact gggaagccgg aaaaccaggc     1620
gctattgcga acgatcaggt gcgttacagc ctgggtgatc atctgggctc gagcacgctg     1680
gagcttgatc agcaaggcgg cctgatcagc caggaaagtt attacccctt tggcggcacg     1740
gcctggtggg cggcgcgtag tgcagtggag gccaagtaca aaacagtgcg ttattcgggt     1800
aaagagcgcg atgccagcgg gctttattat tacgggttca ggtattacgc gccgtggttg     1860
cagcggtgga tcaatcctga cccggcgggg gatgtggatg ggttgaatct gtacaggatg     1920
gtcagaaata atccgcttgt ttacgttgat gcgaagggcc agcaacctga acctgttcca     1980
aaaactattc accagatctg gataggtgaa acaagaatg ccttgagagc tcaggttagc     2040
aatatcaaca gaaccgttga aatggcttgg gggtataaag tgaagttgca tctggaaacg     2100
aggacgccgg aagcttattc ggaaatcgaa aaggatctga gatccgaagt ggttctgctt     2160
cctgattccc aggttttttca aaacttcaag gagaagccgc tttatgcggc ctatgaagat     2220
ttccgaagaa acaatcagaa ttacgctttc gcggtagacg ttttacgtat gcataccgtt     2280
catgagttgg gcgggattta ttcagatgtc gatgacgttt atgcaggtgc ggagactggc     2340
ggaatgacgc agttggggga taatccgctg tttcagaaac ctgatgaggt tttgacgctg     2400
gatcctgttc atgtcccttg ggagccccag aattctgttg aaagtttat ggtcaataac     2460 agctcatttg ccgctcattc aggtgcaggc gtcttacttg acatgatggg ggaaggagcg     2520
aaacgatatg atgaagccgt tgagggcgga agttatccgg atccgacggg catgaacggt     2580
ataggtctaa gtctgctctg gaatcctaac ccggcagtaa gagttcgaac gttatcgaat     2640
gtagtaggcc ccggcttgtt tacagacaca ctgcacgctt cggacacagc atacggtgag     2700 cttttttagta atctgaaagg cgtcgtcttt caaaaacagc cgttcacgtt tgccgaccaa     2760
atggccagga agatgccgct gcatcggcat ataaaaagcg gcgcggcgca aacctggcgc     2820
tga                                                                   2823
```

<210> SEQ ID NO 64
<211> LENGTH: 940
<212> TYPE: PRT
<213> ORGANISM: Pseudomonas syringae pv. tomato DC3000

<400> SEQUENCE: 64

```
Met Ser Ser Ile Thr His Thr Asn Thr Pro Gln Leu Ala Val Ser Asp
 1               5                  10                  15

Ser Arg Gly Leu Pro Val Arg Ser Val Gln Phe Tyr Arg Gly Ala Asp
             20                  25                  30

Gly Gln Pro Val Asp Ala Arg Val Thr Gln His Tyr Phe Asp Lys Ala
         35                  40                  45

Gly Arg Leu Ile Ala Ser Arg Asp Pro Arg Phe Ser Ser Arg Leu Lys
     50                  55                  60

Tyr Gly Val Cys Ala Pro Val Asn Leu Met Gln Ile Val Ser Leu Ser
 65                  70                  75                  80

Gly Ala Leu Leu Leu Ser Lys Ser Val Asp Ser Gly Trp Arg Val Ser
                 85                  90                  95

Leu Asn Gly Glu Ala Gly Gln Leu Val Asp Ser Cys Asp Gly Arg Asp
            100                 105                 110

Asn Pro Arg Gln Ile Glu Tyr Asp Gly Leu Leu Arg Pro Leu Ala Ile
            115                 120                 125

Asn Glu Ser Gly Arg Met Thr Glu Arg Phe Thr Tyr Gly Gly Pro Ala
            130                 135                 140

Thr Ala Glu His Asn Gln Cys Asn Gln Leu Ile Arg His Asp Asp Thr
145                 150                 155                 160

Ala Gly Ser Arg Leu Leu Arg Asp Tyr Gly Leu Ser Gly Arg Ala Leu
                165                 170                 175

Ser Glu Lys Arg Tyr Phe Leu Gln Ser Pro Asp Ser Pro Asp Trp Pro
            180                 185                 190

Leu Ala Glu Pro Asp Arg Asp Ala Leu Leu Glu Pro Val Gly Leu Gln
            195                 200                 205

Thr Arg Trp Ala Phe Asn Ala Gln Gly Glu Asp Leu Ala Gln Thr Asp
            210                 215                 220

Ala Asn Gly Asn Val Gln Arg Phe Ser His Gly Val Ala Gly Gln Leu
225                 230                 235                 240

His Ala Val Glu Leu Thr Leu Ala Asn Thr Ala Gln Arg Gln Thr Leu
                245                 250                 255

Val Ser Ala Ile His Tyr Asp Ala Phe Asn Gln Ala Glu Gln Glu Thr
            260                 265                 270

Ala Gly Asn Gly Val Val Ser Arg Tyr Val Tyr Asp Gln Gln Asp Gly
            275                 280                 285

Arg Leu Thr Glu Leu Ser Ala Leu Ser Ala Asp Gly Ser Val Leu Gln
            290                 295                 300

Lys Leu Asn Tyr Ser Tyr Asp Pro Ala Gly Asn Val Leu Leu Ile Asn
305                 310                 315                 320

Asp Ala Ser Gln Pro Asp Arg Tyr Cys Gly Asn Gln Arg Ile Glu Pro
                325                 330                 335

Ile Asn Arg Tyr Cys Tyr Asp Thr Leu Tyr Gln Leu Ile Glu Ala Thr
            340                 345                 350

Gly Arg Glu Val Arg Asn Gly Ala Ser His Gly Pro Ala Leu Pro Gly
            355                 360                 365

Leu Gln Pro Leu Pro Thr Leu Asp Pro Cys Gln Val Ser Asn Tyr Thr
            370                 375                 380

Gln Arg Tyr Ser Tyr Asp Ala Ala Gly Asn Leu Leu Gln Met Arg His
385                 390                 395                 400

Glu Gly Ala His Asn Phe Thr Arg Asn Met His Val Asp Pro Asp Ser
                405                 410                 415
```

-continued

```
Asn Arg Ser Leu Pro Asp Asn Asp Arg Tyr Val Asp Phe Ala Thr Ser
            420                 425                 430

Phe Asp Ala Asn Gly Asn Leu Leu Gln Leu Val Arg Gly Gln Thr Met
        435                 440                 445

Ser Trp Asp Val Arg Asn Gln Leu Arg Gln Ile Thr Thr Val Gln Arg
    450                 455                 460

Glu Asp Ala Pro Asn Asp Glu Arg Tyr Val Tyr Asp Gly Gln Gly
465                 470                 475                 480

Gln Arg Cys Arg Lys Ile Ser Thr Ala Gln Ala Ser Gly Arg Thr Leu
                485                 490                 495

Thr Asn Glu Val Arg Tyr Leu Pro Gly Leu Glu Val Arg Thr Thr Ala
            500                 505                 510

Asp Gly Glu Thr Leu His Val Val Thr Ala Gln Ala Gly Arg Asn Ser
        515                 520                 525

Val Arg Val Leu His Trp Glu Ala Gly Lys Pro Gly Ala Ile Ala Asn
    530                 535                 540

Asp Gln Val Arg Tyr Ser Leu Gly Asp His Leu Gly Ser Ser Thr Leu
545                 550                 555                 560

Glu Leu Asp Gln Gln Gly Gly Leu Ile Ser Gln Glu Ser Tyr Tyr Pro
                565                 570                 575

Phe Gly Gly Thr Ala Trp Trp Ala Ala Arg Ser Ala Val Glu Ala Lys
            580                 585                 590

Tyr Lys Thr Val Arg Tyr Ser Gly Lys Glu Arg Asp Ala Ser Gly Leu
        595                 600                 605

Tyr Tyr Tyr Gly Phe Arg Tyr Tyr Ala Pro Trp Leu Gln Arg Trp Ile
    610                 615                 620

Asn Pro Asp Pro Ala Gly Asp Val Asp Gly Leu Asn Leu Tyr Arg Met
625                 630                 635                 640

Val Arg Asn Asn Pro Leu Val Tyr Val Asp Ala Lys Gly Gln Gln Pro
                645                 650                 655

Glu Pro Val Pro Lys Thr Ile His Gln Ile Trp Ile Gly Glu Asn Lys
            660                 665                 670

Asn Ala Leu Arg Ala Gln Val Ser Asn Ile Asn Arg Thr Val Glu Met
        675                 680                 685

Ala Trp Gly Tyr Lys Val Lys Leu His Leu Glu Thr Arg Thr Pro Glu
    690                 695                 700

Ala Tyr Ser Glu Ile Glu Lys Asp Leu Arg Ser Glu Val Val Leu Leu
705                 710                 715                 720

Pro Asp Ser Gln Val Phe Gln Asn Phe Lys Glu Lys Pro Leu Tyr Ala
                725                 730                 735

Ala Tyr Glu Asp Phe Arg Arg Asn Asn Gln Asn Tyr Ala Phe Ala Val
            740                 745                 750

Asp Val Leu Arg Met His Thr Val His Glu Leu Gly Gly Ile Tyr Ser
        755                 760                 765

Asp Val Asp Asp Val Tyr Ala Gly Ala Glu Thr Gly Gly Met Thr Gln
    770                 775                 780

Leu Gly Asp Asn Pro Leu Phe Ala Glu Pro Asp Glu Val Leu Thr Leu
785                 790                 795                 800

Asp Pro Val His Val Pro Trp Glu Pro Gln Asn Ser Val Glu Ser Phe
                805                 810                 815

Met Val Asn Asn Ser Ser Phe Ala Ala His Ser Gly Ala Gly Val Leu
            820                 825                 830
```

```
Leu Asp Met Met Gly Glu Gly Ala Lys Arg Tyr Asp Glu Ala Val Glu
            835                 840                 845

Gly Gly Ser Tyr Pro Asp Pro Thr Gly Met Asn Gly Ile Gly Leu Ser
        850                 855                 860

Leu Leu Trp Asn Pro Asn Pro Ala Val Arg Val Arg Thr Leu Ser Asn
865                 870                 875                 880

Val Val Gly Pro Gly Leu Phe Thr Asp Thr Leu His Ala Ser Asp Thr
                    885                 890                 895

Ala Tyr Gly Glu Leu Phe Ser Asn Leu Lys Gly Val Val Phe Gln Lys
                900                 905                 910

Gln Pro Phe Thr Phe Ala Asp Gln Met Ala Arg Lys Met Pro Leu His
            915                 920                 925

Arg His Ile Lys Ser Gly Ala Ala Gln Thr Trp Arg
            930                 935                 940

<210> SEQ ID NO 65
<211> LENGTH: 534
<212> TYPE: DNA
<213> ORGANISM: Pseudomonas syringae pv. tomato DC3000

<400> SEQUENCE: 65
atgccgatca ccgcgcagca gttgctgcag atactcccga gcgctggcca gaaagccggc      60
gtttttgcac ccgtcctgaa cacagcgatg agcaagcacc agatcttgac gccgctgcgc     120
atcgcggctt tcatcgccca ggtcggtcat gagtccggcc aactgcgcta cgtccgcgag     180
atttgggggc cgactccgca gcagctgggt tatgaaggcc gcaaggacct cggcaatacc     240
gtggcgggtg atggttcgaa gtaccgcggg cgcggcctga tccagatcac cggccgggcc     300
aactatgccg aatgcggcga ggcgctgggc ctagacctga tccatcaccc ggaactgctc     360
gagcagccgg agcacgccac aatgtcggca gcgtggtact ggagcagccg tggcctgaac     420 tcgctgccg  acaaagggga cttcttcaa  attacccgaa gaatcaacgg aggcaccaat     480
ggactggcgg atcggcaggc gctgtacgac cgggcgctga aggtgctggc gtga           534

<210> SEQ ID NO 66
<211> LENGTH: 177
<212> TYPE: PRT
<213> ORGANISM: Pseudomonas syringae pv. tomato DC3000

<400> SEQUENCE: 66

Met Pro Ile Thr Ala Gln Gln Leu Leu Gln Ile Leu Pro Ser Ala Gly
  1               5                  10                  15

Gln Lys Ala Gly Val Phe Ala Pro Val Leu Asn Thr Ala Met Ser Lys
                 20                  25                  30

His Gln Ile Leu Thr Pro Leu Arg Ile Ala Ala Phe Ile Ala Gln Val
            35                  40                  45

Gly His Glu Ser Gly Gln Leu Arg Tyr Val Arg Glu Ile Trp Gly Pro
        50                  55                  60

Thr Pro Gln Gln Leu Gly Tyr Glu Gly Arg Lys Asp Leu Gly Asn Thr
65                  70                  75                  80

Val Ala Gly Asp Gly Ser Lys Tyr Arg Gly Arg Gly Leu Ile Gln Ile
                    85                  90                  95

Thr Gly Arg Ala Asn Tyr Ala Glu Cys Gly Glu Ala Leu Gly Leu Asp
                100                 105                 110

Leu Ile His His Pro Glu Leu Leu Glu Gln Pro Glu His Ala Thr Met
            115                 120                 125
```

```
Ser Ala Ala Trp Tyr Trp Ser Ser Arg Gly Leu Asn Ser Leu Ala Asp
    130                 135                 140

Lys Gly Asp Phe Leu Gln Ile Thr Arg Arg Ile Asn Gly Gly Thr Asn
145                 150                 155                 160

Gly Leu Ala Asp Arg Gln Ala Leu Tyr Asp Arg Ala Leu Lys Val Leu
                165                 170                 175
Ala

<210> SEQ ID NO 67
<211> LENGTH: 1137
<212> TYPE: DNA
<213> ORGANISM: Pseudomonas syringae pv. tomato DC3000

<400> SEQUENCE: 67
atgaatctaa cagctttagg ttcaaagctg tctcggtatc gcaagcagct tgcgatgagc      60
gaggaagaag tgtgtgcggt cacccacatc ccccttgagc gcctgcagtc agttgaagcc     120
ggctctcagg cgcctacggg tgatgaagtg cttatcctgg ccgatctcta ccactgcaac     180
ttcaaattct tcatctcgaa cgagccgctc gccccctttg agcagaccga atcctgtat      240 cgcaggcacg gagctgagtt catcaaggag gatcgtagag ccgtccaaga attcctgtac     300
ctctgcgaaa cagaggactt cctgatgagt gagttgaagg ctatgaagct cgaatttccg     360
ctgccgcagg cttctgggaa ttttaagaat gatggaatcc gagcggctga agcctttcgc     420
cttttcaatc agcaccccac aaacgccgtg cctcgggatg tgtatcagga gattcgccaa     480
accggagtgc atgtgttccg tagaaagctt ggtaactcta acatttcggg gcttttcctg     540
gctcacccca cggctgggaa gtgcattctg gtcaactaca gcgaagacgt ataccggcag     600
cggtttagcg ctgcgcatga atttgctcac gctcttttcg atgcgcaggg tggccccagt     660
attacctact cccgtacgac taaggctgac ctagtcgaag tgagagcaaa cacctttgcc     720
tcccggtatc tgatgccttc agaaatcctc cgacagctgc ccaaccctga gcaatggaca     780
caggaaaata cccagtattg ggctcatgag ttgcgagtca gctgcgttgc cttgggcata     840
ggtctgaagt ccgagggctt aattagcgag caagcattcc agaggataaa gtcgtaccgc     900
gttcctcgtg aactgaagat tgacccagaa ttgccggccc aattgacgac gcaacagcgt     960
gagcgaaagg ctaagttact ggaaaagggg ttatctgaca gctacgtcgc actgtgccta    1020
gacgctcaga gccgtggcat catcactcaa ggtcgattgg ctgaagcctt gcttagtgac    1080
ttgggaggcc ttcaagagct gctcagcctt tatggaagat cgcgcaatgg ccattga       1137

<210> SEQ ID NO 68
<211> LENGTH: 378
<212> TYPE: PRT
<213> ORGANISM: Pseudomonas syringae pv. tomato DC3000

<400> SEQUENCE: 68

Met Asn Leu Thr Ala Leu Gly Ser Lys Leu Ser Arg Tyr Arg Lys Gln
1               5                   10                  15

Leu Ala Met Ser Glu Glu Val Cys Ala Val Thr His Ile Pro Leu
            20                  25                  30

Glu Arg Leu Gln Ser Val Glu Ala Gly Ser Gln Ala Pro Thr Gly Asp
        35                  40                  45

Glu Val Leu Ile Leu Ala Asp Leu Tyr His Cys Asn Phe Lys Phe Phe
    50                  55                  60

Ile Ser Asn Glu Pro Leu Ala Pro Phe Glu Gln Thr Glu Ile Leu Tyr
65                  70                  75                  80
```

```
Arg Arg His Gly Ala Glu Phe Ile Lys Glu Asp Arg Arg Ala Val Gln
                85                  90                  95
Glu Phe Leu Tyr Leu Cys Glu Thr Glu Asp Phe Leu Met Ser Glu Leu
            100                 105                 110
Lys Ala Met Lys Leu Glu Phe Pro Leu Pro Gln Ala Ser Gly Asn Phe
        115                 120                 125
Lys Asn Asp Gly Ile Arg Ala Ala Glu Ala Phe Arg Leu Phe Asn Gln
    130                 135                 140
His Pro Thr Asn Ala Val Pro Arg Asp Val Tyr Gln Glu Ile Arg Gln
145                 150                 155                 160
Thr Gly Val His Val Phe Arg Arg Lys Leu Gly Asn Ser Asn Ile Ser
                165                 170                 175
Gly Leu Phe Leu Ala His Pro Thr Ala Gly Lys Cys Ile Leu Val Asn
            180                 185                 190
Tyr Ser Glu Asp Val Tyr Arg Gln Arg Phe Ser Ala Ala His Glu Phe
        195                 200                 205
Ala His Ala Leu Phe Asp Ala Gln Gly Gly Pro Ser Ile Thr Tyr Ser
    210                 215                 220
Arg Thr Thr Lys Ala Asp Leu Val Glu Val Arg Ala Asn Thr Phe Ala
225                 230                 235                 240
Ser Arg Tyr Leu Met Pro Ser Glu Ile Leu Arg Gln Leu Pro Asn Pro
                245                 250                 255
Glu Gln Trp Thr Gln Glu Asn Thr Gln Tyr Trp Ala His Glu Leu Arg
            260                 265                 270
Val Ser Cys Val Ala Leu Gly Ile Gly Leu Lys Ser Glu Gly Leu Ile
        275                 280                 285
Ser Glu Gln Ala Phe Gln Arg Ile Lys Ser Tyr Arg Val Pro Arg Glu
    290                 295                 300
Leu Lys Ile Asp Pro Glu Leu Pro Ala Gln Leu Thr Thr Gln Arg
305                 310                 315                 320
Glu Arg Lys Ala Lys Leu Leu Glu Lys Gly Leu Ser Asp Ser Tyr Val
                325                 330                 335
Ala Leu Cys Leu Asp Ala Gln Ser Arg Gly Ile Ile Thr Gln Gly Arg
            340                 345                 350
Leu Ala Glu Ala Leu Leu Ser Asp Leu Gly Gly Leu Gln Glu Leu Leu
        355                 360                 365
Ser Leu Tyr Gly Arg Ser Arg Asn Gly His
370                 375

<210> SEQ ID NO 69
<211> LENGTH: 714
<212> TYPE: DNA
<213> ORGANISM: Pseudomonas syringae pv. tomato DC3000

<400> SEQUENCE: 69
atgaatatca accccttggc ttcttcatta cagaatcaac agcgcactct cttaggcccg    60
ccccccctca attcatctgc tgctctgccg atcaagatcc ctgtggcgca tgataaagcg   120
cgtgacccta cgctgaatt ctataccacc gaggaaacgc cctggtttgc cggctacaaa   180
aagtcggagg caggacgcgc tattttagag aaaatgtctg agaaggaagc aaaagatatc   240
cgaggcgagt atctgggaaa ctacatgaaa gcctttgacg aaaccatatg tcgtatgtac   300
gacaattttc acgatttcaa acagcagctt ttttacctta atacggagct gtcaaaaaag   360
catttcggct tcacgctggg ctttaatcag gacattcagg tgaccgaccc ggacgaggta   420
```

-continued

```
ctcaccccgg cagagttcac gtacctgacc gagaagctga acgaacgcca acaactgaaa       480
gaggatctgc gtgcgcacgc aaaaattgtg atgacgctgt cgaccatta  caccgaaaaa       540 ttcgataacc ggcacaccct caatctggag agttacagca aggtcatcga ctacggacag       600
atcttcagcc gcaatcatat tggcaatttc atggacacga ttatctacca gatcgagcgc       660
aatgcgccga agcgtgagga agaaccaaaa cctctggttg atgtgcacgc ttga             714
```

<210> SEQ ID NO 70
<211> LENGTH: 237
<212> TYPE: PRT
<213> ORGANISM: Pseudomonas syringae pv. tomato DC3000

<400> SEQUENCE: 70

```
Met Asn Ile Asn Pro Leu Ala Ser Ser Leu Gln Asn Gln Gln Arg Thr
  1               5                  10                  15

Leu Leu Gly Pro Pro Leu Asn Ser Ser Ala Ala Leu Pro Ile Lys
             20                  25                  30

Ile Pro Val Ala His Asp Lys Ala Arg Asp Pro Asn Ala Glu Phe Tyr
         35                  40                  45

Thr Thr Glu Glu Thr Pro Trp Phe Ala Gly Tyr Lys Lys Ser Glu Ala
     50                  55                  60

Gly Arg Ala Ile Leu Glu Lys Met Ser Glu Lys Glu Ala Lys Asp Ile
 65                  70                  75                  80

Arg Gly Glu Tyr Leu Gly Asn Tyr Met Lys Ala Phe Asp Glu Thr Ile
                 85                  90                  95

Cys Arg Met Tyr Asp Asn Phe His Asp Phe Lys Gln Gln Leu Phe Tyr
            100                 105                 110

Leu Asn Thr Glu Leu Ser Lys Lys His Phe Gly Phe Thr Leu Gly Phe
        115                 120                 125

Asn Gln Asp Ile Gln Val Thr Asp Pro Asp Glu Val Leu Thr Pro Ala
    130                 135                 140

Glu Phe Thr Tyr Leu Thr Glu Lys Leu Asn Glu Arg Gln Gln Leu Lys
145                 150                 155                 160

Glu Asp Leu Arg Ala His Ala Lys Ile Val Met Thr Leu Leu Asp His
                165                 170                 175

Tyr Thr Glu Lys Phe Asp Asn Arg His Thr Leu Asn Leu Glu Ser Tyr
            180                 185                 190

Ser Lys Val Ile Asp Tyr Gly Gln Ile Phe Ser Arg Asn His Ile Gly
        195                 200                 205

Asn Phe Met Asp Thr Ile Ile Tyr Gln Ile Glu Arg Asn Ala Pro Lys
    210                 215                 220

Arg Glu Glu Glu Pro Lys Pro Leu Val Asp Val His Ala
225                 230                 235
```

<210> SEQ ID NO 71
<211> LENGTH: 3693
<212> TYPE: DNA
<213> ORGANISM: Pseudomonas syringae pv. tomato DC3000

<400> SEQUENCE: 71

```
atgggcctga tcggcgtcaa acagaacaaa ccgcaacagg cgcagaccta cctgacgcgc       60
ctgcaagcgc tgtcgccagc gccctggcag gcggtgcagc tggagcagga cattgccctc      120
ggccagccgc aaaatcaggc gctgctggat gatgcccgac gctggccga  cgccggtgag      180 cgtgacaagg cgaccggggt gtttcgccag ttgttcaacg gccgtttgcc tcaaggcact      240
```

-continued

```
gtcggccgcg agtactacac caacctgggc ttcaacaatg cggactggcc cgaggcgcgc      300
aagggttttg aacgcctgat gcggcagaac cctgacgact cgattctggc gctgttcttt      360
gccaagcacc tggcccgccg cgaagacagc cgcgccgaag gcatcgccgc tctggcgcgc      420
ctgagcactc atccggacat cgccggcgat gccgatcaga gctggcgcat ggcgctggtc      480
tggatcggcc cgcctgcggc tgcgcaagtg ccactgttcg acgcgtttct caaggttcat      540
cccgacgatc aggaaatccg cgaccagttg aacaagggtc gccagcagca tgccagcggc      600
gctgcctcag gctggcagca agacccgctg gtggcgcgcg gcttgaaggc gctggaaaaa      660
aatgatcatg tggcggccga agaagccttt gccgcccgcc tgaaaatcaa ggcggacgat      720
gccaacgtgc ttggcggcct gggcgtggtg cgtcagcagc agaaccggtt gcctgaagcc      780
gaacaattgc tgacccgcgc cacgcgccag cagggcggtg cgcgctggaa aaacgcgctg      840
gaaaacgtac agctctggac ctcgctgcaa gaggcccgtg acctgcaggc caaagggcag      900
accggcaagg ctcaagcgtt gctggctcag gcgcagcggc aaaaccctga caatatcgac      960
gtgcgtttga ccctggccga cgtgcaggtg caggccgggc aactggacgc cgcgcaagcg     1020
ggctatcgtc aggtactggc gacccagcgc ggtaatccgc aggcaatccg cgggctgatc     1080
aacgtgctgg cccagcgtgg tcaggctgat gaagcgttgc gcctgctcga cacattgtcg     1140
ccaggcgaac aggccaaact gggcgacagc ggtcgcttca aggcgctgcg ctccacccag     1200
gtggcgcggc tggccgagca gcgtggcgat gttcgcgctg cccaggtggc cttgaaagac     1260
gcggtgaaga acgacccgga caatgtctgg acgcgttttg atctggcgcg cctgtacctc     1320
aagaccgacg aagcgcccaa ggcccgcgcg ctgatcgacg agctgctcaa ggctcagccc     1380
aacaatatcg atgcgctcta caccagcgcg ctgctgtcag tggaaatggg ccagtggcag     1440
gacgcgcaga ccacgtttac gcgcatcccg gttgatcagc gcacgccgga catgaaagcg     1500
cttgctgacg aagtcaccat gaccgtgcag atcaatctgg ccatcggcat cgcccggcgc     1560
ggtcagcgcc aggaagcgtt ggcgctgctc gatcgcttgc aaccggtcgc cagcggcagc     1620
ccggagcgtc aactcacgct ggccagcgct tacatcgatg cgggcgagcc cgcgcgcggt     1680
cgggaaatgg cccgtgcggc catcgctcag gccccttttgc cgtcggccga cctgatgctg     1740
caatacgccg gtctgctgct cgcagcgggc gatgacgtgc aggtcaatgc gatcctgcgc     1800
aacgtgcagg gtcagccgat gagcgtgcag acccgcaaac gttttgatga cctttttgtac     1860 cgctaccgca ttcgtcaggc cgatctgctg cgtgaaggcg gtgatctggc gggcgcgtac     1920
gacacgctgg cacctgcttt ggcgcagcgc ccggacgaca ttcaggcggt gtcggccttc     1980
gcccgcatgt acaccgccaa tggcgacagc gcccgagcgt tcgagctgta caagcctttg     2040
ttgcagcgcc agcccaatga cccgcaagtg ttgctgggcg cagccgatgc ggcggtcaaa     2100
gcgcatgatt atggctttgc cgaaaaagcc ctgagccagt tccgcaaact ggagcgtaac     2160
gacccgcaga ccctgacgga ggccgcacgt atctaccaaa gcatgggca gaccggcgcg     2220 gccaccgagt tgctgcgcaa ggccgtggcc atcgaacaga gtgaaaaaca gcgcgcgatg     2280
gctgtgcagg ctgtgtcgac cagcaccacg tcgtccaacc cgtttgcgac gggcggctca     2340
cgtagcctgg cggcggcttc ggctattccg gctccggctc aggtgtcgct cagcggtggg     2400
agagcgcttg aaacaaacag tgcgcctgaa atatctgccc cgcgtgacac cgcttatccc     2460
ggccagatcg ccgcaccaca accgctgtct gccgcacgta cgcaaagtgt gcgcggcaat     2520
ccgttcatgg cagccaccga ccgcgatcag gccagcagcg cacagcaggc gctcaatcgc     2580
attcttgagc agcgcagtgg cttcgtcagt cagggcctgg ccgtgcgcag caataacagc     2640
```

```
gagtcgggtc tgagcaaact gaccgtggtc gagaccccgc tagaggtcaa tttgcctgcc    2700
ggtgataacc gggtggccgt gcgcgtcacg ccggtgtcgc tgaatgctgg cagcttgaag    2760
tcagatgcag gtgcccgttt tggcggtggc accagcggtg ctgccggttc gcagagcgac    2820
aagggtgtcg gtctggcggt ggcgttcgag cgccccgaag aaggcctcaa ggccgatatc    2880
ggcaccacgc cgatgggttt caaatacacc acggttgccg gcggcgcgag tgtcgaccgg    2940
ccgttgggta caacccggga cctgcgctac ggcctcaacg tgtcacggcg tccggtgacg    3000
gacagcgtga cttcgtttgc cggttccaca gacgagcgca gcggcctgtc ctggggcggc    3060
gtcacggcca acggcgggcg cggtcagctc agctatgacg accagaccat cggcggttat    3120
ggctacggct cgtggcacaa actggttggc aacaacgtga atccaacac ccgaggcgaa     3180 gtgggtggcg gcgtttactg gtacctgcgc aatgccgagg acagcaaact gaccgcaggc    3240
ctgagcctga tgggcatgag ctatgacaat gaccagagct acttcacgta cggccacggt    3300
ggctatttca gcccgcagag cttctatgcc atcggcgtgc cggtgatgtg gcacagcgc     3360 accgagcgtt tcagctatca ggtcaagagc tcggtcgggg tccagcactt caagcaggac    3420
ggcgccgaat tcttccccga cgacagcacg ctacaggccg cttccgccca gcgctacaca    3480
gggcaaagca aaaccggaat tggctacaac ctgagcgcgg caggcgagta caagctcgat    3540
tccagcctgt tcatggggc cagtctgggc ctggacaatg cccgggacta tcgccagttc     3600
agcggcgcgc tttacctgcg ttacatgttc gaggacataa ccggcccgat ggcactgccg    3660 gtcagcccctt accgttcacc ttattccaac tga                                3693
```

<210> SEQ ID NO 72
<211> LENGTH: 1230
<212> TYPE: PRT
<213> ORGANISM: Pseudomonas syringae pv. tomato DC3000

<400> SEQUENCE: 72

```
Met Gly Leu Ile Gly Val Lys Gln Asn Lys Pro Gln Gln Ala Gln Thr
  1               5                  10                  15

Tyr Leu Thr Arg Leu Gln Ala Leu Ser Pro Ala Pro Trp Gln Ala Val
             20                  25                  30

Gln Leu Glu Gln Asp Ile Ala Leu Gly Gln Pro Gln Asn Gln Ala Leu
         35                  40                  45

Leu Asp Asp Ala Arg Arg Leu Ala Asp Ala Gly Glu Arg Asp Lys Ala
     50                  55                  60

Thr Gly Val Phe Arg Gln Leu Phe Asn Gly Arg Leu Pro Gln Gly Thr
 65                  70                  75                  80

Val Gly Arg Glu Tyr Tyr Thr Asn Leu Gly Phe Asn Asn Ala Asp Trp
                 85                  90                  95

Pro Glu Ala Arg Lys Gly Phe Glu Arg Leu Met Arg Gln Asn Pro Asp
            100                 105                 110

Asp Ser Ile Leu Ala Leu Phe Ala Lys His Leu Ala Arg Arg Glu
        115                 120                 125

Asp Ser Arg Ala Glu Gly Ile Ala Ala Leu Ala Arg Leu Ser Thr His
    130                 135                 140

Pro Asp Ile Ala Gly Asp Ala Asp Gln Ser Trp Arg Met Ala Leu Val
145                 150                 155                 160

Trp Ile Gly Pro Pro Ala Ala Ala Gln Val Pro Leu Phe Asp Ala Phe
                165                 170                 175

Leu Lys Val His Pro Asp Asp Gln Glu Ile Arg Asp Gln Leu Asn Lys
            180                 185                 190
```

```
Gly Arg Gln Gln His Ala Ser Gly Ala Ala Ser Gly Trp Gln Gln Asp
            195                 200                 205

Pro Leu Val Ala Arg Gly Leu Lys Ala Leu Glu Lys Asn Asp His Val
210                 215                 220

Ala Ala Glu Glu Ala Phe Ala Ala Arg Leu Lys Ile Lys Ala Asp Asp
225                 230                 235                 240

Ala Asn Val Leu Gly Gly Leu Gly Val Arg Gln Gln Asn Arg
                245                 250                 255

Leu Pro Glu Ala Glu Gln Leu Leu Thr Arg Ala Thr Arg Gln Gln Gly
            260                 265                 270

Gly Ala Arg Trp Lys Asn Ala Leu Glu Asn Val Gln Leu Trp Thr Ser
            275                 280                 285

Leu Gln Glu Ala Arg Asp Leu Gln Ala Lys Gly Gln Thr Gly Lys Ala
            290                 295                 300

Gln Ala Leu Leu Ala Gln Ala Arg Gln Asn Pro Asp Asn Ile Asp
305                 310                 315                 320

Val Arg Leu Thr Leu Ala Asp Val Gln Val Gln Ala Gly Gln Leu Asp
                325                 330                 335

Ala Ala Gln Ala Gly Tyr Arg Gln Val Leu Ala Thr Gln Arg Gly Asn
            340                 345                 350

Pro Gln Ala Ile Arg Gly Leu Ile Asn Val Leu Ala Gln Arg Gly Gln
            355                 360                 365

Ala Asp Glu Ala Leu Arg Leu Leu Asp Thr Leu Ser Pro Gly Glu Gln
370                 375                 380

Ala Lys Leu Gly Asp Ser Gly Arg Phe Lys Ala Leu Arg Ser Thr Gln
385                 390                 395                 400

Val Ala Arg Leu Ala Glu Gln Arg Gly Asp Val Arg Ala Ala Gln Val
            405                 410                 415

Ala Leu Lys Asp Ala Val Lys Asn Asp Pro Asp Asn Val Trp Thr Arg
            420                 425                 430

Phe Asp Leu Ala Arg Leu Tyr Leu Lys Thr Asp Glu Ala Pro Lys Ala
            435                 440                 445

Arg Ala Leu Ile Asp Glu Leu Leu Lys Ala Gln Pro Asn Asn Ile Asp
450                 455                 460

Ala Leu Tyr Thr Ser Ala Leu Leu Ser Val Glu Met Gly Gln Trp Gln
465                 470                 475                 480

Asp Ala Gln Thr Thr Phe Thr Arg Ile Pro Val Asp Gln Arg Thr Pro
                485                 490                 495

Asp Met Lys Ala Leu Ala Asp Glu Val Thr Met Thr Val Gln Ile Asn
            500                 505                 510

Leu Ala Ile Gly Ile Ala Arg Arg Gly Gln Arg Gln Glu Ala Leu Ala
            515                 520                 525

Leu Leu Asp Arg Leu Gln Pro Val Ala Ser Gly Ser Pro Glu Arg Gln
            530                 535                 540

Leu Thr Leu Ala Ser Ala Tyr Ile Asp Ala Gly Glu Pro Ala Arg Gly
545                 550                 555                 560

Arg Glu Met Ala Arg Ala Ile Ala Gln Ala Pro Leu Pro Ser Ala
                565                 570                 575

Asp Leu Met Leu Gln Tyr Ala Gly Leu Leu Ala Ala Gly Asp Asp
            580                 585                 590

Val Gln Val Asn Ala Ile Leu Arg Asn Val Gln Gly Gln Pro Met Ser
            595                 600                 605
```

-continued

```
Val Gln Thr Arg Lys Arg Phe Asp Asp Leu Leu Tyr Arg Tyr Arg Ile
    610                 615                 620

Arg Gln Ala Asp Leu Leu Arg Glu Gly Gly Asp Leu Ala Gly Ala Tyr
625                 630                 635                 640

Asp Thr Leu Ala Pro Ala Leu Ala Gln Arg Pro Asp Asp Ile Gln Ala
                645                 650                 655

Val Ser Ala Phe Ala Arg Met Tyr Thr Ala Asn Gly Asp Ser Ala Arg
            660                 665                 670

Ala Phe Glu Leu Tyr Lys Pro Leu Leu Gln Arg Gln Pro Asn Asp Pro
        675                 680                 685

Gln Val Leu Leu Gly Ala Ala Asp Ala Ala Val Lys Ala His Asp Tyr
    690                 695                 700

Gly Phe Ala Glu Lys Ala Leu Ser Gln Phe Arg Lys Leu Glu Arg Asn
705                 710                 715                 720

Asp Pro Gln Thr Leu Thr Glu Ala Ala Arg Ile Tyr Gln Ser Met Gly
                725                 730                 735

Gln Thr Gly Ala Ala Thr Glu Leu Leu Arg Lys Ala Val Ala Ile Glu
            740                 745                 750

Gln Ser Glu Lys Gln Arg Ala Met Ala Val Gln Ala Val Ser Thr Ser
        755                 760                 765

Thr Thr Ser Ser Asn Pro Phe Ala Thr Gly Gly Ser Arg Ser Leu Ala
    770                 775                 780

Ala Ala Ser Ala Ile Pro Ala Pro Ala Gln Val Ser Leu Ser Gly Gly
785                 790                 795                 800

Arg Ala Leu Glu Thr Asn Ser Ala Pro Glu Ile Ser Ala Pro Arg Asp
                805                 810                 815

Thr Ala Tyr Pro Gly Gln Ile Ala Pro Gln Pro Leu Ser Ala Ala
            820                 825                 830

Arg Thr Gln Ser Val Arg Gly Asn Pro Phe Met Ala Thr Asp Arg
        835                 840                 845

Asp Gln Ala Ser Ser Ala Gln Gln Ala Leu Asn Arg Ile Leu Glu Gln
    850                 855                 860

Arg Ser Gly Phe Val Ser Gln Gly Leu Ala Val Arg Ser Asn Asn Ser
865                 870                 875                 880

Glu Ser Gly Leu Ser Lys Leu Thr Val Val Glu Thr Pro Leu Glu Val
                885                 890                 895

Asn Leu Pro Ala Gly Asp Asn Arg Val Ala Val Arg Val Thr Pro Val
            900                 905                 910

Ser Leu Asn Ala Gly Ser Leu Lys Ser Asp Ala Gly Ala Arg Phe Gly
        915                 920                 925

Gly Gly Thr Ser Gly Ala Ala Gly Ser Gln Ser Asp Lys Gly Val Gly
    930                 935                 940

Leu Ala Val Ala Phe Glu Arg Pro Glu Glu Gly Leu Lys Ala Asp Ile
945                 950                 955                 960

Gly Thr Thr Pro Met Gly Phe Lys Tyr Thr Thr Val Ala Gly Gly Ala
                965                 970                 975

Ser Val Asp Arg Pro Leu Gly Asn Asn Pro Asp Leu Arg Tyr Gly Leu
            980                 985                 990

Asn Val Ser Arg Arg Pro Val Thr Asp Ser Val Thr Ser Phe Ala Gly
        995                 1000                1005

Ser Thr Asp Glu Arg Ser Gly Leu Ser Trp Gly Gly Val Thr Ala Asn
    1010                1015                1020
```

Gly Gly Arg Gly Gln Leu Ser Tyr Asp Asp Gln Thr Ile Gly Gly Tyr
1025                1030                1035                1040

Gly Tyr Gly Ser Trp His Lys Leu Val Gly Asn Asn Val Lys Ser Asn
            1045                1050                1055

Thr Arg Gly Glu Val Gly Gly Val Tyr Trp Tyr Leu Arg Asn Ala
        1060                1065                1070

Glu Asp Ser Lys Leu Thr Ala Gly Leu Ser Leu Met Gly Met Ser Tyr
    1075                1080                1085

Asp Asn Asp Gln Ser Tyr Phe Thr Tyr Gly His Gly Gly Tyr Phe Ser
    1090                1095                1100

Pro Gln Ser Phe Tyr Ala Ile Gly Val Pro Val Met Trp Ala Gln Arg
1105                1110                1115                1120

Thr Glu Arg Phe Ser Tyr Gln Val Lys Ser Val Gly Val Gln His
            1125                1130                1135

Phe Lys Gln Asp Gly Ala Glu Phe Phe Pro Asp Asp Ser Thr Leu Gln
        1140                1145                1150

Ala Ala Ser Ala Gln Arg Tyr Thr Gly Gln Ser Lys Thr Gly Ile Gly
    1155                1160                1165

Tyr Asn Leu Ser Ala Ala Gly Glu Tyr Lys Leu Asp Ser Ser Leu Phe
    1170                1175                1180

Met Gly Ala Ser Leu Gly Leu Asp Asn Ala Arg Asp Tyr Arg Gln Phe
1185                1190                1195                1200

Ser Gly Ala Leu Tyr Leu Arg Tyr Met Phe Glu Asp Ile Thr Gly Pro
            1205                1210                1215

Met Ala Leu Pro Val Ser Pro Tyr Arg Ser Pro Tyr Ser Asn
        1220                1225                1230

<210> SEQ ID NO 73
<211> LENGTH: 540
<212> TYPE: DNA
<213> ORGANISM: Pseudomonas syringae pv. tomato DC3000

<400> SEQUENCE: 73
atgaaactga tacgacagat ccgctcgcag ggtcgtcagt cgcccttgtt cgaggacctt      60
gcccagctcg aggggcgcaa gcgtcaatgg ctggccgagc gcgccgtgca gttcgcactg     120
ggcttgcacg gccgccggcc agaggtcgat aaccccttca aggcaaaact gcgtgaagac     180
ctgtgctgca tcatgttcga tgacctgtcg ctgcacaccc tggtcgagcg ttacgcggcc     240
agtgaagccc tgcgacgaca cgacagcgag tacttcagca aactgatcgc acgacacga     300 aataccgtgg aacggcgcat cgtctttcac gggctgctgg aacacttcga caggctgttg     360
cctatcgaaa agagcatcta ccaactcaac taccgcagcg ttcaatacgc gcacctggag     420
caggaagaag ccctgtacgg caaactgata atggaacaac ccattagtgc actgctggaa     480
gtgcacacgc tgagtggct tcttgagaat ctgtcttcgt ttgagttttc gattgattga     540

<210> SEQ ID NO 74
<211> LENGTH: 179
<212> TYPE: PRT
<213> ORGANISM: Pseudomonas syringae pv. tomato DC3000

<400> SEQUENCE: 74

Met Lys Leu Ile Arg Gln Ile Arg Ser Gln Gly Arg Gln Ser Pro Leu
1               5                   10                  15

Phe Glu Asp Leu Ala Gln Leu Glu Gly Arg Lys Arg Gln Trp Leu Ala
            20                  25                  30

```
Glu Arg Ala Val Gln Phe Ala Leu Gly Leu His Gly Arg Arg Pro Glu
         35                  40                  45
Val Asp Asn Pro Phe Lys Gly Lys Leu Arg Glu Asp Leu Cys Cys Ile
     50                  55                  60
Met Phe Asp Asp Leu Ser Leu His Thr Leu Val Glu Arg Tyr Ala Ala
 65                  70                  75                  80
Ser Glu Ala Leu Arg Arg His Asp Ser Glu Tyr Phe Ser Lys Leu Ile
                 85                  90                  95
Ala Thr Thr Arg Asn Thr Val Glu Arg Arg Ile Val Phe His Gly Leu
            100                 105                 110
Leu Glu His Phe Asp Arg Leu Leu Pro Ile Glu Lys Ser Ile Tyr Gln
        115                 120                 125
Leu Asn Tyr Arg Ser Val Gln Tyr Ala His Leu Glu Gln Glu Glu Ala
    130                 135                 140
Leu Tyr Gly Lys Leu Ile Met Glu Gln Pro Ile Ser Ala Leu Leu Glu
145                 150                 155                 160
Val His Thr Pro Glu Trp Leu Leu Glu Asn Leu Ser Ser Phe Glu Phe
                165                 170                 175
Ser Ile Asp

<210> SEQ ID NO 75
<211> LENGTH: 492
<212> TYPE: DNA
<213> ORGANISM: Pseudomonas syringae pv. tomato DC3000

<400> SEQUENCE: 75
atgcgactga ctactaaagg ccgatacgct gtgacagcca tgcttgacct ggcgttacat      60
gcgcagaacg ggccagtgtc tctggccgac atctccgagc ggcagggcat ttccctgtct     120
tatctcgaac agttgttcgc caaactgcgt cgcggcaatc tggtttccag tgttcgtggt     180
ccgggcggcg gttatcagct gtctcgtgac atgaaaggca tccaggtcgc ccaagtcgtc     240
gacgcggtca atgaatcggt cgatgccacg cgttgtcagg gctgggtga ttgccacgct      300
ggcgatacct gcctgaccca ccacttgtgg tgcgatctga ccagcagat tcacgaattt       360
ctaagcggta tcagcttggc ggatcttgtc actcgccgtg aggtacaaga agtcgctcag    420
cgccaggata tgcgccgtgg tcataaccac acgtcgcaac tgggtaagat cgaaacgtcc     480
gccgtcgaat ga                                                        492

<210> SEQ ID NO 76
<211> LENGTH: 163
<212> TYPE: PRT
<213> ORGANISM: Pseudomonas syringae pv. tomato DC3000

<400> SEQUENCE: 76

Met Arg Leu Thr Thr Lys Gly Arg Tyr Ala Val Thr Ala Met Leu Asp
 1               5                  10                  15
Leu Ala Leu His Ala Gln Asn Gly Pro Val Ser Leu Ala Asp Ile Ser
             20                  25                  30
Glu Arg Gln Gly Ile Ser Leu Ser Tyr Leu Glu Gln Leu Phe Ala Lys
         35                  40                  45
Leu Arg Arg Gly Asn Leu Val Ser Ser Val Arg Gly Pro Gly Gly Gly
     50                  55                  60
Tyr Gln Leu Ser Arg Asp Met Lys Gly Ile Gln Val Ala Gln Val Val
 65                  70                  75                  80
Asp Ala Val Asn Glu Ser Val Asp Ala Thr Arg Cys Gln Gly Leu Gly
                 85                  90                  95
```

```
Asp Cys His Ala Gly Asp Thr Cys Leu Thr His His Leu Trp Cys Asp
            100                 105                 110
Leu Ser Gln Gln Ile His Glu Phe Leu Ser Gly Ile Ser Leu Ala Asp
        115                 120                 125
Leu Val Thr Arg Arg Glu Val Gln Glu Val Ala Gln Arg Gln Asp Met
    130                 135                 140
Arg Arg Gly His Asn His Thr Ser Gln Leu Gly Lys Ile Glu Thr Ser
145                 150                 155                 160
Ala Val Glu

<210> SEQ ID NO 77
<211> LENGTH: 3441
<212> TYPE: DNA
<213> ORGANISM: Pseudomonas syringae pv. tomato DC3000

<400> SEQUENCE: 77
```

| | | | | | |
|---|---|---|---|---|---|
| atgaataccg | tcagaaaacc | cataacacca | cggatgctca | gcatgaccga | taaaaacggc | 60 |
| acccatcgac | aacgacgtgc | tgcactgttc | cccaaaaccc | ggcgaccgc | caccagcctg | 120 |
| tgcccttca | gagggcctaa | tatcgccatc | gtcccggtgc | gctatgcgct | ggatcgctcg | 180 |
| cgctatgacg | ctgaccccgc | gcaactgaag | ccactgccca | agacggcca | atgggcccac | 240 |
| ctgccgacgc | tgaaaactcg | cagttacacc | ttacgccaac | tgtacgacgg | ctacgtttac | 300 |
| gtgttcgacg | aaacggccgg | cacgttgcac | gaatacgcag | cctcagccag | cgacggccat | 360 |
| ctgagccgca | tcgtctggac | cgatgcacac | atcggtaacg | accagcgaag | cggtgccggt | 420 |
| gaagggcaac | cctttgtgct | ttacccgcgt | gaccaccgcc | tgcacatcgc | cttttctccc | 480 |
| ctgcaatgga | catggcgaat | gtgcgagcac | atgcgctccc | acgccccaag | ccgcgcgttg | 540 |
| tggatgaagg | cgctggacct | ggccagctac | tgcctcacca | tggccgaacc | ggacaccctg | 600 |
| ccgctggatc | gcatcgccga | ggccgtggcg | gatatcgaca | agactgtgt | tgtggaagat | 660 |
| ggccgtttg | cagattcggc | gattccagt | gttcgcccgc | catcagaagg | tgcagaaccc | 720 |
| tatccgttat | gggcaccgct | gggcgccgat | gtcttctggc | agggcagcgt | ctacgatcag | 780 |
| gacagctctc | tggtcattgc | cctcaatgac | ccgctcgccg | ttttcaacga | cttgggcatg | 840 |
| cagctggcgg | ccgatcaggc | ggcttttcgg | gaatggcaaa | gcgcccacga | cacaagatc | 900 |
| cagattgccc | agaccgtcgc | cacgctgtgc | ggtgcagaga | gcgaagcaga | gaagctgcca | 960 |
| gcatcggtgc | gcggtgatgc | gctgcgcacg | catcagtacc | tgagcgaggt | cgaagcctac | 1020 |
| tttgaacaat | gcattcttga | gaagcacag | atcagcagta | gcaacgttcc | tggagatttt | 1080 |
| ctgctgctgc | cggacatgtt | caagagcctg | acatgcgca | aatcgatcga | aacacgttat | 1140 |
| ggcagcgcgc | cgaccgatga | gggcgcgcag | gcctggaaag | atcgccacaa | atggcggcgc | 1200 |
| gaggtcgatc | tgagcagtgc | gcgtcagtac | cttttgcagc | acctgccgac | cggagacaaa | 1260 |
| cgcctgcaac | aggtgcgtga | cacgcaaagc | gatttccagc | actgggcggc | acatataggc | 1320 |
| accgaaccgc | tcaagctgtt | catcgacacc | acacacccga | aaaccctgct | gtatttgcag | 1380 |
| acgatcatgc | tcaatctgca | gatcatctat | gcgcaggaca | gcgccgcaaa | tgcctggctc | 1440 |
| gccgagcagg | aagccaacac | cagcagcctg | tttggcaccc | tgcgttatgg | tttttcgcca | 1500 |
| gcgctcaagc | acgccctgca | tcaggaagcc | gacgcactgc | tgaacggcct | cggcgacgtc | 1560 |
| actaatctgg | ccacgcgcat | cggtgaactc | aatggcgtgc | tcaaccatca | gggttttgcc | 1620 |
| gacaagccgt | ggatgaaggc | gctgaaacag | cctgttcaag | acaccttcaa | agccctcggc | 1680 |
| gaactggcca | gcggtgccgg | caaagccagg | tttgaaagtg | tattactggc | atgggtgccc | 1740 |

-continued

```
atcgacagcc gcatggccct tggcaagcag cagaacatcg ttgcgttgct tcgcaccctg    1800
ctgatcggcc agatattgct cgactcgaca gcacgcgtcg cgatcaatga gcagacagtg    1860
accaagctca acagtgggt aagtgagtgg caagtcctca acaagcaaat cagcgagctg     1920
gtgcgcagtt ggcaataccc gaacgcctac aacacgcgcc aaagcaccgc tcgcaaattg    1980
caggcccata acacaaact gcgcgttcac gaactgagca tccctgccct gctcgacttt     2040
cagaacaacg aatacgccaa gctattgcag gacgagattc gtcagtactt ccagtctggc    2100
aaaaccctcg ccacggactg gctcgcccgc gccaaaggct ggaccgaccg actgggcggc    2160
gttgctggca cgatcacctg gggcgtggtc atgcttaacc tgatcaatac cgccttcctc    2220
tatcgggacc ttacccggga cggggatttc agtaccaagg acattggcaa ggtgacgtat    2280 ggattgggt acagcttcaa tctgttgatg gcggtgtttg tggacgcgcc gtggagcatc     2340 ataaggacg caacgccagc gctgatcgat ggcaagaatg tggccattct ggacaggtcc     2400
agtgcgtact ggaaagccaa gggaaatgca gcgtggggtg atgcgatacg tgggttcagg    2460
gtttcgatgg tggcgatggg tgggtttggg cttgcggcgg ttacgcttga attatttgat    2520
gttacagatg attttcacgc agctaaaaca tcagaagaaa catatggaat tggcatcaag    2580
gggttttccg tagtggtgat gggattgggt gctgcggccc agctaatggc aggcatttct    2640
cccgctggcg tttttacgat tatcgcaatg agtccgtggt tcagcgtagc gctactggca    2700
gcaggcttga tttatctttt tgctacgatg gcccttaatt acttcaagca agacagtgtc    2760
ggctggtggc tacgcaagtg ctgttggtcc ataacccaag actatcgcta tgctgagact    2820
gcggaaggta agcatgacga agtgcgcgcg ctgatggaaa taaaattatc tccgcaggtc    2880
catgtaaaaa gcaccgtgaa ttatgaaaac cgttatcttg caaaaacga tcactacagc     2940 gtagcggtac aaaatggcgc gggggtacaa gtgcgcttgc cgaatcttct acgcgggctg    3000
tccgtgcatt tcaatatcgt tagtagcaag agaccatggg gcgtgctgcc cgtagaaaaa    3060
atagatcagc cgatacatga agcttttctg gaccacgggc aattcaggaa agtcgaacag    3120
ttcgggatgt ttaccaacaa gcctgctggc aaggcgagtg aagactatac ctaccccgc     3180 atgccacctg aaaacgaaga cctcatctgg gaaacctggg tgccgctcga caaggacgca    3240
acgtatcttg agttgcaaat ctggtacccg gccaatcttt taaatcctgg cggagacgat    3300
agaagctatc tgtttcagat ggagcttggc acaaaaggcg ataccgctat tgacggcctg    3360
gctgcagtgg aactcgaggt aaaggcatca agcaggattg gcgctctgac cctagaagtc    3420
gcagagggca cacctgtatg a                                              3441
```

<210> SEQ ID NO 78
<211> LENGTH: 1146
<212> TYPE: PRT
<213> ORGANISM: Pseudomonas syringae pv. tomato DC3000

<400> SEQUENCE: 78

```
Met Asn Thr Val Arg Lys Pro Ile Thr Pro Arg Met Leu Ser Met Thr
  1               5                  10                  15

Asp Lys Asn Gly Thr His Arg Gln Arg Ala Ala Leu Phe Pro Lys
             20                  25                  30

Thr Pro Ala Thr Ala Thr Ser Leu Cys Pro Phe Arg Gly Pro Asn Ile
         35                  40                  45

Ala Ile Val Pro Val Arg Tyr Ala Leu Asp Arg Ser Arg Tyr Asp Ala
     50                  55                  60
```

```
Asp Pro Ala Gln Leu Lys Pro Leu Pro Lys Asp Gly Gln Trp Ala His
 65                  70                  75                  80

Leu Pro Thr Leu Lys Thr Arg Ser Tyr Thr Leu Arg Gln Leu Tyr Asp
                 85                  90                  95

Gly Tyr Val Tyr Val Phe Asp Glu Thr Ala Gly Thr Leu His Glu Tyr
            100                 105                 110

Ala Ala Ser Ala Ser Asp Gly His Leu Ser Arg Ile Val Trp Thr Asp
            115                 120                 125

Ala His Ile Gly Asn Asp Gln Arg Ser Gly Ala Gly Glu Gly Gln Pro
        130                 135                 140

Phe Val Leu Tyr Pro Arg Asp His Arg Leu His Ile Ala Phe Ser Pro
145                 150                 155                 160

Leu Gln Trp Thr Trp Arg Met Cys Glu His Met Arg Ser His Ala Pro
                165                 170                 175

Ser Arg Ala Leu Trp Met Lys Ala Leu Asp Leu Ala Ser Tyr Cys Leu
            180                 185                 190

Thr Met Ala Glu Pro Asp Thr Leu Pro Leu Asp Arg Ile Ala Glu Ala
            195                 200                 205

Val Ala Asp Ile Asp Lys Asp Cys Val Val Glu Asp Gly Arg Phe Ala
210                 215                 220

Asp Ser Ala Ile Pro Ser Val Arg Pro Ser Glu Gly Ala Glu Pro
225                 230                 235                 240

Tyr Pro Leu Trp Ala Pro Leu Gly Ala Asp Val Phe Trp Gln Gly Ser
                245                 250                 255

Val Tyr Asp Gln Asp Ser Ser Leu Val Ile Ala Leu Asn Asp Pro Leu
            260                 265                 270

Ala Val Phe Asn Asp Leu Gly Met Gln Leu Ala Ala Asp Gln Ala Ala
            275                 280                 285

Phe Arg Glu Trp Gln Ser Ala His Glu His Lys Ile Gln Ile Ala Gln
290                 295                 300

Thr Val Ala Thr Leu Cys Gly Ala Glu Ser Glu Ala Glu Lys Leu Pro
305                 310                 315                 320

Ala Ser Val Arg Gly Asp Ala Leu Arg Thr His Gln Tyr Leu Ser Glu
            325                 330                 335

Val Glu Ala Tyr Phe Glu Gln Cys Ile Leu Glu Glu Ala Gln Ile Ser
            340                 345                 350

Ser Ser Asn Val Pro Gly Asp Phe Leu Leu Pro Asp Met Phe Lys
            355                 360                 365

Ser Leu Asp Met Arg Lys Ser Ile Glu Thr Arg Tyr Gly Ser Ala Pro
370                 375                 380

Thr Asp Glu Gly Ala Gln Ala Trp Lys Asp Arg His Lys Trp Arg Arg
385                 390                 395                 400

Glu Val Asp Leu Ser Ser Ala Arg Gln Tyr Leu Leu Gln His Leu Pro
                405                 410                 415

Thr Gly Asp Lys Arg Leu Gln Gln Val Arg Asp Thr Gln Ser Asp Phe
            420                 425                 430

Gln His Trp Ala Ala His Ile Gly Thr Glu Pro Leu Lys Leu Phe Ile
            435                 440                 445

Asp Thr Thr His Pro Lys Thr Leu Leu Tyr Leu Gln Thr Ile Met Leu
            450                 455                 460

Asn Leu Gln Ile Ile Tyr Ala Gln Asp Ser Ala Ala Asn Ala Trp Leu
465                 470                 475                 480
```

```
Ala Glu Gln Glu Ala Asn Thr Ser Ser Leu Phe Gly Thr Leu Arg Tyr
            485                 490                 495

Gly Phe Ser Pro Ala Leu Lys His Ala Leu His Gln Glu Ala Asp Ala
            500                 505                 510

Leu Leu Asn Gly Leu Gly Asp Val Thr Asn Leu Ala Thr Arg Ile Gly
            515                 520                 525

Glu Leu Asn Gly Val Leu Asn His Gln Gly Phe Ala Asp Lys Pro Trp
            530                 535                 540

Met Lys Ala Leu Lys Gln Pro Val Gln Asp Thr Phe Lys Ala Leu Gly
545                 550                 555                 560

Glu Leu Ala Ser Gly Ala Gly Lys Ala Arg Phe Glu Ser Val Leu Leu
            565                 570                 575

Ala Trp Val Pro Ile Asp Ser Arg Met Ala Leu Gly Lys Gln Gln Asn
            580                 585                 590

Ile Val Ala Leu Leu Arg Thr Leu Leu Ile Gly Gln Ile Leu Leu Asp
            595                 600                 605

Ser Thr Ala Arg Val Ala Ile Asn Glu Gln Thr Val Thr Lys Leu Lys
            610                 615                 620

Gln Trp Val Ser Glu Trp Gln Val Leu Asn Lys Gln Ile Ser Glu Leu
625                 630                 635                 640

Val Arg Ser Trp Gln Tyr Pro Asn Ala Tyr Asn Thr Arg Gln Ser Thr
            645                 650                 655

Ala Arg Lys Leu Gln Ala His Lys His Lys Leu Arg Val His Glu Leu
            660                 665                 670

Ser Ile Pro Ala Leu Leu Asp Phe Gln Asn Asn Glu Tyr Ala Lys Leu
            675                 680                 685

Leu Gln Asp Glu Ile Arg Gln Tyr Phe Gln Ser Gly Lys Thr Leu Ala
            690                 695                 700

Thr Asp Trp Leu Ala Arg Ala Lys Gly Trp Thr Asp Arg Leu Gly Gly
705                 710                 715                 720

Val Ala Gly Thr Ile Thr Trp Gly Val Val Met Leu Asn Leu Ile Asn
            725                 730                 735

Thr Ala Phe Leu Tyr Arg Asp Leu Thr Arg Asp Gly Asp Phe Ser Thr
            740                 745                 750

Lys Asp Ile Gly Lys Val Thr Tyr Gly Leu Gly Tyr Ser Phe Asn Leu
            755                 760                 765

Leu Met Ala Val Phe Val Asp Ala Pro Trp Ser Ile Ile Arg Asp Ala
            770                 775                 780

Thr Pro Ala Leu Ile Asp Gly Lys Asn Val Ala Ile Leu Asp Arg Ser
785                 790                 795                 800

Ser Ala Tyr Trp Lys Ala Lys Gly Asn Ala Ala Trp Gly Asp Ala Ile
            805                 810                 815

Arg Gly Phe Arg Val Ser Met Val Ala Met Gly Gly Phe Gly Leu Ala
            820                 825                 830

Ala Val Thr Leu Glu Leu Phe Asp Val Thr Asp Phe His Ala Ala
            835                 840                 845

Lys Thr Ser Glu Glu Thr Tyr Gly Ile Gly Ile Lys Gly Phe Ser Val
            850                 855                 860

Val Val Met Gly Leu Gly Ala Ala Ala Gln Leu Met Ala Gly Ile Ser
865                 870                 875                 880

Pro Ala Gly Val Phe Thr Ile Ile Ala Met Ser Pro Trp Phe Ser Val
            885                 890                 895
```

```
Ala Leu Leu Ala Ala Gly Leu Ile Tyr Leu Phe Ala Thr Met Ala Leu
            900                 905                 910

Asn Tyr Phe Lys Gln Asp Ser Val Gly Trp Trp Leu Arg Lys Cys Cys
            915                 920                 925

Trp Ser Ile Thr Gln Asp Tyr Arg Tyr Ala Glu Thr Ala Glu Gly Lys
            930                 935                 940

His Asp Glu Val Arg Ala Leu Met Glu Ile Lys Leu Ser Pro Gln Val
945                 950                 955                 960

His Val Lys Ser Thr Val Asn Tyr Glu Asn Arg Tyr Leu Gly Lys Asn
                965                 970                 975

Asp His Tyr Ser Val Ala Val Gln Asn Gly Ala Gly Val Gln Val Arg
            980                 985                 990

Leu Pro Asn Leu Leu Arg Gly Leu Ser Val His Phe Asn Ile Val Ser
            995                 1000                1005

Ser Lys Arg Pro Trp Gly Val Leu Pro Val Glu Lys Ile Asp Gln Pro
    1010                1015                1020

Ile His Glu Ala Phe Leu Asp His Gly Gln Phe Arg Lys Val Glu Gln
1025                1030                1035                1040

Phe Gly Met Phe Thr Asn Lys Pro Ala Gly Lys Ala Ser Glu Asp Tyr
            1045                1050                1055

Thr Tyr Pro Arg Met Pro Pro Glu Asn Glu Asp Leu Ile Trp Glu Thr
            1060                1065                1070

Trp Val Pro Leu Asp Lys Asp Ala Thr Tyr Leu Glu Leu Gln Ile Trp
    1075                1080                1085

Tyr Pro Ala Asn Leu Leu Asn Pro Gly Gly Asp Asp Arg Ser Tyr Leu
    1090                1095                1100

Phe Gln Met Glu Leu Gly Thr Lys Gly Asp Thr Ala Ile Asp Gly Leu
1105                1110                1115                1120

Ala Ala Val Glu Leu Glu Val Lys Ala Ser Ser Arg Ile Gly Ala Leu
            1125                1130                1135

Thr Leu Glu Val Ala Glu Gly Thr Pro Val
            1140                1145

<210> SEQ ID NO 79
<211> LENGTH: 630
<212> TYPE: DNA
<213> ORGANISM: Pseudomonas syringae pv. tomato DC3000

<400> SEQUENCE: 79
atgtgcctgg tggcgagcct gtcggtgctg gcaggcatga ccgatgccat cggcttcatg      60
gccaccggcg atttcgtctc gttcatgagc ggcaacacca cgcgccttgc ggtggcgatc     120
agtgatggcg atttgagcgt cacactccgt ctggccctgg ccatctttgc gtttattgcc     180
ggcaatgcac tgggcgttgt cgttgcgcgc ctgggcaacc ggcgcgccct gcccttactg     240
ctggctatcg ccacgctgtt gtgtgccgct gcggcgtggc cgttggcgaa caatatgctt     300
gccctgatct gggcgattct ggcgatgggc atgctcaacg ccgctgtcga gcaggtcaac     360
gggctgccgg tgggcctgac ctacgtgacc ggcgcgctgt cgcgactggg gcgcggtctg     420
ggccgctgga tgctcggcga acgccgggat ggctggcgca ttcaactggt cccgtgggcc     480
gggatgttca ttggcgcagt gatcggcgcg ttgcttgaac atcgtctggg gctcaatgcc     540
ttgctggtca cgccagcct gtcagcgtta atgcgctgg tgtcgctgaa aatcccgcat      600
cgctggcaac gtcagtacat gccgcgctga                                       630
```

-continued

<210> SEQ ID NO 80
<211> LENGTH: 209
<212> TYPE: PRT
<213> ORGANISM: Pseudomonas syringae pv. tomato DC3000

<400> SEQUENCE: 80

```
Met Cys Leu Val Ala Ser Leu Ser Val Leu Ala Gly Met Thr Asp Ala
 1               5                  10                  15

Ile Gly Phe Met Ala Thr Gly Asp Phe Val Ser Phe Met Ser Gly Asn
            20                  25                  30

Thr Thr Arg Leu Ala Val Ala Ile Ser Asp Gly Asp Leu Ser Val Thr
        35                  40                  45

Leu Arg Leu Ala Leu Ala Ile Phe Ala Phe Ile Ala Gly Asn Ala Leu
    50                  55                  60

Gly Val Val Val Ala Arg Leu Gly Asn Arg Arg Ala Leu Pro Leu Leu
65                  70                  75                  80

Leu Ala Ile Ala Thr Leu Leu Cys Ala Ala Ala Trp Pro Leu Ala
                85                  90                  95

Asn Asn Met Leu Ala Leu Ile Trp Ala Ile Leu Ala Met Gly Met Leu
            100                 105                 110

Asn Ala Ala Val Glu Gln Val Asn Gly Leu Pro Val Gly Leu Thr Tyr
        115                 120                 125

Val Thr Gly Ala Leu Ser Arg Leu Gly Arg Gly Leu Gly Arg Trp Met
    130                 135                 140

Leu Gly Glu Arg Arg Asp Gly Trp Arg Ile Gln Leu Val Pro Trp Ala
145                 150                 155                 160

Gly Met Phe Ile Gly Ala Val Ile Gly Ala Leu Leu Glu His Arg Leu
                165                 170                 175

Gly Leu Asn Ala Leu Leu Val Ser Ala Ser Leu Ser Ala Leu Met Ala
            180                 185                 190

Leu Val Ser Leu Lys Ile Pro His Arg Trp Gln Arg Gln Tyr Met Pro
        195                 200                 205
Arg
```

<210> SEQ ID NO 81
<211> LENGTH: 882
<212> TYPE: DNA
<213> ORGANISM: Pseudomonas syringae pv. tomato DC3000

<400> SEQUENCE: 81

| | | | | | |
|---|---|---|---|---|---|
| atgagagggc | ttggtgttct | gagcatgaac | caccagtttc | aggcaatac | cctgttcaaa | 60 |
| gaaataagcg | gtaccagctt | tccgcgccc | tacatcaccc | atcttgcggg | ccgtctcctt | 120 |
| aacgagcacc | cagaggcatc | ggcgaacctc | ttgcgcgcta | tgctggtgaa | tcatgcgtca | 180 |
| ttgtctagcg | aggtcgagac | gactttctcc | gacgacatga | ggaagggcta | caaagctaat | 240 |
| aaggcgaccc | acaaccgtga | aatatcgcgc | gatgtgagtg | gttacggcca | agtgaatgag | 300 |
| gcagacctgt | ttcggtcttc | cgaccattgc | gttgtgctga | tgtgtgaaga | gtccattgag | 360 |
| aaggactcgt | gccagttcta | cgaactgcct | ttgcccactt | cgtttcttcg | cagggctaga | 420 |
| ggggcaaggc | acctgagcgt | cacgctggct | tattctcctg | ccgtcaggac | aactcggttg | 480 |
| gactatctgg | caactcagat | cagttatcgc | ctagtgaaag | gttcgtcgct | tgaggaagtc | 540 |
| caggcctcgt | ttaactacga | caagcaggac | gaaacgaaga | cccgtggaga | tgacgctgag | 600 |
| cagaatcgag | acatcactgc | tcagttgaga | agccgcggga | ccgtccagtc | ctcgcggtgg | 660 |
| acgttcaaga | agcgaaatcc | agaagaaaaa | tggtttgtag | ttgtgatccg | ccaggatcgg | 720 |

```
gaatggaatc atcccgacgt gctggatcga gaatcttacg ccctggtggt aacagttgct    780
gatcgtgaca acgaacacgc gcagttgtat gccgaaattc aagccaagct gacgcttcaa    840
aatcaggtgc gtgaagaggc aaggcagcgg gctgttctgt aa                       882
```

```
<210> SEQ ID NO 82
<211> LENGTH: 293
<212> TYPE: PRT
<213> ORGANISM: Pseudomonas syringae pv. tomato DC3000

<400> SEQUENCE: 82

Met Arg Gly Leu Gly Val Leu Ser Met Asn His Gln Phe Gln Gly Asn
  1               5                  10                  15

Thr Leu Phe Lys Glu Ile Ser Gly Thr Ser Phe Ser Ala Pro Tyr Ile
                 20                  25                  30

Thr His Leu Ala Gly Arg Leu Leu Asn Glu His Pro Glu Ala Ser Ala
             35                  40                  45

Asn Leu Leu Arg Ala Met Leu Val Asn His Ala Ser Leu Ser Ser Glu
         50                  55                  60

Val Glu Thr Thr Phe Ser Asp Asp Met Arg Lys Gly Tyr Lys Ala Asn
 65                  70                  75                  80

Lys Ala Thr His Asn Arg Glu Ile Ser Arg Asp Val Ser Gly Tyr Gly
                 85                  90                  95

Gln Val Asn Glu Ala Asp Leu Phe Arg Ser Ser Asp His Cys Val Val
                100                 105                 110

Leu Met Cys Glu Glu Ser Ile Glu Lys Asp Ser Cys Gln Phe Tyr Glu
            115                 120                 125

Leu Pro Leu Pro Thr Ser Phe Leu Arg Arg Ala Arg Gly Ala Arg His
        130                 135                 140

Leu Ser Val Thr Leu Ala Tyr Ser Pro Ala Val Arg Thr Thr Arg Leu
145                 150                 155                 160

Asp Tyr Leu Ala Thr Gln Ile Ser Tyr Arg Leu Val Lys Gly Ser Ser
                165                 170                 175

Leu Glu Glu Val Gln Ala Ser Phe Asn Tyr Asp Lys Gln Asp Glu Thr
            180                 185                 190

Lys Thr Arg Gly Asp Asp Ala Glu Gln Asn Arg Asp Ile Thr Ala Gln
        195                 200                 205

Leu Arg Ser Arg Gly Thr Val Gln Ser Ser Arg Trp Thr Phe Lys Lys
    210                 215                 220

Arg Asn Pro Glu Glu Lys Trp Phe Val Val Ile Arg Gln Asp Arg
225                 230                 235                 240

Glu Trp Asn His Pro Asp Val Leu Asp Arg Glu Ser Tyr Ala Leu Val
                245                 250                 255

Val Thr Val Ala Asp Arg Asp Asn Glu His Ala Gln Leu Tyr Ala Glu
            260                 265                 270

Ile Gln Ala Lys Leu Thr Leu Gln Asn Gln Val Arg Glu Glu Ala Arg
        275                 280                 285

Gln Arg Ala Val Leu
        290

<210> SEQ ID NO 83
<211> LENGTH: 846
<212> TYPE: DNA
<213> ORGANISM: Pseudomonas syringae pv. tomato DC3000
```

-continued

```
<400> SEQUENCE: 83
atgggcattg gcggtttgct taaacctttg gtcgattttt taccgaagtt gccgaccta      60
cgcaccaaga tttcctcgcc ttccatcagc tacgcgcgtt tgcaaagcga tgcgtcccag    120
gtacgcagta aattgggatt gggtgagcgc agcgtgctgg ttatgaagc gctgatcgcc    180
gagttcaagg cgtgcgggc ggttctggtg cccgttcttt ggggacaaaa gcagcaacac    240
aagaatgcgt tgcacattct attgccggcg tcagatgtca cctttgtctt cgtcaacctg    300
gataccaagc tggaagactt caagttttgg atggcccacg agttagcgca tgtctacact    360
cctgagcttg cgggtagtga cgaggggag gattttgcgg atgcctttgc cggtgccctg     420
ctgtttcctg aggcttgcgt gcagctagcg tatgccgagg cggcgcaagc gcctagcgca    480
gctggggagg tgagtgtcct tcagcagcat gcccggcatc accaaatttc actgaacacg    540
gtgttccagc aggcgcaggg atatgcggcg gaaaacaatc tgccatcctt acgggtaccg    600
gaaaggacaa ttcacgcggt gcgcaacagc tccacgccgc agttggtcag tacgatcctg    660
tttgatccga ctccacccaa accggcgcaa tacattgccg cagcgtcgaa tgtgtttcag    720
tctgagttct tcctggcgct gaaacgcatg attcgcgagc acgggacggg cccgtcgtat    780
gttcagcaaa tcatggatgt atcactcagt gatgcctccg cgctttacgg cgagctcgcg    840
cgttga                                                               846

<210> SEQ ID NO 84
<211> LENGTH: 281
<212> TYPE: PRT
<213> ORGANISM: Pseudomonas syringae pv. tomato DC3000

<400> SEQUENCE: 84

Met Gly Ile Gly Gly Leu Leu Lys Pro Leu Val Asp Phe Leu Pro Lys
  1               5                  10                  15

Leu Pro Thr Leu Arg Thr Lys Ile Ser Ser Pro Ser Ile Ser Tyr Ala
             20                  25                  30

Arg Leu Gln Ser Asp Ala Ser Gln Val Arg Ser Lys Leu Gly Leu Gly
         35                  40                  45

Glu Arg Ser Val Leu Gly Tyr Glu Ala Leu Ile Ala Glu Phe Lys Ala
     50                  55                  60

Cys Gly Ala Val Leu Val Pro Val Leu Trp Gly Gln Lys Gln Gln His
 65                  70                  75                  80

Lys Asn Ala Leu His Ile Leu Leu Pro Ala Ser Asp Val Thr Phe Val
                 85                  90                  95

Phe Val Asn Leu Asp Thr Lys Leu Glu Asp Phe Lys Phe Trp Met Ala
            100                 105                 110

His Glu Leu Ala His Val Tyr Thr Pro Glu Leu Ala Gly Ser Asp Glu
        115                 120                 125

Gly Glu Asp Phe Ala Asp Ala Phe Ala Gly Ala Leu Leu Phe Pro Glu
    130                 135                 140

Ala Cys Val Gln Leu Ala Tyr Ala Glu Ala Ala Gln Ala Pro Ser Ala
145                 150                 155                 160

Ala Gly Glu Val Ser Val Leu Gln Gln His Ala Arg His Gln Ile
                165                 170                 175

Ser Leu Asn Thr Val Phe Gln Gln Ala Gln Gly Tyr Ala Ala Glu Asn
        180                 185                 190

Asn Leu Pro Ser Leu Arg Val Pro Glu Arg Thr Ile His Ala Val Arg
    195                 200                 205
```

-continued

Asn Ser Ser Thr Pro Gln Leu Val Ser Thr Ile Leu Phe Asp Pro Thr
    210                 215                 220

Pro Pro Lys Pro Ala Gln Tyr Ile Ala Ala Ser Asn Val Phe Gln
225                 230                 235                 240

Ser Glu Phe Phe Leu Ala Leu Lys Arg Met Ile Arg Glu His Gly Thr
                245                 250                 255

Gly Pro Ser Tyr Val Gln Gln Ile Met Asp Val Ser Leu Ser Asp Ala
            260                 265                 270

Ser Ala Leu Tyr Gly Glu Leu Ala Arg
        275                 280

<210> SEQ ID NO 85
<211> LENGTH: 525
<212> TYPE: DNA
<213> ORGANISM: Pseudomonas syringae pv. tomato DC3000

<400> SEQUENCE: 85
atgaagcagc tcgcggcagg cagcaatgtg catgttcttg aaaatgagtc tttccagata      60
gataaggtgc gcttttttggg ggccacagct tggacagatt tcgcaacagg tgaaagcgtg     120
taccaagcgt cccaggaggc aaggcgaggc atgaatgact ttcgcttgat ccgtgcaggc     180
gagggttacc gcgcattgag catcagtgat gtgatcagtc gaaatcatcg aacttacgag     240
tggctcaagg aagagctcgc catggagttc gatggtcaga ccattgtcat cactcatcat     300
tgcccgttgg tcaattactg tggcccagag cagggctcac cgctaatgcc tgcttattca     360
aatgattggc cagaactcgt tcgtcaggct gatgtgtggg tctttgggca cacgcacagt     420
catgtcgatg tcatggtgga aggatgccga ctcattagta accctagagg ttatccaggt     480
gagagttgcg gctttgccaa tgactttgtg gtcgatatta actag                     525

<210> SEQ ID NO 86
<211> LENGTH: 174
<212> TYPE: PRT
<213> ORGANISM: Pseudomonas syringae pv. tomato DC3000

<400> SEQUENCE: 86

Met Lys Gln Leu Ala Ala Gly Ser Asn Val His Val Leu Glu Asn Glu
1               5                   10                  15

Ser Phe Gln Ile Asp Lys Val Arg Phe Leu Gly Ala Thr Ala Trp Thr
            20                  25                  30

Asp Phe Ala Thr Gly Glu Ser Val Tyr Gln Ala Ser Gln Glu Ala Arg
        35                  40                  45

Arg Gly Met Asn Asp Phe Arg Leu Ile Arg Ala Gly Glu Gly Tyr Arg
    50                  55                  60

Ala Leu Ser Ile Ser Asp Val Ile Ser Arg Asn His Arg Thr Tyr Glu
65                  70                  75                  80

Trp Leu Lys Glu Glu Leu Ala Met Glu Phe Asp Gly Gln Thr Ile Val
                85                  90                  95

Ile Thr His His Cys Pro Leu Val Asn Tyr Cys Gly Pro Glu Gln Gly
            100                 105                 110

Ser Pro Leu Met Pro Ala Tyr Ser Asn Asp Trp Pro Glu Leu Val Arg
        115                 120                 125

Gln Ala Asp Val Trp Val Phe Gly His Thr His Ser His Val Asp Val
    130                 135                 140

```
Met Val Glu Gly Cys Arg Leu Ile Ser Asn Pro Arg Gly Tyr Pro Gly
145                 150                 155                 160

Glu Ser Cys Gly Phe Ala Asn Asp Phe Val Val Asp Ile Asn
                165                 170
```

<210> SEQ ID NO 87
<211> LENGTH: 2307
<212> TYPE: DNA
<213> ORGANISM: Pseudomonas syringae pv. tomato DC3000

<400> SEQUENCE: 87

| | | | | | |
|---|---|---|---|---|---|
| atgacgctga | cgcagcgtca | ggcatggcat | cgcgaggcac | agcggtttgg | cgagcaggtg | 60 |
| gtgaacatgc | gcaaagccag | caaggagcac | ttcggccagg | cggaaaatga | cagccgcacc | 120 |
| tatccggcgc | gctttatcga | ccagcaactg | gctcaactgc | tgaaccggct | atccatcgct | 180 |
| gcaacggcgc | aacagatcaa | tatttcactg | acctacagga | cgggcaccga | agtgctcgaa | 240 |
| attcccggcg | cgcctgtatt | gccagaaacc | gagaccgaga | acgtttcact | caggcaactg | 300 |
| gtgcataccc | aggccctgcg | caccaaggcc | aaggatgccg | tgcttctacg | cgctgtcgac | 360 |
| gccgaaggcg | tcccccttgc | gcacttggac | aagcaggcca | taaccgagct | gattgccacg | 420 |
| ctggaagatc | accgatacct | cagtgattac | cttgacctgc | acctgaaaac | ctcggcgtat | 480 |
| gcacagcagc | tcaagcggtc | agaaaaagcc | atgttgcaag | ctcagatgaa | gatggcgctg | 540 |
| ctggagatcg | agcaacaggc | ttttgcacca | gccggtcgcg | agtggatcaa | ggctgtgctg | 600 |
| gattcgccag | cccccaagg | acgtcgaacc | atggcagggg | aaagcattga | agtccgtttt | 660 |
| ttcagcgtca | accaattcaa | gatgaccaat | gtcatgctga | ttgctccagc | cggtaaattc | 720 |
| gagaagggc | cgctggtgct | tgcacgctg | atgcttccg | acggtgtggt | tttccgctgg | 780 |
| tttaacagca | tgtatcacct | gaccaccagc | tttctggaag | aggcacccttt | ccagcagtat | 840 |
| ctgattcagc | aaataccggt | ttccaggcgt | cttgagacgc | tgcatgccat | gcagtacgaa | 900 |
| aaggaagcca | agcattggcg | tccgccagaa | gtattcaccc | aactgacgct | gctaccgatc | 960 |
| ccgtcaaggc | tgctgcgccc | agtcgtgttt | gtcagccaga | gcaaagacat | ttacgaggaa | 1020 |
| aatcacgaga | ccaagatcaa | ccatctgatc | aacgaagcca | aacggcagat | gagcctgtcc | 1080 |
| accggtacag | gcaatcgggg | tcggggcttc | gatctgatcg | cgagcattgc | gattctgttt | 1140 |
| ctgcctggcg | cgatcatgat | gcctgtctcg | ctgggcgctg | gcctttacaa | acctggagc | 1200 |
| gcttttcga | aaatcgatga | aaacgacctg | gaaggtgccg | ccgaggagtt | tctgagcgcc | 1260 |
| ctcagctatc | ttgccattac | cttggtcggc | catttggcgc | tggccttgaa | accggcagga | 1320 |
| agcgccgcaa | aaacggtgag | acgtccgcac | ctggtacgca | gagtcggtcg | tgatgggcag | 1380 |
| gcacagatcg | gctacctcct | gtcgcattca | aaagcgccg | gtttcccaga | ctcgaaattg | 1440 |
| atcgctgcaa | tggaccccaa | acgcttcgtc | gccattgagg | tagaaggcca | gacctgctta | 1500 |
| ataagccggc | gggccaacct | gttcggccac | tcacgccttt | atcgggtaaa | cccgatggat | 1560 |
| gcaacgcaac | tggtgcacga | gcaggagttt | gccttgcgca | gcaccaacgg | cacctggaaa | 1620 |
| atcgtgggca | aacagatcct | gcgcatgagt | cagtccgcaa | tccgcaatgc | ccaggctcaa | 1680 |
| ctgaccagcc | tgacaaatct | ctggccggcg | tctctggagg | aagcaagtag | cgccgaacgc | 1740 |
| ttgagcttcg | agaccgacta | cctggcgctg | cccagacat | ccaacgcaga | aaactattcc | 1800 |
| gaaatagtcg | cctacgtgga | aagcggttca | acagacatca | cccgctgct | gcgaagcggc | 1860 |
| gtgcgcaacg | ccaccacgcg | cagatttta | cgtcagttcc | ataaactcaa | tgcgtgggaa | 1920 |
| ggcactgcct | ttcgcgccac | ctatgtgtcc | agcgacgggg | tggcatgcct | tgagcgcgaa | 1980 |

-continued

```
gtgggttcgg tgttcaccga caacggcgtg cagtctgcat cggtgtcgcg agccaatgcc    2040
tccagatgga gccaggacgg gttcgtgagc agcaacgcca atgccgcaaa ccacccggtg    2100
ttcttcatct ttgcaccggg agtgcccaag aagaacatgt tcaccggctt tcttggcgat    2160
cacgtggcaa tcccgccagg cacgtgcgtg caactgggtg cgaccaagcg ataaacgga     2220 cagctgtttg cctggttcga tgcgcccgaa caaatggtcg atcagaccta cgatctctat    2280
acaggagaac aggaactctg ggtctga                                         2307
```

<210> SEQ ID NO 88
<211> LENGTH: 768
<212> TYPE: PRT
<213> ORGANISM: Pseudomonas syringae pv. tomato DC3000

<400> SEQUENCE: 88

```
Met Thr Leu Thr Gln Arg Gln Ala Trp His Arg Glu Ala Gln Arg Phe
  1               5                  10                  15

Gly Glu Gln Val Val Asn Met Arg Lys Ala Ser Lys Glu His Phe Gly
                 20                  25                  30

Gln Ala Glu Asn Asp Ser Arg Thr Tyr Pro Ala Arg Phe Ile Asp Gln
             35                  40                  45

Gln Leu Ala Gln Leu Leu Asn Arg Leu Ser Ile Ala Ala Thr Ala Gln
         50                  55                  60

Gln Ile Asn Ile Ser Leu Thr Tyr Arg Thr Gly Thr Glu Val Leu Glu
     65                  70                  75                  80

Ile Pro Gly Ala Pro Val Leu Pro Glu Thr Glu Thr Glu Asn Val Ser
                 85                  90                  95

Leu Arg Gln Leu Val His Thr Gln Ala Leu Arg Thr Lys Ala Lys Asp
            100                 105                 110

Ala Val Leu Leu Arg Ala Val Asp Ala Glu Gly Val Pro Leu Ala His
        115                 120                 125

Leu Asp Lys Gln Ala Val Thr Glu Leu Ile Ala Thr Leu Glu Asp His
    130                 135                 140

Arg Tyr Leu Ser Asp Tyr Leu Asp Leu His Leu Lys Thr Ser Ala Tyr
145                 150                 155                 160

Ala Gln Gln Leu Lys Arg Ser Glu Lys Ala Met Leu Gln Ala Gln Met
                165                 170                 175

Lys Met Ala Leu Leu Glu Ile Glu Gln Gln Ala Phe Ala Pro Ala Gly
            180                 185                 190

Arg Glu Trp Ile Lys Ala Val Leu Asp Ser Pro Ala Pro Gln Gly Arg
        195                 200                 205

Arg Thr Met Ala Gly Glu Ser Ile Glu Val Arg Phe Phe Ser Val Asn
    210                 215                 220

Gln Phe Lys Met Thr Asn Val Met Leu Ile Ala Pro Ala Gly Lys Phe
225                 230                 235                 240

Glu Lys Gly Pro Leu Val Leu Cys Thr Leu Asp Ala Ser Asp Gly Val
                245                 250                 255

Val Phe Arg Trp Phe Asn Ser Met Tyr His Leu Thr Thr Ser Phe Leu
            260                 265                 270

Glu Glu Ala Pro Phe Gln Gln Tyr Leu Ile Gln Ile Pro Val Ser
        275                 280                 285

Arg Arg Leu Glu Thr Leu His Ala Met Gln Tyr Glu Lys Glu Ala Lys
    290                 295                 300

His Trp Arg Pro Pro Glu Val Phe Thr Gln Leu Thr Leu Leu Pro Ile
305                 310                 315                 320
```

```
Pro Ser Arg Leu Leu Arg Pro Val Val Phe Val Ser Gln Ser Lys Asp
            325                 330                 335

Ile Tyr Glu Glu Asn His Glu Thr Lys Ile Asn His Leu Ile Asn Glu
            340                 345                 350

Ala Lys Arg Gln Met Ser Leu Ser Thr Gly Thr Gly Gln Ser Gly Arg
            355                 360                 365

Gly Phe Asp Leu Ile Ala Ser Ile Ala Ile Leu Phe Leu Pro Gly Ala
    370                 375                 380

Ile Met Met Pro Val Ser Leu Gly Ala Gly Leu Tyr Lys Thr Trp Ser
385                 390                 395                 400

Ala Phe Ser Lys Ile Asp Glu Asn Asp Leu Glu Gly Ala Ala Glu Glu
                405                 410                 415

Phe Leu Ser Ala Leu Ser Tyr Leu Ala Ile Thr Leu Val Gly His Leu
            420                 425                 430

Ala Leu Ala Leu Lys Pro Ala Gly Ser Ala Ala Lys Thr Val Arg Arg
            435                 440                 445

Pro His Leu Val Arg Arg Val Gly Arg Asp Gly Gln Ala Gln Ile Gly
    450                 455                 460

Tyr Leu Leu Ser His Ser Lys Ala Pro Arg Phe Pro Asp Ser Lys Leu
465                 470                 475                 480

Ile Ala Ala Met Asp Pro Lys Arg Phe Val Ala Ile Glu Val Glu Gly
                485                 490                 495

Gln Thr Cys Leu Ile Ser Arg Arg Ala Asn Leu Phe Gly His Ser Arg
            500                 505                 510

Leu Tyr Arg Val Asn Pro Met Asp Ala Thr Gln Leu Val His Glu Gln
            515                 520                 525

Glu Phe Ala Leu Arg Ser Thr Asn Gly Thr Trp Lys Ile Val Gly Lys
    530                 535                 540

Gln Ile Leu Arg Met Ser Gln Ser Ala Ile Arg Asn Ala Gln Ala Gln
545                 550                 555                 560

Leu Thr Ser Leu Thr Asn Leu Trp Pro Ala Ser Leu Glu Glu Ala Ser
                565                 570                 575

Ser Ala Glu Arg Leu Ser Phe Glu Thr Asp Tyr Leu Ala Leu Ala Gln
            580                 585                 590

Thr Ser Asn Ala Glu Asn Tyr Ser Glu Ile Val Ala Tyr Val Glu Ser
            595                 600                 605

Gly Ser Thr Asp Ile Asn Pro Leu Leu Arg Ser Gly Val Arg Asn Ala
    610                 615                 620

Thr Thr Arg Arg Phe Leu Arg Gln Phe His Lys Leu Asn Ala Trp Glu
625                 630                 635                 640

Gly Thr Ala Phe Arg Ala Thr Tyr Val Ser Ser Asp Gly Val Ala Cys
                645                 650                 655

Leu Glu Arg Glu Val Gly Ser Val Phe Thr Asp Asn Gly Val Gln Ser
            660                 665                 670

Ala Ser Val Ser Arg Ala Asn Ala Ser Arg Trp Ser Gln Asp Gly Phe
            675                 680                 685

Val Ser Ser Asn Ala Asn Ala Ala Asn His Pro Val Phe Phe Ile Phe
    690                 695                 700

Ala Pro Gly Val Pro Lys Lys Asn Met Phe Thr Gly Phe Leu Gly Asp
705                 710                 715                 720

His Val Ala Ile Pro Pro Gly Thr Cys Val Gln Leu Gly Ala Thr Lys
                725                 730                 735
```

| Arg | Ile | Asn | Gly | Gln | Leu | Phe | Ala | Trp | Phe | Asp | Ala | Pro | Glu | Gln | Met |
|---|---|---|---|---|---|---|---|---|---|---|---|---|---|---|---|
| | | | | 740 | | | | | 745 | | | | | 750 | |

| Val | Asp | Gln | Thr | Tyr | Asp | Leu | Tyr | Thr | Gly | Glu | Gln | Glu | Leu | Trp | Val |
|---|---|---|---|---|---|---|---|---|---|---|---|---|---|---|---|
| | | | | 755 | | | | | 760 | | | | | 765 | |

<210> SEQ ID NO 89
<211> LENGTH: 2745
<212> TYPE: DNA
<213> ORGANISM: Pseudomonas syringae pv. tomato DC3000

<400> SEQUENCE: 89

| | |
|---|---|
| atgactcagc taaaccctgc gggacaaccg cccgcagaac cgacccgaat cgtcaaagct | 60 |
| cacattgacc tcatggatcc tgccgaaagc gctgactacg aggcgacccg aatggcattg | 120 |
| ctcgcagcga tgcaaagcgg caatgccgcg atcaacctcg aacagattcg gctcaagccc | 180 |
| gacccagcgt ccgggttcgg cgaatactgc gctgagaaag ctgcgctacc tcacccggtc | 240 |
| caggccgaaa accaggaact cccgtttcag atagacagcg atggcagcgt cagtctggca | 300 |
| ttgatgctgc gctataacta cgggttgtcg ctgccgcaat cgcctgacga acagcgatc | 360 |
| aaaaccctgc tcaatacgct ggcagaactt cgcaccagtc aagaactggg gcttattgat | 420 |
| cagttcgaca tcaaggccat gctgaccatg caaaatctgc aggatctgaa gcgagcctgc | 480 |
| attgagtacc ttggcaccga cggtggcacg ctgctaggca agctgggtgc tgaaataatt | 540 |
| gcctcctgcc cactggcaga tgtgcagaac tccccggtga cggttattgc ccggattctc | 600 |
| agatcggaac cggcaagggc attggggcaa acgctgctgg cacagcttgg tcggcctgaa | 660 |
| gaagaaacgg acgcgtccct gacaacactc gtggaccgga ttttatggta tgccatcagt | 720 |
| agcgatcttc atgatccaga aaaccggaag ccaggagaaa ttgccggcta tccattcacc | 780 |
| caggccgaaa accagggacg ccgccacgct gacatcctga cgatattca aaccacctg | 840 |
| atcaccacgg gcaaggctga gtctgtcaac gaagcaataa ttgcctgctt catacttgca | 900 |
| ctcgatgact gcccggaatg gctggtcagc agtgttcccg atgatctgcc atacggctgt | 960 |
| acagaggtgt gggtcaactt caacatgggg tcacacttg cggaagtcat cgagtttggc | 1020 |
| tcgtcacgct ggatgaactt tgaagacctg atcgagctgc cggtgatttt caacaaaaag | 1080 |
| atggacaccg aagagcagca agtcgcctat gtcgcaacgc gcatgcccat tcttctgact | 1140 |
| tgggcccagg ccaacggtta cattcgtacc cagagcgacc tgccttactc cgaacaagag | 1200 |
| atagaacagg ccgccagcgc gtttgaacac tccgagaaac aatcccttga agctgcgaac | 1260 |
| gccttgatcc ggaaagcgcc agaacgcaaa gccatggcta tcagtgccat gaagaagcg | 1320 |
| cggaggacgc ctgaaataga aaaatactt gagcaggaag attactggtt tccgcccatc | 1380 |
| gatctcggca tcaggctggc ggtgctacgc aaaaatcaca cgcctgtcta tcgcgatcac | 1440 |
| caaggcacgc tctcaccgtc aaatctgcca tacgacccct acggcataaa acacaaggcg | 1500 |
| tcgtcgttgc tggagatcta catggcaggt gaaaacattg atgactggag actgccgggg | 1560 |
| cgcaacagca acgagggcct gcttcccatc aaccgtgaaa tgcagttgtt gtacaaggcg | 1620 |
| ctgccagaca tcaatcaaag gttcgagagt gaatttcagg cttatctggc agatgcccgt | 1680 |
| aaggcgtatg cgacgattat cagaaagttg ctgactcacc tgccgctcaa gcaccgcatg | 1740 |
| gcgatcgaaa atggtgaggt gtcgctacac tcactcagat gccgaccaa ggacgtgctg | 1800 |
| gcggcgacag agagcgaaaa acatcgggag ccgttgcgag gcgcacggg ctttgtcatc | 1860 |
| aaagctgtct acgagggcaa aaccacgttt tacgaggtgt ttccgttatc gatgattgta | 1920 |
| cgctatcgcc ctgatctgga ggcccttctc aagaacggtg tggtcggtat agattttgg | 1980 |

-continued

```
gacattctgc ctcccacccg tataccggta gcggtttata acggaatcac aatgccattt    2040
gatcagggag cctatttgaa cggtcagcta cctgagcctg gggcaagcgc tgtgatgatt    2100
gcagaaacca ttggtgaacg atttgattct tcaagtgcag aggtcgggca acaccagcct    2160
ccgacctcgt tttcaaaacg ctctactggc attgccgaga ccatcacaac atcgcttttc    2220
tacgtcaacg aagatgcact ctttgcacac tgcaaaagcc tcacgcaggt agaaatagat    2280
aacggtgccc aggtgcgct cgaagaggtg tccagctttc tgatacacct gacgccctgg     2340
ccggaaatcg aaaacattct gtccggagag aaagcgctta tgaggggagg agcaatcggt    2400
ctggcgcttt acatgattcc ctatgtggga cccgcgggca gttgctcgc aggcacggca     2460 aaagtcgtta cccgcctggg caaaagcctc ataaccagcg gtagcaaagt ccaggtctcg    2520
aaattgctca tcacggccgg caccaccctg aaagacgccc cgctgatcat gatcagacag    2580
gcccctgaca tgaccagtaa agcaatgact ggcgtttcgc aattcgtcgt gaaacacgtc    2640
acctggaaat ttctggcgat acgtataggt attggtttaa gccgcaggct tgtagccatc    2700
atgagcaggc agcaggccca ggccgcaaag caagaggcca cgtaa                    2745
```

<210> SEQ ID NO 90
<211> LENGTH: 914
<212> TYPE: PRT
<213> ORGANISM: Pseudomonas syringae pv. tomato DC3000

<400> SEQUENCE: 90

```
Met Thr Gln Leu Asn Pro Ala Gly Gln Pro Ala Glu Pro Thr Arg
 1               5                  10                  15

Ile Val Lys Ala His Ile Asp Leu Met Asp Pro Ala Glu Ser Ala Asp
                20                  25                  30

Tyr Glu Ala Thr Arg Met Ala Leu Leu Ala Ala Met Gln Ser Gly Asn
            35                  40                  45

Ala Ala Ile Asn Leu Glu Gln Ile Arg Leu Lys Pro Asp Pro Ala Ser
        50                  55                  60

Gly Phe Gly Glu Tyr Cys Ala Glu Lys Ala Ala Leu Pro His Pro Val
 65                  70                  75                  80

Gln Ala Glu Asn Gln Glu Leu Pro Phe Gln Ile Asp Ser Asp Gly Ser
                 85                  90                  95

Val Ser Leu Ala Leu Met Leu Arg Tyr Asn Tyr Gly Leu Ser Leu Pro
            100                 105                 110

Gln Ser Pro Asp Glu Thr Ala Ile Lys Thr Leu Leu Asn Thr Leu Ala
        115                 120                 125

Glu Leu Arg Thr Ser Gln Glu Leu Gly Leu Ile Asp Gln Phe Asp Ile
    130                 135                 140

Lys Ala Met Leu Thr Met Gln Asn Leu Gln Asp Leu Lys Arg Ala Cys
145                 150                 155                 160

Ile Glu Tyr Leu Gly Thr Asp Gly Thr Leu Gly Lys Leu Gly
                165                 170                 175

Ala Glu Ile Ile Ala Ser Cys Pro Leu Ala Asp Val Gln Asn Ser Pro
            180                 185                 190

Val Thr Val Ile Ala Arg Ile Leu Arg Ser Glu Pro Ala Arg Ala Leu
        195                 200                 205

Gly Gln Thr Leu Leu Ala Gln Leu Gly Arg Pro Glu Glu Thr Asp
    210                 215                 220

Ala Ser Leu Thr Thr Leu Val Asp Arg Ile Leu Trp Tyr Ala Ile Ser
225                 230                 235                 240
```

```
Ser Asp Leu His Asp Pro Glu Asn Arg Lys Pro Gly Glu Ile Ala Gly
            245                 250                 255

Tyr Pro Phe Thr Gln Ala Glu Asn Gln Gly Arg Arg His Ala Asp Ile
            260                 265                 270

Leu Asn Asp Ile His Asn His Leu Ile Thr Thr Gly Lys Ala Glu Ser
            275                 280                 285

Val Asn Glu Ala Ile Ile Ala Cys Phe Ile Leu Ala Leu Asp Asp Cys
290                 295                 300

Pro Glu Trp Leu Val Ser Ser Val Pro Asp Asp Leu Pro Tyr Gly Cys
305                 310                 315                 320

Thr Glu Val Trp Val Asn Phe Gln His Gly Val Thr Leu Ala Glu Val
                325                 330                 335

Ile Glu Phe Gly Ser Ser Arg Trp Met Asn Phe Glu Asp Leu Ile Glu
            340                 345                 350

Leu Pro Val Ile Phe Asn Lys Lys Met Asp Thr Glu Gln Gln Val
            355                 360                 365

Ala Tyr Val Ala Thr Arg Met Pro Ile Leu Leu Thr Trp Ala Gln Ala
        370                 375                 380

Asn Gly Tyr Ile Arg Thr Gln Ser Asp Leu Pro Tyr Ser Glu Gln Glu
385                 390                 395                 400

Ile Glu Gln Ala Ala Ser Ala Phe Glu His Ser Glu Lys Gln Ser Leu
                405                 410                 415

Glu Ala Ala Asn Ala Leu Ile Arg Lys Ala Pro Glu Arg Lys Ala Met
            420                 425                 430

Ala Ile Ser Ala Met Lys Glu Ala Arg Arg Thr Pro Glu Ile Glu Lys
        435                 440                 445

Ile Leu Glu Gln Glu Asp Tyr Trp Phe Pro Ile Asp Leu Gly Ile
    450                 455                 460

Arg Leu Ala Val Leu Arg Lys Asn His Thr Pro Val Tyr Arg Asp His
465                 470                 475                 480

Gln Gly Thr Leu Ser Pro Ser Asn Leu Pro Tyr Asp Pro Tyr Gly Ile
                485                 490                 495

Lys His Lys Ala Ser Ser Leu Leu Glu Ile Tyr Met Ala Gly Glu Asn
            500                 505                 510

Ile Asp Asp Trp Arg Leu Pro Gly Arg Asn Ser Asn Glu Gly Leu Leu
        515                 520                 525

Pro Ile Asn Arg Glu Met Gln Leu Leu Tyr Lys Ala Leu Pro Asp Ile
    530                 535                 540

Asn Gln Arg Phe Glu Ser Glu Phe Gln Ala Tyr Leu Ala Asp Ala Arg
545                 550                 555                 560

Lys Ala Tyr Ala Thr Ile Ile Arg Lys Leu Leu Thr His Leu Pro Leu
                565                 570                 575

Lys His Arg Met Ala Ile Glu Asn Gly Glu Val Ser Leu His Ser Leu
            580                 585                 590

Arg Leu Pro Thr Lys Asp Val Leu Ala Ala Thr Glu Ser Glu Lys His
        595                 600                 605

Arg Glu Pro Leu Arg Gly Arg Thr Gly Phe Val Ile Lys Ala Val Tyr
    610                 615                 620

Glu Gly Lys Thr Thr Phe Tyr Glu Val Phe Pro Leu Ser Met Ile Val
625                 630                 635                 640

Arg Tyr Arg Pro Asp Leu Glu Ala Leu Leu Lys Asn Gly Val Val Gly
                645                 650                 655
```

-continued

```
Ile Asp Phe Trp Asp Ile Leu Pro Pro Thr Arg Ile Pro Val Ala Val
              660                 665                 670
Tyr Asn Gly Ile Thr Met Pro Phe Asp Gln Gly Ala Tyr Leu Asn Gly
          675                 680                 685
Gln Leu Pro Glu Pro Gly Ala Ser Ala Val Met Ile Ala Glu Thr Ile
      690                 695                 700
Gly Glu Arg Phe Asp Ser Ser Ala Glu Val Gly Gln His Gln Pro
705                 710                 715                 720
Pro Thr Ser Phe Ser Lys Arg Ser Thr Gly Ile Ala Glu Thr Ile Thr
                  725                 730                 735
Thr Ser Leu Phe Tyr Val Asn Glu Asp Ala Leu Phe Ala His Cys Lys
              740                 745                 750
Ser Leu Thr Gln Val Glu Ile Asp Asn Gly Ala Pro Gly Ala Leu Glu
          755                 760                 765
Glu Val Ser Ser Phe Leu Ile His Leu Thr Pro Trp Pro Glu Ile Glu
      770                 775                 780
Asn Ile Leu Ser Gly Glu Lys Ala Leu Met Arg Gly Gly Ala Ile Gly
785                 790                 795                 800
Leu Ala Leu Tyr Met Ile Pro Tyr Val Gly Pro Ala Gly Lys Leu Leu
                  805                 810                 815
Ala Gly Thr Ala Lys Val Val Thr Arg Leu Gly Lys Ser Leu Ile Thr
              820                 825                 830
Ser Gly Ser Lys Val Gln Val Ser Lys Leu Leu Ile Thr Ala Gly Thr
          835                 840                 845
Thr Leu Lys Asp Ala Pro Leu Ile Met Ile Arg Gln Ala Pro Asp Met
      850                 855                 860
Thr Ser Lys Ala Met Thr Gly Val Ser Gln Phe Val Val Lys His Val
865                 870                 875                 880
Thr Trp Lys Phe Leu Ala Ile Arg Ile Gly Ile Gly Leu Ser Arg Arg
                  885                 890                 895
Leu Val Ala Ile Met Ser Arg Gln Gln Ala Gln Ala Ala Lys Gln Glu
              900                 905                 910
Ala Thr
```

<210> SEQ ID NO 91
<211> LENGTH: 882
<212> TYPE: DNA
<213> ORGANISM: Pseudomonas syringae pv. tomato DC3000

<400> SEQUENCE: 91

```
atgtctgtta cttcatctgt cctgcgactg tcgcgcctga gcgtgtcgtt atcacttttg     60
ggcatgctgt cgtctgcact gtttgccggc gcggcattcg ccagcgacga gacgcaactg    120
atcgaatccc tcaacgccta ccgtggccag gcgcagcgct gtggcgagca ggtgtccatg    180
gaactgccgc cgctgagcac cgacccgcgt ctggtgctgc cgccagtggg caacctgaac    240
ctgcaacagt cgctgacccg cgcgtcttat ccgatggtca ccgtgcaggc gatcagtctg    300
tccggaccgc gagatgcggc gtcggcgttg aaggcggtgc aggagagttt ctgccgcgtg    360
gtgctggacc gcagttcgt cgatatcggg gtcagccggg acgggcgcga ctggcgcatc    420
gtgctggcgc gctcgctggt ggcatcacgt ctgggtgact ggcaagcaga aggtcagaaa    480
attctggaga tgatcaacac cgcccgtacc caggcgcgtc agtgcggttc gcaatccttc    540
gcggccacta caccgttgag ctggaatcag gtattgggga cggccgcaca aggacactcg    600
caggcaatgg ccaatcagaa cttctttgac cacaaggggc gcgacggccg cacgccgggt    660
```

```
gacagggccg agcttgccgg ctatctgggc cagcagatcg gtgagaatat tgccgcaggc    720
caggacactg cccgcaaggt ggtggacggc tggctggtca gcccgggcca ctgcgcaaac    780
ctgatgaccc ccggttttcg cgagctggga gccgcctacg cgatggaccc caaaagtgac    840
gcggggattt actggacagc catgttcggc acgcagcaat ag                      882
```

<210> SEQ ID NO 92
<211> LENGTH: 293
<212> TYPE: PRT
<213> ORGANISM: Pseudomonas syringae pv. tomato DC3000

<400> SEQUENCE: 92

```
Met Ser Val Thr Ser Val Leu Arg Leu Ser Arg Leu Ser Val Ser
 1               5                  10                  15

Leu Ser Leu Leu Gly Met Leu Ser Ser Ala Leu Phe Ala Gly Ala Ala
                20                  25                  30

Phe Ala Ser Asp Glu Thr Gln Leu Ile Glu Ser Leu Asn Ala Tyr Arg
            35                  40                  45

Gly Gln Ala Gln Arg Cys Gly Glu Gln Val Ser Met Glu Leu Pro Pro
        50                  55                  60

Leu Ser Thr Asp Pro Arg Leu Val Leu Pro Ala Ser Gly Asn Leu Asn
65                  70                  75                  80

Leu Gln Gln Ser Leu Thr Arg Ala Ser Tyr Pro Met Val Thr Val Gln
                85                  90                  95

Ala Ile Ser Leu Ser Gly Pro Arg Asp Ala Ala Ser Ala Leu Lys Ala
            100                 105                 110

Val Gln Glu Ser Phe Cys Arg Val Val Leu Asp Pro Gln Phe Val Asp
        115                 120                 125

Ile Gly Val Ser Arg Asp Gly Arg Asp Trp Arg Ile Val Leu Ala Arg
    130                 135                 140

Ser Leu Val Ala Ser Arg Leu Gly Asp Trp Gln Ala Glu Gly Gln Lys
145                 150                 155                 160

Ile Leu Glu Met Ile Asn Thr Ala Arg Thr Gln Ala Arg Gln Cys Gly
                165                 170                 175

Ser Gln Ser Phe Ala Ala Thr Thr Pro Leu Ser Trp Asn Gln Val Leu
            180                 185                 190

Gly Thr Ala Ala Gln Gly His Ser Gln Ala Met Ala Gln Asn Phe
        195                 200                 205

Phe Asp His Lys Gly Arg Asp Gly Arg Thr Pro Gly Asp Arg Ala Glu
    210                 215                 220

Leu Ala Gly Tyr Leu Gly Gln Gln Ile Gly Glu Asn Ile Ala Ala Gly
225                 230                 235                 240

Gln Asp Thr Ala Arg Lys Val Val Asp Gly Trp Leu Val Ser Pro Gly
                245                 250                 255

His Cys Ala Asn Leu Met Thr Pro Gly Phe Arg Glu Leu Gly Ala Ala
            260                 265                 270

Tyr Ala Met Asp Pro Lys Ser Asp Ala Gly Ile Tyr Trp Thr Ala Met
        275                 280                 285

Phe Gly Thr Gln Gln
        290
```

<210> SEQ ID NO 93
<211> LENGTH: 1533
<212> TYPE: DNA
<213> ORGANISM: Pseudomonas syringae pv. tomato DC3000

```
<400> SEQUENCE: 93
atgccgttat taaactggtc cagacacatg gttcatttaa cagccatcgg ccttatcagc      60
attccggctg cctatgcagc ggacaccctg acccgcgaca atggcgcagc ggtcggcgac     120
aaccagaact ctcagactgc aggcgcccaa gggcctgtcc tgctgcaaga cgtacagctg     180
ctgcagaagc tgcagcgttt tgatcgcgag cgtatcccgg agcgtgtggt ccacgcacgc     240
ggcactggcg tgaaaggcga attcacgcg tccgccgaca tcagcgacct gagcaaggcg      300
accgtcttca aatcgggtga agacccccg gtattcgtac gtttttcttc cgtggtccac      360
ggcaaccact cgccagaaac cctgcgcgac ccgcatggct cgccaccaa gttctacacc      420 gctgatggca actgggacct ggtaggcaac aacttcccga cgttcttcat ccgcgacgcc     480
atcaagttcc cggacatggt gcacgccttc aagcctgacc cgcgtaccaa cctggacaac     540
gactcgcgcc gcttcgactt cttctcgcat gtaccggaag ccacgcgcac gctgaccctg     600
ctgtactcca acgaaggcac accgaccggc tatcgcttca tggacggcaa cggcgttcac     660
gcctacaaac tggtcaacgc caaaggcgaa gtgcactacg tcaagttcca ctggaagacg     720
ctgcaaggca tcaagaacct cgaccctaaa gaagtcgctc aggttcagtc caaggactac     780
agccacctga ccaacgacct ggtcggcgcc atcaagaagg gtgacttccc gaaatgggac     840
ctgtacatcc aggtgctgaa acctgaagac ctggccaagt cgacttcga cccgctggac      900 gccaccaaaa tctggcctga tgtgccagag aagaaaatcg ccagatggt cctgaacaag      960 aacgtcgaca cttcttcca ggaaaccgag caggtcgcca tggcacccgc caacctggtc     1020
cctggtatcg agccttccga agaccgtctg ctgcaaggtc gagtgttctc ctatgccgac    1080
acgcaaatgt atcgcctggg tgccaacggc ctgagcctgc cggtcaacca gccaaaggtt    1140
gcagtgaaca acggcaatca ggatggcgcg atgaacagcg gcaaaaccac cagcggcgtg    1200
aactacgagc ctagccgtct ggaacccgt cctgccgatg agaaagcacg ttacagcgag     1260
ctgccaatca gcggcactac ccagcaggcg aagatcacgc gtgagcagaa cttcaagcag    1320
gcgggtgatc tgtatcgctc ttacaacgcg aaagagcaga ccgacctggt gcagagcttc    1380
ggtgaatcgc tggccgacac tgacaccgaa agcaagaaca tcatgctgtc gttcctctac    1440
aaggcagacc ccaccatgg cactcgggta accgaagcgg ccaaaggcga tctggccaag    1500
gtcaagtcac tggctgccag cctgaaagac tga                               1533

<210> SEQ ID NO 94
<211> LENGTH: 510
<212> TYPE: PRT
<213> ORGANISM: Pseudomonas syringae pv. tomato DC3000

<400> SEQUENCE: 94

Met Pro Leu Leu Asn Trp Ser Arg His Met Val His Leu Thr Ala Ile
  1               5                  10                  15

Gly Leu Ile Ser Ile Pro Ala Ala Tyr Ala Ala Asp Thr Leu Thr Arg
                 20                  25                  30

Asp Asn Gly Ala Ala Val Gly Asp Asn Gln Asn Ser Gln Thr Ala Gly
             35                  40                  45

Ala Gln Gly Pro Val Leu Leu Gln Asp Val Gln Leu Leu Gln Lys Leu
         50                  55                  60

Gln Arg Phe Asp Arg Glu Arg Ile Pro Glu Arg Val His Ala Arg
 65                  70                  75                  80

Gly Thr Gly Val Lys Gly Glu Phe Thr Ala Ser Ala Asp Ile Ser Asp
                 85                  90                  95
```

```
Leu Ser Lys Ala Thr Val Phe Lys Ser Gly Glu Lys Thr Pro Val Phe
            100                 105                 110

Val Arg Phe Ser Ser Val Val His Gly Asn His Ser Pro Glu Thr Leu
            115                 120                 125

Arg Asp Pro His Gly Phe Ala Thr Lys Phe Tyr Thr Ala Asp Gly Asn
            130                 135                 140

Trp Asp Leu Val Gly Asn Asn Phe Pro Thr Phe Phe Ile Arg Asp Ala
145                 150                 155                 160

Ile Lys Phe Pro Asp Met Val His Ala Phe Lys Pro Asp Pro Arg Thr
                165                 170                 175

Asn Leu Asp Asn Asp Ser Arg Arg Phe Asp Phe Ser His Val Pro
            180                 185                 190

Glu Ala Thr Arg Thr Leu Thr Leu Leu Tyr Ser Asn Glu Gly Thr Pro
            195                 200                 205

Thr Gly Tyr Arg Phe Met Asp Gly Asn Gly Val His Ala Tyr Lys Leu
            210                 215                 220

Val Asn Ala Lys Gly Glu Val His Tyr Val Lys Phe His Trp Lys Thr
225                 230                 235                 240

Leu Gln Gly Ile Lys Asn Leu Asp Pro Lys Glu Val Ala Gln Val Gln
            245                 250                 255

Ser Lys Asp Tyr Ser His Leu Thr Asn Asp Leu Val Gly Ala Ile Lys
            260                 265                 270

Lys Gly Asp Phe Pro Lys Trp Asp Leu Tyr Ile Gln Val Leu Lys Pro
            275                 280                 285

Glu Asp Leu Ala Lys Phe Asp Phe Asp Pro Leu Asp Ala Thr Lys Ile
            290                 295                 300

Trp Pro Asp Val Pro Glu Lys Lys Ile Gly Gln Met Val Leu Asn Lys
305                 310                 315                 320

Asn Val Asp Asn Phe Phe Gln Glu Thr Glu Gln Val Ala Met Ala Pro
                325                 330                 335

Ala Asn Leu Val Pro Gly Ile Glu Pro Ser Glu Asp Arg Leu Leu Gln
            340                 345                 350

Gly Arg Val Phe Ser Tyr Ala Asp Thr Gln Met Tyr Arg Leu Gly Ala
            355                 360                 365

Asn Gly Leu Ser Leu Pro Val Asn Gln Pro Lys Val Ala Val Asn Asn
370                 375                 380

Gly Asn Gln Asp Gly Ala Met Asn Ser Gly Lys Thr Thr Ser Gly Val
385                 390                 395                 400

Asn Tyr Glu Pro Ser Arg Leu Glu Pro Arg Pro Ala Asp Glu Lys Ala
            405                 410                 415

Arg Tyr Ser Glu Leu Pro Ile Ser Gly Thr Thr Gln Gln Ala Lys Ile
            420                 425                 430

Thr Arg Glu Gln Asn Phe Lys Gln Ala Gly Asp Leu Tyr Arg Ser Tyr
            435                 440                 445

Asn Ala Lys Glu Gln Thr Asp Leu Val Gln Ser Phe Gly Glu Ser Leu
450                 455                 460

Ala Asp Thr Asp Thr Glu Ser Lys Asn Ile Met Leu Ser Phe Leu Tyr
465                 470                 475                 480

Lys Ala Asp Pro Thr Tyr Gly Thr Arg Val Thr Glu Ala Ala Lys Gly
            485                 490                 495

Asp Leu Ala Lys Val Lys Ser Leu Ala Ala Ser Leu Lys Asp
            500                 505                 510
```

<210> SEQ ID NO 95
<211> LENGTH: 489
<212> TYPE: DNA
<213> ORGANISM: Pseudomonas syringae pv. tomato DC3000

<400> SEQUENCE: 95

| | | |
|---|---|---|
| atgggggttt cgagctgcgg caaaagtgcc gtcggtgcag aaatcgcccg taacagcggc | 60 |
| ggtcgcctga tcgaaggcga tgcgttccat ccccaggcca acatcgacaa gatgagcgcc | 120 |
| ggcaccccc tcaccgacga agaccgtgcc ggctggctga cccgtctggg tgaagaactg | 180 |
| gccgcagccc ttgccaaggg cgaacatccg gtgctgacct gttcggcact caagctcatt | 240 |
| tatcgtgaac gcctgcgtgc ggcggtgccg ggcctgggtt ttgtctttct cgaactgagc | 300 |
| aaagagctgg ccaccgagcg ttgcgccaac cggaccgggc atttcatgcc tgcgagtctg | 360 |
| gtcgatagcc agttcgcgac cctggaacca ccgatcggcg agccactgac cctggtggtc | 420 |
| gatgccagca agcctatcga tgtaattggt gaacaagccg cggcatggtg gaaaggctct | 480 |
| cacgcctga | 489 |

<210> SEQ ID NO 96
<211> LENGTH: 162
<212> TYPE: PRT
<213> ORGANISM: Pseudomonas syringae pv. tomato DC3000

<400> SEQUENCE: 96

Met Gly Val Ser Ser Cys Gly Lys Ser Ala Val Gly Ala Glu Ile Ala
1               5                   10                  15
Arg Asn Ser Gly Gly Arg Leu Ile Glu Gly Asp Ala Phe His Pro Gln
            20                  25                  30
Ala Asn Ile Asp Lys Met Ser Ala Gly Thr Pro Leu Thr Asp Glu Asp
        35                  40                  45
Arg Ala Gly Trp Leu Thr Arg Leu Gly Glu Glu Leu Ala Ala Ala Leu
    50                  55                  60
Ala Lys Gly Glu His Pro Val Leu Thr Cys Ser Ala Leu Lys Leu Ile
65                  70                  75                  80
Tyr Arg Glu Arg Leu Arg Ala Ala Val Pro Gly Leu Gly Phe Val Phe
                85                  90                  95
Leu Glu Leu Ser Lys Glu Leu Ala Thr Glu Arg Cys Ala Asn Arg Thr
            100                 105                 110
Gly His Phe Met Pro Ala Ser Leu Val Asp Ser Gln Phe Ala Thr Leu
        115                 120                 125
Glu Pro Pro Ile Gly Glu Pro Leu Thr Leu Val Val Asp Ala Ser Lys
    130                 135                 140
Pro Ile Asp Val Ile Gly Glu Gln Ala Ala Ala Trp Trp Lys Gly Ser
145                 150                 155                 160
His Ala

<210> SEQ ID NO 97
<211> LENGTH: 3405
<212> TYPE: DNA
<213> ORGANISM: Pseudomonas syringae pv. tomato DC3000

<400> SEQUENCE: 97

| | | |
|---|---|---|
| atgcgaccgg tgtctatgtt ttccctgcgt tccatttgtg ctgccgcact gtttgcgctt | 60 |
| tgcctgtcta tcttcccggc gctggccgcc gagccgccca ccgcgatgc cgtgcagcaa | 120 |
| agcctcgaca gattgccga ccgcaagctg ccggatgccg atcagaaggc cttgcagcag | 180 |
| gtgcttgagc agacgctggc gtttctcaac agcaaagacg acagcgagca aaagctgacc | 240 |

-continued

```
gcgctcaagc agcagctggc tcaagcgcca aaacagacct cggacaacca gcgcgagctg      300
gcccggttga agaaagcaa agtcgttgcc gttgcacagc gctacggtgg cctcgatgtg      360
ccgcaactgg agcaactgct cagccagcgc agcacccagc aaagtgatct gcaaagcgag     420
cttaacgacg ccaacagcct ggccatcacc gcgcaaaccc ggccggagcg ggcgcagact     480
gaaatcagcg ccaatcagac acgcatccag cagatcaatg ccatcctcaa gaatggcaaa     540
gacaacggca agaccctgag tgccgatcag cgcaatctgc tcaatgcgga actggcctcg     600
atcaacgcgc tgaacctgct gcgccgtcag gaactggccg gcaacagcca gttacaggac     660
ctgggcaaca gccagcacga cttgctgacc gaaaagtcg cccgccagga gcaggaaatt      720
caggacctgc aaaccctgat caacgacaag cgccgagccc agtcgcagaa accgtggcg      780 gacctgtctc tggaagcgca gaaatccggt ggcagcagcc tcctggcgac cgagagcgcc     840
gccaacctca agctgtccga ttacctgctg cgcggcaccg accgtctcaa cgagctgacc     900
cagcaaaacc tcaagaccaa gcagcaactg acaaccctga cgcagaccga tcaagccctc     960
agcgagcaga tcaacgtgct gagcggcagc ctgctgctgt ccaagattct ctacaagcaa    1020
aaacagtcgt tgccgcacct ggaactggac aaaggcctgg ctgacgaaat cgccaacatc    1080
cgcctttatc agttcgacat caatcagcaa cgcgagcaga tgagcacacc gaccgcttac    1140
gtcgaacgac tgctcgccac ccagcccccg gaaaatatca ccccgcaact gcgcaggacg    1200
ctgcttgatc tggccatcac ccgcagcgac ctgctcgaac gcctgaaccg cgagctgagc    1260
gcgttgctca cgagtccat cacgctgcaa ttgaaccaga agcagttgac cagtaccgcc     1320
gtcggcctgc gctccacgct ggacgagcag atgttctgga tccccagcaa caagccgctg    1380
gatctggagt ggttccagaa catctggccg cgcctgcaaa acaggtcgc gaccctgccc      1440 tggacgtcca gcctcagcga gctgtcggac ggcttgacac aacgcccgct gctgtttctg    1500
ccattgttac tgctgatcgg tgtactgacc tggaggcgca aggcgcttta ccagaagctc    1560
aaccggctgc acgccgacat cggccacttc aaacgcgaca gtcagtggaa aaccccgttg    1620
gcgctgctga tcaacgtgct gctggccatg ccggtcgcat tggggctggc gctgtgcggc    1680
tacgccttgc aaatcgatgc gcgcgggcaa aacgccaacc ttggcgaggc cttgctgcag    1740
atcgcgctgg cctggctagt gttctacacc gcctaccgcg tgctggcccc gtccggcgtt    1800
gcgcaactgc actttcgctg ggaaccggcg caggtcgcgt tcttgcgcgg ctgggttcgt    1860
cgcctggggt tggtggtgct ggcgctggtc gccgtggtgg cggtcgccga gcatcaaccg    1920
gccgcgctgg ccgacgacgt gctgggtatc ggcgtggtgc tgacctgtta cgcgctgatg    1980
acctggctgc tgggccgatt gctgctctcc agccctacgc accacaacgc gtcgctgttc    2040
cgcaagacgc tgggtgtggc gttcacggca ttgccggtcg cgctgtttct ggcggtgtgc    2100
ttcggctact actacaccgc actcaagctc agcgaccgtc tgatcgacac gctgtacctg    2160
atgatgatct ggctgatggt cgaggccacc ttcgttcgtg gtctgggcgt tgccgcgcgg    2220
cgactggcct accagcgtgc gctggccaaa cgtcaggctg cgcgagaaaa cggtgacagc    2280
gacatccccg tcgaagaacc gaaactggac atcaacagg tcaaccagca gtcgctgcgc     2340
ctgattcgtc tggccttgct ggctggtttc gtcggcgcgt tgtacctggt ctgggccgag    2400
ctgatcacgg tgttcgccta cctggacaac atcatcctct acgaatacac aagcggcaca    2460
ggcgccaaca tgagcatggt gccgatcagc ctgagcgact tcctcggtgc cggggtcatc    2520
atcgtcatta cctttgtgct ggcgggcaac ctgcccggct gctcgaggt gctggttctg     2580 tcacgcatga acctggcgca aggcagcgcc tatgcgacca ccacgctgct ctcctacacc    2640
```

-continued

```
atcgccggca tcggctttgt gaccacgctg tccacattag gcgtgagctg ggacaagctg    2700
cagtggctgg tcgcagcgct gtcggtgggc ctggggttcg gcatgcagga gatcttcgcc    2760
aacttcattt ccggcatcat gatcctcttc gagcgcccgg tacggatcgg cgacaccatc    2820
accatcggcg ccctgtcggg tacggtcagc aagatccgca tccgcgccac gaccatcacc    2880
gacttcgacc gcaaggacat tatcgtcccg aacaagacct tcatcaccgg ccagctcatc    2940
aactggtcac tgactgacac cgtcacccgc gtaacgctca agctgggtgt ggattacggc    3000
tcggacctgg acctcgtgcg ctccctgctg ctgcaagccg cacgggaaaa ccctcgggtg    3060
ctcaaggagc cagagcccat tgtctacttc ctgaacttcg gcgaaagcac cctcgaccac    3120
gaactgcgca tgcacgttcg cgacctgggc gaccgcaacc cggtactcga cgagatcaac    3180
cgcttcatca accgcgagtt caagaaacag cacatcaaca tctcgttccg ccagatggag    3240
atctacctca aaacaccca gggcctggaa tacaaactgg tgcccgccga accaggcgaa    3300
aagcacggcg caccggctgg gcaaaccacg ctgcaaccgg taaacaccaa agtagccccg    3360
gcaaccaaag atgcgccaga gccgccggag ttgaggctgg actga                    3405
```

<210> SEQ ID NO 98
<211> LENGTH: 1134
<212> TYPE: PRT
<213> ORGANISM: Pseudomonas syringae pv. tomato DC3000

<400> SEQUENCE: 98

```
Met Arg Pro Val Ser Met Phe Ser Leu Arg Ser Ile Cys Ala Ala Ala
 1               5                  10                  15

Leu Phe Ala Leu Cys Leu Ser Ile Phe Pro Ala Leu Ala Ala Glu Pro
             20                  25                  30

Pro Thr Arg Asp Ala Val Gln Gln Ser Leu Asp Lys Ile Ala Asp Arg
         35                  40                  45

Lys Leu Pro Asp Ala Asp Gln Lys Ala Leu Gln Val Leu Glu Gln
     50                  55                  60

Thr Leu Ala Phe Leu Asn Ser Lys Asp Asp Ser Glu Gln Lys Leu Thr
 65                  70                  75                  80

Ala Leu Lys Gln Gln Leu Ala Gln Ala Pro Lys Gln Thr Ser Asp Asn
                 85                  90                  95

Gln Arg Glu Leu Ala Arg Leu Lys Glu Ser Lys Val Val Ala Val Ala
            100                 105                 110

Gln Arg Tyr Gly Gly Leu Asp Val Pro Gln Leu Glu Gln Leu Leu Ser
        115                 120                 125

Gln Arg Ser Thr Gln Ser Asp Leu Gln Ser Glu Leu Asn Asp Ala
    130                 135                 140

Asn Ser Leu Ala Ile Thr Ala Gln Thr Arg Pro Glu Arg Ala Gln Thr
145                 150                 155                 160

Glu Ile Ser Ala Asn Gln Thr Arg Ile Gln Gln Ile Asn Ala Ile Leu
                165                 170                 175

Lys Asn Gly Lys Asp Asn Gly Lys Thr Leu Ser Ala Asp Gln Arg Asn
            180                 185                 190

Leu Leu Asn Ala Glu Leu Ala Ser Ile Asn Ala Leu Asn Leu Arg
        195                 200                 205

Arg Gln Glu Leu Ala Gly Asn Ser Gln Leu Gln Asp Leu Gly Asn Ser
    210                 215                 220

Gln His Asp Leu Leu Thr Glu Lys Val Ala Arg Gln Glu Gln Glu Ile
225                 230                 235                 240
```

-continued

```
Gln Asp Leu Gln Thr Leu Ile Asn Asp Lys Arg Arg Ala Gln Ser Gln
                245                 250                 255
Lys Thr Val Ala Asp Leu Ser Leu Glu Ala Gln Lys Ser Gly Gly Ser
            260                 265                 270
Ser Leu Leu Ala Thr Glu Ser Ala Ala Asn Leu Lys Leu Ser Asp Tyr
        275                 280                 285
Leu Leu Arg Gly Thr Asp Arg Leu Asn Glu Leu Thr Gln Gln Asn Leu
    290                 295                 300
Lys Thr Lys Gln Gln Leu Asp Asn Leu Thr Gln Thr Asp Gln Ala Leu
305                 310                 315                 320
Ser Glu Gln Ile Asn Val Leu Ser Gly Ser Leu Leu Ser Lys Ile
                325                 330                 335
Leu Tyr Lys Gln Lys Gln Ser Leu Pro His Leu Glu Leu Asp Lys Gly
                340                 345                 350
Leu Ala Asp Glu Ile Ala Asn Ile Arg Leu Tyr Gln Phe Asp Ile Asn
            355                 360                 365
Gln Gln Arg Glu Gln Met Ser Thr Pro Thr Ala Tyr Val Glu Arg Leu
        370                 375                 380
Leu Ala Thr Gln Pro Pro Glu Asn Ile Thr Pro Gln Leu Arg Arg Thr
385                 390                 395                 400
Leu Leu Asp Leu Ala Ile Thr Arg Ser Asp Leu Leu Glu Arg Leu Asn
                405                 410                 415
Arg Glu Leu Ser Ala Leu Leu Asn Glu Ser Ile Thr Leu Gln Leu Asn
                420                 425                 430
Gln Lys Gln Leu Thr Ser Thr Ala Val Gly Leu Arg Ser Thr Leu Asp
            435                 440                 445
Glu Gln Met Phe Trp Ile Pro Ser Asn Lys Pro Leu Asp Leu Glu Trp
        450                 455                 460
Phe Gln Asn Ile Trp Pro Arg Leu Gln Lys Gln Val Ala Thr Leu Pro
465                 470                 475                 480
Trp Thr Ser Ser Leu Ser Glu Leu Ser Asp Gly Leu Thr Gln Arg Pro
                485                 490                 495
Leu Leu Phe Leu Pro Leu Leu Leu Ile Gly Val Leu Thr Trp Arg
                500                 505                 510
Arg Lys Ala Leu Tyr Gln Lys Leu Asn Arg Leu His Ala Asp Ile Gly
            515                 520                 525
His Phe Lys Arg Asp Ser Gln Trp Lys Thr Pro Leu Ala Leu Leu Ile
        530                 535                 540
Asn Val Leu Leu Ala Met Pro Val Ala Leu Gly Leu Ala Leu Cys Gly
545                 550                 555                 560
Tyr Ala Leu Gln Ile Asp Ala Arg Gly Gln Asn Ala Asn Leu Gly Glu
                565                 570                 575
Ala Leu Leu Gln Ile Ala Leu Ala Trp Leu Val Phe Tyr Thr Ala Tyr
            580                 585                 590
Arg Val Leu Ala Pro Ser Gly Val Ala Gln Leu His Phe Arg Trp Glu
        595                 600                 605
Pro Ala Gln Val Ala Phe Leu Arg Gly Trp Val Arg Arg Leu Gly Leu
    610                 615                 620
Val Val Leu Ala Leu Val Ala Val Ala Val Ala Glu His Gln Pro
625                 630                 635                 640
Ala Ala Leu Ala Asp Asp Val Leu Gly Ile Gly Val Val Leu Thr Cys
                645                 650                 655
```

-continued

```
Tyr Ala Leu Met Thr Trp Leu Leu Gly Arg Leu Leu Leu Ser Ser Pro
            660                 665                 670

Thr His His Asn Ala Ser Leu Phe Arg Lys Thr Leu Gly Val Ala Phe
            675                 680                 685

Thr Ala Leu Pro Val Ala Leu Phe Leu Ala Val Cys Phe Gly Tyr Tyr
            690                 695                 700

Tyr Thr Ala Leu Lys Leu Ser Asp Arg Leu Ile Asp Thr Leu Tyr Leu
705                 710                 715                 720

Met Met Ile Trp Leu Met Val Glu Ala Thr Phe Val Arg Gly Leu Gly
                725                 730                 735

Val Ala Ala Arg Arg Leu Ala Tyr Gln Arg Ala Leu Ala Lys Arg Gln
            740                 745                 750

Ala Ala Arg Glu Asn Gly Asp Ser Asp Ile Pro Val Glu Glu Pro Lys
            755                 760                 765

Leu Asp Ile Glu Gln Val Asn Gln Gln Ser Leu Arg Leu Ile Arg Leu
            770                 775                 780

Ala Leu Leu Ala Gly Phe Val Gly Ala Leu Tyr Leu Val Trp Ala Glu
785                 790                 795                 800

Leu Ile Thr Val Phe Ala Tyr Leu Asp Asn Ile Ile Leu Tyr Glu Tyr
                805                 810                 815

Thr Ser Gly Thr Gly Ala Asn Met Ser Met Val Pro Ile Ser Leu Ser
            820                 825                 830

Asp Phe Leu Gly Ala Gly Val Ile Val Ile Thr Phe Val Leu Ala
            835                 840                 845

Gly Asn Leu Pro Gly Leu Leu Glu Val Leu Val Leu Ser Arg Met Asn
850                 855                 860

Leu Ala Gln Gly Ser Ala Tyr Ala Thr Thr Leu Leu Ser Tyr Thr
865                 870                 875                 880

Ile Ala Gly Ile Gly Phe Val Thr Thr Leu Ser Thr Leu Gly Val Ser
                885                 890                 895

Trp Asp Lys Leu Gln Trp Leu Val Ala Leu Ser Val Gly Leu Gly
                900                 905                 910

Phe Gly Met Gln Glu Ile Phe Ala Asn Phe Ile Ser Gly Ile Met Ile
            915                 920                 925

Leu Phe Glu Arg Pro Val Arg Ile Gly Asp Thr Ile Thr Ile Gly Ala
    930                 935                 940

Leu Ser Gly Thr Val Ser Lys Ile Arg Ile Arg Ala Thr Thr Ile Thr
945                 950                 955                 960

Asp Phe Asp Arg Lys Asp Ile Ile Val Pro Asn Lys Thr Phe Ile Thr
                965                 970                 975

Gly Gln Leu Ile Asn Trp Ser Leu Thr Asp Thr Val Thr Arg Val Thr
            980                 985                 990

Leu Lys Leu Gly Val Asp Tyr Gly Ser Asp Leu Asp Leu Val Arg Ser
            995                 1000                1005

Leu Leu Leu Gln Ala Ala Arg Glu Asn Pro Arg Val Leu Lys Glu Pro
   1010                 1015                1020

Glu Pro Ile Val Tyr Phe Leu Asn Phe Gly Glu Ser Thr Leu Asp His
1025                 1030                1035                1040

Glu Leu Arg Met His Val Arg Asp Leu Gly Asp Arg Asn Pro Val Leu
                1045                1050                1055

Asp Glu Ile Asn Arg Phe Ile Asn Arg Glu Phe Lys Lys Gln His Ile
            1060                1065                1070
```

```
Asn Ile Ser Phe Arg Gln Met Glu Ile Tyr Leu Lys Asn Thr Gln Gly
        1075                1080                1085

Leu Glu Tyr Lys Leu Val Pro Ala Glu Pro Gly Glu Lys His Gly Ala
    1090                1095                1100

Pro Ala Gly Gln Thr Thr Leu Gln Pro Val Asn Thr Lys Val Ala Pro
1105                1110                1115                1120

Ala Thr Lys Asp Ala Pro Glu Pro Glu Leu Arg Leu Asp
        1125                1130
```

<210> SEQ ID NO 99
<211> LENGTH: 1113
<212> TYPE: DNA
<213> ORGANISM: Pseudomonas syringae pv. tomato DC3000

<400> SEQUENCE: 99

```
atgtcaacgt tgaatcatac gtctgctgta aattgccgcg tcagttttga tggtgaccgt      60
tgctatgtag acaccccat ccagatcatg ccgggtgagc gatgggctgt aaatatcgta     120
cctaacgatt tagtcacaat ccactacgag ccgccagca atcacgacta cccttttgctg   180
ctggccagca taaaaatct gtttaccgat gagcgttgtg tcgtgctaaa gcccggcctt    240
acacagcaag ctttgaacat gtatttttca gaggttaaca gccttaaacc taacgcgact    300
catgttcgct tgttgcatcg agcgcagcgt attttctag aaaacatgat ccgtagcgta     360
cagataaccct cgcaaggtat cagcgtcact ttcgcaaccg ccgaattcaa aaattataac   420
taccagctaa aggtggataa atatactttt gcaaggcttg acaagggta ccctctctat     480
tcggagctgg ttgaaaacac ctggataacg aaattatccg tagcccataa tattctgtat   540
tccatctctg tgagcctgga ccactcaagc acaccttata cacttttttc aggaaccctc   600
gcggaagaca atatagtcca gccgatacgg gcgcttttca ccgacaacac catgactcaa   660
ctcacctcct tggccgatca gaaaaccgtg gatgccttgt atacgacggt caatggcaac   720
ccggttatca gcatcaaaaa acgcgcagat tatcggtctt atctgaacat cgcacagaag   780
ttactgcttc caagaaccta caccaaagta gtacggacag tgagcagcct gtctgtgcat   840
tttacggggg aggcgtacaa acaattcaac tacaagatgc ttgtcaacaa tgcttatgca   900
tccgagatca cccgagggaa ggcttattac tccagcgtga gcaatggggt gtggaccact   960
tccggtacgc atgacagcga cgacaactgc aaagtcactt gtgattacaa gggcgcaacc  1020
tacgtcctgt acgagagtaa tgcggcagat agacgcactg aaacctgggc acaagacccg  1080
tacgttactc attgcgaccc gagagacctg taa                              1113
```

<210> SEQ ID NO 100
<211> LENGTH: 370
<212> TYPE: PRT
<213> ORGANISM: Pseudomonas syringae pv. tomato DC3000

<400> SEQUENCE: 100

```
Met Ser Thr Leu Asn His Thr Ser Ala Val Asn Cys Arg Val Ser Phe
  1               5                  10                  15

Asp Gly Asp Arg Cys Tyr Val Asp Thr Pro Ile Gln Ile Met Pro Gly
              20                  25                  30

Glu Arg Trp Ala Val Asn Ile Val Pro Asn Asp Leu Val Thr Ile His
          35                  40                  45

Tyr Glu Ala Ala Ser Asn His Asp Tyr Pro Leu Leu Leu Ala Ser Ile
      50                  55                  60
```

```
Lys Asn Leu Phe Thr Asp Glu Arg Cys Val Val Leu Lys Pro Gly Leu
 65                  70                  75                  80

Thr Gln Gln Ala Leu Asn Met Tyr Phe Ser Glu Val Asn Ser Leu Lys
             85                  90                  95

Pro Asn Ala Thr His Val Arg Leu Leu His Arg Ala Gln Arg Ile Phe
        100                 105                 110

Leu Glu Asn Met Ile Arg Ser Val Gln Ile Thr Ser Gln Gly Ile Ser
    115                 120                 125

Val Thr Phe Ala Thr Ala Glu Phe Lys Asn Tyr Asn Tyr Gln Leu Lys
130                 135                 140

Val Asp Lys Tyr Thr Phe Ala Arg Leu Asp Lys Gly Tyr Pro Leu Tyr
145                 150                 155                 160

Ser Glu Leu Val Glu Asn Thr Trp Ile Thr Lys Leu Ser Val Ala His
                165                 170                 175

Asn Ile Leu Tyr Ser Ile Ser Val Ser Leu Asp His Ser Ser Thr Pro
            180                 185                 190

Tyr Thr Leu Phe Ser Gly Thr Leu Ala Glu Asp Asn Ile Val Gln Pro
        195                 200                 205

Ile Arg Ala Leu Phe Thr Asp Asn Thr Met Thr Gln Leu Thr Ser Leu
210                 215                 220

Ala Asp Gln Lys Thr Val Asp Ala Leu Tyr Thr Thr Val Asn Gly Asn
225                 230                 235                 240

Pro Val Ile Ser Ile Lys Lys Arg Ala Asp Tyr Arg Ser Tyr Leu Asn
                245                 250                 255

Ile Ala Gln Lys Leu Leu Leu Pro Arg Thr Tyr Thr Lys Val Val Arg
            260                 265                 270

Thr Val Ser Ser Leu Ser Val His Phe Thr Gly Glu Ala Tyr Lys Gln
        275                 280                 285

Phe Asn Tyr Lys Met Leu Val Asn Asn Ala Tyr Ala Ser Glu Ile Thr
290                 295                 300

Arg Gly Lys Ala Tyr Tyr Ser Ser Val Ser Asn Gly Val Trp Thr Thr
305                 310                 315                 320

Ser Gly Thr His Asp Ser Asp Asp Asn Cys Lys Val Thr Cys Asp Tyr
                325                 330                 335

Lys Gly Ala Thr Tyr Val Leu Tyr Glu Ser Asn Ala Ala Asp Arg Arg
            340                 345                 350

Thr Glu Thr Trp Ala Gln Asp Pro Tyr Val Thr His Cys Asp Pro Arg
        355                 360                 365

Asp Leu
    370

<210> SEQ ID NO 101
<211> LENGTH: 714
<212> TYPE: DNA
<213> ORGANISM: Pseudomonas syringae pv. tomato DC3000

<400> SEQUENCE: 101
atgcgcctga tcgcgcagat tctgcccggc ctgccggaaa acaccactta cagcgccgcc      60
gctgcgtcca cacccctggc gcgggccatg cccaacgcca ttcgcaatgc gctgggcacc     120
ctggggctgg tggctgcgcg cacccagcca agcatctttc cgttgccgtc gcgcaacgtc     180
agcggtggcg aaaagagga cgacctggag attctgctca aactcgcggc cgccgctgtt     240
tcgcgcctgc aaagccacca gttgggcggc ctggagcaga cccgtaccaa tgccgatggc     300
actcaggtga ctacatggca actggaagtg ccgatgcgca acgcccatga catcgtgccg     360
```

-continued

| | |
|---|---|
| ttgcaggtca aggtgcagcg cgaagacaag cctgatcagg acgccaccga agaccgcgac | 420 |
| gatatcgaga tcaaggaaac ccgtgaaaaa ctctggaaag tcgatctggc tttcgacctg | 480 |
| gagccgcttg ccccatgca ggtgcatgcg caactgctgc gcggcacgct gtccagccag | 540 |
| ttatgggccg agcgcccgga tagcgcaaca ctgatcgaac atgaactggg gcatttgcgc | 600 |
| gagcgcctga ttgcctgcgg cctggccgtc ggggaactgg cgtgcagcca tggcgttccg | 660 |
| ccgcaagggc cgcgcaccgc cctcgaacaa cgctggatcg acgagaacgc ctga | 714 |

<210> SEQ ID NO 102
<211> LENGTH: 237
<212> TYPE: PRT
<213> ORGANISM: Pseudomonas syringae pv. tomato DC3000

<400> SEQUENCE: 102

Met Arg Leu Ile Ala Gln Ile Leu Pro Gly Leu Pro Glu Asn Thr Thr
 1               5                  10                  15
Tyr Ser Ala Ala Ala Ser Asn Thr Leu Ala Arg Ala Met Pro Asn
             20                  25                  30
Ala Ile Arg Asn Ala Leu Gly Thr Leu Gly Leu Val Ala Ala Arg Thr
         35                  40                  45
Gln Pro Ser Ile Phe Pro Leu Pro Ser Arg Asn Val Ser Gly Gly Glu
     50                  55                  60
Lys Glu Asp Asp Leu Glu Ile Leu Leu Lys Leu Ala Ala Ala Val
 65                  70                  75                  80
Ser Arg Leu Gln Ser His Gln Leu Gly Gly Leu Glu Gln Thr Arg Thr
                 85                  90                  95
Asn Ala Asp Gly Thr Gln Val Thr Thr Trp Gln Leu Glu Val Pro Met
            100                 105                 110
Arg Asn Ala His Asp Ile Val Pro Leu Gln Val Lys Val Gln Arg Glu
        115                 120                 125
Asp Lys Pro Asp Gln Asp Ala Thr Glu Asp Arg Asp Ile Glu Ile
    130                 135                 140
Lys Glu Thr Arg Glu Lys Leu Trp Lys Val Asp Leu Ala Phe Asp Leu
145                 150                 155                 160
Glu Pro Leu Gly Pro Met Gln Val His Ala Gln Leu Leu Arg Gly Thr
                165                 170                 175
Leu Ser Ser Gln Leu Trp Ala Glu Arg Pro Asp Ser Ala Thr Leu Ile
            180                 185                 190
Glu His Glu Leu Gly His Leu Arg Glu Arg Leu Ile Ala Cys Gly Leu
        195                 200                 205
Ala Val Gly Glu Leu Ala Cys Ser His Gly Val Pro Pro Gln Gly Pro
    210                 215                 220
Arg Thr Ala Leu Glu Gln Arg Trp Ile Asp Glu Asn Ala
225                 230                 235

<210> SEQ ID NO 103
<211> LENGTH: 690
<212> TYPE: DNA
<213> ORGANISM: Pseudomonas syringae pv. tomato DC3000

<400> SEQUENCE: 103

| | |
|---|---|
| atgagtagcg tcgcagcact gatcaccata tcgactggac agacgcagtt cgttaaagtc | 60 |
| gcgcggacgt cattttctgt gctacgaatc cccctcgccg gcagatgtcg tgtccgggat | 120 |
| cagttgacca ctacaataaa gacagagcag aaacccataa aaatagggg aagagacgtg | 180 |

-continued

```
agcctaaatg atcacttgaa aaaagcattg aattctgatt ccagcgacga gcttgatgaa    240
atcaccgacc tttatgtgac gttgcctgca gaggtcttca gttgcttgac catttcactc    300
gaagggaatt ggaaggaaat tgatagcgtc tggtctgctc ggttagacgc agcagattca    360
aagaataata caaaatgtca cgtccatatc gccaaaacca agcatcgatc ctcaaaaagc    420
aaacaggttt cttggaacag tgatggtagc cggcatgata aaaaaacatt cgatgtaacg    480
ctgggacaga gcagaaaggc ccaggcgata gctaggaaat ttttaggcct tggcgagtcc    540
ataagccttg aaagcaaaga ttccaagcag atggttgaaa gacctctact cagcactgct    600 acatccttt cgaatgatgg aaaagaggtg aaggtcgagt tctacgtgga agaatccacc    660
gcccaccttc ccgcatggtt acgatggtag                                     690
```

<210> SEQ ID NO 104
<211> LENGTH: 229
<212> TYPE: PRT
<213> ORGANISM: Pseudomonas syringae pv. tomato DC3000

<400> SEQUENCE: 104

```
Met Ser Ser Val Ala Ala Leu Ile Thr Ile Ser Thr Gly Gln Thr Gln
 1               5                  10                  15

Phe Val Lys Val Ala Arg Thr Ser Phe Ser Val Leu Arg Ile Pro Leu
            20                  25                  30

Ala Gly Arg Cys Arg Val Arg Asp Gln Leu Thr Thr Thr Ile Lys Thr
        35                  40                  45

Glu Gln Lys Pro Ile Lys Ile Gly Gly Arg Asp Val Ser Leu Asn Asp
    50                  55                  60

His Leu Lys Lys Ala Leu Asn Ser Asp Ser Ser Asp Glu Leu Asp Glu
65                  70                  75                  80

Ile Thr Asp Leu Tyr Val Thr Leu Pro Ala Glu Val Phe Ser Cys Leu
                85                  90                  95

Thr Ile Ser Leu Glu Gly Asn Trp Lys Glu Ile Asp Ser Val Trp Ser
            100                 105                 110

Ala Arg Leu Asp Ala Ala Asp Ser Lys Asn Asn Thr Lys Cys His Val
        115                 120                 125

His Ile Ala Lys Thr Lys His Arg Ser Ser Lys Ser Lys Gln Val Ser
    130                 135                 140

Trp Asn Ser Asp Gly Ser Arg His Asp Lys Lys Thr Phe Asp Val Thr
145                 150                 155                 160

Leu Gly Gln Ser Arg Lys Ala Gln Ala Ile Ala Arg Lys Phe Leu Gly
                165                 170                 175

Leu Gly Glu Ser Ile Ser Leu Glu Ser Lys Asp Ser Lys Gln Met Val
            180                 185                 190

Glu Arg Pro Leu Leu Ser Thr Ala Thr Ser Phe Ser Asn Asp Gly Lys
        195                 200                 205

Glu Val Lys Val Glu Phe Tyr Val Glu Glu Ser Thr Ala His Leu Pro
    210                 215                 220

Ala Trp Leu Arg Trp
225
```

<210> SEQ ID NO 105
<211> LENGTH: 2949
<212> TYPE: DNA
<213> ORGANISM: Pseudomonas syringae pv. tomato DC3000

-continued

```
<400> SEQUENCE: 105
atgaagccaa tccatactgc ccgatacaac gcctggaatc agttggagca ggagaccgcc      60
catgactggc tggggccaa acccttggcc agcagcaccc ttggctaccg ctacgatgac      120
tggaaccagc gatgctgcac cacgaccgat gacaacgtac agacttatga gtattcagac    180
ccgatcggca gcgacgtaca taaaggccca atccagaaaa cctggaaaca gagtggcgac    240
ccggagggcc gcatcagtgg ccgcagcgaa acctggctga atctgttcgg caaaccggac    300
cggatccgga cgctgaccgc tggtaaaacg ggtcgcagcc gcacgcacag catgagccgc    360
agccggaacc tgaccacgac tgagcaggaa ctgagcagga agacctttct gtacgacggg    420
ctgggacgct gcaccgagca gcgcgatgca ctccagcaaa gcaccctgtt cagctacgac    480
aactggtcac gcatggtctc ctccacgctt gcagacggca gcgtcatcaa ccggagttat    540
gcgccgcaaa gcagcagtga gctggcaacg atgctcgagg tcgtgcacca gaacggcacc    600
accagaaccg tggcaggtac acagaaattt gacgggcttg agcgtgtgac gcagaccaaa    660
acaggtgacc gcgtcgaaca gttcaactac gacgccggtg agatgcagcc caggtcgcgc    720
acaacagccg ggctggacaa catcaacttt acctacactc gggcgctcac tgatcagatt    780
ttttccagca cggctccgga tgaaacggcc aaattcgatt atgacaagac cagtgcccgc    840
ctcatcgaag cgacgaaccc gcaaggcacg cgcacttacc gctatgacgt gcacaatcaa    900
ctgacgggag agacttggga caatctgctg ggtcaggctt gggaaacccg acaccaatca    960
tcgctgctgg gtcggccgat caagcgcacc gatctcaaaa aggcgaggc ggcgggcgca    1020 gagacccgtt acgactacga cacgctcggc agaatcaggt ttatcaacca gagcaacctg    1080
cgcaccacaa tcgactatga cgtgctgggc cagctctgca aggtggccac cgaggacctg    1140
caggccggaa ctggcgtgat catcgacatg aatacgacg accagggaca ggaaattctc    1200
agaacccaga ccgcaagcaa ccaagcggcg ttgaccttga ctcaaacgtg ggcagtggac    1260
gggcttttga aaacccgcga cctgcaacag gcgggtagcc ccctgctgca cgaaacgttt    1320
agctacgacc ccagaggccg cctgacactg gtgaattacc tgggtagcag cttgccgaga    1380
gacgaactgc aaagggagat gaccagacaa atattcagct tcgacgagct ggacaacatt    1440
acgctatgcc agaccaggtt taccgatggc acctctgagc gagcagcttt caaatacggc    1500
agccccggcg acgataagca taaagaccgc tgccagcttt tgagtattgc ctacacgccg    1560
cccagaaaaa caccggaccc gacattcagt tacgacgcca acgtaaccag cttaaagac    1620 gagcatggca acagtctgca ttacgatagc cagagccgcc tgctgcaggt cgcagaaacc    1680
ggcggtgccc ctatcagcca ataccgttat gacggccaca atcaactggt cgccaccagg    1740
gatggcaatg aaagcgagat tttgcggttc tatgagggtc atcaactgag cagcacggtg    1800
caggaagatc aacgcactca gtacctgcat ctcggcgaac agccgctggg ccagcagatt    1860
gtggacgacg ccgagcaaac cctgttgcta ctgactgacg caaaccagag cgttatgggt    1920
gaatttcaac aaggccagct gcgcaaggcg gtctacagtg cctacgggga gcgccacagc    1980
gaggaggcgc tgctgagcac tgccgggttt aacggtgaag tacgcgaagc cgccaacggc    2040
tggtatctgt gggcaatgg ctaccgggcc tacaaccctc tcctgatgcg cttccacagc    2100
ccggattttc tcagcccctt cgccgaaggc ggcgtcaacc cctacaccta ctgcctgggc    2160
aaccccatcg ccctgcgcga cccgacagga catgatgcca gcggtcagac tggccggttg    2220
agacggcccg atgaggggggc tttgccaatg caacaaggtg gcggagatat catgggttgg    2280
gtgggtgtag aataggcgt tgttttcacc gtattgggcg ttgccgctac catagccacg    2340
```

-continued

```
ttaggaacag ccacaccggt taccggcccg gtaactgtcc tgggcatttc catgaccgcc    2400
agcgctgccg cggccgtttc gacagtctcg accggtgcgt tgatcgtcgg tacggcattg    2460
acagcggctt caactacggc caatacagtt gccattgtaa ataacgatca gacggccgga    2520
gaagtcggcg gctggttggg tattgccgct gtgcccgttg gcttggtagg gtttggcgcg    2580
ggggctgtgg tggcgagggc agttgcggct gcggctaaag ttgcggctgc caacgctggt    2640
acgatcggtg tccgcagcgt cagcagaata ggcctcgctg ctgctggtgc ccgcagaacc    2700
atttccagcg ctgccagcag cgctcggcgc caaatcagca acatgttagg cagaatctta    2760
ccccgtgctc taaacaggac tgctgctact gcacgccgga ttccaagcgt tacaagtggc    2820
ggatcaggac cagggccatc attatttaca cagactacct ttaacgaatc gattgggatg    2880
acgcagacca ctattttttc aacgaatgcg agcggaatcc caccggccac gcaggtaact    2940
cgaatctag                                                           2949
```

<210> SEQ ID NO 106
<211> LENGTH: 982
<212> TYPE: PRT
<213> ORGANISM: Pseudomonas syringae pv. tomato DC3000

<400> SEQUENCE: 106

```
Met Lys Pro Ile His Thr Ala Arg Tyr Asn Ala Trp Asn Gln Leu Glu
  1               5                  10                  15

Gln Glu Thr Ala His Asp Trp Leu Gly Ala Lys Pro Leu Ala Ser Ser
                 20                  25                  30

Thr Leu Gly Tyr Arg Tyr Asp Asp Trp Asn Gln Arg Cys Cys Thr Thr
             35                  40                  45

Thr Asp Asp Asn Val Gln Thr Tyr Glu Tyr Ser Asp Pro Ile Gly Ser
         50                  55                  60

Asp Val His Lys Gly Pro Ile Gln Lys Thr Trp Lys Gln Ser Gly Asp
 65                  70                  75                  80

Pro Glu Gly Arg Ile Ser Gly Arg Ser Glu Thr Trp Leu Asn Leu Phe
                 85                  90                  95

Gly Lys Pro Asp Arg Ile Arg Thr Leu Thr Ala Gly Lys Thr Gly Arg
            100                 105                 110

Ser Arg Thr His Ser Met Ser Arg Ser Arg Asn Leu Thr Thr Thr Glu
        115                 120                 125

Gln Glu Leu Ser Arg Gln Thr Phe Leu Tyr Asp Gly Leu Gly Arg Cys
    130                 135                 140

Thr Glu Gln Arg Asp Ala Leu Gln Gln Ser Thr Leu Phe Ser Tyr Asp
145                 150                 155                 160

Asn Trp Ser Arg Met Val Ser Ser Thr Leu Ala Asp Gly Ser Val Ile
                165                 170                 175

Asn Arg Ser Tyr Ala Pro Gln Ser Ser Ser Glu Leu Ala Thr Met Leu
            180                 185                 190

Glu Val Val His Gln Asn Gly Thr Thr Arg Thr Val Ala Gly Thr Gln
        195                 200                 205

Lys Phe Asp Gly Leu Glu Arg Val Thr Gln Thr Lys Thr Gly Asp Arg
    210                 215                 220

Val Glu Gln Phe Asn Tyr Asp Ala Gly Glu Met Gln Pro Arg Ser Arg
225                 230                 235                 240

Thr Thr Ala Gly Leu Asp Asn Ile Asn Phe Thr Tyr Thr Arg Ala Leu
                245                 250                 255
```

-continued

```
Thr Asp Gln Ile Phe Ser Ser Thr Ala Pro Asp Glu Thr Ala Lys Phe
            260                 265                 270

Asp Tyr Asp Lys Thr Ser Ala Arg Leu Ile Glu Ala Thr Asn Pro Gln
        275                 280                 285

Gly Thr Arg Thr Tyr Arg Tyr Asp Val His Asn Gln Leu Thr Gly Glu
    290                 295                 300

Thr Trp Asp Asn Leu Leu Gly Gln Ala Trp Glu Thr Arg His Gln Ser
305                 310                 315                 320

Ser Leu Leu Gly Arg Pro Ile Lys Arg Thr Asp Leu Lys Lys Gly Glu
                325                 330                 335

Ala Ala Gly Ala Glu Thr Arg Tyr Asp Tyr Asp Thr Leu Gly Arg Ile
            340                 345                 350

Arg Phe Ile Asn Gln Ser Asn Leu Arg Thr Thr Ile Asp Tyr Asp Val
        355                 360                 365

Leu Gly Gln Leu Cys Lys Val Ala Thr Glu Asp Leu Gln Ala Gly Thr
    370                 375                 380

Gly Val Ile Ile Asp Met Glu Tyr Asp Asp Gln Gly Gln Glu Ile Leu
385                 390                 395                 400

Arg Thr Gln Thr Ala Ser Asn Gln Ala Ala Leu Thr Leu Thr Gln Thr
                405                 410                 415

Trp Ala Val Asp Gly Leu Leu Lys Thr Arg Asp Leu Gln Gln Ala Gly
            420                 425                 430

Ser Pro Leu Leu His Glu Thr Phe Ser Tyr Asp Pro Arg Gly Arg Leu
        435                 440                 445

Thr Leu Val Asn Tyr Leu Gly Ser Ser Leu Pro Arg Asp Glu Leu Gln
    450                 455                 460

Arg Glu Met Thr Arg Gln Ile Phe Ser Phe Asp Glu Leu Asp Asn Ile
465                 470                 475                 480

Thr Leu Cys Gln Thr Arg Phe Thr Asp Gly Thr Ser Glu Arg Ala Ala
                485                 490                 495

Phe Lys Tyr Gly Ser Pro Gly Asp Asp Lys His Lys Asp Arg Cys Gln
            500                 505                 510

Leu Leu Ser Ile Ala Tyr Thr Pro Pro Arg Lys Thr Pro Asp Pro Thr
        515                 520                 525

Phe Ser Tyr Asp Ala Asn Gly Asn Gln Leu Lys Asp Glu His Gly Asn
    530                 535                 540

Ser Leu His Tyr Asp Ser Gln Ser Arg Leu Leu Gln Val Ala Glu Thr
545                 550                 555                 560

Gly Gly Ala Pro Ile Ser Gln Tyr Arg Tyr Asp Gly His Asn Gln Leu
                565                 570                 575

Val Ala Thr Arg Asp Gly Asn Glu Ser Glu Ile Leu Arg Phe Tyr Glu
            580                 585                 590

Gly His Gln Leu Ser Ser Thr Val Gln Glu Asp Gln Arg Thr Gln Tyr
        595                 600                 605

Leu His Leu Gly Glu Gln Pro Leu Gly Gln Gln Ile Val Asp Asp Ala
    610                 615                 620

Glu Gln Thr Leu Leu Leu Thr Asp Ala Asn Gln Ser Val Met Gly
625                 630                 635                 640

Glu Phe Gln Gln Gly Gln Leu Arg Lys Ala Val Tyr Ser Ala Tyr Gly
                645                 650                 655

Glu Arg His Ser Glu Glu Ala Leu Leu Ser Thr Ala Gly Phe Asn Gly
            660                 665                 670
```

-continued

```
            Glu Val Arg Glu Ala Ala Asn Gly Trp Tyr Leu Leu Gly Asn Gly Tyr
                            675                 680                 685

Arg Ala Tyr Asn Pro Leu Leu Met Arg Phe His Ser Pro Asp Phe Leu
                        690                 695                 700

Ser Pro Phe Ala Glu Gly Val Asn Pro Tyr Thr Tyr Cys Leu Gly
            705                 710                 715                 720

Asn Pro Ile Ala Leu Arg Asp Pro Thr Gly His Asp Ala Ser Gly Gln
                            725                 730                 735

Thr Gly Arg Leu Arg Arg Pro Asp Glu Gly Ala Leu Pro Met Gln Gln
                        740                 745                 750

Gly Gly Gly Asp Ile Met Gly Trp Val Gly Val Gly Ile Gly Val Val
                        755                 760                 765

Phe Thr Val Leu Gly Val Ala Ala Thr Ile Ala Thr Leu Gly Thr Ala
            770                 775                 780

Thr Pro Val Thr Gly Pro Val Thr Val Leu Gly Ile Ser Met Thr Ala
            785                 790                 795                 800

Ser Ala Ala Ala Val Ser Thr Val Ser Thr Gly Ala Leu Ile Val
                            805                 810                 815

Gly Thr Ala Leu Thr Ala Ala Ser Thr Thr Ala Asn Thr Val Ala Ile
                        820                 825                 830

Val Asn Asn Asp Gln Thr Ala Gly Glu Val Gly Gly Trp Leu Gly Ile
                        835                 840                 845

Ala Ala Val Pro Val Gly Leu Val Gly Phe Gly Ala Gly Ala Val Val
            850                 855                 860

Ala Arg Ala Val Ala Ala Ala Lys Val Ala Ala Ala Asn Ala Gly
            865                 870                 875                 880

Thr Ile Gly Val Arg Ser Val Ser Arg Ile Gly Leu Ala Ala Ala Gly
                            885                 890                 895

Ala Arg Arg Thr Ile Ser Ser Ala Ala Ser Ser Ala Arg Arg Gln Ile
                        900                 905                 910

Ser Asn Met Leu Gly Arg Ile Leu Pro Arg Ala Leu Asn Arg Thr Ala
                        915                 920                 925

Ala Thr Ala Arg Arg Ile Pro Ser Val Thr Ser Gly Gly Ser Gly Pro
            930                 935                 940

Gly Pro Ser Leu Phe Thr Gln Thr Thr Phe Asn Glu Ser Ile Gly Met
            945                 950                 955                 960

Thr Gln Thr Thr Ile Phe Ser Thr Asn Ala Ser Gly Ile Pro Pro Ala
                            965                 970                 975

Thr Gln Val Thr Arg Ile
                        980
```

<210> SEQ ID NO 107
<211> LENGTH: 495
<212> TYPE: DNA
<213> ORGANISM: Pseudomonas syringae pv. tomato DC3000

<400> SEQUENCE: 107

```
atgcggtgtg tgaggcgatc aagaaggttc tttaagctgc aagctgcaag ctgcaagaaa    60
aagcaggacc gctttagctt agctgacgct ccactgagta ctttccatcg aacgatccga   120 aaaccctgc ctcgaaagct tgtcagaccc ttttctgaat cagctatcga ggtagtcatg    180
tccatcgaac cccaacgtca gaaagaacag ccacccggcc agcacacgcc agcggatcag   240
ggcccggatc gcaatgatcc ggccatcgag ccgcaggttt cggacgtaga gccggagact   300
gaaaaaggtg acggccagac gcaaggccag accctgccc ccagccaaag ccagtcacaa   360
```

-continued

```
agtcagaatc agagccagca gtccaacggc agcgcttacg tgcctgacta tgagccgcag    420
gaaaaaaagg aagaccagcg caatcatcag cccactcaag gcactgatgc tgatatcgac    480
accaatgcgg gctga                                                     495
```

<210> SEQ ID NO 108
<211> LENGTH: 164
<212> TYPE: PRT
<213> ORGANISM: Pseudomonas syringae pv. tomato DC3000

<400> SEQUENCE: 108

```
Met Arg Cys Val Arg Ser Arg Arg Phe Phe Lys Leu Gln Ala Ala
 1               5                  10                  15

Ser Cys Lys Lys Lys Gln Asp Arg Phe Ser Leu Ala Asp Ala Pro Leu
                20                  25                  30

Ser Thr Phe His Arg Thr Ile Arg Lys Thr Leu Pro Arg Lys Leu Val
            35                  40                  45

Arg Pro Phe Ser Glu Ser Ala Ile Glu Val Val Met Ser Ile Glu Pro
        50                  55                  60

Gln Arg Gln Lys Glu Gln Pro Pro Gly Gln His Thr Pro Ala Asp Gln
    65                  70                  75                  80

Gly Pro Asp Arg Asn Asp Pro Ala Ile Glu Pro Gln Val Ser Asp Val
                85                  90                  95

Glu Pro Glu Thr Glu Lys Gly Asp Gly Gln Thr Gln Gly Gln Thr Pro
            100                 105                 110

Ala Pro Ser Gln Ser Gln Ser Gln Ser Gln Asn Gln Ser Gln Gln Ser
        115                 120                 125

Asn Gly Ser Ala Tyr Val Pro Asp Tyr Glu Pro Gln Glu Lys Lys Glu
    130                 135                 140

Asp Gln Arg Asn His Gln Pro Thr Gln Gly Thr Asp Ala Asp Ile Asp
145                 150                 155                 160
Thr Asn Ala Gly
```

<210> SEQ ID NO 109
<211> LENGTH: 702
<212> TYPE: DNA
<213> ORGANISM: Pseudomonas syringae pv. tomato DC3000

<400> SEQUENCE: 109

```
atgcccgtca ctggtgcagg ctttatcaag cgtttgacgc aattgtccct ctgcgccggc     60
atggcgctgg tcccggtggc cgtacaggca gccgaaagcg atccttggga aggcatcaac    120
cgttccattt tcagcttcaa cgataccctt gacgcttata cgctcaagcc gctggcaaag    180
ggttatcagt acatcgctcc gcagtttgtc gaagacggta ttcataactt cttcagcaat    240
atcggcgatg tcggcaatct ggcgaacaac gtcttgcagg ccaaacctga gcggccggt     300 gtagataccg cacgccttat cgtcaacact acgttcggtc tgctgggctt cattgacgtc    360
ggcacccgca tgggcctgca acgcagtgat gaagacttcg ccagacact gggctactgg    420 ggtgtgccaa gcgcccgtt cgtggtgatt ccgctgctgg gcccaagcac ggtgcgtgac    480
gccattgcca agtacccgga cacctacacc tccccgtacc gctatattga tcacgtaccc    540
acccgcaaca cggcgttggg cgtcaatctg gtcgacacgc gtgccagcct gctgtccgcc    600
gagcgcctgg tcagtggtga tcgctacacc ttcatccgca acgcttactt gcagaaccgc    660
gaattcaagg tcaaggacgg gcaggtcgaa gacgattttt aa                      702
```

-continued

<210> SEQ ID NO 110
<211> LENGTH: 233
<212> TYPE: PRT
<213> ORGANISM: Pseudomonas syringae pv. tomato DC3000

<400> SEQUENCE: 110

```
Met Pro Val Thr Gly Ala Gly Phe Ile Lys Arg Leu Thr Gln Leu Ser
1               5                   10                  15
Leu Cys Ala Gly Met Ala Leu Val Pro Val Ala Val Gln Ala Ala Glu
                20                  25                  30
Ser Asp Pro Trp Glu Gly Ile Asn Arg Ser Ile Phe Ser Phe Asn Asp
            35                  40                  45
Thr Leu Asp Ala Tyr Thr Leu Lys Pro Leu Ala Lys Gly Tyr Gln Tyr
    50                  55                  60
Ile Ala Pro Gln Phe Val Glu Asp Gly Ile His Asn Phe Phe Ser Asn
65                  70                  75                  80
Ile Gly Asp Val Gly Asn Leu Ala Asn Asn Val Leu Gln Ala Lys Pro
                85                  90                  95
Glu Ala Ala Gly Val Asp Thr Ala Arg Leu Ile Val Asn Thr Thr Phe
            100                 105                 110
Gly Leu Leu Gly Phe Ile Asp Val Gly Thr Arg Met Gly Leu Gln Arg
        115                 120                 125
Ser Asp Glu Asp Phe Gly Gln Thr Leu Gly Tyr Trp Gly Val Pro Ser
    130                 135                 140
Gly Pro Phe Val Val Ile Pro Leu Leu Gly Pro Ser Thr Val Arg Asp
145                 150                 155                 160
Ala Ile Ala Lys Tyr Pro Asp Thr Tyr Thr Ser Pro Tyr Arg Tyr Ile
                165                 170                 175
Asp His Val Pro Thr Arg Asn Thr Ala Leu Gly Val Asn Leu Val Asp
            180                 185                 190
Thr Arg Ala Ser Leu Leu Ser Ala Glu Arg Leu Val Ser Gly Asp Arg
        195                 200                 205
Tyr Thr Phe Ile Arg Asn Ala Tyr Leu Gln Asn Arg Glu Phe Lys Val
    210                 215                 220
Lys Asp Gly Gln Val Glu Asp Asp Phe
225                 230
```

<210> SEQ ID NO 111
<211> LENGTH: 1194
<212> TYPE: DNA
<213> ORGANISM: Pseudomonas syringae pv. tomato DC3000

<400> SEQUENCE: 111

```
atgacacttt caaccctgcg ccctaccccg cgccagcagt atgaatcgcc cgagtcagcc      60
gaggatttca cccagcggct ggccgacctg acccgcacgc tggccgaaac agccgagcag     120
tacgacatca gcgcgcagtt ccctcacgcc aacttccgct tgctgcacag ccacggactg     180
ctcggcctga ccgtgcctgc cgaactgggc ggcggcgctg ccgacctgtc gcgggcgcag     240
caggtcatca gcgcagtggc cagaggcgag ccttcgacag cgctgattct ggtcatgcag     300
tacctgcagc attccaggct gcaggacaac cgcaactggc cgagccacct cgcgaacag      360 gtggccaaag acgccgtgca cgagggcgcg ctgatcaacg cgctgcgtgt cgaacccgac     420
ctgggcacac tgcgcgtgg  cggcttgccg ggcaccatcg cccggcgcag cgccgaaggc     480
tggcgcatca gcggcagcaa gatctactcc accggcagcc atggcctgac ctggttcgcc     540
```

-continued

```
gtgtgggcgc gcagcgatga cgaggacccg ctggtcggca gttggctggt gcacaaggac    600
acgcccggga tcagcatcgt cgaggactgg gaccatctgg gcatgcgcgc cacctgcagc    660
cacgaggtca ggttcgacaa cgtgcgagtg ccgctcgaac acgcggtcag cgtcagtccg    720
tggagcgccc cgcaatccga gcttgatggt gccggcatgc tgtggatgtc ggtgctgctg    780
tcgtcggtct acgatggcat cgctcaatct gcccgcgact ggctggtgca ctggctggaa    840
cagcgcacgc cttccaacct gggcgccgcg ctgtcgaccc tgccgcgctt tcaggaaaca    900
gtcgggcaga tcgacacact gctgttcgcc aaccgcagcc tgctggagtc cgccgcccaa    960
gggcacacac ccgcacagca tgccgcgcag atcaaatacc tggtgaccgg caatgccatc   1020
cgcgcagtgg aactggccat tgaggcctcg ggcaatcccg ggctttcacg cactaacccg   1080
ctgcagcgtc attaccgcaa cgtgctatgc ggccgggtgc atacgccgca gaacgacgcc   1140
gtgttgatgg gcgtgggcaa agcggtattt gcggcacgca agcagagcca gtaa         1194
```

<210> SEQ ID NO 112
<211> LENGTH: 397
<212> TYPE: PRT
<213> ORGANISM: Pseudomonas syringae pv. tomato DC3000

<400> SEQUENCE: 112

```
Met Thr Leu Ser Thr Leu Arg Pro Thr Pro Arg Gln Gln Tyr Glu Ser
  1               5                  10                  15

Pro Glu Ser Ala Glu Asp Phe Thr Gln Arg Leu Ala Asp Leu Thr Arg
             20                  25                  30

Thr Leu Ala Glu Thr Ala Glu Gln Tyr Asp Ile Ser Ala Gln Phe Pro
         35                  40                  45

His Ala Asn Phe Arg Leu Leu His Ser His Gly Leu Leu Gly Leu Thr
     50                  55                  60

Val Pro Ala Glu Leu Gly Gly Gly Ala Ala Asp Leu Ser Arg Ala Gln
 65                  70                  75                  80

Gln Val Ile Ser Ala Val Ala Arg Gly Glu Pro Ser Thr Ala Leu Ile
                 85                  90                  95

Leu Val Met Gln Tyr Leu Gln His Ser Arg Leu Gln Asp Asn Arg Asn
            100                 105                 110

Trp Pro Ser His Leu Arg Glu Gln Val Ala Lys Asp Ala Val His Glu
        115                 120                 125

Gly Ala Leu Ile Asn Ala Leu Arg Val Glu Pro Asp Leu Gly Thr Pro
    130                 135                 140

Ala Arg Gly Gly Leu Pro Gly Thr Ile Ala Arg Arg Ser Ala Glu Gly
145                 150                 155                 160

Trp Arg Ile Ser Gly Ser Lys Ile Tyr Ser Thr Gly Ser His Gly Leu
                165                 170                 175

Thr Trp Phe Ala Val Trp Ala Arg Ser Asp Asp Glu Asp Pro Leu Val
            180                 185                 190

Gly Ser Trp Leu Val His Lys Asp Thr Pro Gly Ile Ser Ile Val Glu
        195                 200                 205

Asp Trp Asp His Leu Gly Met Arg Ala Thr Cys Ser His Glu Val Arg
    210                 215                 220

Phe Asp Asn Val Arg Val Pro Leu Glu His Ala Val Ser Val Ser Pro
225                 230                 235                 240

Trp Ser Ala Pro Gln Ser Glu Leu Asp Gly Ala Gly Met Leu Trp Met
                245                 250                 255
```

```
Ser Val Leu Leu Ser Val Tyr Asp Gly Ile Ala Gln Ser Ala Arg
            260                 265                 270

Asp Trp Leu Val His Trp Leu Glu Gln Arg Thr Pro Ser Asn Leu Gly
        275                 280                 285

Ala Ala Leu Ser Thr Leu Pro Arg Phe Gln Glu Thr Val Gly Gln Ile
        290                 295                 300

Asp Thr Leu Leu Phe Ala Asn Arg Ser Leu Leu Glu Ser Ala Ala Gln
305                 310                 315                 320

Gly His Thr Pro Ala Gln His Ala Ala Gln Ile Lys Tyr Leu Val Thr
                325                 330                 335

Gly Asn Ala Ile Arg Ala Val Glu Leu Ala Ile Glu Ala Ser Gly Asn
            340                 345                 350

Pro Gly Leu Ser Arg Thr Asn Pro Leu Gln Arg His Tyr Arg Asn Val
        355                 360                 365

Leu Cys Gly Arg Val His Thr Pro Gln Asn Asp Ala Val Leu Met Gly
        370                 375                 380

Val Gly Lys Ala Val Phe Ala Ala Arg Lys Gln Ser Gln
385                 390                 395
```

<210> SEQ ID NO 113
<211> LENGTH: 882
<212> TYPE: DNA
<213> ORGANISM: Pseudomonas syringae pv. tomato DC3000

<400> SEQUENCE: 113

```
atgaatctca caacacttcc tcttgcgctc agcattgctt gcgctgcggc catcacacct      60
gccttcgcgg gcacaagcgt ctctgaggct tcacacaaag tgaatgtgca gcaagttcgt     120
aacgcgacgg taaagatctc ctacggcggc acgacctttc tgatcgaccc gatgctggcc     180
aaaaagggaa cctacccagg gtttgaaaat acctatcgaa gcaatctgcg caatccactg     240
gttgatctga ccgaatcgcc caccgaagtg atcgccggta tcgacgcagt tatcgtcact     300
catacgcacc ttgaccattg gacgatgct gcacaaaaag tgctgcctaa agacatccct     360
ctgttcaccc agcatgaaaa agacgcgcag ctgattcgct ctcaaggttt caagaacgta     420
cgcgtattga ctgatgaagc cgaattcggc ggcgtcaaaa ttaccaagac cggtgggcag     480
catggcaccg acgaaatgta tgccgtgcca gccctcgcga agcctctggg tgaagcaatg     540
ggcgttgtat ttcaagcccc gggctacaag accctctacc tcgctggtga cactgtctgg     600
cgtaaagagg tcgatcaggc tatcgagaac tattgtcccg aagtcatcgt actcaatgcc     660
ggcaaagcaa aaatgacggg gtatgagggg gcgatcatca tggggggaaga ggatgtactg     720
cgcgcttcac aggtcgcgaa gaacgcgaaa atcgtcgctg tacacatgaa tgcaatcaac     780
catatgtccc tgaccgtgat gcaattgcgc gcttacgtca gcagcaggg tatcgaaagt     840
cgtgtagaca taccggaaga tggcgcttca ctggagttct ga                        882
```

<210> SEQ ID NO 114
<211> LENGTH: 293
<212> TYPE: PRT
<213> ORGANISM: Pseudomonas syringae pv. tomato DC3000

<400> SEQUENCE: 114

```
Met Asn Leu Thr Thr Leu Pro Leu Ala Leu Ser Ile Ala Cys Ala Ala
  1               5                  10                  15

Ala Ile Thr Pro Ala Phe Ala Gly Thr Ser Val Ser Glu Ala Ser His
             20                  25                  30
```

-continued

```
Lys Val Asn Val Gln Gln Val Arg Asn Ala Thr Val Lys Ile Ser Tyr
     35                  40                  45
Gly Gly Thr Thr Phe Leu Ile Asp Pro Met Leu Ala Lys Lys Gly Thr
 50                  55                  60
Tyr Pro Gly Phe Glu Asn Thr Tyr Arg Ser Asn Leu Arg Asn Pro Leu
 65                  70                  75                  80
Val Asp Leu Thr Glu Ser Pro Thr Glu Val Ile Ala Gly Ile Asp Ala
                 85                  90                  95
Val Ile Val Thr His Thr His Leu Asp His Trp Asp Ala Ala Gln
                100                 105                 110
Lys Val Leu Pro Lys Asp Ile Pro Leu Phe Thr Gln His Glu Lys Asp
            115                 120                 125
Ala Gln Leu Ile Arg Ser Gln Gly Phe Lys Asn Val Arg Val Leu Thr
130                 135                 140
Asp Glu Ala Glu Phe Gly Gly Val Lys Ile Thr Lys Thr Gly Gly Gln
145                 150                 155                 160
His Gly Thr Asp Glu Met Tyr Ala Val Pro Ala Leu Ala Lys Pro Leu
                165                 170                 175
Gly Glu Ala Met Gly Val Val Phe Gln Ala Pro Gly Tyr Lys Thr Leu
            180                 185                 190
Tyr Leu Ala Gly Asp Thr Val Trp Arg Lys Glu Val Asp Gln Ala Ile
        195                 200                 205
Glu Asn Tyr Cys Pro Glu Val Ile Val Leu Asn Ala Gly Lys Ala Lys
    210                 215                 220
Met Thr Gly Tyr Glu Gly Ala Ile Ile Met Gly Glu Glu Asp Val Leu
225                 230                 235                 240
Arg Ala Ser Gln Val Ala Lys Asn Ala Lys Ile Val Ala Val His Met
                245                 250                 255
Asn Ala Ile Asn His Met Ser Leu Thr Arg Glu Gln Leu Arg Ala Tyr
            260                 265                 270
Val Lys Gln Gln Gly Ile Glu Ser Arg Val Asp Ile Pro Glu Asp Gly
        275                 280                 285
Ala Ser Leu Glu Phe
    290

<210> SEQ ID NO 115
<211> LENGTH: 2379
<212> TYPE: DNA
<213> ORGANISM: Pseudomonas syringae pv. tomato DC3000

<400> SEQUENCE: 115
atgcatctgt tgccgtttgc gcgttacccc ttatcacctg cagaaacacc taaacccaag      60
gtgaccatga aggttggaga tttcagggct tacgacaccg ctccagcacc cggagtgacc     120
actgcgtcct gcggacaact ggcaatcggc accaagttag aaatcatcga gaccgccgag     180
aatggcgaac ttacttatgc caagggtaag attctatctg gcagcgtgaa gcaggggca     240 accaaaaaac gggtcgaggg ggcggaggtc tggttcgctt atttgaaaaa cggcgaaccc     300
tacaaaaact cagtccctaa gcgcatctgg ctcgctgacg atgtgcctga gcagcaaga     360 cccaattact ggcagggtaa ggtcaaagcc tcagtagtga ataagttgcc gctgtacgat     420
gatcctgcca gccctacaaa tggccagcct gcaggcgccc ggaagggac tctggagctg     480 gtcatgaaca gcgtcatcga gtttaactct tcggaagtcg tcaacctggc gctggatggc     540
aagctgcatc ggatggccaa gtgcacgatg ctgagtggcg gcctgcgggg tcatggtgcg     600
```

-continued

```
gttcccccca gcttttgggc atgtgttgaa aatgaccctg ctaataaagt attgaaatgg      660
gactcggtaa cgccgaccag ttttgatacg gtcgttatga cgagcaccgg agtgaaggcg      720
ggcgatccaa ttggctatct tggacaaacc gaaaatctca ccggtgaaaa tggcggcgtc      780
agcagcaaat accaggttca cgtcgaaatt ttcacagccg atgctgaggt taaagacttc      840
ctcaagaaca ccgcgggttt gaagattggg aagcaatacc tgcaccttgc aagcggggct      900
gtactcaagc aaaagcgcc cgcgaccggc accacagcac tcaagcaaga ccatgcggtt       960
gacttggcta agccacaat tgtcaaagaa ggcaccgatg actggtatga ggtcagcgtg      1020
atcgaggaca atcagcctgt agccggcctg ataaaaaaag ccactgcgct agtcatcaca     1080
cagcacgatt gggaaaaatt gggctttcag atcgtagagg agaacaacgc agcagccgat    1140
ggtttcttgg acccggatgc aatgccacag ttcttcaaag acctattcgc gaagatcgac    1200
aagaaccacg atggtgaggt ggagcctgct gaactggctg aggctcttaa gaaaccggaa    1260
accagaaccc agtgggccag gcttgttgcc catcacccta cggagtggaa agataaggca   1320
ggctccccca gtggagcaa gttggataaa ctgctggaaa cgtcgccgaa gatgttgaaa    1380
catgaaaaag aacgcattga taaatatgta ttttgggatg agttgtcagg aaagctaag    1440
atgacctcaa gtttaatatg gcattttcat ccggtagaat tcatttcaac atttagcgca    1500
aaaaaagtct gcgcttgcaa cgccatagtt aaggctactc gctgggtttc ttccagtaag   1560
acgcactatg gcccattgca tacgggtgat aaagagcttg ggagtgcacc tcagtgggat   1620
gacctggtct cagaaggaaa ataacggaa gaggagaaaa aaattattgt tgtaatgtct    1680
ggaaacgagg caaaaattaa cggagtacaa agttatgata gcgaaataat tactgccggc    1740
gcgatgcaga aaacaattaa cttgtccggt ggcggtgagc tgccactaca agttaagaag   1800
tttaaaaatc agcatcccga ggcgtacatc gaatactttg attctcaagg ctggaagttg   1860
gatgagacag gtgattcggc gaaaatgtat tatcaagggc cggctcgagc tagtggcgca   1920
aagctggaag gaaaggcgct gaaggataat ttaaaaattg gttgcagtga atcgacattt    1980
gggaaggtgg ttgactgtca acctgtttca gtgatggcct gcgctatcgc aagtccgtta    2040
tatatccaga tacaaataat ggattttata gaaaggttac gtagttcttt aacgaagaag    2100
cccacaggct ataactttac tgctggggga ttttcaaga cctctctcgg aaaagctgtg    2160
gttttggatc acgatataaa tcgacccggg tatgtgaagg atgacttggg atctgctctt   2220
gacactttt ttgctcaaaa tccaacagtc agccgggata ttgatacatg gggcgcagca    2280
tatagcgtta atgagcgaaa agttttagac ctgtatggcg ctcgaagaag aatgaccaat   2340
gcattgcttc gatacaatca cttgaaggcg gagttataa                          2379
```

<210> SEQ ID NO 116
<211> LENGTH: 792
<212> TYPE: PRT
<213> ORGANISM: Pseudomonas syringae pv. tomato DC3000

<400> SEQUENCE: 116

```
Met His Leu Leu Pro Phe Ala Arg Tyr Pro Leu Ser Pro Ala Glu Thr
 1               5                  10                  15

Pro Lys Pro Lys Val Thr Met Lys Val Gly Asp Phe Arg Ala Tyr Asp
            20                  25                  30

Thr Ala Pro Ala Pro Gly Val Thr Thr Ala Ser Cys Gly Gln Leu Ala
        35                  40                  45

Ile Gly Thr Lys Leu Glu Ile Ile Glu Thr Ala Glu Asn Gly Glu Leu
    50                  55                  60
```

-continued

Thr Tyr Ala Lys Gly Lys Ile Leu Ser Gly Ser Val Lys Gln Gly Ala
 65                  70                  75                  80

Thr Lys Lys Arg Val Glu Gly Ala Glu Val Trp Phe Ala Tyr Leu Lys
                 85                  90                  95

Asn Gly Glu Pro Tyr Lys Asn Ser Val Pro Lys Arg Ile Trp Leu Ala
            100                 105                 110

Asp Asp Val Pro Glu Arg Ala Arg Pro Asn Tyr Trp Gln Gly Lys Val
        115                 120                 125

Lys Ala Ser Val Val Asn Lys Leu Pro Leu Tyr Asp Asp Pro Ala Ser
130                 135                 140

Pro Thr Asn Gly Gln Pro Ala Gly Ala Arg Lys Gly Thr Leu Glu Leu
145                 150                 155                 160

Val Met Asn Ser Val Ile Glu Phe Asn Ser Ser Glu Val Val Asn Leu
                165                 170                 175

Ala Leu Asp Gly Lys Leu His Arg Met Ala Lys Cys Thr Met Leu Ser
            180                 185                 190

Gly Gly Leu Arg Gly His Gly Ala Val Pro Pro Ser Phe Trp Ala Cys
        195                 200                 205

Val Glu Asn Asp Pro Ala Asn Lys Val Leu Lys Trp Asp Ser Val Thr
210                 215                 220

Pro Thr Ser Phe Asp Thr Val Val Met Thr Ser Thr Gly Val Lys Ala
225                 230                 235                 240

Gly Asp Pro Ile Gly Tyr Leu Gly Gln Thr Glu Asn Leu Thr Gly Glu
                245                 250                 255

Asn Gly Gly Val Ser Ser Lys Tyr Gln Val His Val Glu Ile Phe Thr
            260                 265                 270

Ala Asp Ala Glu Val Lys Asp Phe Leu Lys Asn Thr Ala Gly Leu Lys
        275                 280                 285

Ile Gly Lys Gln Tyr Leu His Leu Ala Ser Gly Ala Val Leu Lys Gln
290                 295                 300

Lys Ala Pro Ala Thr Gly Thr Thr Ala Leu Lys Gln Asp His Ala Val
305                 310                 315                 320

Asp Leu Ala Lys Ala Thr Ile Val Lys Glu Gly Thr Asp Asp Trp Tyr
                325                 330                 335

Glu Val Ser Val Ile Glu Asp Gln Pro Val Ala Gly Leu Ile Lys
            340                 345                 350

Lys Ala Thr Ala Leu Val Ile Thr Gln His Asp Trp Glu Lys Leu Gly
        355                 360                 365

Phe Gln Ile Val Glu Glu Asn Asn Ala Ala Ala Asp Gly Phe Leu Asp
370                 375                 380

Pro Asp Ala Met Pro Gln Phe Phe Lys Asp Leu Phe Ala Lys Ile Asp
385                 390                 395                 400

Lys Asn His Asp Gly Glu Val Glu Pro Ala Glu Leu Ala Glu Ala Leu
                405                 410                 415

Lys Lys Pro Glu Thr Arg Thr Gln Trp Ala Arg Leu Val Ala His His
            420                 425                 430

Pro Thr Glu Trp Lys Asp Lys Ala Gly Ser Pro Lys Trp Ser Lys Leu
        435                 440                 445

Asp Lys Leu Leu Glu Thr Ser Pro Lys Met Leu Lys His Glu Lys Glu
450                 455                 460

Arg Ile Asp Lys Tyr Val Phe Trp Asp Glu Leu Ser Gly Lys Ala Lys
465                 470                 475                 480

-continued

```
Met Thr Ser Ser Leu Ile Trp His Phe His Pro Val Glu Phe Ile Ser
            485                 490                 495

Thr Phe Ser Ala Lys Lys Val Cys Ala Cys Asn Ala Ile Val Lys Ala
            500                 505                 510

Thr Arg Trp Val Ser Ser Lys Thr His Tyr Gly Pro Leu His Thr
            515                 520                 525

Gly Asp Lys Glu Leu Gly Ser Ala Pro Gln Trp Asp Asp Leu Val Ser
            530                 535                 540

Glu Gly Lys Ile Thr Glu Glu Lys Ile Ile Val Val Met Ser
545                 550                 555                 560

Gly Asn Glu Ala Lys Ile Asn Gly Val Gln Ser Tyr Asp Ser Glu Ile
                565                 570                 575

Ile Thr Ala Gly Ala Met Gln Lys Thr Ile Asn Leu Ser Gly Gly Gly
            580                 585                 590

Glu Leu Pro Leu Gln Val Lys Lys Phe Lys Asn Gln His Pro Glu Ala
            595                 600                 605

Tyr Ile Glu Tyr Phe Asp Ser Gln Gly Trp Lys Leu Asp Glu Thr Gly
            610                 615                 620

Asp Ser Ala Lys Met Tyr Tyr Gln Gly Pro Ala Arg Ala Ser Gly Ala
625                 630                 635                 640

Lys Leu Glu Gly Lys Ala Leu Lys Asp Asn Leu Lys Ile Gly Cys Ser
                645                 650                 655

Glu Ser Thr Phe Gly Lys Val Val Asp Cys Gln Pro Val Ser Val Met
            660                 665                 670

Ala Cys Ala Ile Ala Ser Pro Leu Tyr Ile Gln Ile Gln Ile Met Asp
            675                 680                 685

Phe Ile Glu Arg Leu Arg Ser Ser Leu Thr Lys Lys Pro Thr Gly Tyr
            690                 695                 700

Asn Phe Thr Ala Gly Gly Phe Phe Lys Thr Ser Leu Gly Lys Ala Val
705                 710                 715                 720

Val Leu Asp His Asp Ile Asn Arg Pro Gly Tyr Val Lys Asp Asp Leu
                725                 730                 735

Gly Ser Ala Leu Asp Thr Phe Phe Ala Gln Asn Pro Thr Val Ser Arg
            740                 745                 750

Asp Ile Asp Thr Trp Gly Ala Ala Tyr Ser Val Asn Glu Arg Lys Val
            755                 760                 765

Leu Asp Leu Tyr Gly Ala Arg Arg Met Thr Asn Ala Leu Leu Arg
            770                 775                 780

Tyr Asn His Leu Lys Ala Glu Leu
785                 790

<210> SEQ ID NO 117
<211> LENGTH: 1554
<212> TYPE: DNA
<213> ORGANISM: Pseudomonas syringae pv. tomato DC3000

<400> SEQUENCE: 117
atgcggccgt tgcctgcgtt cagtattttg cagtttgatc cgttgaaacg ttcgggtcct     60
gcgctgacgg tcgaacgtga tacaccggtc gatagcaagc ctattaatga cgtgcgttgt    120
cgcttccgta cgtgctaccc gaccgaagtt caggcgctgg atctgaccgc gctgaattac    180
tcggtgaaag gcggtggttc gttgctcagc ctgcgcctgg agatgagcgc tgaaggtcac    240
ttgggtgagc ttgaactgag ccgcctgcgt ctgcactttg caggcgagcg ctatatcagc    300
cagatgctgt acctctgcct gctacgcaat ctcgagggta tcgagctgat ccctctggac    360
```

-continued

```
gctgccggca agcccatcga cggtgtcaat ggcgcgccaa tggcgttcaa gatgccgggc      420
gaccgtgtac agccggtagg gtttgccgaa gaagaggcgt tgatcccgta tccgctgaac      480
acgttccgcg gttatcgcta cctgcaggag tacttcgcgt ttcaggacaa gttcctgttc      540
gtcgacatca acggtctgga tctgctcaac gcactgccag aagagacact caaacaagtg      600
cgcggccttg agttgcgctt tgatattcgc aagagcggca ttcagcgtct tcgtcccacc      660
ctggataacg taaagctgta ttgcacgccg atcgtcaact tgttcaagca cgacgccttg      720
ccgattcgcc ttgatggcaa gcaggacgag tacctgctgc tgcccgccga atatggcctg      780
gaaacctgtg gtgtgttttc ggttgaaacc gtgaccggtt ggaagccggg aggtcttggc      840
tatcaggatt atgtgccgtt cgaatccttt gagcacgacc ccagtttcga cgtgcccaac      900
agccgtccgc attacagcat tcgccagcgt tcttctttgc tccatgaagg cctcgacact      960
tatctgagtt tcggcattcg ccatacagaa gcgcacgaaa ccctgtcgat cgagttgatg     1020
tgcaccaatc agaacctgcc acgcaaactc aaactgggcg aaatcaacgt ggcctgcgaa     1080
gatacgccgg agttttgag tttccgcaat atcacaccgg ctacctccag tttcgcgccc     1140
ccgctgaacc gtgacttcct gtggaagttg atcagcaata tgtcgctcaa ttacttgtct     1200
ctggctgacg tcaatgcgct gaaggtgatt ctggaaacct acgatttgcc ccgttactac     1260
gaccagcacg cggaaaaagt cagcaagcgc ctgttgggcg ttttgaaatc gatcaagcat     1320
caacacgtgg acagattgca ccgagggtta ccggtacgcg gattgcgcac tgagctgacc     1380
atcgacccgg aagggtatat cggcgaaggc gacatgtttg tattcgcttc ggttctcaac     1440
gagtttttcg cgctttacgc cagtctcaat tcgtaccacg agctgcgggt aaaaagcaca     1500
cagggagagg tgtaccaatg gacaccacgt atgggcctcc agcccctgct ttaa           1554
```

<210> SEQ ID NO 118
<211> LENGTH: 517
<212> TYPE: PRT
<213> ORGANISM: Pseudomonas syringae pv. tomato DC3000

<400> SEQUENCE: 118

```
Met Arg Pro Leu Pro Ala Phe Ser Ile Leu Gln Phe Asp Pro Leu Lys
  1               5                  10                  15

Arg Ser Gly Pro Ala Leu Thr Val Glu Arg Asp Thr Pro Val Asp Ser
             20                  25                  30

Lys Pro Ile Asn Asp Val Arg Cys Arg Phe Arg Thr Cys Tyr Pro Thr
         35                  40                  45

Glu Val Gln Ala Leu Asp Leu Thr Ala Leu Asn Tyr Ser Val Lys Gly
     50                  55                  60

Gly Gly Ser Leu Leu Ser Leu Arg Leu Glu Met Ser Ala Glu Gly His
 65                  70                  75                  80

Leu Gly Glu Leu Glu Leu Ser Arg Leu Arg Leu His Phe Ala Gly Glu
                 85                  90                  95

Arg Tyr Ile Ser Gln Met Leu Tyr Leu Cys Leu Leu Arg Asn Leu Glu
            100                 105                 110

Gly Ile Glu Leu Ile Pro Leu Asp Ala Ala Gly Lys Pro Ile Asp Gly
        115                 120                 125

Val Asn Gly Ala Pro Met Ala Phe Lys Met Pro Gly Asp Arg Val Gln
    130                 135                 140

Pro Val Gly Phe Ala Glu Glu Ala Leu Ile Pro Tyr Pro Leu Asn
145                 150                 155                 160
```

```
Thr Phe Arg Gly Tyr Arg Tyr Leu Gln Glu Tyr Phe Ala Phe Gln Asp
                165                 170                 175

Lys Phe Leu Phe Val Asp Ile Asn Gly Leu Asp Leu Leu Asn Ala Leu
            180                 185                 190

Pro Glu Glu Thr Leu Lys Gln Val Arg Gly Leu Glu Leu Arg Phe Asp
        195                 200                 205

Ile Arg Lys Ser Gly Ile Gln Arg Leu Arg Pro Thr Leu Asp Asn Val
    210                 215                 220

Lys Leu Tyr Cys Thr Pro Ile Val Asn Leu Phe Lys His Asp Ala Leu
225                 230                 235                 240

Pro Ile Arg Leu Asp Gly Lys Gln Asp Glu Tyr Leu Leu Pro Ala
                245                 250                 255

Glu Tyr Gly Leu Glu Thr Cys Gly Val Phe Ser Val Glu Thr Val Thr
                260                 265                 270

Gly Trp Lys Pro Gly Gly Leu Gly Tyr Gln Asp Tyr Val Pro Phe Glu
            275                 280                 285

Ser Phe Glu His Asp Pro Ser Phe Asp Val Pro Asn Ser Arg Pro His
        290                 295                 300

Tyr Ser Ile Arg Gln Arg Ser Ser Leu Leu His Glu Gly Leu Asp Thr
305                 310                 315                 320

Tyr Leu Ser Phe Gly Ile Arg His Thr Glu Ala His Glu Thr Leu Ser
                325                 330                 335

Ile Glu Leu Met Cys Thr Asn Gln Asn Leu Pro Arg Lys Leu Lys Leu
            340                 345                 350

Gly Glu Ile Asn Val Ala Cys Glu Asp Thr Pro Glu Phe Leu Ser Phe
        355                 360                 365

Arg Asn Ile Thr Pro Ala Thr Ser Ser Phe Ala Pro Pro Leu Asn Arg
    370                 375                 380

Asp Phe Leu Trp Lys Leu Ile Ser Asn Met Ser Leu Asn Tyr Leu Ser
385                 390                 395                 400

Leu Ala Asp Val Asn Ala Leu Lys Val Ile Leu Glu Thr Tyr Asp Leu
                405                 410                 415

Pro Arg Tyr Tyr Asp Gln His Ala Glu Lys Val Ser Lys Arg Leu Leu
            420                 425                 430

Gly Gly Leu Lys Ser Ile Lys His Gln His Val Asp Arg Leu His Arg
        435                 440                 445

Gly Leu Pro Val Arg Gly Leu Arg Thr Glu Leu Thr Ile Asp Pro Glu
    450                 455                 460

Gly Tyr Ile Gly Glu Gly Asp Met Phe Val Phe Ala Ser Val Leu Asn
465                 470                 475                 480

Glu Phe Phe Ala Leu Tyr Ala Ser Leu Asn Ser Tyr His Glu Leu Arg
                485                 490                 495

Val Lys Ser Thr Gln Gly Glu Val Tyr Gln Trp Thr Pro Arg Met Gly
            500                 505                 510

Leu Gln Pro Leu Leu
            515
```

<210> SEQ ID NO 119
<211> LENGTH: 5874
<212> TYPE: DNA
<213> ORGANISM: Pseudomonas syringae pv. tomato DC3000

```
<400> SEQUENCE: 119
atggtcaagg ttacctcttc cggatttact gccaaccctc tctctcatca tgcggacagt      60
gtttcccccg cgaacagtcc ccctcagtta ccggagcctg tgcatctggt tgatttaagc     120
gagtcgtccc gcaagggcgg catgcgaaat cggccgcatg ccagtttgaa cagtcaggtg     180
ctcgaactgc aagcggtgcc gtcgcaacgt ggaaagcatg ttcgtgtcag aagtcatgcc     240
gatggcgaga gtgtcattaa tgcctggctg gcaaagcgcc cctcggttca aagcgaaacc     300
agtcttgata cgatggcaa  actggtgcgt tacaccccg  tgaatcatga gccgctggcg     360
ccgcgcaatg aggcgttttt caccctcggtg ccggggatgt tgatggccgt tttgacggtc    420
cacccccgaga tggaacatgg catcagcggg gacataactg ctgatgctgt ggctgcccgg    480
cttgccgaac cgccaatagg gttgctaacc ggaatctggc agtcttccca tgatcgagcc    540
tatctggagc gtggcggtgt ggtgcatacc gccaatatgg aagagcgctg gcgccgttg     600
acgctgccag gcatcaatcc ccgagagccc ctgcgaatgg ccggtttgca ggccgatggt    660
ggagtctatc tgcataacgg cagccaactg tggcgcttga ccgaaactgc gccgagtcc    720
gtgaccaccg aaaaccttcc tgaaggtgcg gcggtacgca ttggcgccgg tggcgaggtg    780
catgggctgc atgaaggcgc gcttcattcg aatggcattt cccgtccaat cgagctttgg   840
cggccaaaag ctggcgcgcc ggggcgcgag cagagtccgg cgcgcccgt tgatttgctg   900
ccgttaccgg gtggcaccgc tgcactgatc cttgatgaca agggacgtat ttatcacgct   960
gatctgaaag gcacaggcgc tgttgaagcc caccggctga aattacctgc tgactttgcg  1020
cagggtaaag gttgggccgt gaccgccatg ggattgtccc gagacgacac tgttcatctg  1080
atgctgcagg atcagaacgg gcgtcgcatg agcttgcagc gagcaccggg cgaggcgctg  1140
tttcgtcctg cgtacctgct ggatcgcccg ttgctgctgc tctataccga agggctgcat  1200
gttccgtcgg aggccgcggt gcagtcgcac gttcagcttg atggtcatgc tcaactgggg  1260
catatcgatg gcgtgctgca ttataaagcg gctcccgatc agtcatggga acggctaaag  1320
cagtcgggcg gcgaaccgct gacgggtttg actgctcttt attccagccc gctgggattt  1380
atcgacagga aaccggtttt cgctttagtg ggggatgccc ggcaggtggt cgagttgaaa  1440
ctggagggc  gtacatcctg gttgccgagc gatgccgagc ttccgcgtca ccctgcgggc  1500
gggcctttgg cggtgatacc ggatacggta gcgttacgca ccagcccgat cgcgcagttt  1560
gacgagcctg tacaggcgct ggcggttcac ggtaatcgcc gggtcgtcgc gctgacggat  1620
tcggggcgat taatggctgc cgatgcggac accccagccc gccgacttcc cacgttgcag  1680
cgccccatcg ccatcgccgt agggctcaac gatcagttac tggtgctgca tcatccccat  1740
agccagcgcc cccagttgaa acggttgagt gcgaaagatg actgggagcc ggtgccgata  1800
attctgccgg gtattgttca ccccttcaagt cttcgcgcta ctcgcacggg gcaaatacaa  1860
gtgcagctgg agaaaactg  gcatacgttg ctgccatcaa tgacgtcgca cgataatcag  1920
cgcttacctg cccgcgtaaa acctgaacca gaggggatg  aggcgccgtc ggcgaatttc  1980
ctggcgggta gcaacgccct cgccaatcag cagcaagcca gtcgtatcag cacaccgcat  2040
catgacgcat cggtggttac gacgctggcg gggacaacag ccaacaaccc gttgacgatg  2100
gcgtcgagcc tacaggcagt ggttgatacg acccgcgctc aggtaggcgc gttggcgaga  2160
gatgtagtgg gcgcagcggc gaacagcacg atgcgggcaa tggcgcatac cttgggtgtt  2220
gtactgccgc caacgcctca ggagaagcgc ctggccagtt tccataatga ggcgaaacag  2280
gcttatacat caggaaaaat actgtttgag catctgccgt cactcgcgca agtgcgcgtc  2340
```

-continued

```
gcttcagccg tagggccgtc ggacggagaa agattcgggc tgtcacatca gcaaacgcaa    2400
cgcttgttga cgctgcgaga ggggaagctg gaagcgctgt tacgcgactt gcgcaagatc    2460
ggctttcatg aagggtgat catgggcgat atgggcgaca gcgacagtgc gcacggtctt    2520
gtttcgacga catcgacacc aacgttccgg ctggccgagc tatggcgacg gcagcattcg    2580
cgagtggata aggcgctgtc ttccgctgga ttatccagat cggaagatat ttttccggac    2640
ttgaacctaa gtatcaacgc gttggctggc ggcgcggcgc tgaatgcgga tcgtatgagc    2700
gaacgtgaag ctgagttgtt gagcgttttg tgcgaggtca gcgaaaaaat gatgcgcgct    2760
ggcgtacgct tgccggcaga tgatggaagc gttgacagcg cccacagcca ggcgccatac    2820
ggcttgagaa cagcaggatt gattgcaggt ctggtggact atgatgcgct gttgagcagt    2880
accgacgcgc aggcgctgga aatggcggag cgacttcagc aagatgccag gcttgctgca    2940
ttgtgcaaac tcggtctgtc ttcgtggggt caattagcgg ccttcgatga tgtggtgacg    3000
acgtttcgcg aacagatatc gttaccgggc tcggcacgcc gcacccagtt gctcaaaaat    3060
cttggcttgc cacccgatgc cgcgccggac gaaatggcgg cgcgcatgtc cgacttactc    3120
ctggatctgt caaccggag caccttcttt tcgacgcagt cgcgtggtct ggaactgcgc    3180
ggttcgttgg gatcggctga ctggaaacat ctcaatgcgt tcagcgtcgg cgtgactggc    3240
gaggcgcttc aagtgctcgg cgtagagcgc atcggcgatg gcaaggacgg cgatgccggg    3300
ttggtcgcgt tttttgtgcg ccacgccaaa gcctctgtat ctgcgacgtc agggatcgga    3360
atcgatttca agccaggccc cggcactggc ggccgtgtta ttgattcgcg accgggtcgc    3420
tcgatgaact cgacgtgggg aggctctacc aacctgggta tttccggcgc gtaccagcat    3480
ggtcagggcg ccgccgtgat catcgcaccg tcgacgatct ccgatttcgt gcggctgtta    3540
ttcgatgtca accatcccga taccacccaa atcctgcgca ccggtgtgaa cggtggttcg    3600
attggtcttg atctgtttga aaccaatgtg aatgcctctg tgggggcgaa cgtcagcgta    3660
tcgccattca gcctgagcca gaaatatggg ccacagaaac cgacggcaga tgcggccgtc    3720
tctggcccag acaatcggcg cagcaccgcg tcagggtcgt tgtcggtagg cgggacggct    3780
caggctggcg cgcactgggg gcaaatggag ttgcacctgg atcacgcctg gccgatatt    3840 atcggtctgg aatttcaggg ccgcacggat ttcaatcttg aattcaatag cggcctgaat    3900
ctgggaggcg cgctgtcttc cgcgctgggc gataacccc aaaagttgat aaatgcgtcc    3960 actgaaacg gcaatctgca actcgccggc atccgcgtcg cgtcaagcga tgtgcagttg    4020
ccgaccgatg ctgtggttga cgacaagcgc cgtggcccct tcctgtcgac ggccagctat    4080
aaacgcacct tcgataccga agttgccaag cctgttacgg ccggggagtg gagccagatg    4140
cgccagcgcc ttgccaaagc ctttcctgac aatatcgcag agttgggcgc gctcgattac    4200
cccaccaggc ccggtgagcg tatcgcgacc atcaaacagg tgattgaccg catacaaggt    4260
gcgaaggcgc gtagcgtgga agccgtcggt gcaatggacg gaaaggcatt gcaccgtcag    4320
cgtttcgatg ccgcgagaga aatgtcgaac gccggcaaca gcgtatggcg ggcgagttcc    4380
gaaattgagc gcgcctcgat cgtggagatg ctgcatcagt tgcgtcagca ggaacaaagc    4440
gccgtccaga atcacgcccg agccattccc ggcgcgcgtg tggaattcaa cctgttcggt    4500
cgtgaatcgc tggaaacggt ggtctttcac gccatcggtc atctgggct ggcagcaag    4560 ctgaacgatc tggcggagct gcgtcgcaag gtgccgggtc tcgatcaggt catgctgagt    4620
ttccagtcgt tgcccaaggt caatcaggtg cgctacgttt ttgagatgcg ccctcaggcg    4680
aggttcgcca tcaatgacgc gctactggcg cgcgagcagc aggcatcggc acgtgcgctc    4740
```

-continued

```
ggtttgcagg gaccctcggg aagtgaattg aattggcgcg gcgttctgga caagatcaaa    4800
accacgcctg acctttatcg gctggcggcg atcgccgtac ataacaccga tgaaaacccc    4860
gtgacctcaa gaatagggct gccgctgctg aatgtgtcgg ccacaggcgc gacatcgcat    4920
cagttgttcg aggcggaaat ccagttccga tacggtctgt atgacggtct gcaagggggtt   4980 gagttgctgg aggccggaaa cagggcattg cagtcgccgt tacgggcatt acagcaatcc    5040
ggtattcagg ccctggggca gagaacccag gccggggagg ttgcgtatgg cccccccttcg   5100 ccgcgcaaag agtcgccgtt gcgcaccgca gtggatgctg ctgcgctgac aacgagtgac    5160
atcgcgcgac aacttgaggt taaagtccag cgcatgaata ccgcgcatga gcgtgaggcg    5220
aatgctatca gttcgttcca gcaggcttat gggatcgcgt ccgcgcatct agacaggctg    5280
cttttgcgca ttcctgaatt gccattacct gaaattgatg accgcgacgt cgatggagga    5340
cgtgtgcgcg gtacatttgc gtcgctccag cgacatcatc aggcgctgga tgacgctata    5400
agtgccatgc atcaggccag cgaaaaggtg tacacgatac ctggcaagca ggccactcaa    5460
gagcaagacc cggcgctggc tcaactgctc tctgttgaaa acgtcggcg ttcgctcggg     5520 catgccttgg aaacactggc gggcagaggg gtggaagcgg gcacggccac agggcttgaa    5580
cttaacaggg tctcatcgca agtgaatgat ctggtcgctc gccgggacgc gctgctaagg    5640
cagcgtgaaa gcggtgttca ggagggcggt ctggatagcg aagagctgga aatgaaactt    5700
caattgacca cctcagtgct gcagcggttg cgcgccgatt tgctcggcga gcggcaggcg    5760
atggaggcta ccgccaaacg cctggatcag gcgagccgcg ctgccctcga aggtgagcgc    5820
agcttcagcg acgccgtgcg tgacagggcg tggggcgaac tcgataacgt gtag          5874
```

<210> SEQ ID NO 120
<211> LENGTH: 1957
<212> TYPE: PRT
<213> ORGANISM: Pseudomonas syringae pv. tomato DC3000

<400> SEQUENCE: 120

```
Met Val Lys Val Thr Ser Ser Gly Phe Thr Ala Asn Pro Leu Ser His
 1               5                   10                  15

His Ala Asp Ser Val Ser Pro Ala Asn Ser Pro Gln Leu Pro Glu
            20                  25                  30

Pro Val His Leu Val Asp Leu Ser Glu Ser Ser Arg Lys Gly Gly Met
        35                  40                  45

Arg Asn Arg Pro His Ala Ser Leu Asn Ser Gln Val Leu Glu Leu Gln
    50                  55                  60

Ala Val Pro Ser Gln Arg Gly Lys His Val Arg Val Arg Ser His Ala
65                  70                  75                  80

Asp Gly Glu Ser Val Ile Asn Ala Trp Leu Ala Lys Arg Pro Ser Val
                85                  90                  95

Gln Ser Glu Thr Ser Leu Asp Asn Asp Gly Lys Leu Val Arg Tyr Thr
            100                 105                 110

Pro Val Asn His Glu Pro Leu Ala Pro Arg Asn Glu Ala Phe Phe Thr
        115                 120                 125

Ser Val Pro Gly Met Leu Met Ala Val Leu Thr Val His Pro Glu Met
    130                 135                 140

Glu His Gly Ile Ser Gly Asp Ile Thr Ala Asp Ala Val Ala Ala Arg
145                 150                 155                 160

Leu Ala Glu Pro Pro Ile Gly Leu Leu Thr Gly Ile Trp Gln Ser Ser
                165                 170                 175
```

```
His Asp Arg Ala Tyr Leu Glu Arg Gly Gly Val His Thr Ala Asn
            180                 185                 190
Met Glu Glu Arg Trp Ala Pro Leu Thr Leu Pro Gly Ile Asn Pro Arg
            195                 200                 205
Glu Pro Leu Arg Met Ala Gly Leu Gln Ala Asp Gly Val Tyr Leu
210                 215                 220
His Asn Gly Ser Gln Leu Trp Arg Leu Thr Glu Thr Ala Ala Glu Ser
225                 230                 235                 240
Val Thr Thr Glu Asn Leu Pro Glu Gly Ala Ala Val Arg Ile Gly Ala
                245                 250                 255
Gly Gly Glu Val His Gly Leu His Glu Gly Ala Leu His Ser Asn Gly
            260                 265                 270
Ile Ser Arg Pro Ile Glu Leu Trp Arg Pro Lys Ala Gly Ala Pro Gly
        275                 280                 285
Arg Glu Gln Ser Pro Ala Arg Pro Val Asp Leu Leu Pro Leu Pro Gly
    290                 295                 300
Gly Thr Ala Ala Leu Ile Leu Asp Asp Lys Gly Arg Ile Tyr His Ala
305                 310                 315                 320
Asp Leu Lys Gly Thr Gly Ala Val Glu Ala His Arg Leu Lys Leu Pro
                325                 330                 335
Ala Asp Phe Ala Gln Gly Lys Gly Trp Ala Val Thr Ala Met Gly Leu
            340                 345                 350
Ser Arg Asp Asp Thr Val His Leu Met Leu Gln Asp Gln Asn Gly Arg
        355                 360                 365
Arg Met Ser Leu Gln Arg Ala Pro Gly Glu Ala Leu Phe Arg Pro Ala
    370                 375                 380
Tyr Leu Leu Asp Arg Pro Leu Leu Leu Tyr Thr Glu Gly Leu His
385                 390                 395                 400
Val Pro Ser Glu Ala Ala Val Gln Ser His Val Gln Leu Asp Gly His
                405                 410                 415
Ala Gln Leu Gly His Ile Asp Gly Val Leu His Tyr Lys Ala Ala Pro
            420                 425                 430
Asp Gln Ser Trp Glu Arg Leu Lys Gln Ser Gly Gly Glu Pro Leu Thr
        435                 440                 445
Gly Leu Thr Ala Leu Tyr Ser Ser Pro Leu Gly Phe Ile Asp Arg Lys
    450                 455                 460
Pro Val Phe Ala Leu Val Gly Asp Ala Arg Gln Val Val Glu Leu Lys
465                 470                 475                 480
Leu Glu Gly Arg Thr Ser Trp Leu Pro Ser Asp Ala Glu Leu Pro Arg
                485                 490                 495
His Pro Ala Gly Gly Pro Leu Ala Val Ile Pro Asp Thr Val Ala Leu
            500                 505                 510
Arg Thr Ser Pro Ile Ala Gln Phe Asp Glu Pro Val Gln Ala Leu Ala
        515                 520                 525
Val His Gly Asn Arg Val Val Ala Leu Thr Asp Ser Gly Arg Leu
    530                 535                 540
Met Ala Ala Asp Ala Asp Thr Pro Ala Arg Arg Leu Pro Thr Leu Gln
545                 550                 555                 560
Arg Pro Ile Ala Ile Ala Val Gly Leu Asn Asp Gln Leu Leu Val Leu
                565                 570                 575
His His Pro His Ser Gln Arg Pro Gln Leu Lys Arg Leu Ser Ala Lys
            580                 585                 590
```

-continued

```
Asp Asp Trp Glu Pro Val Pro Ile Ile Leu Pro Gly Ile Val His Pro
        595                 600                 605

Ser Ser Leu Arg Ala Thr Arg Thr Gly Gln Ile Gln Val Gln Leu Gly
        610                 615                 620

Glu Asn Trp His Thr Leu Leu Pro Ser Met Thr Ser His Asp Asn Gln
625                 630                 635                 640

Arg Leu Pro Ala Arg Val Lys Pro Glu Pro Glu Gly Asp Glu Ala Pro
                645                 650                 655

Ser Ala Asn Phe Leu Ala Gly Ser Asn Ala Leu Ala Asn Gln Gln Gln
            660                 665                 670

Ala Ser Arg Ile Ser Thr Pro His His Asp Ala Ser Val Val Thr Thr
        675                 680                 685

Leu Ala Gly Thr Thr Ala Asn Asn Pro Leu Thr Met Ala Ser Ser Leu
        690                 695                 700

Gln Ala Val Val Asp Thr Thr Arg Ala Gln Val Gly Ala Leu Ala Arg
705                 710                 715                 720

Asp Val Val Gly Ala Ala Asn Ser Thr Met Arg Ala Met Ala His
                725                 730                 735

Thr Leu Gly Val Val Leu Pro Pro Thr Pro Gln Glu Lys Arg Leu Ala
                740                 745                 750

Ser Phe His Asn Glu Ala Lys Gln Ala Tyr Thr Ser Gly Lys Ile Leu
        755                 760                 765

Phe Glu His Leu Pro Ser Leu Ala Gln Val Arg Val Ala Ser Ala Val
        770                 775                 780

Gly Pro Ser Asp Gly Glu Arg Phe Gly Leu Ser His Gln Gln Thr Gln
785                 790                 795                 800

Arg Leu Leu Thr Leu Arg Glu Gly Lys Leu Glu Ala Leu Leu Arg Asp
                805                 810                 815

Leu Arg Lys Ile Gly Phe His Glu Gly Val Ile Met Gly Asp Met Gly
                820                 825                 830

Asp Ser Asp Ser Ala His Gly Leu Val Ser Thr Thr Ser Thr Pro Thr
        835                 840                 845

Phe Arg Leu Ala Glu Leu Trp Arg Arg Gln His Ser Arg Val Asp Lys
        850                 855                 860

Ala Leu Ser Ser Ala Gly Leu Ser Arg Ser Glu Asp Ile Phe Pro Asp
865                 870                 875                 880

Leu Asn Leu Ser Ile Asn Ala Leu Ala Gly Gly Ala Ala Leu Asn Ala
                885                 890                 895

Asp Arg Met Ser Glu Arg Glu Ala Glu Leu Leu Ser Val Leu Cys Glu
                900                 905                 910

Val Ser Glu Lys Met Met Arg Ala Gly Val Arg Leu Pro Ala Asp Asp
        915                 920                 925

Gly Ser Val Asp Ser Ala His Ser Gln Ala Pro Tyr Gly Leu Arg Thr
        930                 935                 940

Ala Gly Leu Ile Ala Gly Leu Val Asp Tyr Asp Ala Leu Leu Ser Ser
945                 950                 955                 960

Thr Asp Ala Gln Ala Leu Glu Met Ala Glu Arg Leu Gln Gln Asp Ala
                965                 970                 975

Arg Leu Ala Ala Leu Cys Lys Leu Gly Leu Ser Ser Trp Gly Gln Leu
            980                 985                 990

Ala Ala Phe Asp Asp Val Val Thr Thr Phe Arg Glu Gln Ile Ser Leu
        995                 1000                1005
```

```
Pro Gly Ser Ala Arg Arg Thr Gln Leu Leu Lys Asn Leu Gly Leu Pro
    1010                1015                1020
Pro Asp Ala Ala Pro Asp Glu Met Ala Ala Arg Met Ser Asp Leu Leu
1025                1030                1035                1040
Leu Asp Leu Phe Asn Arg Ser Thr Phe Ser Thr Gln Ser Arg Gly
            1045                1050                1055
Leu Glu Leu Arg Gly Ser Leu Gly Ser Ala Asp Trp Lys His Leu Asn
            1060                1065                1070
Ala Phe Ser Val Gly Val Thr Gly Glu Ala Leu Gln Val Leu Gly Val
        1075                1080                1085
Glu Arg Ile Gly Asp Gly Lys Asp Gly Asp Ala Gly Leu Val Ala Phe
    1090                1095                1100
Phe Val Arg His Ala Lys Ala Ser Val Ser Ala Thr Ser Gly Ile Gly
1105                1110                1115                1120
Ile Asp Phe Lys Pro Gly Pro Gly Thr Gly Gly Arg Val Ile Asp Ser
            1125                1130                1135
Arg Pro Gly Arg Ser Met Asn Ser Thr Trp Gly Gly Ser Thr Asn Leu
            1140                1145                1150
Gly Ile Ser Gly Ala Tyr Gln His Gly Gln Gly Ala Ala Val Ile Ile
        1155                1160                1165
Ala Pro Ser Thr Ile Ser Asp Phe Val Arg Leu Leu Phe Asp Val Asn
    1170                1175                1180
His Pro Asp Thr Thr Gln Ile Leu Arg Thr Gly Val Asn Gly Gly Ser
1185                1190                1195                1200
Ile Gly Leu Asp Leu Phe Glu Thr Asn Val Asn Ala Ser Val Gly Ala
            1205                1210                1215
Asn Val Ser Val Ser Pro Phe Ser Leu Ser Gln Lys Tyr Gly Pro Gln
            1220                1225                1230
Lys Pro Thr Ala Asp Ala Ala Val Ser Gly Pro Asp Asn Arg Arg Ser
        1235                1240                1245
Thr Ala Ser Gly Ser Leu Ser Val Gly Gly Thr Ala Gln Ala Gly Ala
    1250                1255                1260
His Trp Gly Gln Met Glu Leu His Leu Asp His Ala Trp Ala Asp Ile
1265                1270                1275                1280
Ile Gly Leu Glu Phe Gln Gly Arg Thr Asp Phe Asn Leu Glu Phe Asn
            1285                1290                1295
Ser Gly Leu Asn Leu Gly Gly Ala Leu Ser Ser Ala Leu Gly Asp Asn
            1300                1305                1310
Pro Gln Lys Leu Ile Asn Ala Ser Thr Gly Asn Gly Asn Leu Gln Leu
        1315                1320                1325
Ala Gly Ile Arg Val Ala Ser Ser Asp Val Gln Leu Pro Thr Asp Ala
    1330                1335                1340
Val Val Asp Asp Lys Arg Arg Gly Pro Phe Leu Ser Thr Ala Ser Tyr
1345                1350                1355                1360
Lys Arg Thr Phe Asp Thr Glu Val Ala Lys Pro Val Thr Ala Gly Glu
            1365                1370                1375
Trp Ser Gln Met Arg Gln Arg Leu Ala Lys Ala Phe Pro Asp Asn Ile
            1380                1385                1390
Ala Glu Leu Gly Ala Leu Asp Tyr Pro Thr Arg Pro Gly Glu Arg Ile
        1395                1400                1405
Ala Thr Ile Lys Gln Val Ile Asp Arg Ile Gln Gly Ala Lys Ala Arg
    1410                1415                1420
```

-continued

```
Ser Val Glu Ala Val Gly Ala Met Asp Gly Lys Ala Leu His Arg Gln
1425                1430                1435                1440

Arg Phe Asp Ala Ala Arg Glu Met Ser Asn Ala Gly Asn Ser Val Trp
            1445                1450                1455

Arg Ala Ser Ser Glu Ile Glu Arg Ala Ser Ile Val Glu Met Leu His
        1460                1465                1470

Gln Leu Arg Gln Gln Glu Gln Ser Ala Val Gln Asn His Ala Arg Ala
    1475                1480                1485

Ile Pro Gly Ala Arg Val Glu Phe Asn Leu Phe Gly Arg Glu Ser Leu
1490                1495                1500

Glu Thr Val Val Phe His Ala Ile Gly His Leu Gly Leu Gly Ser Lys
1505                1510                1515                1520

Leu Asn Asp Leu Ala Glu Leu Arg Arg Lys Val Pro Gly Leu Asp Gln
            1525                1530                1535

Val Met Leu Ser Phe Gln Ser Leu Pro Lys Val Asn Gln Val Arg Tyr
        1540                1545                1550

Val Phe Glu Met Arg Pro Gln Ala Arg Phe Ala Ile Asn Asp Ala Leu
    1555                1560                1565

Leu Ala Arg Glu Gln Gln Ala Ser Ala Arg Ala Leu Gly Leu Gln Gly
1570                1575                1580

Pro Ser Gly Ser Glu Leu Asn Trp Arg Gly Val Leu Asp Lys Ile Lys
1585                1590                1595                1600

Thr Thr Pro Asp Leu Tyr Arg Leu Ala Ala Ile Ala Val His Asn Thr
            1605                1610                1615

Asp Glu Asn Pro Val Thr Ser Arg Ile Gly Leu Pro Leu Leu Asn Val
        1620                1625                1630

Ser Ala Thr Gly Ala Thr Ser His Gln Leu Phe Glu Ala Glu Ile Gln
    1635                1640                1645

Phe Arg Tyr Gly Leu Tyr Asp Gly Leu Gln Gly Val Glu Leu Leu Glu
1650                1655                1660

Ala Gly Asn Arg Ala Leu Gln Ser Pro Leu Arg Ala Leu Gln Gln Ser
1665                1670                1675                1680

Gly Ile Gln Ala Leu Gly Gln Arg Thr Gln Ala Gly Glu Val Ala Tyr
            1685                1690                1695

Gly Pro Pro Ser Pro Arg Lys Glu Ser Pro Leu Arg Thr Ala Val Asp
        1700                1705                1710

Ala Ala Ala Leu Thr Thr Ser Asp Ile Ala Arg Gln Leu Glu Val Lys
    1715                1720                1725

Val Gln Arg Met Asn Thr Ala His Glu Arg Glu Ala Asn Ala Ile Ser
1730                1735                1740

Ser Phe Gln Gln Ala Tyr Gly Ile Ala Ser Ala His Leu Asp Arg Leu
1745                1750                1755                1760

Leu Leu Arg Ile Pro Glu Leu Pro Leu Pro Glu Ile Asp Asp Arg Asp
            1765                1770                1775

Val Asp Gly Gly Arg Val Arg Gly Thr Phe Ala Ser Leu Gln Arg His
        1780                1785                1790

His Gln Ala Leu Asp Asp Ala Ile Ser Ala Met His Gln Ala Ser Glu
    1795                1800                1805

Lys Val Tyr Thr Ile Pro Gly Lys Gln Ala Thr Gln Glu Gln Asp Pro
1810                1815                1820

Ala Leu Ala Gln Leu Leu Ser Val Glu Lys Arg Arg Arg Ser Leu Gly
1825                1830                1835                1840
```

-continued

```
His Ala Leu Glu Thr Leu Ala Gly Arg Gly Val Glu Ala Gly Thr Ala
            1845                1850                1855

Thr Gly Leu Glu Leu Asn Arg Val Ser Ser Gln Val Asn Asp Leu Val
        1860                1865                1870

Ala Arg Arg Asp Ala Leu Leu Arg Gln Arg Glu Ser Gly Val Gln Glu
    1875                1880                1885

Gly Gly Leu Asp Ser Glu Glu Leu Glu Met Glu Leu Gln Leu Thr Thr
1890                1895                1900

Ser Val Leu Gln Arg Leu Arg Ala Asp Leu Leu Gly Glu Arg Gln Ala
1905                1910                1915                1920

Met Glu Ala Thr Ala Lys Arg Leu Asp Gln Ala Ser Arg Ala Ala Leu
                1925                1930                1935

Glu Gly Glu Arg Ser Phe Ser Asp Ala Val Arg Asp Arg Ala Trp Gly
            1940                1945                1950

Glu Leu Asp Asn Val
        1955
```

<210> SEQ ID NO 121
<211> LENGTH: 864
<212> TYPE: DNA
<213> ORGANISM: Pseudomonas syringae pv. tomato DC3000

<400> SEQUENCE: 121

| | |
|---|---|
| atgaacatta cgccgctcac gtcagccgcg ggcaagggct cgtccgcaca aggcacagac | 60 |
| aaaatttcca ttcccaactc cacgcgcatg atcaatgccg cttcaatcaa gtggttgaat | 120 |
| aaggtgcgta gcgccatcag tgaccacatc cgcaccagca tcgagaaagg gaaactgttc | 180 |
| gagctcgcct ccttgggcag caacatgttc ggtgtcccgg ctctttcagc gcgcccctcg | 240 |
| acgctccaac ctgtgttggc gtttgaggct gaccccaatc acgacctgaa ccttgtcagg | 300 |
| gtctatatgc aggacagcgc cggcaagctc actccctggg acccgacgcc caacgcggtc | 360 |
| acgacgacgt cgaatccatc agagcctgat gcgcagagcg atacggcttc gtcatcatta | 420 |
| cctcggcggc ctcccgcagg ctcggtgctg agtttgctgg cattgcgct ggatcacgcg | 480 |
| caacgccaca gtcctcgcgc ggacaggtct gccaagggac gacctggccg agaggagagg | 540 |
| aacggggcaa ggttcaatgc caagcaaaca aagccgacag aggctgaagc ctacggtgat | 600 |
| catcagacac ccaatcctga tttgcacagg caaaaagaga cagctcaacg cgttgctgaa | 660 |
| agcatcaaca gcatgcgaga gcagcaaaat ggaatgcaac gcgccgaagg gcttctcaga | 720 |
| gccaaagaag cgttgcaagc tcgggaagcc gcgcgcaagc agcttctgga cgtgctcgag | 780 |
| gccatccagg ctggccgtga agactccacc gacaagaaga tcagcgccac tgaaaagaac | 840 |
| gccacgggca tcaactacca gtga | 864 |

<210> SEQ ID NO 122
<211> LENGTH: 287
<212> TYPE: PRT
<213> ORGANISM: Pseudomonas syringae pv. tomato DC3000

<400> SEQUENCE: 122

```
Met Asn Ile Thr Pro Leu Thr Ser Ala Ala Gly Lys Gly Ser Ser Ala
1               5                   10                  15

Gln Gly Thr Asp Lys Ile Ser Ile Pro Asn Ser Thr Arg Met Ile Asn
            20                  25                  30

Ala Ala Ser Ile Lys Trp Leu Asn Lys Val Arg Ser Ala Ile Ser Asp
        35                  40                  45
```

His Ile Arg Thr Ser Ile Glu Lys Gly Lys Leu Phe Glu Leu Ala Ser
        50                  55                  60

Leu Gly Ser Asn Met Phe Gly Val Pro Ala Leu Ser Ala Arg Pro Ser
 65                  70                  75                  80

Thr Leu Gln Pro Val Leu Ala Phe Glu Ala Asp Pro Asn His Asp Leu
                 85                  90                  95

Asn Leu Val Arg Val Tyr Met Gln Asp Ser Ala Gly Lys Leu Thr Pro
            100                 105                 110

Trp Asp Pro Thr Pro Asn Ala Val Thr Thr Ser Asn Pro Ser Glu
            115                 120                 125

Pro Asp Ala Gln Ser Asp Thr Ala Ser Ser Ser Leu Pro Arg Arg Pro
130                 135                 140

Pro Ala Gly Ser Val Leu Ser Leu Leu Gly Ile Ala Leu Asp His Ala
145                 150                 155                 160

Gln Arg His Ser Pro Arg Ala Asp Arg Ser Ala Lys Gly Arg Pro Gly
                165                 170                 175

Arg Glu Glu Arg Asn Gly Ala Arg Phe Asn Ala Lys Gln Thr Lys Pro
            180                 185                 190

Thr Glu Ala Glu Ala Tyr Gly Asp His Gln Thr Pro Asn Pro Asp Leu
        195                 200                 205

His Arg Gln Lys Glu Thr Ala Gln Arg Val Ala Glu Ser Ile Asn Ser
210                 215                 220

Met Arg Glu Gln Gln Asn Gly Met Gln Arg Ala Glu Gly Leu Leu Arg
225                 230                 235                 240

Ala Lys Glu Ala Leu Gln Ala Arg Glu Ala Arg Lys Gln Leu Leu
                245                 250                 255

Asp Val Leu Glu Ala Ile Gln Ala Gly Arg Glu Asp Ser Thr Asp Lys
            260                 265                 270

Lys Ile Ser Ala Thr Glu Lys Asn Ala Thr Gly Ile Asn Tyr Gln
        275                 280                 285

<210> SEQ ID NO 123
<211> LENGTH: 837
<212> TYPE: DNA
<213> ORGANISM: Pseudomonas syringae pv. tomato DC3000

<400> SEQUENCE: 123
atgaccttaa gaatcaatac tcgttctgct accccggttg tacctctgga aacaggctct      60
acatcgcagc cgacaccacc gccggtcacg gcaagagcga ctgagcctcc cccgtcgcc     120 aatcctgcgg cgcctaaatc agcgccaggt gttcagcaag cacacgggct gaagacgcgc     180
atcgctggca agctttccga acgtcagacc aatttcagtc tcgggattcc cggcactggt     240
cgtactctca accggccctt gcgcagcggg attccggagg aaggtgagca ggtatcgaac     300
gaggagagtc atgatccgtt gctcaaggaa gcgcatgaac tgcagcgtat ggtggagtcg     360
gcgctgaccc atctgaaggc ggcaccgacg tctctctggg agcgtcccgc cccttcaacg     420
gtaaggcgta ttaccaccaa gattttccg tggctaaagc ctgccccgct gcgcgaagtc     480
gcaagcaatg gcagcaacgc caagaccaag atcaagatca actcacagca aagccctgaa     540
accatcgcag cggcggtgaa agagctgagc accggctcg atcaccagag caaggtgctc     600
gccacagcca cccacgcact ggtcgctgcg cgtgagcatc ttgaatcgct cgaacaggcc     660
accccgccct cgtcgaccga accactggac catgccaggg ctcgcgttca acaagccgac     720

```
tccaccaccc gcctggccag tcagcaactt cgtgagctga ttcagggtac agacgtgttg    780
caactgggcg cgctgagtga agggcaggat caggttgaac agaaagccga gttttct      837
```

<210> SEQ ID NO 124
<211> LENGTH: 279
<212> TYPE: PRT
<213> ORGANISM: Pseudomonas syringae pv. tomato DC3000

<400> SEQUENCE: 124

```
Met Thr Leu Arg Ile Asn Thr Arg Ser Ala Thr Pro Val Val Pro Leu
  1               5                  10                  15

Glu Thr Gly Ser Thr Ser Gln Pro Thr Pro Pro Val Thr Ala Arg
             20                  25                  30

Ala Thr Glu Pro Pro Pro Val Ala Asn Pro Ala Ala Pro Lys Ser Ala
         35                  40                  45

Pro Gly Val Gln Gln Ala His Gly Leu Lys Thr Arg Ile Ala Gly Lys
     50                  55                  60

Leu Ser Glu Arg Gln Thr Asn Phe Ser Leu Gly Ile Pro Gly Thr Gly
 65                  70                  75                  80

Arg Thr Leu Asn Arg Pro Leu Arg Ser Gly Ile Pro Glu Glu Gly Glu
                 85                  90                  95

Gln Val Ser Asn Glu Glu Ser His Asp Pro Leu Leu Lys Glu Ala His
            100                 105                 110

Glu Leu Gln Arg Met Val Glu Ser Ala Leu Thr His Leu Lys Ala Ala
        115                 120                 125

Pro Thr Ser Leu Trp Glu Arg Pro Ala Pro Ser Thr Val Arg Arg Ile
    130                 135                 140

Thr Thr Lys Ile Phe Pro Trp Leu Lys Pro Ala Pro Leu Arg Glu Val
145                 150                 155                 160

Ala Ser Asn Gly Ser Asn Ala Lys Thr Lys Ile Lys Ile Asn Ser Gln
                165                 170                 175

Gln Ser Pro Glu Thr Ile Ala Ala Val Lys Glu Leu Ser Thr Arg
            180                 185                 190

Leu Asp His Gln Ser Lys Val Leu Ala Thr Ala Thr His Ala Leu Val
        195                 200                 205

Ala Ala Arg Glu His Leu Glu Ser Leu Glu Gln Ala Thr Pro Pro Ser
    210                 215                 220

Ser Thr Glu Pro Leu Asp His Ala Arg Ala Arg Val Gln Gln Ala Asp
225                 230                 235                 240

Ser Thr Thr Arg Leu Ala Ser Gln Gln Leu Arg Glu Leu Ile Gln Gly
                245                 250                 255

Thr Asp Val Leu Gln Leu Gly Ala Leu Ser Glu Gly Gln Asp Gln Val
            260                 265                 270

Glu Gln Lys Ala Glu Phe Ser
        275
```

<210> SEQ ID NO 125
<211> LENGTH: 615
<212> TYPE: DNA
<213> ORGANISM: Pseudomonas syringae pv. tomato DC3000

<400> SEQUENCE: 125

```
ataggtaata tttgcggcac ctcgggctca cgtcatgtgt atagcccatc ccatacacaa    60
cgaataactt cagctccctc tacatccact catgttggtg gagatacact gacatccatt   120
catcagcttt cgcatagtca gagagagcag tttctgaaca tgcatgatcc aatgagagta   180
```

```
atgggacttg accatgatac cgagcttttc agaacgacgg atagtcgcta tataaaaaac    240
gataaactcg cgggcaatcc acaatccatg gcgagtatcc ttatgcatga agaactgcgc    300
cccaatcgtt ttgccagcca tacaggtgcc caaccacacg aagcaagggc gtacgttccg    360
aaaagaataa aagccaccga tctaggagtt ccatcactga acgtaatgac tggctcgcta    420
gcgcgagacg gaattagagc ttatgatcac atgagtgata atcaggtctc tgtcaaaatg    480
cgactgggag attttctcga aagggtggc aaggtctatg ccgacgcttc gtctgtagct    540
gacgatgggg aaacatcaca agctctgatt gtcacattgc ccaaaggaca gaaagtgccg    600
gtcgaaaggg tctga                                                    615
```

<210> SEQ ID NO 126
<211> LENGTH: 204
<212> TYPE: PRT
<213> ORGANISM: Pseudomonas syringae pv. tomato DC3000

<400> SEQUENCE: 126

```
Met Gly Asn Ile Cys Gly Thr Ser Gly Ser Arg His Val Tyr Ser Pro
  1               5                  10                  15

Ser His Thr Gln Arg Ile Thr Ser Ala Pro Ser Thr Ser Thr His Val
             20                  25                  30

Gly Gly Asp Thr Leu Thr Ser Ile His Gln Leu Ser His Ser Gln Arg
         35                  40                  45

Glu Gln Phe Leu Asn Met His Asp Pro Met Arg Val Met Gly Leu Asp
     50                  55                  60

His Asp Thr Glu Leu Phe Arg Thr Thr Asp Ser Arg Tyr Ile Lys Asn
 65                  70                  75                  80

Asp Lys Leu Ala Gly Asn Pro Gln Ser Met Ala Ser Ile Leu Met His
                 85                  90                  95

Glu Glu Leu Arg Pro Asn Arg Phe Ala Ser His Thr Gly Ala Gln Pro
            100                 105                 110

His Glu Ala Arg Ala Tyr Val Pro Lys Arg Ile Lys Ala Thr Asp Leu
        115                 120                 125

Gly Val Pro Ser Leu Asn Val Met Thr Gly Ser Leu Ala Arg Asp Gly
    130                 135                 140

Ile Arg Ala Tyr Asp His Met Ser Asp Asn Gln Val Ser Val Lys Met
145                 150                 155                 160

Arg Leu Gly Asp Phe Leu Glu Arg Gly Gly Lys Val Tyr Ala Asp Ala
                165                 170                 175

Ser Ser Val Ala Asp Asp Gly Glu Thr Ser Gln Ala Leu Ile Val Thr
            180                 185                 190

Leu Pro Lys Gly Gln Lys Val Pro Val Glu Arg Val
        195                 200
```

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: HIV TAT
      domain -continued

```
<400> SEQUENCE: 127

Tyr Gly Arg Lys Lys Arg Arg Gln Arg Arg Arg
  1               5                   10

<210> SEQ ID NO 128
<211> LENGTH: 34
<212> TYPE: DNA
<213> ORGANISM: Artificial Sequence
<220> FEATURE:
<223> OTHER INFORMATION: Description of Artificial Sequence:  primer

<400> SEQUENCE: 128
agtaggatcc atagaaaaat accatagggg tgca                                34

<210> SEQ ID NO 129
<211> LENGTH: 55
<212> TYPE: DNA
<213> ORGANISM: Artificial Sequence
<220> FEATURE:
<223> OTHER INFORMATION: Description of Artificial Sequence:  primer

<400> SEQUENCE: 129
agtatctaga tcacttgtca tcgtcgtcct tgtagtcgtc aatcacatgc gcttg         55

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 130
atgcggatcc cgtatgacct tgtaaaat                                      28

<210> SEQ ID NO 131
<211> LENGTH: 58
<212> TYPE: DNA
<213> ORGANISM: Artificial Sequence
<220> FEATURE:
<223> OTHER INFORMATION: Description of Artificial Sequence:  primer

<400> SEQUENCE: 131
atgctctaga tcaagcgtaa tctggaacat cgtatgggta gccgttgtaa aactgctt     58

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence:  primer

<400> SEQUENCE: 132
agtcggatcc gataatcctg gatgatccat tg                                 32

<210> SEQ ID NO 133
<211> LENGTH: 55
<212> TYPE: DNA
<213> ORGANISM: Artificial Sequence
<220> FEATURE:
<223> OTHER INFORMATION: Description of Artificial Sequence:  primer

<400> SEQUENCE: 133
agtcctcgag tcacttgtca tcgtcgtcct tgtagtcttg atgtgccctg tactt         55
```

```
<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 134
agtaaagctt acgggcaggt attgcaag                                    28

<210> SEQ ID NO 135
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 135
agtatctaga tcacttgtca tcgtcgtcct tgtagtcttt tttgggcagc cagcg      55

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 136
agtaggatcc tgcctccaac tattggct                                    28

<210> SEQ ID NO 137
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 137
agtatctaga tcacttgtca tcgtcgtcct tgtagtctct cgctttgaac gcctg      55

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 138
ataggatccc gagaacggcg cggacgtg                                    28

<210> SEQ ID NO 139
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 139
atatctagat catttatcat catcatcttt ataatcctcg tcagagctct ctgc       54

<210> SEQ ID NO 140
<211> LENGTH: 27
<212> TYPE: DNA
<213> ORGANISM: Artificial Sequence
<220> FEATURE:
<223> OTHER INFORMATION: Description of Artificial Sequence: primer
```

```
<400> SEQUENCE: 140
gatggatcca cgcacataac aacggtg                                              27

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 141
atatctagat catttatcat catcatcttt ataatcaatc tgacttaata c                   51

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 142
attggtacct ctagaggatc caaccttcaa tctgaa                                    36

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 143
atgtcgactt agcggtagag cattgcg                                              27

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 144
gcgaattcgt tagttgattt tgtctagcg                                            29

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 145
gaggatccgc cgttgtaaaa ctgcttaga                                            29

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 146
gtaaaacgac ggccagt                                                         17
```

```
<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 147
atgagaattc gcatctccat gcatctt                                    27

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 148
cggactcgag ctcagggcgc gaaactga                                   28

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 149
gtatggtacc ccgacctggc aaccgcag                                   28

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 150
agtcctcgag actaaagagg gtatacgaat gggaaatata                      40

<210> SEQ ID NO 151
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 151
agtcgatatc tcattgccag ttacggtacg ggc                             33

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 152
gatggatcca agtaaccggt ctgcaca                                    27

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: primer
```

```
<400> SEQUENCE: 153
atatctagat catttatcat catcatcttt atatgacttt tgagccgcct g        51

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 154
ggcctcgaga tggacgggtc cggggagcag ctt                            33

<210> SEQ ID NO 155
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 155
ggcactagtt cagcccatct tcttccagat ggtg                           34

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 156
cacctattta attcgttgag aaacaatgaa aata                           34

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 157
gacatctcgt ctcgccaagc c                                         21

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 158
caccaagcaa cgtctggagg caacaatgca                                30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 159
gtcgcctagg aaattattta gttcccatga                                30
```

<210> SEQ ID NO 160
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 160
caccaagatc ggagaggatc agaatatggc g                          31

<210> SEQ ID NO 161
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 161
ggggactatt ctaaaagcat acttggc                               27

<210> SEQ ID NO 162
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 162
caccttagcg taaggagcta acaatgaacc c                          31

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 163
gtttcgcgcc ctgagcgc                                         18

<210> SEQ ID NO 164
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 164
cacccatagg ggtgcaataa caatgaatag a                          31

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 165
gtcaatcaca tgcgcttggc c                                     21

<210> SEQ ID NO 166
<211> LENGTH: 44
<212> TYPE: DNA
<213> ORGANISM: Artificial Sequence
<220> FEATURE:
<223> OTHER INFORMATION: Description of Artificial Sequence: primer

```
<400> SEQUENCE: 166
aaaaagcagg cttcgaagga gatagaacca tgtatagccc atcc                44

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 167
agaaagctgg gtaacagacc ctttcgac                                  28

<210> SEQ ID NO 168
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 168
cacccacata ggatatgtaa acaatgcaaa taaagaac                       38

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 169
gccgttgtaa aactgcttag aggc                                      24

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 170
caccacaaag aggttttcaa acaatgaatc                                30

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 171
gcagtagagc gtgtcgcgac                                           20

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 172
atacataacg ctggccta                                             18
```

```
<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 173
cggatccatg acaatcgt                                                    18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 174
gcaaatcctt taagctct                                                    18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 175
tgtttcgcta agccactg                                                    18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 176
tcgcgccaaa ccagggag                                                    18

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 177
tcccacattc tgcaacgc                                                    18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 178
aaccccattc agtcacgc                                                    18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence:  primer
```

<400> SEQUENCE: 179
tttgccatgc gtgattgc                                                      18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 180
cctctacgat ctattcaa                                                      18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 181
ggcaatgctc gcggcctg                                                      18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 182
tccggtagct cgtcagcg                                                      18

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 183
gtggatgacc acatagttat g                                                  21

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 184
agcccatccc atacacaa                                                      18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 185
cactttctgt cctttggg                                                      18

```
<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 186
tattcagctt caagaatg                                                        18

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 187
acccgcatag acctgtctg                                                       19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 188
atcactccgt ctcgatatc                                                       19

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 189
tgccctgtac ttcatgcg                                                        18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 190
ctatgtattt caaaacac                                                        18

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 191
atcaccctct gtaattccc                                                       19

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: primer
```

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 193
cagcaccgga agcccttc                                                 18

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 194
ggtaatattt gtggtacttc                                               20

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 195
cagatgtaac gtgacatc                                                 18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 196
acagtcagca atcactcg                                                 18

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 197
tacactccat acactgctg                                                19

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 198
ttgaattcat gaaaatacat aacgctgg                                      28

<210> SEQ ID NO 199
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 199
ttctcgagtc agacatctcg tctcgc                26

<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 200
ttggatccgt atgcacgcaa atcctttaag ctc                33

<210> SEQ ID NO 201
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 201
ttctcgagtc agtcgcctag gaaattattt agttcc                36

<210> SEQ ID NO 202
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 202
ttgaattcat gaatagagtt tccggtagct c                31

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 203
ttctcgagtc agtcaatcac atgcgcttgg                30

<210> SEQ ID NO 204
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 204
ttgaattcat gggtaatatt tgcggcacct c                31

<210> SEQ ID NO 205
<211> LENGTH: 26
<212> TYPE: DNA
<213> ORGANISM: Artificial Sequence
<220> FEATURE:
<223> OTHER INFORMATION: Description of Artificial Sequence: primer -continued

```
<400> SEQUENCE: 205
ttctcgagtc agacccttc gaccgg                                          26

<210> SEQ ID NO 206
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 206
ttgaattcat gcaaataaag aacagtcatc tc                                  32

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 207
ttctcgagtc agccgttgta aaactgctta gag                                 33

<210> SEQ ID NO 208
<211> LENGTH: 1185
<212> TYPE: DNA
<213> ORGANISM: Pseudomonas syringae pv. tomato DC3000

<400> SEQUENCE: 208
atgactgcct acgatgtaga aaggaatgg agcagaattt ccaatactgc cgctaaaact      60
caccagaaca acgatttga aggtttcacc taccaggact tcagaaccca cgtaccgatc     120
atggacaagg aaggcttcgc ggcacaaacc gaacgctgcc ttgagcgcaa cgagcgcaac     180
tgcctgatcg gctttaccag tggcaccagc ggcaacctca acgctgtta ttactactac     240 gactgtgaag tcgatgaaga cagttcccgc tccaacgtct ccgcagcaa tggtttcatt     300 caacccggtg atcgctgcgc caacctgttc accatcaacc tgttttctgc cctgaacaac    360
atcaccacca tgatggccgg taactgcggt gcgcatgtgg tgtccgtagg cgatatcacc    420
ctgctgacca agagtcactt cgaggcgctc aactcgatca agctcaacgt actgctcggc    480
gtaccctcga ccatcctgca gttcatcgat gccatgcagc agcacggtgt gcacatcgat    540
atcgaaaagg tcgtcttcaa tggcgagggc ctgaaaacct tcagaagaa atcatcagg      600 gaagcctttg gcaacaggt ctccatcgtc ggcgtatatg gcagttccga gggcggcatt     660
ctgggtttca ccaacagccc ttgccacacc gaatacgagt ttctttccga caaatacttc    720
atcgagaaag aaggcgacag catcctcatc acctcgttga cccgcgagaa cttcacaccg    780
ctgctccggt atcgcctggg agacaccgca acgctttcgc tgaaaggcga caagctctat    840
ttgactgaca tccagcggga ggacatgagc ttcaacttca tgggcaacct cattggtctg    900
ggcatcattc aacaagcgat caaacagaca ctgggccgca cgctggaaat ccaggttcac    960
ctgtcagtga ctgatgcgcg caaagaactg gtgaccgttt tcgttcaggc ctcggaagtc   1020
aacgaagatg aacgcgccag aatcgaaaca gccatcgccg atattccgga catcaacgag   1080
gcctatcaga aagaccaggg cagcgtgctg gttgtgcgca aggatgccag agactacgcc   1140
gtctcggagc gaggcaaaat gctctacatc attgaccgca ggaat                   1185
```

-continued

<210> SEQ ID NO 209
<211> LENGTH: 395
<212> TYPE: PRT
<213> ORGANISM: Pseudomonas syringae pv. tomato DC3000

<400> SEQUENCE: 209

```
Met Thr Ala Tyr Asp Val Glu Lys Glu Trp Ser Arg Ile Ser Asn Thr
 1               5                  10                  15

Ala Ala Lys Thr His Gln Asn Asn Asp Phe Glu Gly Phe Thr Tyr Gln
            20                  25                  30

Asp Phe Arg Thr His Val Pro Ile Met Asp Lys Glu Gly Phe Ala Ala
        35                  40                  45

Gln Thr Glu Arg Cys Leu Glu Arg Asn Glu Arg Asn Cys Leu Ile Gly
    50                  55                  60

Phe Thr Ser Gly Thr Ser Gly Asn Leu Lys Arg Cys Tyr Tyr Tyr Tyr
65                  70                  75                  80

Asp Cys Glu Val Asp Glu Ser Ser Arg Ser Asn Val Phe Arg Ser
            85                  90                  95

Asn Gly Phe Ile Gln Pro Gly Asp Arg Cys Ala Asn Leu Phe Thr Ile
            100                 105                 110

Asn Leu Phe Ser Ala Leu Asn Asn Ile Thr Thr Met Met Ala Gly Asn
        115                 120                 125

Cys Gly Ala His Val Val Ser Val Gly Asp Ile Thr Leu Leu Thr Lys
    130                 135                 140

Ser His Phe Glu Ala Leu Asn Ser Ile Lys Leu Asn Val Leu Leu Gly
145                 150                 155                 160

Val Pro Ser Thr Ile Leu Gln Phe Ile Asp Ala Met Gln Gln His Gly
                165                 170                 175

Val His Ile Asp Ile Glu Lys Val Val Phe Asn Gly Glu Gly Leu Lys
            180                 185                 190

Thr Phe Gln Lys Lys Ile Ile Arg Glu Ala Phe Gly Glu Gln Val Ser
        195                 200                 205

Ile Val Gly Val Tyr Gly Ser Ser Glu Gly Ile Leu Gly Phe Thr
    210                 215                 220

Asn Ser Pro Cys His Thr Glu Tyr Glu Phe Leu Ser Asp Lys Tyr Phe
225                 230                 235                 240

Ile Glu Lys Glu Gly Asp Ser Ile Leu Ile Thr Ser Leu Thr Arg Glu
                245                 250                 255

Asn Phe Thr Pro Leu Leu Arg Tyr Arg Leu Gly Asp Thr Ala Thr Leu
            260                 265                 270

Ser Leu Lys Gly Asp Lys Leu Tyr Leu Thr Asp Ile Gln Arg Glu Asp
        275                 280                 285

Met Ser Phe Asn Phe Met Gly Asn Leu Ile Gly Leu Gly Ile Ile Gln
    290                 295                 300

Gln Ala Ile Lys Gln Thr Leu Gly Arg Thr Leu Glu Ile Gln Val His
305                 310                 315                 320

Leu Ser Val Thr Asp Ala Arg Lys Glu Leu Val Thr Val Phe Val Gln
                325                 330                 335

Ala Ser Glu Val Asn Glu Asp Glu Arg Ala Arg Ile Glu Thr Ala Ile
            340                 345                 350

Ala Asp Ile Pro Asp Ile Asn Glu Ala Tyr Gln Lys Asp Gln Gly Ser
        355                 360                 365
```

```
-continued

Val Leu Val Val Arg Lys Asp Ala Arg Asp Tyr Ala Val Ser Glu Arg
        370             375                 380

Gly Lys Met Leu Tyr Ile Ile Asp Arg Arg Asn
385                 390                 395
```

US 7,220,583 B2

PSEUDOMONAS AVR AND HOP PROTEINS, THEIR ENCODING NUCLEIC ACIDS, AND USE THEREOF

This application claims benefit of U.S. Provisional Patent Application Ser. Nos. 60/356,408, filed Feb. 12, 2002, and 60/380,185, filed May 10, 2002, each of which is hereby incorporated by reference in its entirety.

This work was supported by National Science Foundation Grant Nos. MCB-9982646 and IBN-0096348, National Science Foundation Plant Genome Research Program Cooperative Agreement DBI-0077622, and National Research Initiative Competitive Grants Program, U.S. Department of Agriculture, Grant No. 01-35319-10019. The U.S. Government may have certain rights in this invention.

FIELD OF THE INVENTION

The present invention relates to isolated DNA molecules corresponding to the open reading frames of *Pseudomonas syringae* pv. *tomato* DC3000, the isolated avirulence effector proteins and hrp-dependent outer proteins encoded thereby, as well as their various uses.

BACKGROUND OF THE INVENTION

The plant pathogenic bacterium *Pseudomonas syringae* is noted for its diverse and host-specific interactions with plants. A specific strain may be assigned to one of at least 40 pathovars based on its host range among different plant species and then further assigned to a race based on differential interactions among cultivars of the host. In host plants the bacteria typically grow to high population levels in leaf intercellular spaces and then produce necrotic lesions. In nonhost plants or in host plants with race-specific resistance, the bacteria elicit the hypersensitive response (HR), a rapid, defense-associated programmed death of plant cells in contact with the pathogen (Alfano & Collmer, *J. Bacteriol.* 179:5655–5662 (1997)). The ability to produce either of these reactions in plants appears to be directed by hrp (HR and pathogenicity) and hrc (HR and conserved) genes that encode a type III protein secretion pathway and by avr (avirulence) and hop (Hrp-dependent outer protein) genes that encode effector proteins injected into plant cells by the pathway (Alfano & Collmer, *J. Bacteriol.* 179:5655–5662 (1997)). These effectors may also betray the parasite to the HR-triggering R-gene surveillance system of potential hosts (hence the avr designation), and plant breeding for resistance based on such gene-for-gene (avr-R) interactions may produce complex combinations of races and differential cultivars (Keen, *Annu. Rev. Genet.* 24:447–463 (1990)). hrp/hrc genes are probably universal among necrosis-causing gram-negative plant pathogens, and they have been sequenced in *P. syringae* pv. syringae (Psy) 61, *Erwinia amylovora* Ea321, *Xanthomonas campestris* pv. *vesicatoria* (Xcv) 85-10, and *Ralstonia solanacearum* GMI1000 (Alfano & Collmer, *J. Bacteriol.* 179:5655–5662 (1997)). Based on their distinct gene arrangements and regulatory components, the hrp/hrc gene clusters of these four bacteria can be divided into two groups: I (*Pseudomonas* and *Erwinia*) and II (*Xanthomonas* and *Ralstonia*). The discrepancy between the distribution of these groups and the phylogeny of the bacteria provides some evidence that hrp/hrc gene clusters have been horizontally acquired and, therefore, may represent pathogenicity islands (Pais) (Alfano & Collmer, *J. Bacteriol.* 179:5655–5662 (1997)).

Virulence effector proteins delivered to or into host cells by type III secretion systems are key factors in the pathogenicity of many bacteria, including animal pathogens in the genera *Salmonella, Yersinia, Shigella*, and *Escherichia*, and plant pathogens in the genera *Pseudomonas, Erwinia, Xanthomonas, Ralstonia*, and *Pantoea* (Galán & Collmer, *Science* 284:1322–1328 (1999)). In plant pathogens, the type III secretion machinery is referred to as the hypersensitive response and pathogenicity (Hrp) system because secretion mutants typically lose their ability to elicit the defense-associated hypersensitive response in nonhost plants and to grow parasitically or be pathogenic in host plants (Alfano & Collmer, *J. Bacteriol.* 179:5655–5662 (1997)). These phenotypes demonstrate the importance of the Hrp system in bacterium-plant interactions, and global identification of effectors will be important for understanding the pathogenesis of bacteria that use type III secretion systems. Unfortunately, several factors have hindered searches for type III effector genes. These factors include: (i) effectors are often redundant with mutants having only subtle phenotypes; (ii) with few exceptions (see e.g., Miao & Miller, *Proc. Natl. Acad. Sci. USA* 97:7539–7544 (2000)) motifs that can identify proteins as substrates for type III secretion have not been recognized (Lloyd et al., *Mol. Microbiol.* 39:520–523) (2001); (iii) many effectors show no similarity to known proteins; and (iv) some pathogens have multiple type III secretion systems which deliver different sets of effectors (Cornelis & Van Gijsegem, *Annu. Rev. Microbiol.* 54:735–774 (2000)). Thus, a complete inventory of type III effector genes is lacking for any pathogen, although it seems that pathogens such as *Salmonella* may have many such genes (Worley et al., *Mol. Microbiol.* 36:749–761 (2000)).

Plant pathogen type III effector proteins are mostly designated Avr or Hop, depending on whether their primary phenotype involves plant reaction or secretion behavior. Many effectors were initially discovered through their ability to betray the pathogen to the host R (resistance) gene surveillance system, thereby rendering the pathogen avirulent on a test plant (Keen, *Annu. Rev. Genet.* 24:447–463 (1990)). Over 25 effector genes have been identified by Avr or Hop phenotypes in various *P. syringae* pathovars and races (Vivian & Arnold, *J. Plant Pathol.* 82:163–178 (2000); Alfano et al., *Proc. Natl. Acad. Sci. USA* 97:4856–4861 (2000)). The encoded effectors seem to determine both basic pathogenicity and host range, but the number of such proteins produced by any single strain has not been systematically investigated. *P. s. tomato* DC3000 is known to carry at least three avr genes, avrPto (Ronald et al., *J. Bacteriol.* 174:1604–1611 (1992)), avrPtoB (Kim et al., *Cell* 109: 589–598 (2002)), and avrE (Lorang & Keen, *Mol. Plant-Microbe Interact.* 8:49–57 (1995)), with the latter being in the Hrp pathogenicity island along with five other candidate effector genes (Alfano et al., *Proc. Natl. Acad. Sci. USA* 97:4856–486 (2000); Lorang & Keen, *Mol. Plant-Microbe Interact.* 8:49–57 (1995)).

The present invention is a further advance in the effort to identify, clone, and sequence Avr and Hop proteins or polypeptides from plant pathogens.

SUMMARY OF THE INVENTION

One aspect of the present invention relates to an isolated nucleic acid molecule that includes a nucleotide sequence which (i) encodes a protein or polypeptide having the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, or SEQ ID NO: 209; or (ii) hybridizes, under stringency conditions comprising a hybridization medium which includes 0.9×SSC at a temperature of 42° C., to a DNA molecule complementary to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, OR SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, or SEQ ID NO: 208; or (iii) is complementary to the nucleic acid molecules of (i) and (ii). Expression vectors, host cells, and transgenic plants which include the DNA molecules of the present invention are also disclosed. Methods of making such host cells and transgenic plant are disclosed.

A further aspect of the present invention relates to isolated effector proteins or polypeptides encoded by the nucleic acid molecules of the present invention. Compositions which contain the proteins or polypeptides are also disclosed.

Yet another aspect of the present invention relates to methods of imparting disease resistance to a plant. According to one approach, this method is carried out by transforming a plant cell with a heterologous DNA molecule of the present invention and regenerating a transgenic plant from the transformed plant cell, wherein the transgenic plant expresses the heterologous DNA molecule under conditions effective to impart disease resistance. According to another approach, this method is carried out by treating a plant with a protein or polypeptide of the present invention under conditions effective to impart disease resistance to the treated plant.

A further aspect of the present invention relates to a method of causing eukaryotic cell death which includes: introducing into a eukaryotic cell a cytotoxic Pseudomonas protein of the present invention, said introducing being performed under conditions effective to cause cell death.

A still further aspect of the present invention relates to a method of treating a cancerous condition which includes introducing a cytotoxic Pseudomonas protein of the present invention into cancer cells of a patient under conditions effective to cause death of cancer cells, thereby treating the cancerous condition.

Yet another aspect of the present invention relates to a method of inhibiting programmed cell death which includes introducing into a eukaryotic cell susceptible to programmed cell death, a protein of the present invention that is a hypersensitive response suppressor, said introducing being performed under conditions effective to inhibit programmed cell death of the eukaryotic cell.

Yet another aspect of the present invention relates to a method of modifying a metabolic pathway in a cell which includes: introducing into a cell a protein or polypeptide of the present invention which interacts with a native cellular protein involved in a metabolic pathway, wherein the protein or polypeptide modifies the metabolic pathway through its interaction with the native cellular protein.

It is believed that bacteria have evolved effector proteins to make exquisite alterations in host metabolism. While plant disease resistance, suppression of programmed cell death, and cancer cell toxicity are important uses, as mentioned above, it is believed that these effector proteins can be used to modify or effect metabolic targets in eukaryotes, including both yeasts and higher order species, such as plants and animals. It is noteworthy that several of the effector proteins disclosed herein have homologs in other phytopathogenic bacteria. Thus, these proteins appear to represent a set of effectors that are conserved among *Pseudomonas*, *Erwinia*, *Xanthomonas*, and *Ralstonia* spp. By disrupting or augmenting the function of these effectors through, for example, transgenic expression thereof in a host plant, it is believed that use of these effectors may lead to widely applicable means for controlling diseases of plants.

BRIEF DESCRIPTION OF THE DRAWINGS

FIGS. 1A–C illustrate assays for Hrp system-dependent secretion in culture or translocation in planta of candidate effector proteins. *P. s. tomato* DC3000 and a Hrp secretion mutant derivative were used for tests of newly identified candidate effectors (1A–B). DC3000 or a DC3000 hrcC mutant (Yuan & He, *J. Bacteriol.* 178:6399–6402 (1996), which is hereby incorporated by reference in its entirety) carrying test ORFs (i.e., candidate effectors) fused to either the FLAG (F) or hemagglutinin (HA) epitopes were grown in Hrp-inducing media, and cultures were separated into cell (lanes 1–3) and supernatant (lanes 4 and 5) fractions and analyzed by SDS/PAGE and immunobloting. Lanes 1 and 4, wild-type DC3000; lanes 2 and 5, wild-type DC3000 (pTestORF); lanes 3 and 6, DC3000 hrcC mutant (pTestORF). As an additional control against leakage, pCPP2318 was included in all strains, which encodes the mature form of β-lactamase (β-lac). The presence of an epitope-tagged protein in the supernatant fraction of the wild type (lane 5), but absence in the hrcC secretion mutant (lane 6), indicated that the test ORF encoded a secreted product. In FIG. 1C, an AvrRpt2 translocation assay was performed with DC3000 HopPtoG. Test strains were infiltrated into *A. thaliana* Col-0 (RPS2) and Col-0 rps2-201 (rps2) plants. Plant responses were scored 18 h after inoculation for hypersensitive response (HR) or no visible response (N).

FIG. 2A is a schematic representation of the pHIR11-based suppression assay in *P. fluorescens* (Pf) 55. When DC3000 effectors are individually expressed in trans in Pf(pHIR11), they can potentially suppress the HopPsyA-dependent HR. FIG. 2B shows *N. tabacum* cv. *xanthi* leaves that were infiltrated with Pf(pHIR11) (left panel) or Pf(pHIR11, phopPtoE)(right panel). 'N' denotes no HR. FIG. 2C shows quantitative differences in the ability of DC3000 wild-type (WT), hopP-toE mutant UNL139, and complemented mutant UNL139 (phopPtoE) to elicit the HR in *N. tabacum* cv. *xanthi* leaves. Different dilutions of bacterial cells/ml (1, $10^8$ cells/ml; 2, $10^7$ cells/ml; 3, $10^6$ cells/ml; and 4, $10^5$ cells/ml) were infiltrated into leaves, then leaves were photographed after 24 hr.

FIG. 3A is an image of an immunoblot showing that AvrPto is type III-secreted from DC3000 (WT), but not from a secretiondefective DC3000 hrcC mutant (hrcC). β-Lactamase (β-Lac) was used as a lysis control. C, cell pellet fractions; S, supernatant fractions. FIG. 3B is an image showing that the HR elicited in *N. tabacum* cv. *xanthi* by DC3000 is inhibited when hopPtoE is expressed in trans. FIG. 3C shows the results of *P. fluorescens*(pHIR11) mixing experiments in *N. tabacum* cv. *Xanthi*, demonstrating that HR suppression can occur when HopPtoE and HopPsyA are TTSS-delivered by different bacteria. pLN18 is a pHIR11 derivative that lacks hopPsyA, but encodes a functional TTSS. pCPP2089 (Huang et al., *Mol. Plant-Microbe Interact.* 4:469–476 (1991), which is hereby incorporated by reference in its entirety) is a pHIR11 derivative encoding a defective TTSS.

FIGS. 4A–C identify *P. s. tomato* DC3000 effectors that suppress the HR on tobacco and *Arabidopsis*. FIG. 4A lists DC3000 effectors that were tested in the pHIR11 assay. A 'y' indicates that the effector inhibited the HR, an 'n' indicates that it did not, and a 'y*' indicates that it partially suppressed the HR. Refer to the Materials and Methods for information regarding effector constructs. The nucleic acid and amino acid sequences of AvrPphE$_{Pto}$, AvrPpiB1$_{Pto}$, HopPtoB, HopPtoC, HopPtoD1, HopPtoD2, HopPtoF (previously designated AvrPphF$_{Pto}$ ORF2), HopPtoJ, and HopPtoK are disclosed in U.S. patent application Ser. No. 09/825,414 to Collmer et al., filed Apr. 2, 2002, which is hereby incorporated by reference in its entirety. The nucleic acid and amino acid sequence of AvrPto is reported at Genbank Accession L20425; Salmeron & Staskawicz, *Mol. Gen. Genet.* 239: 6–16 (1993), each of which is hereby incorporated by reference in its entirety. The nucleic acid and amino acid sequence of AvrPtoB is reported at Genbank Accession AY074795 and Kim et al., *Cell* 109:589–598 (2002), each of which is hereby incorporated by reference in its entirety. AvrPtoB was independently shown to suppress the programmed cell death elicited by AvrPto or by heterologously-expressed BAX in *Nicotiana benthamiana* (Abramovitch et al., *EMBO J.* 22:60–69 (2003), which is hereby incorporated by reference in its entirety). FIG. 4B is an image of *N. tabacum* cv. *xanthi* leaves that were infiltrated with *P. fluorescens*(pHIR11) with different effector constructs (noted above each picture). Complete suppression of the HR is denoted with 'N'. FIG. 4C is an image of the same strains (as illustrated in FIG. 4B) infiltrated into *Arabidopsis* Ws-0, producing identical results.

In FIG. 5A, *N. tabacum* cv. *xanthi* leaves were co-infiltrated with *A. tumefaciens* C58C1 carrying phopPsyA and another strain carrying each candidate suppressor. All of the suppressive effectors identified in the pHIR11 screen also suppressed the HR elicited by HopPsyA in this test. In FIG. 5B, an immunoblot of plant tissues with different agroinfiltrations shows that each HA epitope-tagged effector was made in planta. The asterisks indicates a protein of the predicted size of the effector in that lane.

In FIG. 7A, *Agrobacterium* C58C1 strains carrying binary vectors that encode Bax or a specific effector were co-infiltrated into *N. benthamiana* leaves. Leaves were photographed after 7 days. N* indicates that the HR was nearly absent. Effector constructs were the same as in FIG. 4. In FIG. 7B, yeast strain EGY48 carrying plasmids that encoded for Bax (pJG4-5-Bax) and a specific effector were spotted on plates at 5-fold dilutions. Expression of Bax was induced by galactose, whereas effector expression was constitutive. Only AvrPpiB1 was unable to suppress Bax-induced killing. Bcl-xL (pGilda-Bcl-xL), an animal protein known to inhibit Bax-induced PCD, was used as a positive control.

DETAILED DESCRIPTION OF THE INVENTION

Figure 2A:
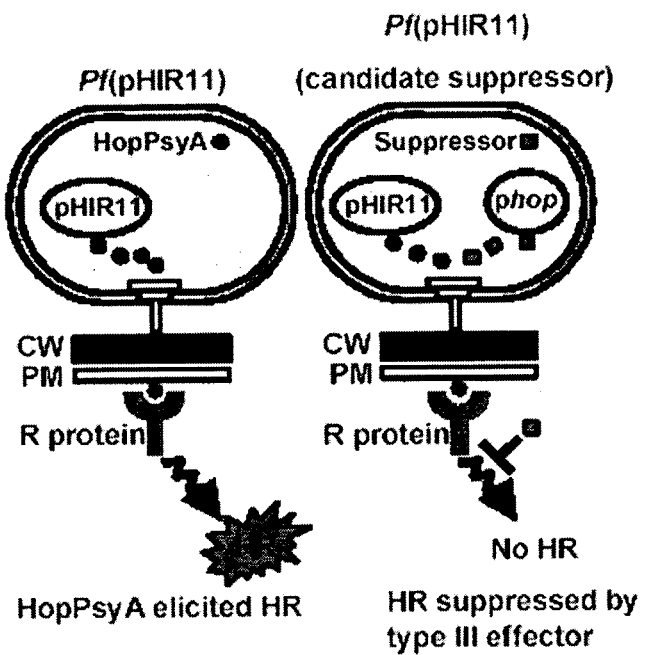
FIGS. 2A–C illustrate pHIR11-dependent HR is suppressed by HopPtoE, and a *P. s. tomato* DC3000 hopPtoE mutant exhibits an enhanced HR.

One aspect of the present invention relates to *Pseudomonas syringae* pv. *syringae* DC 3000 nucleic acid molecules which encode Avr or Hop effector proteins.

A first nucleic acid molecule encodes HopPtoI (ORF1) and has a nucleotide sequence according to SEQ ID NO: 1 as follows:

```
atgcttatcgggcacagcttgcatcacatgcgacccactgctgtggattctagcctaccaacttccgca actagccagactatcagcaataccaaaagtcggctggatccgcatcgtgtccgtgaacttacattcatc ggagtgggtagtagtgttgcctacctactcaatgagcttaatggtcgctttgccgatagcggggtaaca acgccgttttaggaaaagtcagtattgtaggcaaggacgactcttgggccgagaatgttcgtgggaaa ggttatattaaccaccagactgaaattataagccaatgggaccaacaggttccaaaatatgatcctaac
```

-continued

```
tatgctgctcgtgccgaattttctgcgagtaaccgaagacagttgacgcgaacagtggagttaggcgca
gaacatttgaaagcacaggtaacaggcatttcgcgattggatgacggttgttttcgaataaatctggac
aatggccagattttgcaaagccgacagattgtactggggactggtgccggaccccataccagtatctgg
aacagcgttacatcacacactcaagcagaaaaacgactggacaacatcaaattgcatgagcagaaagcc
ttgcgtggcaaggtgctggacctggatgagtttatgcgagcgagtgatgcctctccccagacgtttgct
ggaaaaacggtggtgatacatggaccaaatgcaggcattgatgcagctaacgtgccggggagcttggg
gcaaatgcggtttggtttacccgcagtacgaatccggtattgctggatggcaatcaactaaaattcgcg
ccagagctggccaaaagcgctatacataaagttgacaaattagatattcgcccaacaaaactagagaat
ggtttcgcattgcgactacattacagttcgctaggacaagactcacgggagccaaagaaggtgctagat
gcggactattatgtgtacgccatgggtcaagatattcataagccgggtagcgcagcggccatactaggc
agtcttcttgaccacctagaacctatatatgactacgatcaagtctatagcgaccagcctttcaagaca
gtaataggcttgcaaagtcgcggctccaatagcgataatggtttaattattgtcggggcggcagttgct
cagctggccactaatgttcagcatagctataaggaccacgcgttggatcgtatacttgaggaaatgacc
aggctccccgaaaagcaaacagaaaagctatcacaaatgctgttagaaggtgcgccatcagtacagatc
cagacatatctaaaaacctggcagttagatagcggtcaaccgccagataaacaggtactgcagaatcaa
gtagaaaactatctggcggcccgagactacttccagcggcaaaccaacgaacaaaagggcaacctggac
ggggttgccgcagaggtaaaaaatcaaaccttaaccgaggttgcatcggtcatcgtgtcaccacagtta
ggcacgatcaaggcctccgctgcagcattgtcgggacttatgccagcatatgtggctaacggcgaaaat
aactttaccaccgataatcgaactatgctccgtgccggcattgcagcaagatatccgaatataggtaac
gctgaagccagtgcatttatcgatgaagtagtaactttgcgtcaccttaatagtcagcgttttattgag
aaggtagcaggcgaaatgatggacaaaggagctcaaccactggtgtcgttacgcccccggtcctaggt
gtcccggcgtcggtcaggactgcttatgaggcttacttgcacgcgctgaattctggagcgcacgatggt
acgccgttaagtcagcgctggctgcccaaaaaatag
```

The HopPtoI protein encoded by this nucleic acid molecule has an amino acid sequence according to SEQ ID NO: 2 as follows:

```
MLIGHSLHHMRPTAVDSSLPTSATSQTISNTKSRLDPHRVRELTFIGVGSSVAYLLNELNGRFADSGVT

TPFLGKVSIVGKDDSWAENVRGKGYINHQTEIISQWDQQVPKYDPNYAARAEFSASNRRQLTRTVELGA

EHLKAQVTGISRLDDGCFRINLDNGQILQSRQIVLGTGAGPHTSIWNSVTSHTQAEKRLDNIKLHEQKA

LRGKVLDLDEFMRASDASPQTFAGKTVVIHGPNAGIDAAERAGELGANAVWFTRSTNPVLLDGNQLKFA

PELAKSAIHKVDKLDIRPTKLENGFALRLHYSSLGQDSREPKKVLDADYYVYAMGQDIHKPGSAAAILG

SLLDHLEPIYDYDQVYSDQPFKTVIGLQSRGSNSDNGLIIVGAAVAQLATNVQHSYKDHALDRILEEMT

RLPEKQTEKLSQMLLEGAPSVQIQTYLKTWQLDSGQPPDKQVLQNQVENYLAARDYFQRQTNEQKGNLD

GVAAEVKNQTLTEVASVIVSPQLGTIKASAAALSGLMPAYVANGENNFTTDNRTMLRAGIAARYPNIGN

AEASAFIDEVVTLRHLNSQRFIEKVAGEMMDKGAQPLVSLRPPVLGVPASVRTAYEAYLHALNSGAHDG

TPLSQRWLPKK
```

HopPtoI has been shown to be a protein that is secreted by DC3000.

A second nucleic acid molecule encodes HopPtoH (ORF2) and has a nucleotide sequence according to SEQ ID NO: 3 as follows:

```
atgatcactccgtctcgatatccaggcatctatatcgcccccctcagtaacgaaccgacagcagctcac acatttaaagaacaagcagaggaagcacttgaccatatcagcgccgcaccctctggcgataagctattg cgaaaaatatccactcttgccagtcaaaaagatagaaaagtcacgctaaaagagattgaaataataac cagtgttataccgaagctgttctgagcagraggcaactggaaaagtacgaaccagaaaactttaacgag aaccggcacattgcatcacagctatcacgaaaggggaccttaccaaaggtgaaggaagcaacgcgatt attggctggtcaccagacaaagcaagcatacgcttaaatcagaatggctcaccgttacaccttggaatg gataacgacgacaaaatcacgaccctagctcatgagctcgttcatgctcgacatgtgttaggtggcagc tccttagcggatggcggagatcgctataatccacgtacgggatctggcaaagaggaacttagggccgtt ggattagataagtaccgctattcacttacaaaaaaaccgtcagagaactccatccgagctgaacacggc ctgcctctgcgcatgaagtacagggcacatcaatag
```

The HopPtoH protein encoded by this nucleic acid molecule has an amino acid sequence according to SEQ ID NO: 4 as follows:

```
MITPSRYPGIYIAPLSNEPTAAHTFKEQAEEALDHISAAPSGDKLLRKISTLASQKDRKVTLKEIEINN

QCYTEAVLSRRQLEKYEPENFNENRHIASQLSRKGTFTKGEGSNAIIGWSPDKASIRLNQNGSPLHLGM

DNDDKITTLAHELVHARHVLGGSSLADGGDRYNPRTGSGKEELRAVGLDKYRYSLTKKPSENSIRAEHG

LPLRMKYRAHQ
```

HopPtoH has been shown to be a protein that is secreted by DC3000. HopPtoH has significant homology (1e-114), as detected by BLAST search, to ORF3 from *Pseudomonas syringae* pv. *pisi* avrPpiC2 locus (Arnold et al., *Microbiology* 147:1171–1182 (2001); GenBank Accession No. CAC16702, each of which is hereby incorporated by reference in its entirety.

A third nucleic acid molecule encodes HopPtoE (ORF3) and has a nucleotide sequence according to SEQ ID NO: 5 as follows:

```
atgaatagagtttccggtagctcgtcagcgacttggcaggcagtcaacgatcttgtggagcaagtaagc gagagaaccacgttgtctacgacaggttatcagacggcaatgggccgcttgaacaaaccggaaaaatca gatgcggatgcgctgatgactatgaggagggcgcaacagtacacggatagcgcgaagcgaacttatatt tcggaaacgctgatgaatctggcagatttgcagcaaaggaaaatctatcgcaccaacagcgggaacttg cgtggcgcgattgagatgacgcctacgcaactcacagattgcgtacagaagtgccgcgaagagggttc tccaattgtgacatacaggcgctggaaatcggcttgcaccttcgacataagttaggaatctcagatttc accatctacagcaaccgtaagttaagccataactatgtggtcatccaccccagcaatgcatttccgaaa ggagcgattgtagactcttggacgggacagggcgtggtggagctggacttcaagacccgattgaaattc aagcaccgggaagagaactacgcagtgaacgccaatatgcacgagtggatcgagagatacggccaagcg catgtgattgactga
```

The HopPtoE protein encoded by this nucleic acid molecule has an amino acid sequence according to SEQ ID NO: 6 as follows:

MNRVSGSSSATWQAVNDLVEQVSERTTLSTTGYQTAMGRLNKPEKSDADALMTMRRAQQYTDSAKRTYI

SETLMNLADLQQRKIYRTNSGNLRGAIEMTPTQLTDCVQKCREEGFSNCDIQALEIGLHLRHKLGISDF

TIYSNRKLSHNYVVIHPSNAFPKGAIVDSWTGQGVVELDFKTRLKFKHREENYAVNANMHEWIERYGQA

HVID

HopPtoE has been shown to be a protein that is secreted by DC3000 as well as translocated in planta.

A fourth nucleic acid molecule encodes HopPtoG (ORF4) and has a nucleotide sequence according to SEQ ID NO: 7 as follows:

atgcaaataaagaacagtcatctctattcagcttcaagaatggtgcagaatacttttaatgcctcgcct aagatggaagtaactaatgcaatagcaaaaaataatgaacctgctgcgctgagcgctacgcaaactgca aagacacacgaaggcgattcaaaaggccaatccagcaataactctaaattgcccttccgcgccatgagg tacgctgcataccttgcaggcagcgcctacctctacgataaaactgccaataatttttttctttctacc acttctctgcatgatggcaaaggtggttttaccagcgatgccaggcttaacgatgcacaagataaagcg cgaaagcgctaccaaaacaaccatagcagcactcttgaaaataaaaactcgcttttaagcccgcttagg ctttgcggagagaatcagttcttaacgatgattgattatcgtgcagcaactaagatttacctctccgac ctagttgacacggagcaagcgcacacatcaattctgaagaatattatgtgcctgaaaggtgagcttacc aatgaagaggcaataaaaaaactcaacccggaaaaaacaccaaaagactatgaccttacaaatagcgaa gcctatataagcaagaacaaatattctttgaccggcgttaaaaatgaggagacgggatctactggttat acatctcgttctatcacaaagccatttgtggaaaaaggcctgaaacactttataaaagcgactcatggc gaaaaagctctcacgcccaagcagtgtatggaaactcttgataacttacttcgaaaaagtatcacgctc aacagtgattcccaattcgcagcaggccaggcacttttggttttcagacaggtctatgcgggtgaagac gcttgggggatgcggaacgggtcatattgaaaagccattataatcggggcactgtactccaagatgaa gctgataaaatagaactaagtaggccgttctcagagcaagatttagcaaagaacatgtttaagaggaat accagcattgcagggccagtgctctaccacgcatatatttatatacaagaaaaaatcttcaagctaccc cccgacaaaatagaagatttgaaacataaatcaatggcagacttgaaaaacctgcctttgactcatgtt aagcttagcaattccggtgtgggatttgaagacgcctcagggttaggagactcgtttacagctctcaac gcgacgtcctgtgttaatcacgcaagaataatgagtggtgagcctcccttgtcaaaagatgatgttgtg attctgataggttgcctcaacgccgtatacgacaattcgagcggaataaggcattctctccgcgaaatt gcacgagggtgctttgtgggtgctggttttacggtccaggacggtgacgacttctacaaacagatctgc aaaaacgcctctaagcagttttacaacggctaa The HopPtoG protein encoded by this nucleic acid molecule has an amino acid sequence according to SEQ ID NO: 8 as follows:

MQIKNSHLYSASRMVQNTFNASPKMEVTNAIAKNNEPAALSATQTAKTHEGDSKGQSSNNSKLPFRAMR

YAAYLAGSAYLYDKTANNFFLSTTSLHDGKGGFTSDARLNDAQDKARKRYQNNHSSTLENKNSLLSPLR

-continued

LCGENQFLTMIDYRAATKIYLSDLVDTEQAHTSILKNIMCLKGELTNEEAIKKLNPEKTPKDYDLTNSE

AYISKNKYSLTGVKNEETGSTGYTSRSITKPFVEKGLKHFIKATHGEKALTPKQCMETLDNLLRKSITL

NSDSQFAAGQALLVFRQVYAGEDAWGDAERVILKSHYNRGTVLQDEADKIELSRPFSEQDLAKNMFKRN

TSIAGPVLYHAYIYIQEKIFKLPPDKIEDLKHKSMADLKNLPLTHVKLSNSGVGFEDASGLGDSFTALN

ATSCVNHARIMSGEPPLSKDDVVILIGCLNAVYDNSSGIRHSLREIARGCFVGAGFTVQDGDDFYKQIC

KNASKQFYNG

HopPtoG has been shown to be a protein that is secreted by DC3000 as well as translocated in planta by recombinant *Pseudomonas syringae* pv. *pisi*. Thus, HopPtoG appears to be a Hrp-injected effector protein. HopPtoG has significant homology, as detected by BLAST search (1e-137), to a hypothetical protein of *Ralstonia solanacearum* (see GenBank Accession No. NP_521884, which is hereby incorporated by reference in its entirety).

A fifth nucleic acid molecule encodes HopPtoS1 (ORF5) and has a nucleotide sequence according to SEQ ID NO: 9 as follows:

Chem. 269:27451–27457 (1994); GenBank Accession No. P55807, each of which is hereby incorporated by reference in its entirety), as well as significant homology to a type III-secreted ADP-ribosyltransferase from *P. aeruginosa* (Yahr et al., *Mol. Microbiol.* 22:991–1003 (1996), which is hereby incorporated by reference in its entirety). Further confirming its similarity to ADP-ribosyltransferases, HopPtoS1 has been determined to possess an ART domain (pfam1129).

```
atgggtaatatttgtggtacttctggctccaatcatgtgtatagtccgcctattagccctcaacatgca tctggttcgtccacaccagtgcccagtgcttctgggacgatgctttctctcagtcatgaacaaatatta agccagaactatgctagcaatataaaggggaaatatcgcacgaaccccgaaaaggaccatctcctagg ctttctgatacgctgatgaagcaggcgctgtcttcagtgatcacacaagagaaaaagcgacttaaaagt caaccaaagtcaatagcccaagatattcagcctccaaacagcatgatcaaaaatgcacttgatgaaaaa gacagccacccttttggtgattgcttttcagacgatgaatttcttgcgatccatctctatacgagttgt ctttacagaccgatcaaccatcatctgcggtatgccccgaaaaatgatgtcgcgcctgttgtggaggca atgaatagcggtttggccaaacttgctcaatacccctgattatcaggtgtctggtcagctgcatagaggc atcaagcaaaagatggatgatggtgaagttatgagtcgcttcaagccgggtaatacttatcgtgatgac gcgttcatgagcacatcgactagaatggatgttacagaagaatttacttccgatgtcacgttacatctg cagtcctcatcagccgtcaatataggtcccttttcaaaaaacccatacgaggacgaagcgctcatcccg cccctgacgcctttcaaagtaaccggtctgcacaagcaggacgataggtggcacgtccacttgaacgag atcgcagagagctctgacgagtga
```

The HopPtoS1 protein encoded by this nucleic acid molecule has an amino acid sequence according to SEQ ID NO: 10 as follows:

A sixth nucleic acid molecule encodes ORF6 and has a nucleotide sequence according to SEQ ID NO: 11 as follows:

MGNICGTSGSNHVYSPPISPQHASGSSTPVPSASGTMLSLSHEQILSQNYASNIKGKYRTNPRKGPSPR

LSDTLMKQALSSVITQEKKRLKSQPKSIAQDIQPPNSMIKNALDEKDSHPFGDCFSDDEFLAIHLYTSC

LYRPINHHLRYAPKNDVAPVVEAMNSGLAKLAQYPDYQVSGQLHRGIKQKMDDGEVMSRFKPGNTYRDD

AFMSTSTRMDVTEEFTSDVTLHLQSSSAVNIGPFSKNPYEDEALIPPLTPFKVTGLHKQDDRWHVHLNE

IAESSDE

HopPtoS1 has been shown to be a protein that is secreted by DC3000 as well as translocated in planta. HopPtoS1 has significant homology, as detected by BLAST search (1e-5), to a chicken ADP-ribosyltransferases (Tsuchiya, *J. Biol.*

```
atgagcttatcgccgacgctgcaaaagctaactaatatattgggcccgac aaaaaatgccaagcctgtcacagaggctatccagtggcaggaaggcatgg
```

```
atataacgctgcatgtcagcggcgacagccttaccttactagctaaaatc atagaactgcgtacagaccctaaagacgacattttattgcgcaagctgct tacccatacgtttccgggcctgcgtctgcgccgtggcgcgcttaccatca accctgatggaagtgccctggttttctcttatgaacacgattttcacctt ctggacaaagcccgttttgagagcctgctggccaactttgctgaaacggc gcaggagcttcgagacacagcgacacattttcgttttaactga
```

The protein encoded by this nucleic acid molecule has an amino acid sequence according to SEQ ID NO: 12 as follows:

MSLSPTLQKLTNILGPTKNAKPVTEAIQWQEGMDITLHVSGDSLTLLAKI
IELRTDPKDDILLRKLLTHTFPGLRLRRGALTINPDESALVFSYEHDFHL
LDKARFEsLLANFAETAQELRDTATHFRFN

Although the protein of SEQ ID NO: 12 possesses N-terminal Hop features and features shared by type III chaperones, this protein was shown not to be secreted by DC3000. Because ORF6 is located directly upstream of ORF17 (described infra), it is believed that the protein of SEQ ID NO: 12 is a type III chaperone for the protein encoded by ORF17.

A seventh nucleic acid molecule encodes ORF7 and has a nucleotide sequence according to SEQ ID NO: 13 as follows:

```
atgaaacaacgagcgacagtcatctgcaaacgtgacggccaggtgcttta cgtacgcaaaccaaaatcccgctgggctttgccaggtggcaagattgaag ccggggaaacgcctttccaggctgccgtgcgcgagctttgcgaagaaacc ggtctggaaaatctcgatctgttgtacctggcggtgtacgagaaaggtga ggtcacgcactacgtgttcaccactcaggttcctgcctacagcgagcctt cgccccagaacgagatttctgcctgcaaatggcttgcgcccaaaaatctt ggcgaccttaaggccagcagcgcgaccaaggctatcgtcaagtcgtatgg ccgccaggctgaagacggtttactcagcgctaactag
```

The protein encoded by this nucleic acid molecule has an amino acid sequence according to SEQ ID NO: 14 as follows:

MKQRATVICKRDGQVLYVRKPKSRWALPGGKIEAGETPFQAAVRELCEET
GLENLDLLYLAVYEKGEVTHYVFTTQVPAYSEPSPQNEISACKWLAPKNL
GDLKASSATKAIVKSYGRQAEDGLLSAN

This protein shares significant homology, as detected by BLAST analysis (3e-7), to MutT mutator of *Mesorhizobium loti* (Genbank Accession No. NP_104556, which is hereby incorporated by reference in its entirety). The protein of SEQ ID NO: 12 was shown not to be secreted by DC3000. Although this protein is not secreted, it may still be an effector protein, because AvrB similarly is not secreted in culture although it is translocated in planta (see van Dijk et al., *J. Bacteriol.* 181:4790–4797 (1999); Gopalan et al., *Plant Cell* 8:1095–1105 (1996), each of which is hereby incorporated by reference in its entirety).

An eighth nucleic acid molecule encodes ORF8 and has a nucleotide sequence according to SEQ ID NO: 15 as follows:

```
gtgctcgcttttgcatacgtcagcctgattagagagcagaaattggacatcaaaaaacgttggccttcc agtgagcaggagttggtagaagtccgacggtttaacaaaaccctcgcccggctgccgcgtttccaggtt cgcaatcgcctcacgccccgcttgattcdggcgctgctgcgggcggctcagattggtcgcgcgttgaaa ccggtcaaacatgacctgcggattgaaacaaccatcgtcagcaccggtaacgtccctgtttcagtgcga atcataaggcccaaaggcaaacccaaaggcgtggtgtttgatattcacggcggcggttgggtgatcggc aacgcccagatgaacgatgacctcaatatcggtatcgttaacgcgtgcaacgtggcggtcgtgtccgtt gattacagattggctttatcgaccccgtcgaagggctgatggatgactgcttttctgccgcatgctgg ctgctgggtagcgactgtaaggagtttgccggcctgccggttattgtcgtcggtgagtccgcgggcggg catcttgccgcagccactttgctcaaattgaaagccaggcccgacttgctcaagcgcgtagtcggcacg gttctgtattacggcgtgtacgacctgaccgggacaaaaagcgttcgtaccgcaggcccggaaacgctg gtgctcgacggccgggcatggtcggcgcaatgcgcttgctcgccccggacagaacgacgagaagcgc cgcgagccgccgttatcgcccttgtatggcgacctcacggatctgccgcccgccctgatgtttgtcggc gaactcgacccgctgctggacgacacgctggaaatggccgagcgatggaaaaactcggcagacgttgaa atgcatcttctgcccgagtctccacatgggttcatccacttcccgactgccttggcgcgcaaggtactt gcgcgcagccacgagtggataaacgcgaggatggaaggacggccttaa
```

The protein encoded by this nucleic acid molecule has an amino acid sequence according to SEQ ID NO: 16 as follows:

VLAFAYVSLIREQKLDIKKRWPSSEQELVEVRRFNKTLARLPRFQVRNRL
TPRLIQALLRAAQIGRALKPVKHDLRIETTIVSTGNVPVSVRIIRPKGKP
KGVVFDIHGGGWVIGNAQMNDDLNIGIVNACNVAVVSVDYRLALSTPVEG
LMDDCESAAcWLLGSDCKEFAGLPVIVVGESAGGHLAAATLLKLKARPDL
LKRVVGTVLYYGVYDLTGTKSVRTAGPETLVLDGPGMVGAMRLLAPDRTD
EKRREPPLSPLYGDLTDLPPALMFVGELDPLLDDTLEMAERWKNSADVEM
HLLPESPHGFIHFPTALARKVLARSHEWINARMEGRP

This protein shares significant homology, as detected by BLAST analysis (1e-12), to a putative esterase/lipase of *Mesorhizobium loti* (Genbank Accession No. NP_105776, which is hereby incorporated by reference in its entirety). The protein of SEQ ID NO: 16 was shown not to be secreted by DC3000. Although this protein is not secreted, it may still be an effector protein, because AvrB similarly is not secreted in culture although it is translocated in planta (see van Dijk et al., *J. Bacteriol.* 181:4790–4797 (1999); Gopalan et al., *Plant Cell* 8:1095–1105 (1996), each of which is hereby incorporated by reference in its entirety).

A ninth nucleic acid molecule encodes ORF9 and has a nucleotide sequence according to SEQ ID NO: 17 as follows:

```
atgcaaacctatatacccatccaaaaaaccctcccaccgttggtacagttctgctgacttcctatggc
tcattcgcccatgaaaacgagatacctaaatcttgtgctgccgacgctttaagagtaggcaaagagctc
gctgatggtttcgatggcgaggttcatcatctaggcgctctgatgctgatgatttccgactttccagca
gagccgctgctgaaagcatctgctgctaagaaaggttctttgctaggaattacttcgcttggctaccta
ttatcctatggatctactggtgaaaaagcgaagcgaatcatcgaagcaggttgtggtattttctcgtc
agagtgagtggtgatattgaaaacccctaaagcaaaaattgaagtttatagctcttggtctgaataccag
aagttccttgaacccattttgaagacaggtgactttatccagtgaaaacgtcgtcgttttccgaataa
```

The protein encoded by this nucleic acid molecule has an amino acid sequence according to SEQ ID NO: 18 as follows:

MQTYIPYPKNPPTVGTVLLTSYGSFAHENETPKSCAADALRVGKELADGF
DGEVHHLGALMLMISDFPAEPLLKASAAKKGSLLGITSLGYLLSYGSTGE
KAKRIIEAGCGIFLVRVSGDIENPKAKIEVYSSWSEYQKFLEPILKTGDF
YPVKTSSFSE

This protein shares significant homology, as detected by BLAST analysis (3e-50), to ORF4 of *Pseudomonas serioboryae* (Genbank Accession No. BAA87063, which is hereby incorporated by reference in its entirety).

A tenth nucleic acid molecule encodes ORF10 and has a nucleotide sequence according to SEQ ID NO: 19 as follows:

```
atgatcaacctcacccacattgcgtcttcattggcgcgggcagcgctcagcgattcgacaaagccgaag
atggagcgcgcgataaacgtcgcgagccacatcgctggcaaagtcgcgttgcaggtcaccagctcatta
ctggagcagaaaggtctgcttaacgagcgtcagcagaaagggctctcgatgattctgaaggccttgagc
ggcaaggagccggtgaacaatgtcgagacgcacgaaggggaggccgattcaatctggcgcgagccgcc
ttcgacgtggccagcgttgtctgggagcgcgacaagtcgatgcataacgtgatgagctttctgggcgtc
agcgacagcaagggcaagatgttgttctctctgggcaagaagctggcggatgcaatggccaagcctgag
cctggcaaggacaacagtgaggccacaaatgcgcgccatgcctatttctccagcaacttgaaactgaac
```

-continued
```
aagttgatgaacgacctcactgaccaggttttcaacaagattcgccagtcgaacggtgatcgcgtgcga cgacccatgccagaaccattctggagaccttacggcgcccaacagcaagcgcgcccgcaaacgcctccc ggcactcgcccacaagccaacagcgcccgccaccgccgccgaaagcagagccacgacctgcgtcgggc cggcctgacggcgcccaacagcaggcgcgcccggaaacgccgcctcgtactcgaccgcaggccaatagc actccgccaccgccgccgaaagcagagccacgacctgcgtcgggccggcctgacggcgcccagcagcaa gcacgcccggaaacgccgccgcgcactcgcccgcaggcgaacagcacgccgccaccgccgcccaaggca gagccacgacctgcgtccggccggcctgacggcgcccaacagcaagcacgcccggaaacgccacctcgc actcgccccaagcgaacagcgcgccgcctccgccgcccaaagcagagccacgacctgcgtccggccgg cctgacggcacccaacagcaagcacgcccggaaacgccacctcgcactcgcccccaagcgaacagcgcg ccgcctccgccgcccaaagcagaacccagcgcaggcggcgaacggccttcaacggcgcggcccaataac acatcggctgctgacgcatctgccagggtgggcgattccgcacctgccaagccgcccgtcaagccgttg tacgagcacttgggcctcactgacatgtcggtagacttatccgccgttaaaaaggcttacagagatgcc gcgatgaagaaccaccctgataaaaaccgcggcaacgaggccgaggcggccgagcgcttcaaagtcatt tcaaatgcgtacaagattttgtccgacccggagttgcgcaaagcatacgacaacggccgtatcaatgag gctggtaatagggcatga
```

The protein encoded by this nucleic acid molecule has an amino acid sequence according to SEQ ID NO: 20 as follows:

```
MINLTHIASSLARAALSDSTKPKMERAINVASHIAGKVALQVTSSLLEQKGLLNERQQKGLSMILKALS

GKEPVNNVETHEGGGRFNLAPAAFDVASVVWERDKSMHNVMSFLGVSDSKGKMLFSLGKKLADAMAKPE

PGKDNSEATNARHAYFSSNLKLNKLMNDLTDQVFNKIRQSNGDRVRRPMPEPFWRPYGAQQQARPQTPP

GTRPQANSAPPPPPKAEPRPASGRPDGAQQQARPETPPRTRPQANSTPPPPPKAEPRPASGRPDGAQQQ

ARPETPPRTRPQANSTPPPPPKAEPRPASGRPDGAQQQARPETPPRTRPQANSAPPPPPKAEPRPASGR

PDGTQQQARPETPPRTRPQANSAPPPPPKAEPSAGGERPSTARPNNTSAADASARVGDSAPAKPPVKPL

YEHLGLTDMSVDLSAVKKAYRDAAMKNHPDKNRGNEAEAAERFKVISNAYKILSDPELRKAYDNGRINE

AGNRA.
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and shares significant homology, as detected by BLAST analysis (2e-11), to DnaJ protein (Genbank Accession No. BAB17689, which is hereby incorporated by reference in its entirety).

An eleventh nucleic acid molecule encodes ORF11 and has a nucleotide sequence according to SEQ ID NO: 21 as follows:

```
atgaacattacgccgctcacgtcagccgcgggcaagggctcgtccgcacaaggcacagacaaaatttcc attcccaactccacgcgcatgatcaatgccgcttcaatcaagtggttgaataaggtgcgtagcgccatc agtgaccacatccgcaccagcatcgagaaagggaaactgttcgagctcgcctccttgggcagcaacatg ttcggtgtcccggctcttcagcgcgcccctcgacgctccaacctgtgttggcgtttgaggctgacccc aatcacgacctgaaccttgtcagggtctatatgcaggacagcgccggaaagctcactccctgggacccg acgcccaacgcggtcacgacgacgtcgaatccatcagagcctgatgcgcagagcgatacggcttcgtca tcattacctcggcggcctcccgcaggctcggtgctgagtttgctgggcattgcgctggatcacgcgcaa
```

```
cgccacagtcctcgcgcggacaggtctgccaagggacgacctggccgagaggagaggaacggggcaagg ttcaatgccaagcaaacaaagccgacagaggctgaagcctacggtgatcatcagacacccaatcctgat ttgcacaggcaaaagagacagctcaacgcgttgctgaaagcatcaacagcatgcgagagcagcaaaat ggaatgcaacgcgccgaagggcttctcagagccaaagaagcgttgcaagctcgggaagccgcgcgcaag cagcttctggacgtgctcgaggccatccaggctggccgtgaagactccaccgacaagaagatcagcgcc actgaaaagaacgccacgggcatcaactaccagtga
```

The protein encoded by this nucleic acid molecule has an amino acid sequence according to SEQ ID NO: 22 as follows:

```
MNITPLTSAAGKGSSAQGTDKISIPNSTRMINAASIKWLNKVRSAISDHIRTSIEKGKLFELASLGSNM

FGVPALSARPSTLQPVLAFEADPNHDLNLVRVYMQDSAGKLTPWDPTPNAVTTTSNPSEPDAQSDTASS

SLPRRPPAGSVLSLLGIALDHAQRHSPRADRSAKGRPGREERNGARFNAKQTKPTEAEAYGDHQTPNPD

LHRQKETAQRVAESINSMREQQNGMQRAEGLLRAKEALQAREAARKQLLDVLEAIQAGREDSTDKKISA

TEKNATGINYQ
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (5e-7), to a HrpA-like protein (Genbank Accession No. AAB00126.1, which is hereby incorporated by reference in its entirety).

A twelfth nucleic acid molecule encodes ORF13 and has a nucleotide sequence according to SEQ ID NO: 23 as follows:

```
atgcgcacatccgttaatggtctgcttgagcacagcctgaagaccctgggctttgatacttcggcattg caggccttgcgcgacgacggttatttactgtggcaaggcaaggataagcaagccagtcttctggttccc tctactgacggcgacgcgcttttcgctatctgtaccttgagccgtgtcgatcccgagcacgacggacgt ctgctggcgcttgcattgcacctgaacctgtctcctgtccacacgatgagcgcatgtatagcdcttgat gtcgagcaaaacacgttgtgtcttcgctacacccatgaccttggcgggaacggggcagataccctgttg cttgcgctcgaaaacgcccaagcgcttgctgaacagatcaagcaggtaatcgaaaactttaggcacgat cagggacgccgatag
```

The protein encoded by this nucleic acid molecule has an amino acid sequence according to SEQ ID NO: 24 as follows:

```
MRTSVNGLLEHSLKTLGFDTSALQALRDDGYLLWQGKDKQASLLVPSTDGDALEAICTLSRVDPEHDGR

LLALALHLNLSPVHTMSACIALDVEQNTLCLRYTHDLGGNGADTLLLALENAQALAEQIKQVIENFRHD

QGRR
```

Because ORF13 shares features common to type III chaperones and is located directly upstream of hopPtoS1 (ORF5), it is believed that the protein of SEQ ID NO: 24 is a type III chaperone for HopPtoS1.

A thirteenth nucleic acid molecule encodes ORF14 and has a nucleotide sequence according to SEQ ID NO: 25 as follows:

atgatcgcgttcgcaaccggactgctagaacacagcctgaaacggcttggatacgacgccgcagatttg caatcccttcgggatgaagggtatttgctgtggcacgggaaaaacggtcacaccagcctgttggtgccc gctgctggcgggatgcgcttttgtcatcagcaccctgagctacatcgatcctgaacaggacgggcgg ctgctggcgcttgcgctgcatttgaacttgtcgccagcccacactctgggcgccagtatcgcgctggat atcgagcaaaataccttgtgcctgcgttacacgcacgacctcactgggcacggcacagacaatttgtcc cgcgcgcttgaaagcactcaggcacttgccgagcagatcaagcaggtcatcgaaacttccgcagtgaa ttcggacgcccgccaatgcccgcccacacagcccgacggccagatgccctggcgctttag The protein encoded by this nucleic acid molecule has an amino acid sequence according to SEQ ID NO: 26 as follows:

MIAFATGLLEHSLKRLGYDAADLQSLRDEGYLLWHGKNGHTSLLVPAAGGDALFVISTLSYIDPEQDGR

LLALALHLNLSPAHTLGASIALDIEQNTLCLRYTHDLTGHGTDNLSRALESTQALAEQIKQVIETFRSE

FGRPPMPAHTARRPDAVAL

ORF14 shares features common to type III chaperones and shares weak similarity with ORF8 of the DC3000 Conserved Effector Locus ("CEL") (U.S. patent application Ser. No. 09/825,414 to Collmer et al., filed Apr. 3, 2001, which is hereby incorporated by reference in its entirety), which is a candidate chaperone for the protein encoded by CEL ORF7. Thus, the protein of SEQ ID NO: 26 is likely a chaperone for the protein of SEQ ID NO: 28.

A fourteenth nucleic acid molecule encodes ORF15 and has a nucleotide sequence according to SEQ ID NO: 27 as follows:

gtgaaaaagtctggcgctggaactcaagcctatgcgttgttcgcctctgcgacgggaagctcgtcgaag ggcgttctaagtaccattgccaggcacctgacgggatgttttgcacccaacaagactgcgcttcattca gcaacagccgtttcgtatgagctattgccgggcaattattctgtcgccgccagtgtgcatggcttgtcg gttgatcaccgccagccggcgctgacacgactgagtaacgtgctgttcaatcaggcactggcgctggac ctggagcgttttgacgagggcgcgccagccgacgaaatgttcaggccttcactgaaacgcgaacgtgcc catccccgattggccgactcactgggtggcgagcaactggctgtgcaaaccatggagaagggccttaaa cggctggcagaggatcctgcgcagtcctttgcgcgatgccattcattttttacccgatcagtagtgat accacttcacctcaagcatcacttcattctgtggcgagctcatctggctga The protein encoded by this nucleic acid molecule has an amino acid sequence according to SEQ ID NO: 28 as follows:

VKKSGAGTQAYALFASATGSSSKGVLSTIARHLTGCFAPNKTALHSATAVSYELLPGNYSVAASVHGLS

VDHRQPALTRLSNVLFNQALALDLERFDEGAPADEMFRPSLKREGAHPRLADSLGGEQLAVQTMEKGLK

RLAEDPAQSFARCHSFFYPISSDTTSPQASLHSVASSSG

The protein of SEQ ID NO: 28 does not share all of the N-terminal features associated with known Hops, however, it is 34% identical with the product of ORF 26, which does.

A fifteenth nucleic acid molecule encodes HopPtoT1 (ORF16) and has a nucleotide sequence according to SEQ ID NO: 29 as follows:

```
atgaaaacagtcagcaatcactcgatacccagtacaaatctcgtcgtggatgcgggaacggaaacttcg
gcgcagaaatcccagccggtttgcagcgaaatccagcgtaacagcaagatcgaaaaagcagtcatcgaa
cacattgccgaccacccggcagcgaaaatgacaataagcgcgctggttgacacgttgacagacgttttt
gtcagggctcatggggaggttaaggggtgggccgaaatcgtccaggcagtctctcgccctcatgacagt
aatcgacacggcagtggagtgctcagcccgcgctttgatgtaatggggagtgttggttggaatgcggca
gctatccgggccaccagtcgcgtcgggacgcttcgagagaaaggtacactgttcactaaccttatgctc
agtaacaactttaaacatttgcttaaacgagtggttaacgatccagccttgcagcaaaagctcgacggt
gggttagacctcaactatctgaaggcttgtgaaggcgatctttatgtcdtgtcagggtgggctgcacgg
gctagcgaaagtcgtgaacaaattggcaaagcccggtatgaaacggcatcaaatcttagccagacgctg
atcagtgcacgtgagttggcttttcatcgtcacaatccggttaatcatccgtctgcccaaacgaaagtg
ggcttcgataagggtttgcctgaggaatctgatctgcaggttctgagaggccatggcagcagtgtatgg
agtgtaaaaccgggcagcgatttcgcaaagcgtgctgaagtttctggaaagcctattatcgccggcccg
tccggtaccgcttcgcgcatggtcgctgttgcgcgttttctggcaccggcttgtttgaaaagcctgggt
attgagagtgagcagaacctgaaagagcttgtgcggtatgcctgctatgcctatttcggtcaggacagc
caccattcgatgcttgaagtgaatcttggtgtcgcttcccatggaatgccggaacaatgggacgacacg
ctttataacgagcctttcagtaattcaattaaaggtcgcgggtttggtatagacaatctcgcgcatagg
caagtcgtcaggcaggcggctcaaaagtcatga
```

The protein encoded by this nucleic acid molecule has an amino acid sequence according to SEQ ID NO: 30 as follows:

```
MKTVSNHSIPSTNLVVDAGTETSAQKSQPVCSEIQRNSKIEKAVIEHIADHPAAKMTISALVDTLTDVF
VRAHGFVKGWAEIVQAVSRPHDSNRHGSGVLSPRFDVMGSVGWNAAAIRATSRVGTLREKGTLFTNLML
SNNFKHLLKRVVNDPALQQKLDGGLDLNYLKACEGDLYVMSGWAARASESREQIGKARYETASNLSQTL
ISARELAFHRHNPVNHPSAQTKVGFDKGLPEESDLQVLRGHGSSVWSVKPGSDFAKRAEVSGKPIIAGP
SGTASRMVAVARFLAPAcLKSLGIESEQNLKELVRYACYAYEGQDSHHSMLEVNLGVASHGMPEQWDDT
LYNEPFSNSIKGRGFGIDNLAHRQVVRQAAQKS
```

HopPtoT1 has been shown to be translocated by DC3000 in planta.

A sixteenth nucleic acid molecule encodes ORF17 and has a nucleotide sequence according to SEQ ID NO: 31 as follows:

```
atgcggtttgatgctgcccgaggccagaagcccaaagcccctatggatgcaccgtcatcattacgtttg
cgagcgatagcaggtggcatgcccagtgaagaagcaggaacgactgcacctgctgacgtgaatcagcct
ccacctgctgatgttcgtccagaaatgggtgtaggtcctgtgagactcttcgttaaactgatggtagga
actctggcgctgtcgacaggagtccgttttgcaagatacccaggtgatttcgcgaaggatccgggaggc
agtgtatgggcagcaatcaatctgcagcatcgctcgagcgtcacacatcttgaacaaggcaataagacg
gttcttgagcgtttcggtgcacatattccaaaagacagtgcgtgtttcaaagctcgcgctgacgtcaca
```

-continued

```
cacgatgttccctcaggcgtggcagggcagtggaaccacaaaacccaacgggtaaaactgaaccctaac attcatttcgagagccatccggcacaggtcgccggacatgagttcatacactgttacacgcatcctgag tttgtcgaacgccatataaaacatccgcactggaaagccctgaacgaagggttgacgactcgtttgaca gagaaactgccagaccctaagcgtctcttgcccattcccttggcaaaggatccctatcatggtttcaag ctgtccaccggggactcctggccggatgcggccaggcgaatcgaagacgaagttggcgaagatgtgttg ttgaaagcgttctttggcggcgatgaccaggctattagtgaagtagctaaagccgctgctcagatctac cccaagattgcctcacgtattaccgagagggagttgtatcaagcgggcagcatgcgtggaggacaacag ctggccgagtgttacgtaggtgctttgctcaaaaacggtcagaaactgcctgacagttttacgaattat ctgctacctgtatttagctattcagatataagccctggtcacgcgaaaaaaatacaggcgcaagcggaa aaaagtcaaaagcggatgggaattgtgttcgatacagcgttttttttcacctgacctgaagacccagaga ctggcacttggcatgctacgggaggacctgctgatgcactggaaaaaagttattccggatagaaagtaa
```

The protein encoded by this nucleic acid molecule has an amino acid sequence according to SEQ ID NO: 32 as follows:

```
MRFDAARGQKPKAPMDAPSSLRLRAIAGGMPSEEAGTTAPADVNQPPPADVRPEMGVGPVRLFVKLMVG

TLALSTGVRFARYPGDFAKDPGGSVWAAINLQHRSSVTHLEQGNKTVLERFGAHIPKDSACFKARADVT

HDVPSGVAGQWNHKTQRVKLNPNIHFESHPAQVAGHEFIHCYTHPEFVERHIKHPHWKALNEGLTTRLT

EKLPDPKRLLPIPLAKDPYHGFKLSTGDSWPDAARRIEDEVGEDVLLKAFFGGDDQAISEVAKAAAQIY

PKIASRITERELYQAGSMRGGQQLAECYVGALLKNGQKLPDSFTNYLLPVFSYSDISPGHAKKIQAQAE

KSQKRMGIVFDTAFFSPDLKTQRLALGMLREDLLMHWKKVIPDRK
```

While the protein of SEQ ID NO: 32 does not possess several N-terminal features associated with known Hops, ORF17 is preceded by a good candidate chaperone protein, encoded by ORF6. Furthermore, the protein of SEQ ID NO: 32 has been shown to be translocated by DC3000 in planta.

A seventeenth nucleic acid molecule encodes ORF18 and has a nucleotide sequence according to SEQ ID NO: 33 as follows:

```
atgaacaggcttcacaagaccagtctgctggcggctatattgaccgcatcccctgcattatggcagct aacgctcatgctatgagttgtcctgtcccgcaaagcgtgaagtacgttaatggtatctatatcgcgccg gaaacgtttgctggttgggaggggaactgggtttctcaaccacacaagaaacactccattaaagagttt tccactgctttatatctttcagtggataaaagtcagaagggaggaacattgactaactgtagttattca ctaagcggagataatggcgtaatagatcttgagtatcgaaaatcaggaaatgagaatagactaaagaca cttatcgtttccattgaaggtcagcacaattggattaaagagcgtggcgcggttggaattcaaggatat gaatgtacaaagtcagcatctgagtgtcagttcgttccgctgcggctaaacgaggactga
```

The protein encoded by this nucleic acid molecule has an amino acid sequence according to SEQ ID NO: 34 as follows:

MNRLHKTSLLAAILTASPCIMAANAHAMSCPVPQSVKYVNGIYIAPETFA
GWEGNWVSQPHKKHSIKEFSTALYLSVDKSQKGGTLTNCSYSLSGDNGVI
DLEYRKSGNENRLKTLIVSIEGQHNWIKERGAVGIQGYECTKSASECQFV
PLRLNED

This protein has significant homology, as detected by BLAST analysis (1e-6), to a putative *Yersinia pestis* exported protein (Genbank Accession No. NP_406993, which is hereby incorporated by reference in its entirety).

An eighteenth nucleic acid molecule encodes ORF19 and has a nucleotide sequence according to SEQ ID NO: 35 as follows:

atgcatcgtcctatcaccgcaggccataccacctcacgtctcatcctagatcagtcaaaacaaatatca
cgtaccccatcggaaagtagcgcgcaatcagcgctttctcagcaagcaagcatgagcagcccagttttg
gagcggtcgaaaagtgcgccagctttattgactgcggcacagcgcacgatgcttgcacaagtgggagcc
tgtaacgctcatctgacctcagatgaaaacatggccatcaacgaactgacatcacacaagccccttta
cctaaggatacgtggttttttcactgatcctaacaaggacccagatgatgtcgtgacctacaccttgggc
aagcaattgcaggctgagggctttgtgcacatcacgatgtagtggcgacactgggtgatgctgaagtt
cgctctcaacgtgccgagatggccaaaggcgtgttcaacaagcttgagttgcatgacgtgcatgtgtcg
cgtggtcgggattacgcaatgaattcgcttcagtcgaaggaacatgccaaattttactggaaggtcat
gctttaagggctggacctggtgaaatacaccgcgacagcttgcaggacatgagcaggcgcctggcccgt
gcgccacatggagtcggtattgtcgtaattgcaggcatgagtgatatcaatgcgctcatcactacctgc
ccggatatggtgcgcgaacgggttgatgacatcaccatcatgggcggcgtcgagcctttaaaggacgca
gatggttttgtacagcctgatgcacgcgcttacaacaatgcgaccgacatggacgctgcgcgcagtctt
tatcggaaagcgcaggagcttggcattccacttcgtatagtgacaaaggaggcggcctataaaacggcg
gtttcgccttcattttacgaagggatagcggggagcggacatccagtaggccactacctgagagacgtt
cagaagagtgcgttgaaaggcctctgggaaggtattcaagctggattgcttcccggggttggatgactca
tggttctttcggacgttcatgccgaatgcacagattgaagcagcacaactggataaaaataaagagagt
tcgtttgaagatatctggcctaaggtgacgaagctaaacctgtatgatcctctgacattactggcctca
gtgccaggggcggcaaaactgctatttaaaccaaaagctatacacacagaaggatttggtgttgtagag
caagtaggtccagatgatgtgacgcatccagagaaagcaaagttattgatgtccgctttagccaaatct
gcgcttgtccagtcgacggtagccccagattga The protein encoded by this nucleic acid molecule has an amino acid sequence according to SEQ ID NO: 36 as follows:

MHRPITAGHTTSRLILDQSKQISRTPSESSAQSALSQQASMSSPVLERSKSAPALLTAAQRTMLAQVGA
CNAHLTSDENMAINELRSHKPLLPKDTWFFTDPNKDPDDVVTYTLGKQLQAEGFVHITDVVATLGDAEV
RSQRAEMAKGVFNKLELHDVHVSRGRDYAMNSLQSKEHAKFLLEGHALRAGPGEIHRDSLQDMSRRLAR
APHGVGIVVIAGMSDINALITTCPDMVRERVDDITIMGGVEPLKDADGFVQPDARAYNNATDMDAARSL
YRKAQELGIPLRIVTKEAAYKTAVSPSFYEGIAGSGHPVGHYLRDVQKSALKGLWEGIQAGLLPGLDDS
WFFRTFMPNAQIEAAQLDKNKESSFEDIWPKVTKLNLYDPLTLLASVPGAAKLLFKPKAIHTEGFGVVE
QVGPDDVTHPEKAKLLMSALAKSALVQSTVAPD

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (2e-92), to a putative protein of *Ralstonia solacearum* (Genbank Accession No. NP_518366, which is hereby incorporated by reference in its entirety). Furthermore, the protein of SEQ ID NO: 36 has been shown to be translocated by DC3000 in planta.

A nineteenth nucleic acid molecule encodes ORF20 and has a nucleotide sequence according to SEQ ID NO: 37 as follows:

```
atgcgttccagggttataactacatcgctggtagtcattatgctctcatgtgcatcagccgctccagct
tgcttctccgcagacatgactcccagcgtgtcgaacgagagcacgtcggaggcggattttcagcaatgg
ctggctactttccgcagcaatgcaactactaagggcatcgacacagccacactcgatcttgctttccaa
aacatcacgcttgacccgactgtgcaccagttggatatggcgcaaccagagttcacgacggccatctgg
gattatttgtctgaacgtctgactccgaagaatatccagcaagggcaggagcttctgcaaaaagagcca
gttctgaacgaggtagagcgtcactacggtgtggatgcgaagattatcgcggccatctggtgtattgaa
agcggctacggtaaggatattggtagtcgcgatgtgattcgttccttggccacgcttgcttacaagggc
cggcggatggattacggggctacacagttgatggccgcccttcatatcgtgcaaaacaaagacatcgcc
cgtgcgcaattgattggctcgtgggctggcgcgatggggcagacgcaattcatcccgacgacctatctc
gactatgcagttgattttaaccacgacaatcggcgcgacgtttggagttcccgggccgatgcgctggcc
tccactgcctcttatttacaacgcagcgcttggaactcgcgcgtctcttggggacaggaggtgcagttg
cccgagaatttcgattacgctcaggctgacatgtcgatcaagaagcccgttgccgaatggcaacggctc
ggggtgatgggaacgaagcaagcgattccgggcgagctcgcacaggagcaagcatcggtcctgctgccc
gcaggttatcgcgggccagcatttatggtcctaagtaatttccgtagcatcctgcgctataacaactcc
actgcctatgcgctaacgatcgggctactagccgacagttatgctggcgggaccggcgtgtctcacccg
tggccaactgataatcctcccttgggcagcattgcgcaggtaaccgatttgcagaaactgctgactgct
aagggctactccctgggtgctgctgacggtgttataggggcgatgacccgggcggccatccgggcttac
cagaaggatcagcatttgccacccgacggttacgccagcactgtactactggagagcctgcgccgatag
```

```
gtgaaaatcaatctccccgcgctcagaacaacgtcttcacgcgtgcagat
ctgcttgaccgcagtcctgctgtgcacaccgctgctgttttccgcgcatg
cccaggcagccggcacggcttctgaacaagccaatgtggaagtgatgatt
cgtcagctcaacgcgctcgaggccgtcgcccagcgcagtgtcgatcttcc
acaagacccggcccaacgctatcacctggactatccccggttggtcagcg
acatcgcgcgcatccgccagggcttgcaagactacctgtcgccgtcccgc
gcacagccccgcgacccgtggagctatcaggccattacaacgtcagcgg
tgatcacacgccatga
```

The protein encoded by this nucleic acid molecule has an amino acid sequence according to SEQ ID NO: 38 as follows:

```
VKINLPALRTTSSRVQICLTAVLLCTPLLFSAHAQAAGTASEQANVEVMI
RQLNALEAVAQRSVDLPQDPAQRYHLDYPRLVSDIARIRQGLQDYLSPSR
AQPRDPVELSGHYNVSGDHTP
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A twentieth nucleic acid molecule encodes ORF21 and has a nucleotide sequence according to SEQ ID NO: 39 as follows:

The protein encoded by this nucleic acid molecule has an amino acid sequence according to SEQ ID NO: 40 as follows:

```
MRSRVITTSLVVIMLSCASAAPACFSADMTPSVSNESTSEADFQQWLATF
RSNATTKGIDTATLDLAFQNITLDPTVHQLDMAQPEFTTAIWDYLSERLT
PKNIQQGQELLQKEPVLNEVERHYGVDAKIIAAIWCIESGYGKDIGSRDV
IRSLATLAYKGRRMDYGATQLMAALHIVQNKDIARAQLIGSWAGAMGQTQ
FIPTTYLDYAVDFNHDNRRDVWSSRADALASTASYLQRSAWNSRVSWGQE
VQLPENFDYAQADMSIKKPVAEWQRLGVMGTKQAIPGELAQEQASVLLPA
GYRGPAFMVLSNFRSILRYNNSTAYALTIGLLADSYAGGTGVSHPWPTDN
PPLGSIAQVTDLQKLLTAKGYSLGAADGVIGAMTRAAIRAYQKDQHLPPD
GYASTVLLESLRR
```

This protein has significant homology, as detected by BLAST analysis (1e-106), to a putative transglycolase from *Pseudomonas aeruginosa* and *Ralstonia solanacearum* (respectively, Genbank Accession Nos. NP_252681 and NP_522801, each of which is hereby incorporated by reference in its entirety).

A twenty-first nucleic acid molecule encodes ORF22 and has a nucleotide sequence according to SEQ ID NO: 41 as follows:

```
atgcttgctcctgacggcgtagaaatcgatatcgtgctatcaggtatatgcggaactgatctggcggta
ttgtcgggccgtgaaggtggagaggtgggcattatacgcgggcacgaagcagttggcattattatcgat
gtaggtaaggatgtagtacacctacaaaaagggatgcgggtggtggttgatcccaacgaatactgtggc
gtttgcgaaccttgccgtcttgctaaaacgcacctatgcaatgggggggtgaacgctggggttggatatc
gcaggtgtcaacaaacatggaacttttgccgagcgcttcgttactcgtgagcgttttgtgtatcaattg
ccagacgatatgagctgggcagctggtgtgttggttgagcctgttgcctgcattctgaataatatagac
caggcgttcattcgagcgggagagcgtgtgttgatcctagggtctggccctatgagtctgattgcgcag
atcgttctgcgctcaatgggagttgacacgctcgccactgatcgaaacacacatcgcatacagttcggc
cgctcacaaagtcttgatgttatacatgccgatgatcttgagttgcagatgcagcaccaagaaaagttt
gatgttgttatcgatactgtcggtaatcagatcgatacagcttcacgctacatcggtcgcggtgggaga
attgtacttttttggatttgatagtgactatcactacatgctgcctgtaaagtacttcctggttaacgct
atcagtattatttctgctggagaatacaatcagcactttcctagagcaattcgtcttgtgcaaaaactt
cctgagctagggcggctggtaacgcatcgctacgtactagaaaatcactcggaggttttcgatgcactt
ctgaacgatgcttccgccccaatataaaaagcgtattcacaccaaatctcgcttatctttaa
```

The protein encoded by this nucleic acid molecule has an amino acid sequence according to SEQ ID NO: 42 as follows:

```
MLAPDGVEIDIVLSGICGTDLAVLSGREGGEVGIIRGHEAVGIIIDVGKD
VVHLQKGMRVVVDPNEYCGVCEPCRLAKTHLCNGGVNAGLDIAGVNKHGT
FAERFVTRERFVYQLPDDMSWAAGVLVEPVACILNNIDQAFIRAGERVLI
LGSGPMSLIAQIVLRSMGVDTLATDRNTHRIQFGRSQSLDVIHADDLELQ
MQHQEKFDVVIDTVGNQIDTASRYIGRGGRIVLFGFDSDYHYMLPVKYFL
VNAISIISAGEYNQHFPRAIRLVQKLPELGRLVTHRYVLENHSEVFDALL
NDASAPNIKSVFTPNLAYL
```

This protein has significant homology, as detected by BLAST analysis (2e-18), to a putative sorbitol dehydrogenase (Genbank Accession No. NP_389115, which is hereby incorporated by reference in its entirety).

A twenty-second nucleic acid molecule encodes ORF23 and has a nucleotide sequence according to SEQ ID NO: 43 as follows:

```
atgaaagttactgtattcagtcagatatcaattgatggcaagttgacgatgggcaaaggcgcatccagc
aagccgttgtttcagaactttgatgatgatgacatgcgttttattcataagttccgcggcgaagtcgac
gcaatcatggtagggcgcaatacaattgttactgacgatccacaattgaccaatcgctatgagtcgggt
cgtaacccaatacgtatcattcccaccacctccttagatctgcctacttccgccagtattttcaaatca
ccagagaaaactattatcgcaactagcgaacaggctcgtgatcatgaaatggtcaaacatatccgtgct
tgtggaaaggaggtgctctttgccggtgcaaagcatgtcgactttacacgacttttccctatgctggag
gcgcgcggaataaaccacatcatggttgagggcggtggccacctgaactggcaggtattcaatctcgat
ctggtagatgaaattatactcatgcaggtgcctatcatcataggtggtgcggcaactgcaacgcttgct
gacggggtggggtatcgggatatcaacatggccaattcgtttacgctgcatgctttagaagcacgcccc
cattacaatctcatgcacttcaagcgcgaatcgaacaatcggagcccgtactga
```

The protein encoded by this nucleic acid molecule has an amino acid sequence according to SEQ ID NO: 44 as follows:

MKVTVFSQISIDGKLTMGKGASSKPLFQNFDDDDMRFIHKFRGEVDAIMV
GRNTIVTDDPQLTNRYESGRNPIRIIPTTSLDLPTSASIFKSPEKTIIAT
SEQARDHEMVKHIRACGKEVLFAGAKHVDFTRLFPMLEARGINHIMVEGG
GHLNWQVFNLDLVDEIILMQVPIIIGGAATATLADGVGYRDINMANSFTL
HALEARPHYNLMHFKRESNNRSPY

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (8e-38), to a riboflavin specific deaminase (Genbank Accession No. NP_213307, which is hereby incorporated by reference in its entirety).

A twenty-third nucleic acid molecule encodes ORF24 and has a nucleotide sequence according to SEQ ID NO: 45 as follows:

atggagcaggaaaagagttcctgtttgcgctacggcgtgacccttaatga
aaaagatctgtcacgtttttgggaactacacagcactacatgtggagca
cgattaaaaatgagtacgcgctcactgaatccatcgaccacttgatggca
cagcatcaacagcaattaatgcgctcaatcagttttgaattgtttcaatc
catgcctggcgtggaggcgcttctcaatttactggagcataccggagtgc
cctgtgccgtagcctcttcgtctccacgtaatttggtcgagcttatattg
aagaaaacgaaattgcgtcgatttttcaaagaggttatttgtggtactga
tgttaaagagagtaaaccgaatccggagattttcttacggcggccaagg
gacttggagtgtcacctcgtgcatgtctggttattgaagactcccatcac
ggtgttaccgctgcgaaggccgcccatatgttttgtataggtttgcgtca
ttccagctcatttcagcaggatctgagcgctgctgatctgatcgccaata
atcattatgacatcaagcaatggtttgcagaaaaatag The protein encoded by this nucleic acid molecule has an amino acid sequence according to SEQ ID NO: 46 as follows:

MEQEKSSCLRYGVTLNEKDLSRFLGTTQHYMWSTIKNEYALTESIDHLMA
QHQQQLMRSISFELFQSMPGVEALLNLLEHTGVPCAVASSSPRNLVELIL
KKTKLRRFFKEVICGTDVKESKPNPEIFLTAAKGLGVSPRACLVIEDSHH
GVTAAKAAHMFCIGLRHSSSFQQDLSAADLIANNHYDIKQWFAEK

This protein has significant homology, as detected by BLAST analysis (5e-32), to a putative phosphatase from Clostridium (Genbank Accession No. NP_347269, which is hereby incorporated by reference in its entirety).

A twenty-fourth nucleic acid molecule encodes ORF25 and has a nucleotide sequence according to SEQ ID NO: 47 as follows:

atgaatgcgttcgcaaccggtcagcttgaatacagcctgaaaaagctggg
atacgatgccgccgctttgcaggccctgcgcgaagaagggtacttgctgt
ggaaagggaaaaacgaccagaccagcttgctggtgccctcggccgatctg
gatgcacttttcgttatcaacacgttgagctacatcgaccccgagcatga
cgcacgtctgctggcgcttgcattgcaccttaacctgtccctgtccata
cgatgagcgcctgcatagccctcgatgtcgagcaaaacacgttatgcctg
cgctacacccatgaccttggcgggagcggggctgataccctgttgcttgc
gctcgaaaacgcccaggcgctggccgaacaggtcaggcaggtgatcgaaa
ccttcaggcgtgaccaagggcgtccgtccgggcaaacgtctttgtcccgg
caatccagtgctctgatgcgataa The protein encoded by this nucleic acid molecule has an amino acid sequence according to SEQ ID NO: 48 as follows:

MNAFATGQLEYSLKKLGYDAAALQALREEGYLLWKGKNDQTSLLVPSADL
DALFVINTLSYTDPEHDGRLLALALHLNLSPVHTMSACIALDVEQNTLCL
RYTHDLGGSGADTLLLALENAQALAEQVRQVIETFRRDQGRPSGQTSLSR
QSSALMR

This protein shares features common to type III chaperones and is a putative chaperone for the product of ORF26 (described below).

A twenty-fifth nucleic acid molecule encodes ORF26 and has a nucleotide sequence according to SEQ ID NO: 49 as follows:

atgaaaatatccggctccacatcgcctgcacacacttcaacgaattccgc
gcagaagtcctcttcaaaagggctgctgagtggtttggccaagcatttca
aggggatgctcgtttctggcaacacttctggtcattcggcgctcgggcat
tacgcgtcatccagcagcggctccaaaggcaaggcaccggtacgggacga
ttacagcaacggaccgcaaacacgccttaacaacacacctctgaaacgag
cactggcccgagagcttgatcgctttggctacggttcatcggcgaccgag
tcttttgaccgctcattgcagcgtaaggataaaaatccagagcttgggaa
ggtctga The protein encoded by this nucleic acid molecule has an amino acid sequence according to SEQ ID NO: 50 as follows:

MKISGSTSPAHTSTNSAQKSSSKGLLSGLAKHFKGMLVSGNTSGHSALGH
YASSSSGSKGKAPVRDDYSNGPQTRLNNTPLKRALARELDRFGYGSSATE
SFDRSLQRKDKNPELGKV

The protein of SEQ ID NO: 50 has been shown to be translocated by DC3000 in planta.

A twenty-sixth nucleic acid molecule encodes ORF27 and has a nucleotide sequence according to SEQ ID NO: 51 as follows:

```
atgaaaaaatgtattgctctgctccttactctggtcgtctgcgaaggtgcattggcaggdacggcacgt
gatgaacagaacatcacgtcttacatcgacagtcacggcaccgaacagatcgcgttgcttgagaagctg
gtcaacatcaacagcgggacagacaacgttgagggtgtcgtcaaggtcggtaacctgatcaagccggag
ctggaggcgttgggtttcgagaccgcctggcacgacctgccctcggcaatgaaccatgccggcagcctt
gtcgctgtgcatgacggcagcaagtctgcaaaacgtattctgctgataggccatctggatacggtcttt
cctcaaacaagccgctttcagacgttcgcttacctggacggcggcaaaaaagccaagggcccggcgtc
attgatgacaaaggcggcgtggtcacgatgctttatgcattgcaggcgctcaagcacagcggcgcgctg
gaaaagatgaacatctcggtagtcttgataggcgatgaagagctggcggccaaaccgaccgagatttcc
agagagtggctgatcgccgaagccaaaagaagcgacattgcgctgggcttcgaattcgccttgtcgccc
aatcaactgatcaccgagcgaagagggctgagcgaatggttttttgaccagcaccggcatcgacaaacat
tcagcgacgatctttcagcctgagaccggttttggtgcgatgtacgagtcggcccgagtgcttgacgag
attcgtcagaaactgtcgaacgagcagggcctgaccatcaatccgggactcattctgggcggctcaacg
gctgtggaagatagcgccagtgggcaaggcacggcttctggaagaaagacaacagttgcccggatcacg
tcggtgcatggtgatttgcgcttcagcagtgaagaccagagggcctctgcggaaacccgaatgaaggac
atagccagtcacccgctgccgcagaccaacagcgacctgaaaataaaagccatcatgccggtcatggcg
gatcgcgaaagcaatcgccaactactggcagcctacagtcaggtcagccaggatctcgacggacctgct
ttggagtcggcgccttcagcagaacgaggcggcgcagatatttcctatgtgaacaagtatgtgactgcg
agcctggacggtcttggtgcgtgggggggcaggtgcgcacagtgaaaatgaaaccatcgagttgggctcc
ttgcccgtggtgacgaaacgggcggctattttcctgagccgctatggtaaccagtga
```

The protein encoded by this nucleic acid molecule has an amino acid sequence according to SEQ ID NO: 52 as follows:

```
MKKCIALLLTLVVCEGALAGTARDEQNITSYIDSHGTEQIALLEKLVNINSGTDNVEGVVKVGNLIKPE
LEALGFETAWHDLPSAMNHAGSLVAVHDGSKSAKRILLIGHLDTVFPQTSRFQTFAYLDGGKKAKGPGV
IDDKGGVVTMLYALQALKHSGALEKMNISVVLIGDEELAAKPTEISREWLIAEAKRSDIALGFEFALSP
NQLITERRGLSEWFLTSTGIDKHSATIFQPETGFGAMYESARVLDEIRQKLSNEQGLTINPGLILGGST
AVEDSASGQGTASGRKTTVARITSVHGDLRFSSEDQRASAETRMKDIASHPLPQTNSDLKIKAIMPVMA
DRESNRQLLAAYSQVSQDLDGPALESAPSAERGGADISYVNKYVTASLDGLGAWGAGAHSENETTELGS
LPVVTKPAAIFLSRYGNQ
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis, to a carboxypeptidase from Bacillus (4e-29) and a hydrolase from Ralstonia (5e-22) (Genbank Accession Nos. NP_241218 and NP_521834, respectively, each of which is hereby incorporated by reference in its entirety).

A twenty-seventh nucleic acid molecule encodes ORF28 and has a nucleotide sequence according to SEQ ID NO: 53 as follows:

```
atgaaccctataacacacagctttagtcatcttgggttttcaaacgctcaaagtacgtcagcgctggcg
cccggcggtaataaagtgccgaactttgtttcgcgagggcgaggcaaaggagtcccgcttgagcatttc
aacaccgctgatgagtatcgtttggcacgccagcagggcggcgtgctgaaatcaatagacggcagagag
ttcatgctactgctgcagaagtacacggccgccgaaacaagcgacgaagaatttgcggatttgagggcc
```

-continued

```
gccataccgcgctattccattgacctggccgagccgggtcaaactaaagtgctttatcgggggatatcg ctgccggagaagactgcggcgcgattactgaatatctcttggggttacgaaagtcgcgdaatagcccat ggtcttatccatggcttgcgggtagttaaggaaggtctgaagtag
```

The protein encoded by this nucleic acid molecule has an amino acid sequence according to SEQ ID NO: 54 as follows:

```
MNPITHSFSHLGFSNAQSTSALAPGGNKVPNFVSRGRGKGVPLEHFNTADEYRLARQQGGVLKSIDGRE

FMLLLQKYTAAETSDEEFADLRAAIPRYSIDLAEPGQTKVLYRGISLPEKTAARLLNISWGYESREIAH

GLIHGLRVVKEGLK
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. Furthermore, the protein of SEQ ID NO: 54 has been shown to be translocated by DC3000 in planta.

A twenty-eighth nucleic acid molecule encodes HopPtoL (ORF29) and has a nucleotide sequence according to SEQ ID NO: 55 as follows:

```
atgactactctgaccaccagacagatacaactcgcccacgcttggacatccgttcatacaggcgctggc ctggccctggactgggtcgccgatgtggccgaaaaggtcgaggaaatcgccaccaaggccgacgccctc agccgtgacttgcaccgcgcgcgcaacctgtcccgcagccttgggcgggtctcgacgacacccatgggt atcggtttcttcggcttgtctcaggcaggcaagagctacctgatttccgctctggcggcggacgagaaa ggccagttgctgacccggctgggtactcagcaactggacttcatcaagcacgtgaacccggtgggcggc ggtaaggaggccaccggtctggtcacgcggttcacccgcaccgccgcgccaagtctggacccgcacttt ccggtggagctgcgtctgtttcgcgaggtcgagatcgccatcattttggccaacgcctggtttgaggat ttcgatcatcagcgcttgaacagccaagtcaccgatgcgcagatcgatgccttttgcagcgtttcgag gggcaattggcagccgctccgacacctggcgtcagcagtgacgacgtggtgctgctatgggattacctg gagcaccattacgctaacgccatgcgcccgctgaacgcccgttattggccttgcgtggtcaaactggcg ccgcgcttgtcggcacgcgagcgcgctcaattgttcgagccgctgtggggcggcatcggcaaaatgacc gaaacctatgagcaactggcctcggccctgcaccgcctgggcgtggcagagacagttttgcgcccatc agcgcgctggtcaccgagcgcgatgggcaactggtacaaagcaaaagcatcatcaacgtcgacattctc agccgtcttggcggcagcgcggactcggccatcgaggtacgtccggccagtgaaggcactttgcgccct gccgtgtcggtgaatcgggccgaactggcggcgctcaccaacgagttgattttcgcctggataacgaa ccggccaacgccatcgtcaatagcgtcgatctgctcgacttcccgggctaccgcagccggcagaagctg atgagcatcaacagaggccagcgaagtcgacagcaatggcaccgccaacaatccggtcgccaggctgttg ctgcgcggcaaggtcgcttacttgtttgagcgttacaccaacgagcaggaaatgaacgcgctggtgatg tgcaccagcaccttcaagcagagcgaagtggtgagcgtcggtccggtactcaagagctggatcgacaag acccaaggcaccagcccccagcagcgcgatggtcgggccagcggtctgatctgggcgttgaccatgtgt gacggctttatcggcggcgcgctcaacggcgaggttgtgcagtttcccgaaggttgcgacaacatgctc
```

-continued

```
aaactgaccatgatcgagcgattcggcaacgaagactggatgaaacaatggggcagcacgcctttcaaa
aacacctatctggtgcgcaagccgcgcttcaagaccagcttcatcgagttggcggcggacggtgaagaa
cgcgcttacaacgactcatcgcactctgcgttacaggcattgcaacaagcgttcagcaacagtgaactg
gtcaagcgccatgtggcagaaccgcaggacgcctggcaggcaatgctgacactgaacgacggcggcatg
actcgtttcagctcggcgttcagcccgattgccaacatcgacttcaagttacagcgtattgccgagcaa
ctggacgagttgatggtgcaattactgccgcgcctggagcagtactacgaagccggtggcgaagacgaa
cgggccaggaagaaggttatcgccaacctgattgcccgcccgttcgcgaccacgccgcacggcaaacac
gtgcttggcgaactgctcggttacatgtcgttgccggaacagcagttgcgcgacctttacctgaacggt
gatttcgccagccctgccagcgacgccactgcaccggtgcaggccgtcggcaagcctgaagtggaatac
gacatattcggcgaggccatcgcagccactgccacggtggaaatacccgcggcaccggccgtagcgccg
caataccagagccacgaacaccgtttcgcccgagcggccttcgacctgtgggcaacgcacctgcgcaac
ctcagccgtcgccagcacctgctggacctgttggagctgcctgccgaggccatcgccctgctggtcaag
gaactggtggtctgcgccgagcgcctggacttgccattgcagctcagcaacgcgctgctcaagcgcgcc
cagagcggtgtgcgcaaagaaaacctggtgcagcgccaagtgctgaccgcgcaactgctgctcaacgac
ttcgccgcctggttcgggcacaccgcccagccggcgggtcagcggccaacgggcctgctgggtgccaaa
caaccgctgtttgctttttatcaaaaggaaatgccagggcgcttcccgcacctcgcagcgcaagccgac
gaccagagcgtgattttcgccgatgactggatttctggcattgccattcatacccagaaaaacgtcggc
caccgcaagggcaaagaaatcactcctgagcagaacgaggccatgggccgcgtcatccaggcgttcaaa
gcgagataa
```

The HopPtoL protein encoded by this nucleic acid molecule has an amino acid sequence according to SEQ ID NO: 56 as follows:

```
MTTLTTRQIQLAHAWTSVHTGAGLALDWVADVAEKVEEIATKADALSRDLHRARNLSRSLGRVSTTPMG
IGFFGLSQAGKSYLISALAADEKGQLLTRLGTQQLDFIKHVNPVGGGKEATGLVTRFTRTAAPSLDPHF
PVELRLFREVEIAIILANAWFEDFDHQRLNSQVTDAQIDALLQRFEGQLAAAPTPGVSSDDVVLLWDYL
EHHYANAMRPLNARYWPCVVKLAPRLSARERAQLFEPLWGGIGKMTETYEQLASALHRLGLAETVFAPI
SALVTERDGQLVQSKSIINVDILSRLGGSADSAIEVRPASEGTLRPAVSVNRAELAALTNELIFRLDNE
PANAIVNSVDLLDFPGYRSRQKLMSINEASEVDSNGTANNPVARLLLRGKVAYLFERYTNFQEMNALVM
CTSTFKQSEVVSVGPVLKSWIDKTQGTSPQQRDGRASGLIWALTMCDGFIGGALNGEVVQFPEGCDNML
KLTMIERFGNEDWMKQWGSTPFKNTYLVRKPREKTSFIELAADGEERAYNDSSHSALQALQQAFSNSEL
VKRHVAEPQDAWQAMLTLNDGGMTRFSSAFSPIANIDFKLQRIAEQLDELMVQLLPRLEQYYEAGGEDE
RARKKVIANLIARPFATTPHGKHVLGELLGYMSLPEQQLRDLYLNGDFASPASDATAPVQAVGKPEVEY
DIFGEAIAATATVEIPAAPAVAPQYQSHEHRFARAAFDLWATHLRNLSRRQHLLDLLELPAEAIALLVK
ELVVCAERLDLPLQLSNALLKRAQSGVRKENLVQRQVLTAQLLLNDFAAWFGHTAQPAGQRPTGLLGAK
QPLFAFYQKEMPGRFPHLAAQADDQSVIFADDWISGIAIHTQKNVGHRKGKEITPEQNEAMGRVIQAFK
AR
```

HopPtoL has been shown to be a protein that is secreted by DC3000. HopPtoL has significant homology, as detected by BLAST search (1e-21), to an SPI-2 regulated SrfC (see Worley et al., *Mol. Microbiol.* 36:749–761 (2000); GenBank Accession No. AAF74575, each of which is hereby incorporated by reference in its entirety).

A twenty-ninth nucleic acid molecule encodes HopPtoS2 (ORF30) and has a nucleotide sequence according to SEQ ID NO: 57 as follows:

```
atgaatataaatcgacaactgcctgtatcaggctcggagcgattgttgactcccgacgtgggcgtatct
cgccaggcttgttccgaaaggcattattctactggacaggatcggcatgattttaccgttttgctgcc
aggctacatgtggatgcgcagtgttttggtctgtcaatagacgatttgatggataagttttctgacaag
cacttcagggctgagcatcctgaatacagggatgtctatccggaggaatgttctgccatttatatgcat
accgctcaagactattctagtcacctcgtaagggggaaataggaacgccgctgtaccgagaggtcaat
aattatcttcgacttcaacatgagaattctgggcgagaagctgaaattgataatcacgacgaaaagcta
tcgcctcacataaaaatgctttcatctgcgcttaatcgtttaatggatgtcgccgcttttagaggaacg
gtttatagaggcattcgcggtgatttagataccattgctcggctctaccatctattcgatacgagcggc
cggtacgtagagcccgctttcatgagtacaactcgaataaaggacagtgcccaggtgtttgagccaggc
acgccaaacaacatagctttccagataagcctaaaaagaggcgccgacatttcgggatcttcccaagcg
ccctcagaggaagaaatcatgctacccatgatgagtgagttcgtcattgaacatgcatccgctctttcc
gaaggaaagcatttatttgtattaagtcagatttga
```

The HopPtoS2 protein encoded by this nucleic acid molecule has an amino acid sequence according to SEQ ID NO: 58 as follows:

```
MNINRQLPVSGSERLLTPDVGVSRQACSERHYSTGQDRHDFYRFAARLHVDAQCFGLSIDDLMDKFSDK
HFRAEHPEYRDVYPEECSAIYMHTAQDYSSHLVRGEIGTPLYREVNNYLRLQHENSGREAEIDNHDEKL
SPHIKMLSSALNRLMDVAAFRGTVYRGIRGDLDTIARLYHLFDTGGRYVEPAFMSTTRIKDSAQVFEPG
TPNNIAFQISLKRGADISGSSQAPSEEEIMLPMMSEFVIEHASALSEGKHLFVLSQI
```

HopPtoS2 has been shown to be a protein that is secreted by DC3000. HopPtoS2 has significant homology, as detected by BLAST search (1e-5), to Clostridium exoenzyme C3 ADP-ribosyltransferase, (Nolling et al., *J. Bacteriol.* 183: 4823–4838 (2001); GenBank Accession No. NP_346979, each of which is hereby incorporated by reference in its entirety). Further confirming that HopPtoS2 has similarity to ADP-ribosyltransferases, it was determined to possess an ART domain (pfam1129). In addition, HopPtoS2 has 20.5% identity to the HopPtoS1 as determined using EMBOSS software.

A thirtieth nucleic acid molecule encodes HopPtoS3 (ORF31) and has a nucleotide sequence according to SEQ ID NO: 59 as follows:

```
atgaatatcagtcctgtatcgggtgcccacggtagcagctacccttcagctcaatccacagcatcgacg
gcatcgaaaggtccctctggatcctttctcaaacagctcggcggctgttttcaccctgcctgggtagc
agctctactggggccatactttctcccgctcatgagcaggtattgagccacacctattccagcaatatt
aaaggaaagttgcgcacgacgcccccaaaaggaccgtcgcccaggttgtctgacacacctatgaagcag
gcgctttcttcaatgatcgtacaggagcgaaaacggcttaaaagtcaacccaagtcattggcctcggat
atagaacgtccagacagtatgatcaaaaaagcgcttgatgaaaaagacggccacccgtttggcgagcgc
ttttcagacgacgaatttcttgcgattcatctctatacgagctgtctttataggccgatcaatcatcat
ctgcggtatgccccgaacaatgatgttgcaccggttgtcgaggcactgaaaagtggtttggcaaagctt
gctcaagaccctgattatcaagtgtctagccagcttcatagaggcatcaagcaaaagatgagtgatggc
gaggtcatgagtcgtttcaaaccgggtaagacctatcgtgatgaagcgttcatgagcacatcaactcat
atgcaggtttcagaagagtttacctccgacgttacgttgcacctgcggtcctcatcagctgtcaatata
ggcccctttcgaaaaatccatacgaggacgaagcgcttatctcgccctgacgcctttcaaagtaacc
ggtctgcgcaagcaggacgataagtggcacgtcgatttgaacgagatagcagataattcagacgagtga
```

HopPtoS3 has an amino acid sequence according to SEQ ID NO: 60 as follows:

MNISPVSGAHGSSYRSAQSTASTASKGPSGSFLKQLGGCFSPCLGSSSTGAILSPAHEQVLSHTYSSNI

KGKLRTTPPKGPSPRLSDTPMKQALSSMIVQERKRLKSQPKSLASDIERPDSMIKKALDEKDGHPFGER

FSDDEFLAIHLYTSCLYRPINHHLRYAPNNDVAPVVEALKSGLAKLAQDPDYQVSSQLHRGIKQKMSDG

EVMSRFKPGKTYRDEAFMSTSTHMQVSEEFTSDVTLHLRSSSAVNIGPFSKNPYEDEALISPLTPFKVT

GLRKQDDKWHVDLNEIADNSDE

HopPtoS3 has significant homology, as detected by BLAST analysis (5e-3), to chicken ADP-ribosyltransferase (Tsuchiya et al., *J. Biol. Chem.* 269:27451–27457 (1994); Genbank Accession No. P55807, each of which is hereby incorporated by reference in its entirety). Further confirming that HopPtoS3 is an ADP-ribosyltransferase, it was determined to possess an ART domain (pfam1129). In addition, HopPtoS3 has 71.7% identity to HopPtoS1 as determined using EMBOSS software.

A thirty-first nucleic acid molecule encodes ORF32 and has a nucleotide sequence according to SEQ ID NO: 61 as follows:

atgaatattaacccttccctgggcgctcatggcagcgcctactcgtcgcctcaaagtgatacttcgaag gccactggaaaagcacctgcgccttcttttttcaaacagttgggcggctgttttcgccgtgccttggt tcccatgcgtcaagcagccaacaactgtccgccagtcatgcgcagacgctcagtcagaattactccagc aacattcaggggacgagccgcacacgccagccgagagcaccctcgccacgcctgtcagatacgcccatg aagcaggcgctttcctcaatgatcgaacgcgagcgtttgcggcttcaaggtcttcgggaggaatgttc tcgggcattgactccgccgatgccatgattggtcgagcgctcacgaagaaggattcaaacccaaaggct gcgcgttttagtgatgatgagtttctcgccgttcacctctacacaacttgcctctacagacctatcaat catcatcttcggtatcaacactag The protein encoded by this nucleic acid molecule has an amino acid sequence according to SEQ ID NO: 62 as follows:

MNINPSLGAHGSAYSSPQSDTSKATGKAPAPSFFKQLGGCFSPCLGSHAS

SSQQLSASHAQTLSQNYSSNIQGTSRTRQPRAPSPRLSDTPMKQALSSMI

ERERLRLQGLSGGMFSGIDSADAMIGRALTKKDSNPKAARFSDDEFLAVH

LYTTCLYRPINHHLRYQH

This protein has significant homology, as detected by BLAST analysis (5e-3), to chicken ADP-ribosyltransferase (Tsuchiya et al., *J. Biol. Chem.* 269:27451–27457 (1994); Genbank Accession No. P55807, each of which is hereby incorporated by reference in its entirety). Further confirming that protein of SEQ ID NO: 62 is an ADP-ribosyltransferase, it was determined to possess an ART domain (pfam1129). In addition, this protein has 51.3% identity to HopPtoS1 as determined using EMBOSS software.

A thirty-second nucleic acid molecule encodes ORF33 and has a nucleotide sequence according to SEQ ID NO: 63 as follows:

atgagctcgatcacgcacaccaacacgccgcaattggcggtcagcgattcacggggtctgccggtacgc agtgtgcagttctatcgtggcgctgatggtcagcctgttgacgcgagggtgacgcagcactatttcgac -continued

```
aaggccgggcgactgatcgccagtcgcgatccacgttttccagtcgtttgaaatacggtgtctgtgcg
cctgtgaacctgatgcaaatcgtcagcttgtccggggctttgctgttatcgaaaagtgtcgattcagt
tggcgggtgagcctgaacggcgaagcggggcagttagtcgacagctgtgacggacgtgacaacccgcgc
cagatcgaatacgacgggctgttgcgccctttggcgatcaacgaatcaggccgaatgaccgagcgcttc
acttatggcgggcctgccactgctgagcataaccagtgcaatcaactgattcgccatgacgatacggca
ggctcgcgcttgctgcgggactatggactgtcgggtagggcgttgagcgaaaaaaggtacttcctgcag
tcgcccgacagcccggactggccacttgccgagcctgatcgtgatgcactgctcgagccggtcggcctg
cagacgcgctgggctttcaacgcgcagggcgaggacctggcgcagactgacgcaaacggtaatgtccag
cgtttcagtcacggtgtggctgggcaactgcacgctgttgaactgaccctggccaatacggcacagcgg
caaacgctggtcagtgcaattcactacgacgcgttcaatcaggccgagcaggagacggcaggaaatggt
gtggtcagtcgctatgtgtatgatcaacaggacggtcggctgactgagctcagtgcgctatctgccgac
ggctcagtgttgcaaaaactgaactacagctatgacccggcaggtaacgttctactcatcaacgatgcc
tcgcaaccagaccggtattgcggcaatcagcgtatcgagccgataaaccgttactgttacgacacgttg
tatcagttgatcgaagccacggggcgggaggtcagaaacggggccagccatggtccggcgctacccggt
ctgcaacctctgccgacgctcgatccttgccaggtcagcaactacacacagcgttacagctacgacgct
gcgggtaacctgctgcaaatgcgccacgaaggcgcgcacaacttcacccgcaacatgcacgttgatccc
gacagcaatcgcagcctgcccgacaatgacaggtatgtggatttcgccacgagttttgatgccaacggc
aatctgctgcaactcgtgcgtgggcagaccatgagctgggatgtgcgtaatcagttgcggcaaatcact
accgtgcaacgtgaagacgcaccgaatgatgaagagcgctatgtatacgacggccagggccagcgctgc
cgcaagatcagcaccgcgcaggcatcaggtcgcacactgaccaatgaagttcgctacctgccgggactg
gaagttcggaccacggccgatggagaaactcttcacgtcgttacggctcaggcgggtcgcaacagcgtg
cgggtgttgcactgggaagccggaaaaccaggcgctattgcgaacgatcaggtgcgttacagcctgggt
gatcatctgggctcgagcacgctggagcttgatcagcaaggcggcctgatcagccaggaaagttattac
ccctttggcggcacggcctggtgggcggcgcgtagtgcagtggaggccaagtacaaaacagtgcgttat
tcgggtaaagagcgcgatgccagcgggctttattattacgggttcaggtattacgcgccgtggttgcag
cggtggatcaatcctgacccggcggggatgtggatgggttgaatctgtacaggatggtcagaaataat
ccgcttgtttacgttgatgcgaagggccagcaacctgaacctgttccaaaaactattcaccagatctgg
ataggtgaaaacaagaatgccttgagagctcaggttagcaatatcaacagaaccgttgaaatggcttgg
gggtataaagtgaagttgcatctggaaacgaggacgccggaagcttattcggaaatcgaaaaggatctg
agatccgaagtggttctgcttcctgattcccaggtttttcaaaacttcaaggagaagccgctttatgcg
gcctatgaagatttccgaagaaacaatcagaattacgctttcgcggtagacgttttacgtatgcatacc
gttcatgatttgggcgggatttattcagatgtcgatgacgtttatgcaggtgcggagactggcggaatg
acgcagttgggggataatccgctgtttgcagaacctgatgaggttttgacgctggatcctgttcatgtc
ccttgggagccccagaattctgttgaaagttttatggtcaataacagctcatttgccgctcattcaggt
gcaggcgtcttacttgacatgatgggggaaggagcgaaacgatatgatgaagccgttgagggcggaagt
tatccggatccgacgggcatgaacggtataggtctaagtctgctctggaatcctaacccggcagtaaga
gttcgaacgttatcgaatgtagtaggcccggcttgtttacagacacactgcacgcttcggacacagca
tacggtgagcttttagtaatctgaaaggcgtcgtctttcaaaaacagccgttcacgtttgccgaccaa
atggccaggaagatgccgctgcatcggcatataaaaagcggcgcggcgcaaacctggcgctga
```

The protein encoded by this nucleic acid molecule has an amino acid sequence according to SEQ ID NO: 64 as follows:

MSSITHTNTPQLAVSDSRGLPVRSVQFYRGADGQPVDARVTQHYFDKAGRLIASRDPRFSSRLKYGVCA

PVNLMQIVSLSGALLLSKSVDSGWRVSLNGEAGQLVDSCDGRDNPRQIEYDGLLRPLAINESGRMTERF

TYGGPATEAHNQCNQLIRHDDTAGSRLLRDYGLSGRALSEKRYFLQSPDSPDWPLAEPDRDALLEPVGL

QTRWAFNAQGEDLAQTDANGNVQRFSHGVAGQLHAVELTLANTAQRQTLVSAIHYDAFNQAEQETAGNG

VVSRYVYDQQDGRLTELSALSADGSVLQKLNYSYDPAGNVLLINDASQPDRYCGNQRIEPINRYCYDTL

YQLIEATGREVRNGASHGPALPGLQPLPTLDPCQVSNYTQRYSYDAAGNLLQMRHEGAHNFTRNMHVDP

DSNRSLPDNDRYVDFATSFDANGNLLQLVRGQTMSWDVRNQLRQITTVQREDAPNDEERYVYDGQGQRC

RKISTAQASGRTLTNEVRYLPGLEVRTTADGETLHVVTAQAGRNSVRVLHWEAGKPGAIANDQVRYSLG

DHLGSSTLELDQQGGLISQESYYPFGGTAWWAARSAVEAKYKTVRYSGKERDASGLYYYGFRYYAPWLQ

RWINPDPAGDVDGLNLYRMVRNNPLVYVDAKGQQPEPVPKTIHQIWIGENKNALRAQVSNINRTVEMAW

GYKVKLHLETRTPEAYSEIEKDLRSEVVLLPDSQVFQNFKEKPLYAAYEDFRRNNQNYAFAVDVLRMHT

VHELGGIYSDVDDVYAGAETGGMTQLGDNPLFAEPDEVLTLDPVHVPWEPQNSVESFMVNNSSFAAHSG

AGVLLDMMGEGAKRYDEAVEGGSYPDPTGMNGIGLSLLWNPNPAVRVRTLSNVVGPGLFTDTLHASDTA

YGELFSNLKGVVFQKQPFTFADQMARKMPLHRHIKSGAAQTWR

This protein has significant homology, as detected by BLAST analysis (1e-128), to SepC insecticidal toxin (Hurst et al., *J. Bacteriol.* 182:5127–5138 (2000); Genbank Accession No. NP_065279, each of which is hereby incorporated by reference in its entirety). This protein also has significant homology (2e-128), as detected by BLAST search, to putative insecticidal toxin from *Yersinia pestis* (Parkhill et al., *Nature* 413:523–527 (2001); GenBank Accession NC_003143.1, each of which is hereby incorporated by reference in its entirety).

A thirty-third nucleic acid molecule encodes ORF34 and has a nucleotide sequence according to SEQ ID NO: 65 as follows:

The protein encoded by this nucleic acid molecule has an amino acid sequence according to SEQ ID NO: 66 as follows:

MPITAQQLLQILPSAGQKAGVFAPVLNTAMSKHQILTPLRIAAFIAQVGH

ESGQLRYVREIWGPTPQQLGYEGRKDLGNTVAGDGSKYRGRGLIQITGRA

NYAECGEALGLDLIHHPELLEQPEHATMSAAWYWSSRGLNSLADKGDFLQ

ITRRINGGTNGLADRQALYDRALKVLA

This protein has significant homology, as detected by BLAST analysis (3e-36), to a lytic enzyme (Nakayama et al., *Mol. Microbiol.* 38:213–231 (2000); Genbank Accession No. BAA83137, each of which is hereby incorporated by reference in its entirety).

A thirty-fourth nucleic acid molecule encodes ORF35 and has a nucleotide sequence according to SEQ ID NO: 67 as follows:

atgccgatcaccgcgcagcagttgctgcagatactcccgagcgctggccagaaagccggcgttttgca cccgtcctgaacacagcgatgagcaagcaccagatcttgacgccgctgcgcatcgcggctttcatcgcc caggtcggtcatgagtccggccaactgcgctacgtccgcgagatttggggccgactccgcagcagctg ggttatgaaggccgcaaggacctcggcaataccgtggcgggtgatggttcgaagtaccgcgggcgcggc ctgatccagatcaccggccgggccaactatgccgaatgcggcgaggcgctgggcctagacctgatccat cacccggaactgctcgagcagccggagcacgccacaatgtcggcagcgtggtactggagcagccgtggc ctgaactcgctggccgacaaaggggactttcttcaaattacccgaagaatcaacggaggcaccaatgga ctggcggatcggcaggcgctgtacgaccgggcgctgaaggtgctggcgtga

```
atgaatctaacagctttaggttcaaagctgtctcggtatcgcaagcagcttgcgatgagcgaggaagaa
gtgtgtgcggtcacccacatccccttgagcgcctgcagtcagttgaagccggctctcaggcgcctacg
ggtgatgaagtgcttatcctggccgatctctaccactgcaacttcaaattcttcatctcgaacgagccg
ctcgccccctttgagcagaccgaaatcctgtatcgcaggcacggagctgagttcatcaaggaggatcgt
agagccgtccaagaattcctgtacctctgcgaaacagaggacttcctgatgagtgagttgaaggctatg
aagctcgaatttccgctgccgcaggcttctgggaatttttaagaatgatggaatccgagcggctgaagcc
tttcgccttttcaatcagcacccacaaacgccgtgcctcgggatgtgtatcaggagattcgccaaacc
ggagtgcatgtgttccgtagaaagcttggtaactctaacatttcgggctttcctggctcacccacg
gctgggaagtgcattctggtcaactacagcgaagacgtataccggcagcggtttagcgctgcgcatgaa
tttgctcacgctcttttcgatgcgcagggtggccccagtattacctactcccgtacgactaaggctgac
ctagtcgaagtgagagcaaacacctttgcctcccggtatctgatgccttcagaaatcctccgacagctg
cccaaccctgagcaatggacacaggaaaatacccagtattgggctcatgagttgcgagtcagctgcgtt
gccttgggcataggtctgaagtccgagggcttaattagcgagcaagcattccagaggataaagtcgtac
cgcgttcctcgtgaactgaagattgacccagaattgccggcccaattgacgacgcaacagcgtgagcga
aaggctaagttactggaaaaggggttatctgacagctacgtcgcactgtgcctagacgctcagagccgt
ggcatcatcactcaaggtcgattggctgaagccttgcttagtgacttgggaggccttcaagagctgctc
agcctttatggaagatcgcgcaatggccattga
```

The protein encoded by this nucleic acid molecule has an amino acid sequence according to SEQ ID NO: 68 as follows:

```
MNLTALGSKLSRYRKQLAMSEEEVCAVTHIPLERLQSVEAGSQAPTGDEVLILADLYHCNFKFFISNEP
LAPFEQTEILYRRHGAEFIKEDRRAVQEFLYLCETEDFLMSELKAMKLEFPLPQASGNFKNDGIRAAEA
FRLFNQHPTNAVPRDVYQEIRQTGVHVFRRKLGNSNISGLFLAHPTAGKCILVNYSEDVYRQRFSAAHE
FAHALFDAQGGPSITYSRTTKADLVEVRANTFASRYLMPSEILRQLPNPEQWTQENTQYWAHELRVSCV
ALGIGLKSEGLISEQAFQRIKSYRVPRELKIDPELPAQLTTQQRERKAKLLEKGLSDSYVALCLDAQSR
GIITQGRLAEALLSDLGGLQELLSLYGRSRNGH
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-fifth nucleic acid molecule encodes ORF36 and has a nucleotide sequence according to SEQ ID NO: 69 as follows:

```
atgaatatcaacccttggcttcttcattacagaatcaacagcgcactctcttaggcccgcccccctc
aattcatctgctgctctgccgatcaagatccctgtggcgcatgataaagcgcgtgaccctaacgctgaa
ttctataccaccgaggaaacgccctggttgccggctacaaaaagtcggaggcaggacgcgctatttta
gagaaaatgtctgagaaggaagcaaaagatatccgaggcgagtatctgggaaactacatgaaagccttt
gacgaaaccatatgtcgtatgtacgacaattttcacgatttcaaacagcagcttttttaccttaatacg
gagctgtcaaaaaagcatttcggcttcacgctgggctttaatcaggacattcaggtgaccgacccggac
gaggtactcaccccggcagagttcacgtacctgaccgagaagctgaacgaacgccaacaactgaaagag
```

```
gatctgcgtgcgcacgcaaaaattgtgatgacgctgctcgaccattacaccgaaaaattcgataaccgg cacaccctcaatctggagagttacagcaaggtcatcgactacggacagatcttcagccgcaatcatatt ggcaatttcatggacacgattatctaccagatcgagcgcaatgcgccgaagcgtgaggaagaaccaaaa cctctggttgatgtgcacgcttga
```

The protein encoded by this nucleic acid molecule has an amino acid sequence according to SEQ ID NO: 70 as follows:

```
MNINPLASSLQNQQRTLLGPPPLNSSAALPIKIPVAHDKARDPNAEFYTT

EETPWFAGYKKSEAGRAILEKMSEKEAKDIRGEYLGNYMKAFDETICRMY

DNFHDFKQQLFYLNTELSKKHFGFTLGFNQDIQVTDPDEVLTPAEFTYLT

EKLNERQQLKEDLRAHAKIVMTLLDHYTEKFDNRHTLNLESYSKVIDYGQ

IFSRNHIGNFMDTIIYQIERNAPKREEEPKPLVDVHA
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-sixth nucleic acid molecule encodes ORF37 and has a nucleotide sequence according to SEQ ID NO: 71 as follows:

```
atgggcctgatcggcgtcaaacagaacaaaccgcaacaggcgcagacctacctgacgcgcctgcaagcg ctgtcgccagcgccctggcaggcggtgcagctggagcaggacattgccctcggccagccgcaaaatcag gcgctgctggatgatgcccgacgcctggccgacgccggtgagcgtgacaaggcgaccggggtgtttcgc cagttgttcaacggccgtttgcctcaaggcactgtcggccgcgagtactacaccaacctgggcttcaac aatgcggactgccccgaggcgcgcaagggttttgaacgcctgatgcggcagaaccctgacgactcgatt ctggcgctgttctttgccaagcacctggcccgccgcgaagacagccgcgccgaaggcatcgccgctctg gcgcgcctgagcactcatccggacatcgccggcgatgccgatcagagctggcgcatggcgctggtctgg atcggcccgctgcggctgcgcaagtgccactgttcgacgcgtttctcaaggttcatcccgacgatcag gaaatccgcgaccagttgaacaagggtcgccagcagcatgccagcggcgctgcctcaggctggcagcaa gacccgctggtggcgcgcggcttgaaggcgctggaaaaaaatgatcatgtggcggccgaagaagcctt gccgccgcctgaaaatcaaggcggacgatgccaacgtgcttggcggcctgggcgtggtgcgtcagcag cagaaccggttgcctgaagccaacaattgctgacccgcgccacgcgccagcagggcggtgcgcgctgg aaaaacgcgctggaaaacgtacagctctggacctcgctgcaagaggcccgtgacctgcaggccaaggg cagaccggcaaggctcaagcgttgctggctcaggcgcagcggcaaaaccctgacaatatcgacgtgcgt ttgaccctggccgacgtgcaggtgcaggccgggcaactggacgccgcgcaagcgggctatcgtcaggta ctggcgacccagcgcggtaatccgcaggcaatccgcgggctgatcaacgtgctggcccagcgtggtcag gctgatgaagcgttgcgcctgctcgacacattgtcgccaggcgaacaggccaaactgggcgacagcggt cgcttcaaggcgctgcgctccacccaggtggcgcggctggccgagcagcgtggcgatgttcgcgctgcc caggtggccttgaaagacgcggtgaagaacgacccggacaatgtctggacgcgttttgatctggcgcgc ctgtacctcaagaccgacgaagcgcccaaggcccgcgcgctgatcgacgagctgctcaaggctcagccc aacaatatcgatgcgctctacaccagcgcgctgctgtcagtggaaatgggccagtggcaggacgcgcag accacgtttacgcgcatcccggttgatcagcgcacgccggacatgaaagcgcttgctgacgaagtcacc atgaccgtgcagatcaatctggccatcggcatcgcccggcgcggtcagcgccaggaagcgttggcgctg ctcgatcgcttgcaaccggtcgccagcggcagcccggagcgtcaactcacgctggccagcgcttacatc gatgcgggcgagcccgcgcgcggtcgggaaatggcccgtgcggccatcgctcaggcccctttgccgtcg gccgacctgatgctgcaatacgccggtctgctgctcgcagcgggcgatgacgtgcaggtcaatgcgatc
```

-continued

```
ctgcgcaacgtgcagggtcagccgatgagcgtgcagacccgcaaacgttttgatgaccttttgtaccgc
taccgcattcgtcaggccgatctgctgcgtgaaggcggtgatctggcgggcgcgtacgacacgctggca
cctgctttggcgcagcgcccggacgacattcaggcggtgtcggccttcgcccgcatgtacaccgccaat
ggcgacagcgcccgagcgttcgagctgtacaagcctttgttgcagcgccagcccaatgacccgcaagtg
ttgctgggcgcagccgatgcggcggtcaaagcgcatgattatggctttgccgaaaaagccctgagccag
ttccgcaaactggagcgtaacgacccgcagaccctgacggaggccgcacgtatctaccaaagcatgggg
cagaccggcgcggccaccgagttgctgcgcaaggccgtggccatcgaacagagtgaaaaacagcgcgcg
atggctgtgcaggctgtgtcgaccagcaccacgtcgtccaacccgtttgcgacgggcggctcacgtagc
ctggcggcggcttcggctattccggctccggctcaggtgtcgctcagcggtgggagagcgcttgaaaca
aacagtgcgcctgaaatatctgccccgcgtgacaccgcttatcccggccagatcgccgcaccacaaccg
ctgtctgccgcacgtacgcaaagtgtgcgcggcaatccgttcatggcagccaccgaccgcgatcaggcc
agcagcgcacagcaggcgctcaatcgcattcttgagcagcgcagtggcttcgtcagtcagggcctggcc
gtgcgcagcaataacagcgagtcgggtctgagcaaactgaccgtggtcgagacccgctagaggtcaat
ttgcctgccggtgataaccgggtggccgtgcgcgtcacgccggtgtcgctgaatgctggcagcttgaag
tcagatgcaggtgcccgttttggcggtggcaccagcggtgctgccggttcgcagagcgacaagggtgtc
ggtctggcggtggcgttcgagcgccccgaagaaggcctcaaggccgatatcggcaccacgccgatgggt
ttcaaatacaccacggttgccggcggcgcgagtgtcgaccggccgttggctaacaacccggacctgcgc
tacggcctcaacgtgtcacggcgtccggtgacggacagcgtgacttcgtttaccggttccacagacgag
cgcagcggcctgtcctggggcggcgtcacggccaacggcgggcgcggtcagctcagctatgacgaccag
accatcggcggttatggctacggctcgtggcacaaactggttggcaacaacgtgaaatccaacacccga
ggcgaagtgggtggcggcgtttactggtacctgcgcaatgccgaggacagcaaactgaccgcaggcctg
agcctgatgggcatgagctatgacaatgaccagagctacttcacgtacggccacggtggctatttcagc
agcctgatgggcatgagctatgacaatgaccagagctacttcacgtacggccacggtggctatttcagc
ccgcagagcttctatgccatcggcgtgccggtgatgtgggcacagcgcaccgagcgtttcagctatcag
gtcaagagctcggtcggggtccagcacttcaagcaggacggcgccgaattcttccccgacgacagcacg
ctacaggccgcttccgcccagcgctacacagggcaaagcaaaaccggaattggctacaacctgagcgcg
gcaggcgagtacaagctcgattccagcctgttcatggggccagtctgggcctggacaatgcccgggac
tatcgccagttcagcggcgcgctttacctgcgttacatgttcgaggacataaccggcccgatggcactg
ccggtcagcccttaccgttcaccttattccaactga
```

The protein encoded by this nucleic acid molecule has an amino acid sequence according to SEQ ID NO: 72 as follows:

```
MGLIGVKQNKPQQAQTYLTRLQALSPAPWQAVQLEQDIALGQPQNQALLDDARRLADAGERDKATGVFR

QLFNGRLPQGTVGREYYTNLGFNNADWPEARKGFERLMRQNPDDSILALFFAKHLARREDSRAEGIAAL

ARLSTHPDIAGDADQSWRMALVWIGPPAAAQVPLPDAFLKVHPDDQEIRDQLNKGRQQHASGAASGWQQ

DPLVARGLKALEKNDHVAAEEAFAARLKIKADDANVLGGLGVVRQQQNRLPEAWQLLTRATRQQGGARW

KNALENVQLWTSLQEARDLQAKGQTGKAQALLAQAQRQNPDNIDVRLTLADVQVQAGQLDAAQAGYRQV

LATQRGNPQAIRGLINVLAQRGQADEALRLLDTLSPGEQAKLGDSGRFKALRSTQVARLAEQRGDVRAA

QVALKDAVKNDPDNVWTRFDLARLYLKTDEAPKARALIDELLKAQPNNIDALYTSALLSVEMGQWQDAQ
```

-continued

```
TTFTRIPVDQRTPDMKALADEVTMTVQINLAIGIARRGQRQEALALLDRLQPVASGSPERQLTLASAYI

DAGEPARGREMARAAIAQAPLPSADLMLQYAGLLLAAGDDVQVNAILRNVQGQPMSVQTRKRFDDLLYR

YRIRQADLLREGGDLAGAYDTLAPALAQRPDDIQAVSAFARMYTANGDSARAFELYKPLLQRQPNDPQV

LLGAADAAVKAHDYGFAEKALSQFRKLERNDPQTLTEAARIYQSMGQTGAATELLRKAVAIEQSEKQRA

MAVQAVSTSTTSSNPFATGGSRSLAAASAIPAPAQVSLSGGRALETNSAPEISAPRDTAYPGQIAAPQP

LSAARTQSVRGNPFMAATDRDQASSAQQALNRILEQRSGFVSQGLAVRSNNSESGLSKLTVVETPLEVN

LPAGDNRVAVRVTPVSLNAGSLKSDAGARFGGGTSGAAGSQSDKGVGLAVAFERPEEGLKADIGTTPMG

FKYTTVAGGASVDRPLGNNPDLRYGLNVSRRPVTDSVTSFAGSTDERSGLSWGGVTANGGRGQLSYDDQ

TIGGYGYGSWHKLVGNNVKSNTRGEVGGGVYWYLRNAEDSKLTAGLSLMGMSYDNDQSYFTYGHGGYFS

PQSFYAIGVPVMWAQRTERFSYQVKSSVGVQHFKQDGAEFFPDDSTLQAASAQRYTGQSKTGIGYNLSA

AGEYKLDSSLFMGASLGLDNARDYRQFSGALYLRYMFEDITGPLALPVSPYRSPYSN
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (e=0), as detected by BLAST search, to cellulose synthase from *Pseudomonas fluorescens* (Spiers et al., *Genetics* 161:33–46 (2002); GenBank Accession P58937, each of which is hereby incorporated by reference in its entirety).

A thirty-seventh nucleic acid molecule encodes ORF38 and has a nucleotide sequence according to SEQ ID NO: 73 as follows:

```
atgaaactgatacgacagatccgctcgcagggtcgtcagtcgcccttgttcgaggaccttgcccagctc gaggggcgcaagcgtcaatggctggccgagcgcgccgtgcagttcgcactgggcttgcacggccgccgg ccagaggtcgataacccttcaaaggcaaactgcgtgaagacctgtgctgcatcatgttcgatgacctg tcgctgcacaccctggtcgagcgttacgcggccagtgaagccctgcgacgacacgacagcgagtacttc agcaaactgatcgccacgacacgaaataccgtggaacggcgcatcgtctttcacgggctgctggaacac ttcgacaggctgttgcctatcgaaaagagcatctaccaactcaactaccgcagcgttcaatacgcgcac ctggagcaggaagaagccctgtacggcaaactgataatggaacaacccattagtgcactgctggaagtg cacacgcctgagtggcttcttgagaatctgtcttcgtttgagttttcgattgattga
```

The protein encoded by this nucleic acid molecule has an amino acid sequence according to SEQ ID NO: 74 as follows:

```
MKLIRQIRSQGRQSPLFEDLAQLEGRKRQWLAERAVQFALGLHGRRPEVD

NPFKGKLREDLCCIMFDDLSLHTLVERYAASEALRRHDSEYFSKLIATTR

NTVERRIVFHGLLEHFDRLLPIEKSIYQLNYRSVQYAHLEQEEALYGKLI

MEQPISALLEVHTPEWLLENLSSFEFSID
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-eighth nucleic acid molecule encodes ORF39 and has a nucleotide sequence according to SEQ ID NO: 75 as follows:

```
atgcgactgactactaaaggccgatacgctgtgacagccatgcttgacctggcgttacatgcgcagaac gggccagtgtctctggccgacatctccgagcggcagggcatttccctgtcttatctcgaacagttgttc
```

-continued

```
gccaaactgcgtcgcggcaatctggtttccagtgttcgtggtccgggcggcggttatcagctgtctcgt gacatgaaaggcatccaggtcgcccaagtcgtcgacgcggtcaatgaatcggtcgatgccacgcgttgt caggggctgggtgattgccacgctggcgatacctgcctgacccaccacttgtggtgcgatctgagccag cagattcacgaatttctaagcggtatcagcttggcggatcttgtcactcgccgtgaggtacaagaagtc gctcagcgccaggatatgcgccgtggtcataaccacacgtcgcaactgggtaagatcgaaacgtccgcc gtcgaatga
```

The protein encoded by this nucleic acid molecule has an amino acid sequence according to SEQ ID NO: 76 as follows:

MRLTTKGRYAVTAMLDLALHAQNGPVSLADISERQGISLSYLEQLFAKLR

RGNLVSSVRGPGGGYQLSRDMKGIQVAQVVDAVNESVDATRCQGLGDCHA

GDTCLTHHLWCDLSQQIHEFLSGISLADLVTRREVQEVAQRQDMRRGHNH

TSQLGKIETSAVE

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-ninth nucleic acid molecule encodes ORF40 and has a nucleotide sequence according to SEQ ID NO: 77 as follows:

```
atgaataccgtcagaaaacccataacaccacggatgctcagcatgaccgataaaaacggcacccatcga caacgacgtgctgcactgttccccaaaacccggcgaccgccaccagcctgtgccctttcagagggcct aatatcgccatcgtcccggtgcgctatgcgctggatcgctcgcgctatgacgctgaccccgcgcaactg aagccactgcccaaagacggccaatgggcccacctgccgacgctgaaaactcgcagttacaccttacgc caactgtacgacggctacgtttacgtgttcgacgaaacggccggcacgttgcacgaatacgcagcctca gccagcgacggccatctgagccgcatcgtctggaccgatgcacacatcggtaacgaccagcgaagcggt gccggtgaagggcaaccctttgtgctttacccgcgtgaccaccgcctgcacatcgccttttctcccctg caatggacatggcgaatgtgcgagcacatgcgctcccacgccccaagccgcgcgttgtggatgaaggcg ctggacctggccagctactgcctcaccatggccgaaccggacaccctgccgctggatcgaatcgccgag gccgtggcggatatcgacaaagactgtgttgtggaagatggccgttttgcagattcggcgattcccagt gttcgcccgccatcagaaggtgcagaaccctatccgttatgggcaccgctgggcgccgatgtcttctgg cagggcagcgtctacgatcaggacagctctctggtcattgccctcaatgacccgctcgccgttttcaac gacttgggcatgcagctggcgccgatcaggcggcttttcgggaatggcaaagcgcccacgaacacaag atccagattgcccagaccgtcgccacgctgtgcggtcagagagcgaagcagagaagctgccagcatcg gtgcgcggtgatgcgctgcgcacgcatcagtacctgagcgaggtcgaagcctactttgaacaatgcatt cttgaagaagcacagatcagcagtagcaacgttcctggagattttctgctgctgccggacatgttcaag agcctggacatgcgcaaatcgatcgaaacacgttatggcagcgcgccgaccgatgagggcgcgcaggcc tggaaagatcgccacaaatggcggcgcgaggtcgatctgagcagtgcgcgtcagtaccttttgcagcac ctgccgaccggagacaaacgcctgcaacaggtgcgtgacacgcaaagcgatttccagcactgggcggca catataggcaccgaaccgctcaagctgttcatcgacaccacacacccgaaaaccctgctgtatttgcag acgatcatgctcaatctgcagatcatctatgcgcattacagcgccgcaaatgcctggctcgccgagcag gaagccaacaccagcagcctgtttggcaccctgcgttatggttttcgccagcgctcaagcacgccctg catcaggaagccgacgcactgctgaacggcctcggcgacgtcactaatctggccacgcgcatcggtgaa ctcaatggcgtgctcaaccatcagggttttgccgacaagccgtggatgaaggcgctgaaacagcctgtt caagacaccttcaaagccctcggcgaactggccagcggtgccggcaaagccaggtttgaaagtgtatta
```

-continued

```
ctggcatgggtgcccatcgacagccgcatggcccttggcaagcagcagaacatcgttgcgttgcttcgc accctgctgatcggccagatattgctcgactcgacagcacgcgtcgcgatcaatgagcagacagtgacc aagctcaaacagtgggtaagtgagtggcaagtcctcaacaagcaaatcagcgagctggtgcgcagttgg caatacccgaacgcctacaacacgcgccaaagcaccgctcgcaaattgcaggcccataaacacaaactg cgcgttcacgaactgagcatccctgccctgctcgactttcagaacaacgaatacgccaagctattgcag gacgagattcgtcagtacttccagtctggcaaaaccctcgccacggactggctcgcccgcgccaaaggc tggaccgaccgactgggcggcgttgctggcacgatcacctggggcgtggtcatgcttaacctgatcaat accgccttcctctatcgggaccttacccgggacggggatttcagtaccaaggacattggcaaggtgacg tatggattggggtacagcttcaatctgttgatggcggtgtttgtggacgcgccgtggagcatcataagg gacgcaacgccagcgctgatcgatggcaagaatgtggccattctggacaggtccagtgcgtactggaaa gccaagggaaatgcagcgtggggtgatgcgatacgtgggttcagggtttcgatggtggcgatgggtggg tttgggcttgcggcggttacgcttgaattatttgatgttacagatgattttcacgcagctaaaacatca gaagaaacatatggaattggcatcaaggggttttccgtagtggtgatgggattgggtgctgcggcccag ctaatggcaggcatttctcccgctggcgtttttacgattatcgcaatgagtccgtggttcagcgtagcg ctactggcagcaggcttgatttatcttttttgctacgatggcccttaattacttcaagcaagacagtgtc ggctggtggctacgcaagtgctgttggtccataacccaagactatcgctatgctgagactgcggaaggt aagcatgacgaagtgcgcgcgctgatggaaataaaattatctccgcaggtccatgtaaaaagcaccgtg aattatgaaaccgttatcttggcaaaaacgatcactacagcgtagcggtacaaaatggcgcgggggta caagtgcgcttgccgaatcttctacgcgggctgtccgtgcatttcaatatcgttagtagcaagagacca tggggcgtgctgcccgtagaaaaaatagatcagccgatacatgaagcttttctggaccacgggcaattc aggaaagtcgaacagttcgggatgtttaccaacaagcctgctggcaaggcgagtgaagactataccta ccccgcatgccacctgaaaacgaagacctcatctgggaaacctgggtgccgctcgacaaggacgcaacg tatcttgagttgcaaatctggtacccggccaatcttttaaatcctggcggagacgatagaagctatctg tttcagatggagcttggcacaaaaggcgataccgctattgacggcctggctgcagtggaactcgaggta aaggcatcaagcaggattggcgctctgaccctagaagtcgcagagggcacacctgtatga
```

The protein encoded by this nucleic acid molecule has an amino acid sequence according to SEQ ID NO: 78 as follows:

```
MNTVRKPITPRMLSMTDKNGTHRQRRAALFPKTPATATSLCPFRGPNIAIVPVRYALDRSRYDADPAQL

KPLPKDGQWAHLPTLKTRSYTLRQLYDGYVYVFDETAGTLHEYAASASDGHLSRIVWTDAHIGNDQRSG

AGEGQPFVLYPRDHRLHIAFSPLQWTWRMCEHMRSHAPSRALWNKALDLASYCLTMAEPDTLPLDRIAE

AVADIDKDCVVEDGRFADSAIPSVRPPSEGAEPYPLWAPLGADVFWQGSVYDQDSSLVIALNDPLAVFN

DLGMQLAADQAAFREWQSAHEHKIQIAQTVATLCGAESEAEKLPASVRGDALRTHQYLSEVEAYFEQCI

LEEAQISSSNVPGDFLLLPDMFKSLDMRKSIETRYGSAPTDEGAQAWKDRHKWRREVDLSSARQYLLQH

LPTGDKRLQQVRDTQSDFQHWAAHIGTEPLKLFIDTTHPKTLLYLQTIMLNLQIIYAQDSAANAWLAEQ

EANTSSLFGTLRYGFSPALKHALHQEADALLNGLGDVTNLATRIGELNGVLNHQGFADKPWMKALKQPV

QDTFKALGELASGAGKARFESVLLAWVPIDSRMALGKQQNIVALLRTLLIGQILLDSTARVAINEQTVT

KLKQWVSEWQVLNKQISELVRSWQYPNAYNTRQSTARKLQAHKHKLRVHELSIPALLDFQNNEYAKLLC

DEIRQYFQSGKTLATDWLARAKGWTDRLGGVAGTITWGVVMLNLINTAFLYRDLTRDGDFSTKDIGKVT
```

```
YGLGYSFNLLMAVFVDAPWSIIRDATPALIDGKNVAILDRSSAYWKAKGNAAWGDAIRGFRVSMVAMGG

FGLAAVTLELFDVTDDFHAAKTSEETYGIGIKGFSVVVMGLGAAAQLMAGISPAGVFTIIAMSPWFSVA

LLAAGLIYLFATMALNYFKQDSVGWWLRKCCWSITQDYRYAETAEGKHDEVRALMEIKLSPQVHVKSTV

NYENRYLGKNDHYSVAVQNGAGVQVRLPNLLRGLSVHFNIVSSKRPWGVLPVEKIDQPIHEAFLDHGQF

RKVEQFGMFTNKPAGKASEDYTYPRMPPENEDLIWETWVPLDKDATYLELQIWYPANLLNPGGDDRSYI

FQMELGTKGDTAIDGLAAVELEVKASSRIGALTLEVAEGTPV
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fortieth nucleic acid molecule encodes ORF41 and has a nucleotide sequence according to SEQ ID NO: 79 as follows:

```
atgtgcctggtggcgagcctgtcggtgctggcaggcatgaccgatgccatcggcttcatggccaccggc gatttcgtctcgttcatgagcggcaacaccacgcgccttgcggtggcgatcagtgatggcgatttgagc gtcacactccgtctggccctggccatcttttgcgtttattgccggcaatgcactgggcgttgtcgttgcg cgcctgggcaaccggcgcgccctgcccttactgctggctatcgccacgctgttgtgtgccgctgcggct tggccgttggcgaacaatatgcttgccctgatctgggcgattctggcgatgggcatgctcaacgccgct gtcgagcaggtcaacgggctgccggtgggcctgacctacgtgaccggcgcgctgtcgcgactggggcgc ggtctgggccgctggatgctcggcgaacgccggatggctggcgcattcaactggtcccgtgggccggg atgttcattggcgcagtgatcggcgcgttgcttgaacatcgtctggggctcaatgccttgctggtcagc gccagcctgtcagcgttaatggcgctggtgtcgctgaaaatcccgcatcgctggcaacgtcagtacatg ccgcgctga
```

The protein encoded by this nucleic acid molecule has an amino acid sequence according to SEQ ID NO: 80 as follows:

```
MCLVASLSVLAGMTDAIGFMATGDFVSFMSGNTTRLAVAISDGDLSVTLR

LALAIFAFIAGNALGVVVARLGNRRALPLLLAIATLLCAAAAWPLANNML

ALIWAILAMGMLNAAVEQVNGLPVGLTYVTGALSRLGRGLGRWMLGERRD

GWRIQLVPWAGMFIGAVIGALLEHRLGLNALLVSASLSALMALVSLKIPH

RWQRQYM
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-first nucleic acid molecule encodes ORF42 and has a nucleotide sequence according to SEQ ID NO: 81 as follows:

```
atgagagggcttggtgttctgagcatgaaccaccagtttcagggcaatacctgttcaaagaaataagc ggtaccagcttttccgcgccctacatcacccatcttgcgggccgtctccttaacgagcacccagaggca tcggcgaacctcttgcgcgctatgctggtgaatcatgcgtcattgtctagcgaggtcgagacgactttc tccgacgacatgaggaagggctacaaagctaataaggcgacccacaaccgtgaaatatcgcgcgatgtg agtggttacggccaagtgaatgaggcagacctgtttcggtcttccgaccattgcgttgtgctgatgtgt gaagagtccattgagaaggactcgtgccagttctacgaactgcctttgcccacttcgtttcttcgcagg gctagaggggcaaggcacctgagcgtcacgctggcttattctcctgccgtcaggacaactcggttggac tatctggcaactcagatcagttatcgcctagtgaaaggttcgtcgcttgaggaagtccaggcctcgttt
```

-continued

```
aactacgacaagcaggacgaaacgaagacccgtggagatgacgctgagcagaatcgagacatcactgct cagttgagaagccgcgggaccgtccagtcctcgcggtggacgttcaagaagcgaaatccagaagaaaaa tggtttgtagttgtgatccgccaggatcgggaatggaatcatcccgacgtgctggatcgagaatcttac gccctggtggtaacagttgctgatcgtgacaacgaacacgcgcagttgtatgccgaaattcaagccaag ctgacgcttcaaaatcaggtgcgtgaagaggcaaggcagcgggctgttctgtaa
```

The protein encoded by this nucleic acid molecule has an amino acid sequence according to SEQ ID NO: 82 as follows:

```
MRGLGVLSMNHQFQGNTLFKEISGTSFSAPYITHLAGRLLNEHPEASANLLRAMLVNHASLSSEVETTF

SDDMRKGYKANKATHNREISRDVSGYGQVNEADLFRSSDHCVVLMCEESIEKDSCQFYELPLPTSFLRR

ARGARHLSVTLAYSPAVRTTRLDYLATQISYRLVKGSSLEEVQASFNYDKQDETKTRGDDAEQNRDITA

QLRSRGTVQSSRWTFKKRNPEEKWFVVVIRQDREWNHPDVLDRESYALVVTVADRDNEHAQLYAEIQAK

LTLQNQVREEARQRAVL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-second nucleic acid molecule encodes ORF43 and has a nucleotide sequence according to SEQ ID NO: 83 as follows:

```
atgggcattggcggtttgcttaaacctttggtcgattttttaccgaagttgccgaccttacgcaccaag atttcctcgccttccatcagctacgcgcgtttgcaaagcgatgcgtcccaggtacgcagtaaattggga ttgggtgagcgcagcgtgctggggttatgaagcgctgatcgccgagttcaaggcgtgcggggcggttctg gtgcccgttctttggggacaaaagcagcaacacaagaatgcgttgcacattctattgccggcgtcagat gtcacctttgtcttcgtcaacctggataccaagctggaagacttcaagttttggatggcccacgagtta gcgcatgtctacactcctgagcttgcgggtagtgacgaggggaggattttgcggatgcctttgccggt gccctgctgtttcctgaggcttgcgtgcagctagcgtatgccgaggcggcgcaagcgcctagcgcagct ggggaggtgagtgtccttcagcagcatgcccggcatcaccaaatttcactgaacacggtgttccagcag gcgcagggatatgcggcggaaaacaatctgccatccttacgggtaccggaaaggacaattcacgcggtg cgcaacatctccacgccgcagttggtcagtacgatcctgtttgatccgactccacccaaaccggcgcaa tacattgccgcagcgtcgaatgtgtttcagtctgagttcttcctggcgctgaaacgcatgattcgcgag cacgggacgggcccgtcgtatgttcagcaaatcatggatgtatcactcagtgatgcctccgcgctttac ggcgagctcgcgcgttga
```

The protein encoded by this nucleic acid molecule has an amino acid sequence according to SEQ ID NO: 84 as follows:

```
MGIGGLLKPLVDFLPKLPTLRTKISSPSISYARLQSDASQVRSKLGLGERSVLGYEALIAEFKACGAVL

VPVLWGQKQQHKNALHILLPASDVTFVFVNLDTKLEDFKFWMAHELAHVYTPELAGSDEGEDFADAFAG
```

```
                                                 -continued
ALLFPEACVQLAYAEAAQAPSAAGEVSVLQQHARHHQISLNTVFQQAQGYAAENNLPSLRVPERTIHAV

RNSSTPQLVSTILFDPTPPKPAQYIAAASNVFQSEFFLALKRMIREHGTPSYVQQIMDVSLSDASALY

GELAR
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-third nucleic acid molecule encodes ORF44 and has a nucleotide sequence according to SEQ ID NO: 85 as follows:

```
atgaagcagctcgcggcaggcagcaatgtgcatgttcttgaaaatgagtctttccagatagataaggtg cgcttttgggggccacagcttggacagatttcgcaacaggtgaaagcgtgtaccaagcgtcccaggag gcaaggcgaggcatgaatgactttcgcttgatccgtgcaggcgagggttaccgcgcattgagcatcagt gatgtgatcagtcgaaatcatcgaacttacgagtggctcaaggaagagctcgccatggagttcgatggt cagaccattgtcatcactcatcattgcccgttggtcaattactgtggcccagagcagggctcaccgcta atgcctgcttattcaaatgattggccagaactcgttcgtcaggctgatgtgtgggtctttgggcacacg cacagtcatgtcgatgtcatggtggaaggatgccgactcattagtaaccctagaggttatccaggtgag agttgcggctttgccaatgactttgtggtcgatattaactag
```

The protein encoded by this nucleic acid molecule has an amino acid sequence according to SEQ ID NO: 86 as follows:

```
MKQLAAGSNVHVLENESFQIDKVRFLGATAWTDFATGESVYQASQEARRG

MNDFRLIRAGEGYRALSISDVISRNHRTYEQLKEELAMEFDGQTIVITHH
```

```
                                                 -continued
CPLVNYCGPEQGSPLMPAYSNDWPELVRQADVWVFGHTHSHVDVMVEGCR

LISNPRGYPGESCGFANDFVVDIN.
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-fourth nucleic acid molecule encodes ORF45 and has a nucleotide sequence according to SEQ ID NO: 87 as follows:

```
atgacgctgacgcagcgtcaggcatggcatcgcgaggcacagcggtttggcgagcaggtggtgaacatg cgcaaagccagcaaggcgcacttcggccaggcggaaaatgacagccgcacctatccggcgcgctttatc gaccagcaactggctcaactgctgaaccggctatccatcgctgcaacgcgcaacagatcaatatttca ctgacctacaggacgggcaccgaagtgctcgaaattcccggcgcgcctgtattgccagaaaccgagacc gagaacgtttcactcaggcaactggtgcatacccaggccctgcgcaccaaggccaaggatgccgtgctt ctacgcgctgtcgacgccgaaggcgtcccccttgcgcacttggacaagcaggccgtaaccgagctgatt gccacgctggaagatcaccgatacctcagtgattaccttgacctgcacctgaaaacctcggcgtatgca cagcagctcaagcggtcagaaaaagccatgttgcaagctcagatgaagatggcgctgctggagatcgag caacaggcttttgcaccagccggtcgcgagtggatcaaggctgtgctggattcgccagcccccaagga cgtcgaaccatggcaggggaaagcattgaagtccgttttttcagcgtcaaccaattcaagatgaccaat gtcatgctgattgctccagccggtaaattcgagaaggggccgctggtgctttgcacgctggatgcttcc gacggtgtggttttccgctggtttaacagcatgtatcacctgaccaccagctttctggaagaggcaccc ttccagcagtatctgattcagcaaataccggtttccaggcgtcttgagacgctgcatgccatgcagtac
```

-continued

```
gaaaaggaagccaagcattggcgtccgccagaagtattcacccaactgacgctgctaccgatcccgtca
aggctgctgcgcccagtcgtgtttgtcagccagagcaaagacatttacgaggaaaatcacgagaccaag
atcaaccatctgatcaacgaagccaaacggcagatgagcctgtccaccggtacagggcaatcgggtcgg
ggcttcgatctgatcgcgagcattgcgattctgtttctgcctggcgcgatcatgatgcctgtctcgctg
ggcgctggcctttacaaaacctggagcgcttttcgaaaatcgatgaaaacgacctggaaggtgccgcc
gaggagtttctgagcgccctcagctatcttgccattaccttggtcggccatttggcgctggccttgaaa
ccggcaggaagcgccgcaaaaacggtgagacgtccgcacctggtacgcagagtcggtcgtgatgggcag
gcacagatcggctacctcctgtcgcattcaaaagcgccgcgtttcccagactcgaaattgatcgctgca
atggaccccaaacgcttcgtcgccattgaggtagaaggccagacctgcttaataagccggcgggccaac
ctgttcggccactcacgcctttatcgggtaaacccgatggatgcaacgcaactggtgcacgagcaggag
tttgccttgcgcagcaccaacggcacctggaaaatcgtgggcaaacagatcctgcgcatgagtcagtcc
gcaatccgcaatgcccaggctcaactgaccagcctgacaaatctctggccggcgtctctggaggaagca
agtagcgccgaacgcttgagcttcgagaccgactacctggcgctggcccagacatccaacgcagaaaac
tattccgaaatagtcgcctacgtggaaagcggttcaacagacatcaacccgctgctgcgaagcggcgtg
cgcaacgccaccacgcgcagatttttacgtcagttccataaactcaatgcgtgggaaggcactgcctt
cgcgccacctatgtgtccagcgacggggtggcatgccttgagcgcgaagtgggttcggtgttcaccgac
aacggcgtgcagtctgcatcggtgtcgcgagccaatgcctccagatggagccaggacgggttcgtgagc
agcaacgccaatgccgcaaccacccggtgttcttcatctttgcaccgggagtgcccaagaagaacatg
ttcaccggctttcttggcgatcacgtggcaatcccgccaggcacgtgcgtgcaactgggtgcgaccaag
cggataaacggacagctgtttgcctggttcgatgcgcccgaacaaatggtcgatcagacctacgatctc
tatacaggagaacaggaactctgggtctga
```

The protein encoded by this nucleic acid molecule has an amino acid sequence according to SEQ ID NO: 88 as follows:

MTLTQRQAWHREAQRFGEQVVNMRKASKEHFGQAENDSRTYPARFIDQQLAQLLNRLSIAATAQQINIS

LTYRTGTEVLEIPGAPVLPETETENVSLRQLVHTQALRTKAKDAVLLRAVDAEGVPLAHLDKQAVTELI

ATLEDHRYLSDYLDLHLKTSAYAQQLKRSEKAMLQAQMKMALLEIEQQAFAPAGREWIKAVLDSPAPQG

RRTMAGESIEVRFFSVNQFKMTNVMLIAPAGKFEKGPLVLCTLDASDGVVFRWFNSMYHLTTSFLEEAP

FQQYLIQQIPVSRRLETLHAMQYEKEAKHWRPPEVFTQLTLLPIPSRLLRPVVFVSQSKDIYEENHETK

INHLINEAKRQMSLSTGTGQSGRGFDLIASIAILFLPGAIMMPVSLGAGLYKTWSAFSKIDENDLEGAA

EEFLSALSYLAITLVGHLALALKPAGSAAKTVRRPHLVRRVGRDGQAQIGYLLSHSKAPRFPDSKLIAA

MDPKRFVAIEVEGQTCLISRRANLFGHSRLYRVNPMDATQLVHEQEFALRSTNGTWKIVGKQILRMSQS

AIRNAQAQLTSLTNLWPASLEEASSAERLSFETDYLALAQTSNAENYSEIVAYVESGSTDINPLLRSGV

RNATTRRFLRQFHKLNAWEGTAFRATYVSSDGVACLEREVGSVFTDNGVQSASVSRANASRWSQDGFVS

SNANAANHPVFFIFAPGVPKKNMFTGFLGDHVAIPPGTCVQLGATKRINGQLFAWFDAPEQMVDQTYDL

YTGEQELWV

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-fifth nucleic acid molecule encodes ORF46 and has a nucleotide sequence according to SEQ ID NO: 89 as follows:

```
atgactcagctaaaccctgcgggacaaccgcccgcagaaccgacccgaatcgtcaaagctcacattgac
ctcatggatcctgccgaaagcgctgactacgaggcgacccgaatggcattgctcgcagcgatgcaaagc
ggcaatgccgcgatcaacctcgaacagattcggctcaagcccgacccagcgtccggttcggcgaatac
tgcgctgagaaagctgcgctacctcacccggtccaggccgaaaaccaggaactcccgtttcagatagac
agcgatggcagcgtcagtctggcattgatgctgcgctataactacgggttgtcgctgccgcaatcgcct
gacgaaacagcgatcaaaaccctgctcaatacgctggcagaacttcgcaccagtcaagaactggggctt
attgatcagttcgacatcaaggccatgctgaccatgcaaaatctgcaggatctgaagcgagcctgcatt
gagtaccttggcaccgacggtggcacgctgctaggcaagctgggtgctgaaataattgcctcctgccca
gagtaccttggcaccgacggtggcacgctgctaggcaagctgggtgctgaaataattgcctcctgccca
ctggcagatgtgcagaactccccggtgacggttattgcccggattctcagatcggaaccggcaagggca
ttggggcaaacgctgctggcacagcttggtcggcctgaagaagaaacggacgcgtccctgacaacactc
gtggaccggatttatggtatgccatcagtagcgatcttcatgatccagaaaaccggaagccaggagaa
attgccggctatccattcacccaggccgaaaaccagggacgccgccacgctgacatcctgaacgatatt
cacaaccacctgatcaccacgggcaaggctgagtctgtcaacgaagcaataattgcctgcttcatactt
gcactcgatgactgcccggaatggctggtcagcagtgttcccgatgatctgccatacggctgtacagag
gtgtgggtcaactttcaacatggggtcacacttgcggaagtcatcgagtttggctcgtcacgctggatg
aactttgaagacctgatcgagctgccggtgattttcaacaaaaagatggacaccgaagagcagcaagtc
gcctatgtcgcaacgcgcatgcccattcttctgacttgggcccaggccaacggttacattcgtacccag
agcgacctgccttactccgaacaagagatagaacaggccgccagcgcgtttgaacactccgagaaacaa
tcccttgaagctgcgaacgccttgatccggaaagcgccagaacgcaaagccatggctatcagtgccatg
aaagaagcgcggaggacgcctgaaatagaaaaaatacttgagcaggaagattactggtttccgcccatc
gatctcggcatcaggctggcggtgctacgcaaaaatcacacgcctgtctatcgcgatcaccaaggcacg
ctctcaccgtcaaatctgccatacgacccctacggcataaaacacaaggcgtcgtcgttgctggagatc
tacatggcaggtgaaaacattgatgactggagactgccggggcgcaacagcaacgagggcctgcttccc
atcaaccgtgaaatgcagttgttgtacaaggcgctgccagacatcaatcaaaggttcgagagtgaattt
caggcttatctggcagatgcccgtaaggcgtatgcgacgattatcagaaagttgctgactcacctgccg
ctcaagcaccgcatggcgatcgaaaatggtgaggtgtcgctacactcactcagattgccgaccaaggac
gtgctggcggcgacagagagcgaaaaacatcgggagccgttgcgagggcgcacgggctttgtcatcaaa
gctgtctacgagggcaaaaccacgttttacgaggtgtttccgttatcgatgattgtacgctatcgccct
gatctggaggcccttctcaagaacggtgtggtcggtatagattttgggacattctgcctcccacccgt
ataccggtagcggtttataacggaatcacaatgccatttgatcagggagcctatttgaacggtcagcta
cctgagcctggggcaagcgctgtgatgattgcagaaaccattggtgaacgatttgattcttcaagtgca
gaggtcgggcaacaccagcctccgacctcgttttcaaaacgctctactggcattgccgagaccatcaca
acatcgcttttctacgtcaacgaagatgcactctttgcacactgcaaaagcctcacgcaggtagaaata
gataacggtgccccaggtgcgctcgaagaggtgtccagctttctgatacacctgacgccctggccggaa
atcgaaaacattctgtccggagagaaagcgcttatgaggggaggagcaatcggtctggcgctttacatg
attccctatgtgggacccgcgggcaagttgctcgcaggcacggcaaaagtcgttaccgcctgggcaaa
```

-continued
```
agcctcataaccagcggtagcaaagtccaggtctcgaaattgctcatcacggccggcaccaccctgaaa gacgccccgctgatcatgatcagacaggcccctgacatgaccagtaaagcaatgactggcgtttcgcaa ttcgtcgtgaaacacgtcacctggaaatttctggcgatacgtataggtattggtttaagccgcaggctt gtagccatcatgagcaggcagcaggcccaggccgcaaagcaagaggccacgtaa
```

The protein encoded by this nucleic acid molecule has an amino acid sequence according to SEQ ID NO: 90 as follows:

```
MTQLNPAGQPPAEPTRIVKAHIDLMDPAESADYEATRMALLAAMQSGNAAINLEQIRLKPDPASGFGEY

CAEKAALPHPVQAENQELPFQIDSDGSVSLALMLRYNYGLSLPQSPDETAIKTLLNTLAELRTSQELGL

IDQFDIKAMLTMQNLQDLKRACIEYLGTDGGTLLGKLGAEIIASCPLADVQNSPVTVIARILRSEPARA

LGQTLLAQLGRPEEETDASLTTLVDRILWYAISSDLHDPENRKPGEIAGYPFTQAENQGRRHADILNDI

HNHLITTGKAESVNEAIIACFILALDDCPEWLVSSVPDDLPYGCTEVWVNFQHGVTLAEVIEFGSSRWM

NFEDLIELPVIFNKKMDTEEQQVAYVATRMPILLTWAQANGYIRTQSDLPYSEQEIEQAASAFEHSEKQ

SLEAANALIRKAPERKAMAISAMKEARRTPEIEKILEQEDYWFPPIDLGIRLAVLRKNHTPVYRDHQGT

LSPSNLPYDPYGIKHKASSLLEIYMAGENIDDWRLPGRNSNEGLLPINREMQLLYKALPDINQRFESEF

QAYLADARKAYATIIRKLLTHLPLKHRMAIENGEVSLHSLRLPTKDVLAATESEKHREPLRGRTGFVIK

AVYEGKTTFYEVFPLSMIVRYRPDLEALLKNGVVGIDFWDILPPTRIPVAVYNGITMPFDQGAYLNGQL

PEPGASAVMIAETIGERFDSSSAEVGQHQPPTSFSKRSTGIAETITTSLFYVNEDALFAHCKSLTQVEI

DNGAPGALEEVSSFLIHLTPWPEIENILSGEKALMRGGAIGLALYMIPYVGPAGKLLAGTAKVVTRLGK

SLITSGSKVQVSKLLITAGTTLKDAPLIMIRQAPDMTSKAMTGVSQFVVKHVTWKFLAIRIGIGLSRRL

VAIMSRQQAQAAKQEAT
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-sixth nucleic acid molecule encodes ORF47 and has a nucleotide sequence according to SEQ ID NO: 91 as follows:

```
atgtctgttacttcatctgtcctgcgactgtcgcgcctgagcgtgtcgttatcacttttgggcatgctg tcgtctgcactgtttgccggcgcggcattcgccagcgacgagacgcaactgatcgaatccctcaacgcc taccgtggccaggcgcagcgctgtggcgagcaggtgtccatggaactgccgccgctgagcaccgacccg cgtctggtgctgcccgccagtggcaacctgaacctgcaacagtcgctgacccgcgcgtcttatcc9atg gtcaccgtgcaggcgatcagtctgtccggaccgcgagatgcggcgtcggcgttgaaggcggtgcaggag agtttctgccgcgtggtgctggacccgcagttcgtcgatatcggggtcagccgggacgggcgcgactgg cgcatcgtgctggcgcgctcgctggtggcatcacgtctgggtgactggcaagcagaaggtcagaaaatt ctggagatgatcaacaccgcccgtacccaggcgcgtcagtgcggttcgcaatccttcgcggccactaca ccgttgagctggaatcaggtattgggacggccgcacaaggacactcgcaggcaatggccaatcagaac ttctttgaccacaaggggcgcgacggccgcacgccgggtgacagggccgagcttgccggctatctgggc cagcagatcggtgagaatattgccgcaggccaggacactgcccgcaaggtggtggacggctggctggtc agcccgggccactgcgcaaacctgatgaccccccggttttcgcgagctgggagccgcctacgcgatggac cccaaaagtgacgcggggatttactggacagccatgttcggcacgcagcaatag
```

The protein encoded by this nucleic acid molecule has an amino acid sequence according to SEQ ID NO: 92 as follows:

MSVTSSVLRLSRLSVSLSLLGMLSSALFAGAAFASDETQLIESLNAYRGQ

AQRCGEQVSMELPPLSTDPRLVLPASGNLNLQQSLTRASYPMVTVQAISL

SGPRDAASALKAVQESFCRVVLDPQFVDIGVSRDGRDWRIVLARSLVASR

LGDWQAFGQKILEMINTARTQARQCGSQSFAATTPLSWNQVLGTAAQGHS

QAMANQNFFDHKGRDGRTPGDRAELAGYLGQQIGENIAAGQDTARKVVDG

WLVSPGHCANLMTPGFRELGAAYAMDPKSDAGIYWTAMFGTQQ

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-seventh nucleic acid molecule encodes ORF48 and has a nucleotide sequence according to SEQ ID NO: 93 as follows:

atgccgttattaaactggtccagacacatggttcatttaacagccatcggccttatcagcattccggct gcctatgcagcggacaccctgacccgcgacaatggcgcagcggtcggcgacaaccagaactctcagact gcaggcgcccaagggcctgtcctgctgcaagacgtacagctgctgcagaagctgcagcgttttgatcgc gggcgtatcccggagcgtgtggtccacgcacgcggcactggcgtgaaaggcgaattcacagcgtccgcc gacatcagcgacctgagcaaggcgaccgtcttcaaatcgggtgagaagacccggtattcgtacgtttt tcttccgtggtccacggcaaccactcgccagaaaccctgcgcggcccgcatggcttcgccaccaagttc tacaccgctgatggcaactgggacctggtaggcaacaacttcccgacgttcttcatccgcgacgccatc aagttcccggacatggtgcacgccttcaagcctgacccgcgtaccaacctggacaacgactcgcgccgc ggcggcttcttctcgcatgtaccggaagccacgcgcacgctgaccctgctgtactccaacgaaggcaca ccgaccggctatcgcttcatggacggcaacggcgttcacgcctacaaactggtcaacgccaaaggcgaa gtgcactacgtcaagttccactggaagacgctgcaaggcatcaagaacctcgaccctaaagaagtcgct gaggttcagtccaaggactacagccacctgaccaacgacctggtcggcgccatcaagaagggtgacttc gcgaaatgggacctgtacatccaggtgctgaaacctgaagacctggccaagttcgacttcgacccgctg gacgccaccaaaatctggcctgatgtgccagagaagaaaatcggccagatggtcctgaacaagaacgtc gacaacttcttccaggaaaccgagcaggtcgccatggcacccgccaacctggtccctggtatcgagcct tccgaagaccgtctgctgcaaggtcgagtgttctcctatgccgacacgcaaatgtatcgcctgggtgcc gacagcggcaaaaccaccagcggcgtgaactacgagcctagccgtctggaacccgtcctgccgatgag aaagcacgttacagcgagctgccaatcagcggcactacccagcaggcgaagatcacgcgtgagcagaac ttcaagcaggcgggtgatctgtatcgctcttacaacgcgaaagagcagaccgacctggtgcagagcttc ggtgaatcgctggccgacactgacaccgaaagcaagaacatcatgctgtcgttcctctacaaggcagac cccacctatggcactcgggtaaccgaagcggccaaaggcgatctggccaaggtcaagtcactggctgcc agcctgaaagactga The protein encoded by this nucleic acid molecule has an amino acid sequence according to SEQ ID NO: 94 as follows:

MPLLNWSRHMVHLTAIGLISIPAAYAADTLTRDNGAAVGDNQNSQTAGAQ

GPVLLQDVQLLQKLQRFDRERIPERVVHARGTGVKGEFTASADISDLSKA

TVFKSGEKTPVFVRPSSVVHGNHSPETLRDPHGFATKFYTADGNWDLVGN

NFPTFFIRDAIKFPDMVHAFKPDPRTNLDNDSRRFDFFSHVPEATRTLTL

LYSNEGTPTGYRFMDGNGVHAYKLVNAKGEVHYVKFHWKTLQGIKNLDPK

EVAQVQSKDYSHLTNDLVGAIKKGDFPKWDLYIQVLKPEDLAKFDFDPLD

ATKIWPDVPEKKIGQMVLNKNVDNFFQETEQVAMAPANLVPGIEPSEDRL

LQGRVESYADTQMYRLGANGLSLPVNQPKVAVNNGNQDGAMNSGKTTSGV

NYEPSRLEPREADEKARYSELPISGTTQQAKITREQNFKQAGDLYRSYNA

KEQTDLVQSFGESLADTDTESKNIMLSFLYKADPTYGTRVTEAAKGDLAK

VKSLAASLKD.

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

This protein also has significant homology (e=0), as detected by BLAST search, to catalase isozyme catalytic subunit CatF from *Pseudomonas syringae* pv. *syringae* (GenBank Accession AAC61659, which is hereby incorporated by reference in its entirety).

A forty-eighth nucleic acid molecule encodes ORF49 and has a nucleotide sequence according to SEQ ID NO: 95 as follows:

```
atgggggtttcgagctgcggcaaaagtgccgtcggtgcagaaatcgcccg taacagcggcggtcgcctgatcgaaggcgatgcgttccatccccaggcca acatcgacaagatgagcgccggcaccccctcaccgacgaagaccgtgcc ggctggctgacccgtctgggtgaagaactggccgcagccttgccaaggg cgaacatccggtgctgacctgttcggcactcaagctcatttatcgtgaac gcctgcgtgcgcggtgccgggcctgggttttgtctttctcgaactgagc aaagagctggccaccgagcgttgcgccaaccggacccgggcatttcatgcc tgcgagtctggtcgatagccagttcgcgaccctggaaccaccgatcggcg agccactgaccctggtggtcgatgccagcaagcctatcgatgtaattggt gaacaagccgcggcatggtggaaaggctctcacgcctga
```

The protein encoded by this nucleic acid molecule has an amino acid sequence according to SEQ ID NO: 96 as follows:

MGVSSCGKSAVGAETARNSGGRLIEGDAFHPQANIDKMSAGTPLTDEDRA

GWLTRLGEELAAALAKGEHPVLTCSALKLIYRERLRAAVPGLGFVFLELS

KELATERCANRTGHFMPASLVDSQFATLEPPIGEPLTLVVDASKPIDVIG

EQAAAWWKGSHA

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (1.1e-52), as detected by BLAST search, to gluconokinase from *Pseudomonas aeruginosa* (Stover et al., *Nature* 406:959–964 (2000); GenBank Accession AAG05709, each of which is hereby incorporated by reference in its entirety).

A forty-ninth nucleic acid molecule encodes ORF50 and has a nucleotide sequence according to SEQ ID NO: 97 as follows:

```
atgcgaccggtgtctatgttttccctgcgttccatttgtgctgccgcactgtttgcgctttgcctgtct
atcttcccggcgctggccgccgagccgcccacccgcgatgccgtgcagcaaagcctcgacaagattgcc
gaccgcaagctgccggatgccgatcagaaggccttgcagcaggtgcttgagcagacgctggcgtttctc
aacagcaaagacgacagcgagcaaaagctgaccgcgctcaagcagcagctggctcaagcgccaaaacag
acctcggacaaccagcgcgagctggcccggttgaaagaaagcaaagtcgttgccgttgcacagcgctac
ggtggcctcgatgtgccgcaactggagcgactgctcagccagcgcagcacccagcaaagtgatctgcaa
agcgagcttaacgacgccaacagcctggccatcaccgcgcaaacccggccgagcgggcgcagactgaa
atcagcgccaatcagacacgcatccagcagatcaatgccatcctcaagaatgcaaagacaacggcaag
accctgagtgccgatcagcgcaatctgctcaatgcggaactggcctcgatcaacgcgctgaacctgctg
cgccgtcaggaactggccggcaacagccagttacaggacctgggcaacagccagcacgacttgctgacc
gaaaaagtcgcccgccaggagcaggaaattcaggacctgcaaaccctgatcaacgacaagcgccgagcc
cagtcgcagaaaaccgtggcggacctgtctctggaagcgcagaaatccggtggcagcagcctcctggcg
accgagagcgccgccaacctcaagctgtccgattacctgctgcgcggcaccgaccgtctcaacgagctg
acccagcaaaacctcaagaccaagcagcaactggacaacctgacgcagaccgatcaagccctcagcgag
cagatcaacgtgctgagcggcagcctgctgctgtccaagattctctacaagcaaaaacagtcgttgccg
cacctggaactggacaaaggcctggctgacgaaatcgccaacatccgcctttatcagttcgacatcaat
cagcaacgcgagcagatgagcacaccgaccgcttacgtcgaacgactgctcgccacccagccccggaa
aatatcaccccgcaactgcgcaggacgctgcttgatctggccatcacccgcagcgacctgctcgaacgc
ctgaaccgcgagctgagcgcgttgctcaacgagtccatcacgctgcaattgaaccagaagcagttgacc
agtaccgccgtcggcctgcgctccacgctggacgagcagatgttctggatcccagcaacaagccgctg
gatctggagtggttccagaacatctggccgcgcctgcaaaaacaggtcgcgaccctgccctggacgtcc
agcctcagcgagctgtcggacggcttgacacaacgcccgctgctgtttctgccattgttactgctgatc
ggtgtactgacctggaggcgcaaggcgctttaccagaagctcaaccggctgcacgccgacatcggccac
ttcaaacgcgacagtcagtggaaaacccgttggcgctgctgatcaacgtgctgctggccatgccggtc
gcattggggctggcgctgtgcggctacgccttgcaaatcgatgcgcgcgggcaaaacgccaaccttggc
```

-continued

```
gaggccttgctgcagatcgcgctggcctggctagtgttctacaccgcctaccgcgtgctggcccgtcc
ggcgttgcgcaactgcactttcgctgggaaccggcgcaggtcgcgttcttgcgcggctgggttcgtcgc
ctggggttggtggtgctggcgctggtcgccgtggtggcggtcgccgagcatcaaccggccgcgctggcc
gacgacgtgctgggtatcggcgtggtgctgacctgttacgcgctgatgacctggctgctgggccgattg
ctgctctccagccctacgcaccacaacgcgtcgctgttccgcaagacgctgggtgtggcgttcacggca
ttgccggtcgcgctgtttctggcggtgtgcttcggctactacaccgcactcaagctcagcgaccgt
ctgatcgacacgctgtacctgatgatgatctggctgatggtcgaggccaccttcgttcgtggtctgggc
gttgccgcgcggcgactggcctaccagcgtgcgctggccaaacgtcaggctgcgcgagaaaacggtgac
agcgacatccccgtcgaagaaccgaaactggacatcgaacaggtcaaccagcagtcgctgcgcctgatt
cgtctggccttgctggctggtttcgtcggcgcgttgtacctggtctgggccgagctgatcacggtgttc
gcctacctggacaacatcatcctctacgaatacaagcggcacaggcgccaacatgagcatggtgccg
atcagcctgagcgacttcctcggtgccggggtcatcatcgtcattacctttgtgctggcgggcaacctg
cccggcttgctcgagtgctggttctgtcacgcatgaacctggtcgcaaggcagcgcctatgcgaccacc
acgctgctctcctacaccatcgccggcatcggctttgtgaccacgctgtccacattaggcgtgagctgg
gacaagctgcagtggctggtcgcagcgctgtcggtgggcctggggttcggcatgcaggagatcttcgcc
aacttcatttccggcatcatgatcctcttcgagcgcccggtacggatcggcgacaccatcaccatcggc
gccctgtcgggtacggtcagcaagatccgcatccgcgccacgaccatcaccgacttcgaccgcaaggac
attatcgtcccgaacaagaccttcatcaccggccagctcatcaactggtcactgactgacaccgtcacc
cgcgtaacgctcaagctgggtgtggattacggctcggacctggacctcgtgcgctccctgctgctgcaa
gccgcacgggaaaaccctcgggtgctcaaggagccagagcccattgtctacttcctgaacttcggcgaa
agcaccctcgaccacgaactgcgcatgcacgttcgcgacctgggcgaccgcaacccggtactcgacgag
atcaaccgcttcatcaaccgcgagttcaagaaacagcacatcaacatctcgttccgccagatggagatc
tacctcaaaaacacccagggcctggaatacaaactggtgcccgccgaaccaggcgaaaagcacggcgca
ccggctgggcaaaccacgctgcaaccggtaaacaccaaagtagccccggcaaccaaagatgcgccagag
ccgccggagttgaggctggactga
```

The protein encoded by this nucleic acid molecule has an amino acid sequence according to SEQ ID NO: 98 as follows:

```
MRPVSMFSLRSICAAALFALCLSIFPALAAEPPTRDAVQQSLDKIADRKLPDADQKALQQVLEQTLAFL
NSKDDSEQKLTALKQQLAQAPKQTSDNQRELARLKESKVVAVAQRYGGLDVPQLEQLLSQRSTQQSDLQ
SELNDANSLAITAQTRPERAQTEISANQTRIQQINAILKNGKDNGKTLSADQRNLLNAELASINALNLL
RRQELAGNSQLQDLGNSQHDLLTEKVARQEQEIQDLQTLINDKRRAQSQKTVADLSLEAQKSGGSSLLA
TESAANLKLSDYLLRGTDRLNELTQQNLKTKQQLDNLTQTDQALSEQINVLSGSLLLSKILYKQKQSLP
HLELDKGLADEIANIRLYQFDINQQREQMSTPTAYVERLLATQPPENITPQLRRTLLDLAITRSDLLER
LNRELSALLNESITLQLNQKQLTSTAVGLRSTLDEQMFWIPSNKPLDLEWPQNIWPRLQKQVATLPWTS
SLSELSDGLTQRPLLFLPLLLLIGVLTWRRKALYQKLNRLHADIGHFKRDSQWKTPLALLINVLLAMPV
ALGLALCGYALQIDARGQNANLGEALLQIALAWLVFYTAYRVLAPSGVAQLHFRWEPAQVAFLRGWVRR
LGLVVLALVAVVAVAEHQPAALADDVLGIGVVLTCYALMTWLLGRLLLSSPTHHNASLERKTLGVAFTA
LPVALFLAVCFGYYYTALKLSDRLIDTLYLMMIWLMVFGATFVRGLGVAARRLAYQRALAKRQGRENGD
```

-continued

```
SDIPVEEPKLDIEQVNQQSLRLIRLALLAGFVGALYLVWAELITVFAYLDNIILYEYTSGTGANMSMVP

ISLSDFLGAGVIIVITFVLAGNLPGLLEVLVLSRMNLAQGSAYATTTLLSYTIAGIGFVTTLSTLGVSW

DKLQWLVAALSVGLGFGMQEIFANFISGIMILFFRPVRIGDTITIGALSGTVSKIRIRATTITDFDRKD

IIVPNKTFITGQLINWSLTDTVTRVTLKLGVDYGSDLDLVRSLLLQAARENPRVLKEPEPIVYFLNFGE

STLDHELRMHVRDLGDRNPVLDEINRFINREFKKQHINISFRQMEIYLKNTQGLEYKLVPAEPGEKHGA

PAGQTTLQPVNTKVAPATKDAPRPPERLRD
```

The protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (e=0), as detected by BLAST search, to putative potassium efflux system from *Yersinia pestis* (Parkhill et al., *Nature* 413:523–527 (2001); GenBank Accession No. NP_406604, each of which is hereby incorporated by reference in its entirety).

A fiftieth nucleic acid molecule encodes ORF51 and has a nucleotide sequence according to SEQ ID NO: 99 as follows:

atgtcaacgttgaatcatacgtctgctgtaaattgccgcgtcagttttgatggtgaccgttgctatgta gacacccccdtccagatcatgccgggtgagcgatgggctgtaaatatcgtacctaacgatttagtcaca atccactacgaggccgccagcaatcacgactaccctttgctgctggccagcataaaaaatctgtttacc gatgagcgttgtgtcgtgctaaagcccggccttacacagcaagctttgaacatgtatttttcagaggtt aacagccttaaacctaacgcgactcatgttcgcttgttgcatcgagcgcagcgtatttttctagaaaac atgatccgtagcgtacagataacctcgcaaggtatcagcgtcactttcgcaaccgccgaattcaaaaat tataactaccagctaaaggtggataaatatacttttgcaaggcttgacaaggggtaccctctctattcg gagctggttgaaaacacctggataacgaaattatccgtagcccataatattctgtattccatctctgtg agcctggaccactcaagcacaccttatacactttttttcaggaaccctcgcggaagacaatatagtccag ccgatacgggcgcttttcaccgacaacaccatgactcaactcacctccttggccgatcagaaaaccgtg gatgccttgtatacgacggtcaatggcaaccccggttatcagcatcaaaaaacgcgcagattatcggtct tatctgaacatcgcacagaagttactgcttccaagaacctacaccaaagtagtacggacagtgagcagc ctgtctgtgcattttacgggggaggcgtacaaacaattcaactacaagatgcttgtcaacaatgcttat gcatccgagatcacccgagggaaggcttattactccagcgtgagcaatggggtgtggaccacttccggt acgcatgacagcgacgacaactgcaaagtcacttgtgattacaagggcgcaacctacgtcctgtacgag agtaatgcggcagatagacgcactgaaacctgggcacaagacccgtacgttactcattgcgacccgaga gacctgtaa The protein encoded by this nucleic acid molecule has an amino acid sequence according to SEQ ID NO: 100 as follows:

MSTLNHTSAVNCRVSFDGDRCYVDTPIQIMPGERWAVNIVPNDLVTIHYE

AASNHDYPLLLASIKNLFTDERCVVLKPGLTQQALNMYFSEVNSLKPNAT

HVRLLHRAQRIFLENMIRSVQITSQGISVTFATAEFKNYNYQLKVDKYTF

ARLDKGYPLYSELVENTWITKLSVAHNILYSISVSLDHSSTPYTLFSGTL

AEDNIVQPIRALFTDNTMTQLTSLADQKTVDALYTTVNGNPVISIKKRAD

YRSYLNIAQKLLLPRTYTKVVRTVSSLSVHFTGEAYKQFNYKMLVNNAYA

-continued

```
SEITRGKAYYSSVSNGVWTTSGTHDSDDNCKVTCDYKGATYVLYESNAAD

RRTETWAQDPYVTHCDPRDL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-first nucleic acid molecule encodes ORF52 and has a nucleotide sequence according to SEQ ID NO: 101 as follows:

```
atgcgcctgatcgcgcagattctgcccggcctgccggaaaacaccacttacagcgccgccgctgcgtcc aacaccctggcgcgggccatgcccaacgccattcgcaatgcgctgggcaccctggggctggtggctgcg cgcacccagccaagcatctttccgttgccgtcgcgcaacgtcagcggtggcgaaaagaggacgacctg gagattctgctcaaactcgcggccgccgctgtttcgcgcctgcaaagccaccagttgggcggcctggag cagacccgtaccaatgccgatggcactcaggtgactacatggcaactggaagtgccgatgcgcaacgcc catgacatcgtgccgttgcaggtcaaggtgcagcgcgaagacaagcctgatcaggacgccaccgaagac cgcgacgatatcgagatcaaggaaacccgtgaaaaactctggaaagtcgatctggctttcgacctggag ccgcttggcccatgcaggtgcatgcgcaactgctgcgcggcacgctgtccagccagttatgggccgag cgcccggatagcgcaacactgatcgaacatgaactggggcatttgcgcgagcgcgagcgccgattgccg ctggccgtcggggaactggdgtgcagccatggcgttccgccgcaagggccgcgcaccgccctcgaacaa cgctggatcgacgagaacgcctga
```

The protein encoded by this nucleic acid molecule has an amino acid sequence according to SEQ ID NO: 102 as follows:

```
MRLIAQILPGLPENTTYSAAAASNTLARAMPNAIRNALGTLGLVAARTQPSIFPLPSRNVSGGEKEDDL

EILLKLAAAAVSRLQSHQLGGLEQTRTNADGTQVTTWQLEVPMRNAHDIVPLQVKVQREDKPDQDATED

RDDIETKETREKLWKVDLAFDLEPLGPMQVHAQLLRGTLSSQLWAERPDSATLIEHELGHLRERLIACG

LAVGEIACSHGVPPQGPRTALEQRWIDENA
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-second nucleic acid molecule encodes ORF53 and has a nucleotide sequence according to SEQ ID NO: 103 as follows:

```
atgagtagcgtcgcagcactgatcaccatatcgactggacagacgcagttcgttaaagtcgcgcggacg tcattttctgtgctacgaatcccctcgccggcagatgtcgtgtgtcgtgtccgggatcagttgaccac aagacagagcagaaacccataaaaatagggggaagagacgtgagcctaaatgatcacttgaaaaaagca ttgattctgatccagcgacgagcttgatgaaatcaccgacctttatgtgacgttgcctgcagaggtcga ttcagttgcttgaccatttcactcgaagggaattggaaggaaattgatagcgtctggtctgctcggtta gacgcagcagattcaaagaataatacaaaatgtcacgtccatatcgccaaaaaccaagcatcatcgatc aaaagcaaacaggtttcttggaacagtgatggtagccggcatgataaaaaaacattcgatgtgaacgct
```

The protein encoded by this nucleic acid molecule has an amino acid sequence according to SEQ ID NO: 104 as follows:

MSSVAALITISTGQTQFVKVARTSFSVLRIPLAGRCRVRDQLTTTIKTEQKPIKIGGRDVSLNDHLKKA

LNSDSSDELDEITDLYVTLPAEVFSCLTISLEGNWKEIDSVWSARLDAADSKNNTKCHVHIAKTKHRSS

KSKQVSWNSDGSRHDKKTFDVTLGQSRKAQAIARKFLGLGESISLESKDSKQMVERPLLSTATSFSNDG

KEVKVEFYVEESTAHLPAWLRW

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-third nucleic acid molecule encodes ORF54 and has a nucleotide sequence according to SEQ ID NO: 105 as follows:

atgaagccaatccatactgcccgatacaacgcctggaatcagttggagcaggagaccgcccatgactgg ctggggccaaacccttggccagcagcacccttggctaccgctacgatgactggaaccagcgatgctgc accacgaccgatgacaacgtacagacttatgagtattcagacccgatcggcagcgacgtacataaggc ccaatccagaaaacctggaaacagagtggcgacccggagggccgcatcagtggccgcagcgaaacctgg ctgaatctgttcggcaaaccggaccggatccggacgctgaccgctggtaaaacgggtcgcagccgcacg cacagcatgagccgcagccggaacctgaccacgactgagcaggaactgagcaggcagacctttctgtac gacgggctgggacgctgcaccgagcagcgcgatgcactccagcaaagcaccctgttcagctacgacadc tggtcacgcatggtctcctccacgcttgcagacggcagcgtcatcaaccggagttatgcgccgcaaagc agcagtgagctggcaacgatgctcgaggtcgtgcaccagaacggcaccaccagaaccgtggcaggtaca cagaaatttgacgggcttgagcgtgtgacgcagaccaaaacaggtgaccgcgtcgaacagttcaactac gacgccggtgagatgcagcccaggtcgcgcacaacagccgggctggcaacatcaactttacctacact cgggcgctcactgatcagatttttccagcacggctccggatgaaacggccaaattcgattatgacaag accagtgcccgcctcatcgaagcgacgaacccgcaaggcacgcgcacttaccgctatgacgtgcacaat caactgacgggagagacttgggacaatctgctgggtcaggcttgggaaacccgacaccaatcatcgctg ctgggtcggccgatcaagcgcaccgatctcaaaaaaggcgaggcggcgggcgcagagacccgttacgac tacgacacgctcggcagaatcaggtttatcaaccagagcaacctgcgcaccacaatcgactatgacgtg ctgggccagctctgcaaggtggccaccgaggacctgcaggccggaactggcgtgatcatcgacatggaa tacgacgaccagggacaggaaattctcagaacccagaccgcaagcaaccaagcggcgttgaccttgact caaacgtgggcagtggacgggcttttgaaaacccgcgacctgcaacaggcgggtagcccctgctgcac gaaacgtttagctacgaccccagaggccgcctgacactggtgaattacctgggtagcagcttgccgaga gacgaactgcaaagggagatgaccagacaaatattcagcttcgacgagctggacaacattacgctatgc cagaccaggtttaccgatggcacctctgagcgagcagctttcaaatacggcagcccggcgacgataag cataaagaccgctgccagcttttgagtattgcctacacgccgcccagaaaaacaccggaccgacattc agttacgacgccaacggtaaccagcttaaagacgagcatggcaacagtctgcattacgatagccagagc cgcctgctgcaggtcgcagaaaccggcggtgcccctatcagccaataccgttatgacggccacaatcaa ctggtcgccaccagggatggcaatgaaagcgagattttgcggttctatgagggtcatcaactgagcagc acggtgcaggaagatcaacgcactcagtacctgcatctcggcgaacagccgctgggccagcagattgtg gacgacgccgagcaaaccctgttgctactgactgacgcaaaccagagcgttatgggtgaatttcaacaa -continued

```
ggccagctgcgcaaggcggtctacagtgcctacggggagcgccacagcgaggaggcgctgctgagcact gccgggtttaacggtgaagtacgcgaagccgccaacggctggtatctgttgggcaatggctaccgggcc tacaaccctctcctgatgcgcttccacagcccggattttctcagcccttcgccgaaggcggcgtcaac ccctacacctactgcctgggcaacccatcgccctgcgcgacccgacaggacatgatgccagcggtcag actggccggttgagacggcccgatgaggggctttgccaatgcaacaaggtggcggagatatcatgggt tgggtgggtgtaggaataggcgttgttttcaccgtattgggcgttgccgctaccatagccacgttagga acagccacaccggttaccggcccggtaactgtcctgggcatttccatgaccgccagcgctgccgcggcc gtttcgacagtctcgaccggtgcgttgatcgtcggtacggcattgacagcggcttcaactacggccaat acagttgccattgtaaataacgatcagacggccggagaagtcggcggctggttgggtattgccgctgtg cccgttggcttggtagggtttggcgcggggctgtggtggcgagggcagttgcggctgcggctaaagtt gcggctgccaacgctggtacgatcggtgtccgcagcgtcagcagaataggcctcgctgctgctggtgcc cgcagaaccatttccagcgctgccagcagcgctcggcgccaaatcagcaacatgttaggcagaatctta ccccgtgctctaaacaggactgctgctactgcacgccggattccaagcgttacaagtggcggatcagga ccagggccatcattatttacacagaetaccttttaacgaategattgggatgacgcagaecaetatttt tcaacgaatgcgagcggaatcccaccggccacgcaggtaactcgaatctag
```

The protein encoded by this nucleic acid molecule has an amino acid sequence according to SEQ ID NO: 106 as follows:

```
MKPTHTARYNAWNQLEQETAHDWLGAKPLASSTLGYRYDDWNQRCCTTTDDNVQTYEYSDPIGSDVHKG

PIQKTWKQSGDPEGRISGRSETWLNLFGKPDRIRTLTAGKTGRSRTHSMSRSRNLTTTEQELSRQTFLY

DGLGRCTEQRDALQQSTLFSYDNWSRMVSSTLADGSVTNRSYAPQSSSELATMLEVVHQNGTTRTVAGT

QKFDGLERVTQTKTGDRVEQFNYDAGFMQPRSRTTAGLDNINFTYTRALTDQIFSSTAPDETAKFDYDK

TSARLIEATNPQGTRTYRYDVHNQLTGETWDNLLGQAWETRHQSSLLGRPIKRTDLKKGEAAGAETRYD

YDTLGRIRFINQSNLRTTIDYDVLGQLcKVATEDLQAGTGVIIDMEYDDQGQEILRTQTASNQAALTLT

QTWAVDGLLKTRDLQQAGSPLLHETFSYDPRGRLTLVNYLGSSLPRDELQREMTRQIFSFDELDNITLC

QTRFTDGTSERKAFKYGSPGDDKHKDRCQLLSIAYTPPRKTPDPTFSYDANGNQLKDEHGNSLHYDSQS

RLLQVAETGGAPISQYRYDGHNQLVATRDGNESEILRFYEGHQLSSTVQEDQRTQYLHLGEQPLGQQIV

DDAEQTLLLLTDANQSVMGEFQQGQLRKAVYSAYGERHSEEALLSTAGFNGEVREAANGWYLLGNGYRA

YNPLLMRFHSPDFLSPFAEGGVNPYTYCLGNPIALRDPTGHDASGQTGRLRRPDEGALPMQQGGGDIMG

WVGVGIGVVFTVLGVAATIATLGTATPVTGPVTVLGISMTASAAAAVSTVSTGALIVGTALTAASTTAN

TVAIVNNDQTAGEVGGWLGIAAVPVGLVGFGAGAVVARAVAAAAKVAAANAGTIGVRSVSRIGLAAAGA

RRTISSAASSARRQISNMLGRILPRALNRTAATARRIPSVTSGGSGPGPSLFTQTTFNESIGMTQTTIF

STNASGIPPATQVTRI
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-fourth nucleic acid molecule encodes ORF55 and has a nucleotide sequence according to SEQ ID NO: 107 as follows:

```
atgcggtgtgtgaggcgatcaagaaggttctttaagctgcaagctgcaagctgcaagaaaaagcaggac cgctttagcttagctgacgctccactgagtactttccatcgaacgatccgaaaaaccctgcctcgaaag
```

-continued

```
cttgtcagacccttttctgaatcagctatcgaggtagtcatgtccatcgaacccaacgtcagaaagaa cagccacccggccagcacacgccagcggatcagggcccggatcgcaatgatccggccatcgagccgcag gtttcggacgtagagccggagactgaaaaaggtgacggccagacgcaaggccagacccctgcccccagc caaagccagtcacaaagtcagaatcagagccagcagtccaacggcagcgcttacgtgcctgactatgag ccgcaggaaaaaaggaagaccagcgcaatcatcagcccactcaaggcactgatgctgatatcgacacc aatgcgggctga
```

The protein encoded by this nucleic acid molecule has an amino acid sequence according to SEQ-ID NO: 108 as follows:

```
MRCVRRSRRFFKLQAASCKKKQDRFSLADAPLSTFHRTIRKTLPRKLVRPFSESAIEVVMSIEPQRQKE

QPPGQHTPADQGPDRNDPAIEPQVSDVEPETEKGDGQTQGQTPAPSQSQSQSQNQSQQSNGSAYVPDYE

PQEKKEDQRNHQPTQGTDADIDTNAG
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-fifth nucleic acid molecule encodes ORF56 and has a nucleotide sequence according to SEQ ID NO: 109 as follows:

```
atgcccgtcactggtgcaggctttatcaagcgtttgacgcaattgtccctctgcgccggcatggcgctg gtcccggtggccgtacaggcagccgaaagcgatccttgggaaggcatcaaccgttccattttcagcttc aacgatacccttgacgcttatacgctcaagccgctggcaaagggttatcagtacatcgctccgcagttt gtcgaagacggtattcataacttcttcagcaatatcggcgatgtcggcaatctggcgaacaacgtcttg caggccaaacctgaagcggccggtgtagataccgcacgccttatcgtcaacactacgttcggtctgctg ggcttcattgacgtcggcacccgcatgggcctgcaacgcagtgatgaagacttcggccagacactgggc tactggggtgtgccaagcggcccgttcgtggtgattccgctgctgggcccaagcacggtgcgtgacgcc attgccaagtacccggacacctacacctcccgtaccgctatattgatcacgtacccacccgcaacacg gcgttgggcgtcaatctggtcgacacgcgtgccagcctgctgtccgccgagcgcctggtcagtggtgat cgctacaccttcatccgcaacgcttacttgcagaaccgcgaattcaaggtcaaggacgggcaggtcgaa gacgattttttaa
```

The protein encoded by this nucleic acid molecule has an amino acid sequence according to SEQ ID NO: 110 as follows:

```
MPVTGAGFIKRLTQLSLCAGMALVPVAVQAAESDPWEGINRSIFSFNDTLDAYTLKPLAKGYQYIAPQF

VEDGIHNFFSNIGDVGNLANNVLQAKPEAAGVDTARLIVNTTFGLLGFIDVGTRMGLQRSDEDFGQTLG

YWGVPSGPFVVIPLLGPSTVRDAIAKYPDTYTSPYRYIDHVPTRNTALGVNLVDTRASLLSAERLVSGD

RYTFIRNAYLQNRFFKVKDGQVEDDF
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-sixth nucleic acid molecule encodes ORF57 and has a nucleotide sequence according to SEQ ID NO: 111 as follows:

```
atgacactttcaaccctgcgccctaccccgcgccagcagtatgaatcgcccgagtcagccgaggatttc
acccagcggctggccgacctgacccgcacgctggccgaaacagccgagcagtacgacatcagcgcgcag
ttccctcacgccaacttccgcttgctgcacagccacggactgctcggcctgaccgtgcctgccgaactg
ggcggcggcgctgccgacctgtcgcgggcgcagcaggtcatcagcgcagtggccagaggcgagccttcg
acagcgctgattctggtcatgcagtacctgcagcattccaggctgcaggacaaccgcaactggccgagc
cacctgcgcgaacaggtggccaaagacgccgtgcacgagggcgcgctgatcaacgcgctgcgtgtcgaa
cccgacctgggcacacctgcgcgtggcggcttgccgggcaccatcgcccggcgcagcgccgaaggctgg
cgcatcagcggcagcaagatctactccaccggcagccatggcctgacctggttcgccgtgtgggcgcgc
agcgatgacgaggaccgctggtcggcagttggctggtgcacaaggacacgcccgggatcagcatcgtc
gaggactgggaccatctgggcatgcgcgccacctgcagccacgaggtcaggttcgacaacgtgcgagtg
ccgctcgaacacgcggtcagcgtcagtccgtggagcgccccgcaatccgagcttgatggtgccggcatg
ctgtggatgtcggtgctgctgtcgtcggtctacgatggcatcgctcaatctgcccgcgactggctggtg
cactggctggaacagcgcacgccttccaacctgggcgccgcgctgtcgaccctgccgcgctttcaggaa
acagtcgggcagatcgacacactgctgttcgccaaccgcagcctgctggagtccgccgcccaagggcac
acacccgcacgcatgccgcgcagatcaaatacctggtgaccggcaatgccatccgcgcagtggaactg
gccattgaggcctcgggcaatcccgggctttcacgcactaacccgctgcagcgtcattaccgcaacgtg
ctatgcggccgggtgcatacgccgcagaacgacgccgtgttgatgggcgtgggcaaagcggtatttgcg
gcacgcaagcagagccagtaa
```

The protein encoded by this nucleic acid molecule has an amino acid sequence according to SEQ ID NO: 112 as follows:

MTLSTLRPTPRQQYESPESAEDFTQRLADLTRTLAETAEQYDISAQFPHA

NFRLLHSHGLLGLTVPAELGGGAADLSRAQQVISAVARGEPSTALILVMQ

YLQHSRLQDNRNWPSHLREQVAKDAVHEGALINALRVEPDLGTPARGGLP

GTIARRSAEGWRISGSKIYSTGSHGLTWFAVWARSDDEDPLVGSWLVHKD

TPGISIVEDWDHLGMRATCSHEVRFDNVRVPLEHAVSVSPWSAPQSELDG

AGMLWMSVLLSSVYDGIAQSARDWLVHWLEQRTPSNLGAALSTLPRFQET

VGQIDTLLFANRSLLESAAQGHTPAQHAAQIKYLVTGNAIRAVELAIEAS

GNPGLSRTNPLQRHYRNVLCGRVHTPQNDAVLMGVGKAVFAARKQSQ

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-seventh nucleic acid molecule encodes ORF58 and has a nucleotide sequence according to SEQ ID NO: 113 as follows:

```
atgaatctcacaacacttcctcttgcgctcagcattgcttgcgctgcggccatcacacctgccttcgcg
ggcacaagcgtctctgaggcttcacacaaagtgaatgtgcagcaagttcgtaacgcgacggtaaagatc
tcctacggcggcacgacctttctgatcgacccgatgctggccaaaaagggaacctacccagggtttgaa
aatacctatcgaagcaatctgcgcaatccactggttgatctgaccgaatcgcccaccgaagtgatcgcc
ggtatcgacgcagttatcgtcactcatacgcaccttgaccattgggacgatgctgcacaaaaagtgctg
cctaaagacatccctctgttcacccagcatgaaaaagacgcgcagctgattcgctctcaaggtttcaag
aacgtacgcgtattgactgatgaagccgaattcggcggcgtcaaaattaccaagaccggtgggcagcat
ggcaccgacgaaatgtatgccgtgccagcccctcgcgaagcctctgggtgaagcaatgggcgttgtattt
```

```
caagccccgggctacaagaccctctacctcgctggtgacactgtctggcgtaaagaggtcgatcaggct atcgagaactattgtcccgaagtcatcgtactcaatgccggcaaagcaaaaatgacggggtatgagggg gcgatcatcatgggggaagaggatgtactgcgcgcttcacaggtcgcgaagaacgcgaaaatcgtcgct gtacacatgaatgcaatcaaccatatgtccctgacccgtgagcaattgcgcgcttacgtcaagcagcag ggtatcgaaagtcgtgtagacataccggaagatggcgcttcactggagttctga
```

The protein encoded by this nucleic acid molecule has an amino acid sequence according to SEQ ID NO: 114 as follows:

MNLTTLPLALSIACAAAITPAFAGTSVSEASHKVNVQQVRNATVKISYG

GTTFLIDPMLAKKGTYPGFNTYRSNLRNPLVDLTESPTEVIAGIDAVIVT

HTHLDHWDDAAQKVLPKDIPLFTQHEKDAQLIRSQGFKNVRVLTDEAEFG

GVKITKTGGQHGTDEMYAVPALAKPLGEANGVVFQAPGYKTLYLAGDTVW

RKEVDQAIENYCPEVIVLNAGKAKMTGYEGAIIMGEEDVLRASQVAKNAK

IVAVHMNAINHMSLTREQLRAYVKQQGIESRVDIPEDGASLEF

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-eighth nucleic acid molecule encodes ORF59 and has a nucleotide sequence according to SEQ ID NO: 115 as follows:

```
atgcatctgttgccgtttgcgcgttaccccttatcacctgcagaaacacctaaacccaaggtgaccatg aaggttggagatttcagggcttacgacaccgctccagcacccggagtgaccactgcgtcctgcggacaa ctggcaatcggcaccaagttagaaatcatcgagaccgccgagaatggcgaacttacttatgccaaggt aagattctatctggcagcgtgaagcaggggcaaccaaaaaacgggtcgaggggcggaggtctggttc gcttatttgaaaaacggcgaaccctacaaaaactcagtccctaagcgcatctggctcgctgacgatgtg cctgagcgagcaagacccaattactggcagggtaaggtcaaagcctcagtagtgaataagttgccgctg tacgatgatcctgccagccctacaaatggccagcctgcaggcgcccggaaggggactctggagctggtc atgaacagcgtcatcgagtttaactcttcggaagtcgtcaacctggcgctggatggcaagctgcatcgg atggccaagtgcacgatgctgagtggcggcctgcgggtcatggtgcggttccccccagcttttgggca tgtgttgaaaatgaccctgctaataaagtattgaaatgggactcggtaacgccgaccagttttgatacg gtcgttatgacgagcaccggagtgaaggcgggcgatccaattggctatcttggacaaaccgaaaatctc accggtgaaaatggcggcgtcagcagcaaataccaggttcacgtcgaaattttcacagccgatgctgag gttaaagacttcctcaagaacaccgcgggtttgaagattgggaagcaatacctgcaccttgcaagcggg gctgtactcaagcaaaaagcgcccgcgaccggcaccacagcactcaagcaagaccatgcggttgacttg gctaaagccacaattgtcaaagaaggcaccgatgactggtatgaggtcagcgtgatcgaggacgatcag cctgtagccggcctgataaaaaaagccactgcgctagtcatcacacagcacgattgggaaaaattgggc tttcagatcgtagaggagaacaacgcagcagccgatggtttcttggacccggatgcaatgccacagttc ttcaaagacctattcgcgaagatcgacaagaaccacgatggtgaggtggagcctgctgaactggctgag gctcttaagaaaccggaaccagaacccagtgggccaggcttgttgcccatcaccctacggagtggaaa gataaggcaggctcccccaagtggagcaagttggataaactgctggaaacgtcgccgaagatgttgaaa catgaaaaagaacgcattgataaatatgtattttgggatgagttgtcagggaaagctaagatgacctca agtttaatatggcattttcatccggtagaattcatttcaacatttagcgcaaaaaagtctgcgcttgc aacgccatagttaaggctactcgctgggtttcttccagtaagacgcactatggcccattgcatacgggt gataaagagcttgggagtgcacctcagtgggatgacctggtctcagaaggaaaaataacggaagaggag
```

-continued

```
aaaaaaattattgttgtaatgtctggaaacgaggcaaaaattaacggagtacaaagttatgatagcgaa ataattactgccggcgcgatgcdgaaaacaattaacttgtccggtggcggtgagctgccactacaagtt aagaagtttaaaaatcagcatcccgaggcgtacatcgaatactttgattctcaaggctggaagttggat gagacaggtgattcggcgaaaatgtattatcaagggccggctcgagctagtggcgcaaagctggaagga aaggcgctgaaggataatttaaaaattggttgcagtgaatcgacatttgggaaggtggttgactgtcaa cctgtttcagtgatggcctgcgctatcgcaagtccgttatatatccagatacaaataatggatttata gaaaggttacgtagttctttaacgaagaagcccacaggctataactttactgctgggggattttcaag acctctctcggaaaagctgtggttttggatcacgatataaatcgacccgggtatgtgaaggatgacttg ggatctgctcttgacactttttttgctcaaaatccaacagtcagccgggatattgatacatgggcgca gcatatagcgttaatgagcgaaaagttttagacctgtatggcgctcgaagaagaatgaccaatgcattg cttcgatacaatcacttgaaggcggagttataa
```
20

The protein encoded by this nucleic acid molecule has an amino acid sequence according to SEQ ID NO: 116 as follows:

```
MHLLPFARYPLSPAETPKPKVTMKVGDFRAYDTAPAPGVTTAScGQLAIGTKLEIIETAENGELTYAKG

KILSGSVKQGATKKRVEGAEVWFAYLKNGEPYKNSVPKRIWLADDVPERARPNYWQGKVKASVVNKLPL

YDDPASPTNGQPAGARKGTLELVMNSVIEFNSSEVVNLALDGKLHRNAKCTMLSGGLRGHGAVPPSFWA

CVENDPANKVLKWDSVTPTSFDTVVMTSTGVKAGDPIGYLGQTENLTGENGGVSSKYQVHVEIFTADAE

VKDFLKNTAGLKIGKQYLHLASGAVLKQKAPATGTTALKQDHAVDLAKATIVKEGTDDWYEVSVIEDDQ

PVAGLIKKATALVITQHDWEKLGFQIVEENNAAADGFLDPDAMPQFFKDLFAKIDKNHDGEVEPAELAE

ALKKPETRTQWARLVAHHPTEWKDKAGSPKWSKLDKLLETSPKMLKHEKERIDKYVFWDELSGKAKMTS

SLIWHFHPVEFISTFSAKKVCACNATVKATRWVSSSKTHYGPLHTGDKELGSAPQWDDLVSEGKITEEE

KKIIVVMSGNEAKINGVQSYDSEIITAGAMQKTINLSGGGELPLQVKKFKNQHPEAYIEYFDSQGWKLD

ETGDSAKMYYQGPARASGAKLEGKALKDNLKIGCSESTFGKVVDCQPVSVMACAIASPLYIQIQIMDFI

ERLRSSLTKKPTGYNFTAGGFFKTSLGKAVVLDHDINRPGYVKDDLGSALDTFFAQNPTVSRDIDTWGA

AYSVNERKVLDLYGARRRMTNALLRYNHLKAEL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-ninth nucleic acid molecule encodes ORF60 and has a nucleotide sequence according to SEQ ID NO: 117 as follows:

```
atgcggccgttgcctgcgttcagtattttgcagtttgatccgttgaaacgttcgggtcctgcgctgacg gtcgaacgtgatacaccggtcgatagcaagcctattaatgacgtgcgttgtcgcttccgtacgtgctac ccgaccgaagttcaggcgctggatctgaccgcgctgaattactcggtgaaaggcggtggttcgttgctc agcctgcgcctggagatgagcgctgaaggtcacttgggtgagcttgaactgagccgcctgcgtctgcac tttgcaggcgagcgctatatcagccagatgctgtacctctgcctgctacgcaatctcgagggtatcgag ctgatccctctggacgctgccggcaagcccatcgacggtgtcaatggcgcgccaatggcgttcaagatg ccgggcgaccgtgtacagccggtagggtttgccgaagaagaggcgttgatcccgtatccgctgaacacg ttccgcggttatcgctacctgcaggagtacttcgcgtttcaggacaagttcctgttcgtcgacatcaac ggtctggatctgctcaacgcactgccagaagagacactcaaacaagtgcgcggccttgagttgcgcttt
```

```
gatattcgcaagagcggcattcagcgtcttcgtccccaccctggataaagtaaagctgtattgcacgccg
atcgtcaacttgttcaagcacgacgccttgccgattcgccttgatggcaagcaggacgagtacctgctg
ctgcccgccgaatatggcctggaaacctgtggtgtgttttcggttgaaaccgtgaccggttggaagccg
ggaggtcttggctatcaggattatgtgccgttcgaatccttcgagcacgaccccagtttcgacgtgccc
aacagccgtccgcattacagcattcgccagcgttcttctttgctccatgaaggcctcgacaacttatctg
agtttcggcattcgccataagaagcgcaacgaaaacctgtcgatcgagttgatgtgcaccaatcagaac
ctgccacgcaaactcaaactgggcgaaatcaacgtggcctgcgaagatacgccggcttttttgagttttc
cgcaatatcaacaacggctaacctccagtttcgccgccccccgctgaaacgtgacttcctgtggaagttgatc
agcaatatgtcgctcaattacttgtctctggctgacgtcaatgcgctgaaggtgattctggaaactac
gatttgccccgttactacgaaccagcacgcggaaaaagtcagcaagcgcctgttgggcggtttgaaatcg
atcaagcatcaaacaagtggacagattcgaaccgaagggttaaccgtacgcggattcgcaatgagctgaacc
atcgaaacggaagggtatatcggcgaaggcgacatgtttgtattcgcttcggttctcaaacgagttttttc
gcgctttacgccagtctcaattcgtaacagagctgcgggtaaaaagcacacaggagaggtgtaccaa
tggacaacacaagtatgggcctcagccccctgctttaa
```

The protein encoded by this nucleic acid molecule has an amino acid sequence according to SEQ ID NO: 118 as follows:

```
MRPLPAFSILQFDPLKRSGPALTVERDTPVDSKPINDVRCRFRTCYPTEV
QALDLTALNYSVKGGGSLLSLRLEMSAEGHLGELELSRLRLHFAGERYIS
QMLYLCLLRNLEGIELIPLDAAGKPIDGVNGAPMAFKMPGDRVQBVGFAE
EEALIPYPLNTFRGYRYLQEYFAFQDKFLFVDINGLDLLNALPEETLKQV
RGLELRFDIRKSGIQRLRPTLDNVKLYCTPIVNLFKHDALPIRLDGKQDE
YLLLPAEYGLETCGVFSVETVTGWKPGGLGYQDYVPFESFEHDPSFDVPN
SRPHYSIRQRSSLLHEGLDTYLSFGIRHTEAHETLSIELMCTNQNLPRKL
KLGEINVACEDTPEFLSFRNITPAISSPAPPLNRDFLWKLISNMSLNYLS
LADVNALKVILETYDLPRYYDQHAEKVSKRLLGGLKSKHQIIVDRLHRGL
PVRGLRTELTIDPEGYIGEGDMPVFASVLNEFFALYASLNSYHELRVKST
QGEVYQWTPRMGLQPLL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixtieth nucleic acid molecule encodes ORF61 and has a nucleotide sequence according to SEQ ID NO: 119 as follows:

```
atggtcaaggttacctcttccggatttactgccaaccctctctctcatcatgcggacagtgtttccccc
gcgaacagtccccctcagttaccggagcctgtgcatctggttgatttaagcgagtcgtcccgcaagggc
ggcatgcgaaatcggccgcatgccagtttgaacagtcaggtgctcgaactgcaagcggtgccgtcgcaa
cgtggaaagcatgttcgtgtcagaagtcatgccgatggcgagagtgtcattaatgcctggctggcaaag
cgcccctcggttcaaagcgaaaccagtcttgataacgatggcaaactggtgcgttacaccccgtgaat
catgagccgctggcgccgcgcaatgaggcgttttcacctcggtgccggggatgttgatggccgttttg
acggtccaccccgagatggaacatggcatcagcggggacataactgctgatgctgtggctgcccggctt
gccgaaccgccaatagggttgctaaccggaatctggcagtcttcccatgatcgagcctatctggagcgt
ggcggtgtggtgcataccgccaatatggaagagcgctgggcgccgttgacgctgccaggcatcaatccc
cgagagcccctgcgaatggccggtttgcaggccgatggtggagtctatctgcataacggcagccaactg
tggcgcttgaccgaaactgccgccgagtccgtgaccaccgaaaaccttcctgaaggtgcggcggtacgc
attggcgccggtggcgaggtgcatgggctgcatgaaggcgcgcttcattcgaatggcatttcccgtcca
atcgagctttgccggccaaaagctggcgcgccggggcgcgagcagagtccggcgcgcccgttgatttg
```

-continued

```
ctgccgttaccgggtggcaccgctgcactgatccttgatgacaagggacgtatttatcacgctgatctg aaaggcacaggcgctgttgaagcccaccggctgaaattacctgctgactttgcgcagggtaaaggttgg gccgtgaccgccatgggattgtcccgagacgacactgttcatctgatgctgcaggatcagaacggcgt cgcatgagcttgcagcgagcaccgggcgaggcgctgtttcgtcctgcgtacctgctggatcgcccgttg ctgctgctctataccaagggctgcatgttccgtcggaggccgcggtgcagtcgcacgttcagcttgat tgtcatgctcaactggggcatatcgatggcgtgctgcattataaagcggctcccgatcagtcatgggaa gggctaaagcagtcgggcggcgaaccgctgacgggtttgactgctctttattccagcccgctgggattt atcgacaggaaaccggttttcgctttagtggggatgcccggcaggtggtcgagttgaaactggagggg cgtacatcctggttgccgagcgatgccgagcttccgcgtcaccctgcgggcgggcctttggcggtgata ccggatacggtagcgttacgcaccagcccgatcgcgcagtttgacgagcctgtacaggcgctggcggtt cacggtaatcgccgggtcgtcgcgctgacggattcggggcgattaatggctgccgatgcggacacccca gcccgccgacttcccacgttgcagcgcccatcgccatcgccgtagggctcaacgatcagttactggtg ctgcatcatccccatagccagcgcccccagttgaaacggttgagtgcgaaagatgactgggagccggtg ccgataattctgccgggtattgttcacccttcaagtcttcgcgctactcgcacggggcaaatacaagtg cagctgggagaaaactggcatacgttgctgccatcaatgacgtcgcacgataatcagcgcttacctgcc cgcgtaaaacctgaaccagaggggatgaggcgccgtcggcgaatttcctggcgggtagcaacgccctc gccaatcagcagcaagccagtcgtatcagcacaccgcatcatgacgcatcggtggttacgacgctggcg gggacaacagccaacaacccgttgacgatggcgtcgagcctacaggcagtggttgatacgacccgcgct caggtaggcgcgttggcgagagatgtagtgggcgcagcggcgaacagcacgatgcgggcdatggcgcat accttgggtgttgtactgccgccaacgcctcaggagaagcgcctggccagtttccataatgaggcgaaa caggcttatacatcaggaaaaatactgtttgagcatctgccgtcactcgcgcaagtgcgcgtcgcttca gccgtagggccgtcggacggagaaagattcgggctgtcacatcagcaaacgcaacgcttgttgacgctg cgagaggggaagctggaagcgctgttacgcgacttgcgcaagatcggctttcatgaagggggtgatcatg ggcgatatgggcgacagcgacagtgcgcacggtcttgtttcgacgacatcgacaccaacgttccggctg gccgagctatggcgacggcagcattcgcgagtggataaggcgctgtcttccgctggattatccagatcg gaagatattttccggacttgaacctaagtatcaacgcgttggctggcggcgcggcgctgaatgcggat cgtatgagcgaacgtgaagctgagttgttgagcgttttgtgcgaggtcagcgaaaaaatgatgcgcgct ggcgtacgcttgccggcagatgatggaagcgttgacagcgcccacagccaggcgccatacggcttgaga acagcaggattgattgcaggtctggtggactatgatgcgctgttgagcdgtaccgacgcgcaggcgctg gaaatggcggagcgacttcagcaagatgccaggcttgctgcattgtgcaaactcggtctgtcttcgtgg ggtcaattagcggccttcgatgatgtggtgacgacgtttcgcgaacagatatcgttaccgggctcggca cgccgcacccagttgctcaaaaatcttggcttgccacccgatgccgcgccggacgaaatggcggcgcgc atgtccgacttactcctggatctgttcaaccggagcaccttcttttcgacgcagtcgcgtggtctggaa ctgcgcggttcgttgggatcggctgactggaaacatctcaatgcgttcagcgtcggcgtgactggcgag gcgcttcaagtgctcggcgtagagcgcatcggcgatggcaaggacgcgatgccgggttggtcgcgttt tttgtgcgccacgccaaagcctctgtatctgcgacgtcagggatcggaatcgatttcaagccaggcccc ggcactgcggccgtgttattgattcgcgaccgggtcgctcgatgaactcgacgtggggaggctctacc aacctgggtatttccggcgcgtaccagcatggtcagggcgccgccgtgatcatcgcaccgtcgacgatc tccgatttcgtgcggctgttattcgatgtcaaccatcccgataccacccaaatcctgcgcaccggtgtg aacggtggttcgattggtcttgatctgttttgaaaccaatgtgaatgcctctgtgggggcgaacgtcagc
```

-continued

```
gtatcgccattcagcctgagccagaaatatgggccacagaaaccgacggcagatgcggccgtctctgac ccagacaatcggcgcagcaccgcgtcagggtcgttgtcggtaggcgggacggctcaggctggcAcgcac tgggggcaaatggagttgcacctggatcacgcctgggccgatattatcggtctggaatttcaggaccgc acggatttcaatcttgaattcaatagcggcctgaatctgggaggcgcgctgtcttccgcgctgggcgat aaccccaaaagttgataaatgcgtccactggaaacggcaatctgcaactcgccggcatccgcgtcgcg tcaagcgatgtgcagttgccgaccgatgctgtggttgacgacaagcgccgtggccccttcctgtcgacg gccagctataaacgcaccttcgataccgaagttgccaagcctgttacggccggggagtggagccagatg cgccagcgccttgccaaagcctttcctgacaatatcgcagagttgggcgcgctcgattacccaccagg cccggtgagcgtatcgcgaccatcaaacaggtgattgaccgcatacaaggtgcgaaggcgcgtagcgtg gaagccgtcggtgcaatggacggaaaggcattgcaccgtcagcgtttcgatgccgcgagagaaatgtcg aacgccggcaacagcgtatggcgggcgagttccgaaattgagcgcgcctcgatcgtggagatgctgcat cagttgcgtcagcaggaacaaagcgccgtccagaatcacgcccgagccattcccggcgcgcgtgtggaa ttcaacctgttcggtcgtgaatcgctggaaacggtggtctttcacgccatcggtcatctggggcttggc agcaagctgaacgatctggcggagctgcgtcgcaaggtgccgggtctcgatcaggtcatgctgagtttc cagtcgttgcccaaggtcaatcaggtgcgctacgtttttgagatgcgccctcaggcgaggttcgccatc aatgacgcgctactggcgcgcgagcagcaggcatcggcacgtgcgctcggtttgcagggaccctcggga agtgaattgaattggcgcggcgttctggacaagatcaaaaccacgcctgacctttatcggctggcggcg atcgccgtacataacaccgatgaaaacccgtgacctcaagaatagggctgecgetgctgaatgtgtcg gccacaggcgcgacatcgcatcagttgttcgaggcggaaatccagttccgatacggtctgtatgacggt ctgcaagggttgagttgctggaggccggaaacagggcattgcagtcgccgttacgggcattacagcaa tccggtattcaggccctggggcagagaacccaggccggggaggttgcgtatggcccccttcgccgcgc aaagagtcgccgttgcgcaccgcagtggatgctgctgcgctgacaacgagtgacatcgcgcgacaactt gaggttaaagtccagcgcatgaataccgcgcatgagcgtgaggcgaatgctatcagttcgttccagcag gcttatgggatcgcgtccgcgcatctagacaggctgcttttgcgcattcctgaattgccattacctgaa attgatgaccgcgacgtcgatggaggacgtgtgcgcggtacatttgcgtcgctccagcgacatcatcag gcgctggatgacgctataagtgccatgcatcaggccagcgaaaaggtgtacacgatacctggcaagcag gccactcaagagcaagacccggcgctggctcaactgctctctgttgaaaaacgtcggcgttcgctcggg catgccttggaaacactggcgggcagaggggtggaagcgggcacggccacagggcttgaacttaacagg gtctcatcgcaagtgaatgatctggtcgctcgccgggacgcgctgctaaggcagcgtgaaagcggtgtt caggagggcggtctggatagcgaagagctggaaatggaacttcaattgaccacctcagtgctgcagcgg ttgcgcgccgatttgctcggcgagcggcaggcgatggaggctaccgccaaacgcctggatcaggcgagc cgcgctgccctcgaaggtgagcgcagcttcagcgacgccgtgcgtgacagggcgtggggcgaactcgat aacgtgtag
```

The protein encoded by this nucleic acid molecule has an amino acid sequence according to SEQ ID NO: 120 as follows:

```
MVKVTSSGFTANPLSHHADSVSPANSPPQLPEPVHLVDLSESSRKGGMRNRPHASLNSQVLELQAVPSQ

RGKHVRVRSHADGESVINAWLAKRPSVQSETSLDNDGKLVRYTPVNHEPLAPRNEAFFTSVPGMLMAVL

TVHPEMEHGISGDITADAVAARLAEPPIGLLTGIWQSSHDRAYLERGGVVHTANMEERWAPLTLPGINP
```

-continued

```
REPLRMAGLQADGGVYLHNGSQLWRLTETAAESVTTENLPEGAAVRIGAGGEVHGLHEGALHSNGISRP

IELWRPKAGAPGREQSPARPVDLLPLPGGTAALILDDKGRIYHADLKGTGAVEAHRLKLPADFAQGKGW

AVTAMGLSRDDTVHLMLQDQNGRRMSLQRAPGEALFRPAYLLDRPLLLLYTEGLHVPSEAAVQSHVQLD

GHAQLGHIDGVLHYKAAPDQSWERLKQSGGEPLTGLTALYSSPLGFIDRKPVFALVGDARQVVELKLEG

RTSWLPSDAELPRHPAGGPLAVIPDTVALRTSPIAQFDEPVQALAVHGNRRVVALTDSGRLMAADADTP

ARRLPTLQRPIAIAVGLNDQLLVLHHPHSQRPQLKRLSAKDDWEPVPIILPGIVHPSSLRATRTGQIQV

QLGENWHTLLPSMTSHDNQRLPARVKPEPEGDEAPSANFLAGSNALANQQQASRISTPHHDASVVTTLA

GTTANNPLTMASSLQAVVDTTRAQVGALARDVVGAAANSTMPAMAHTLGVVLPPTPQEKRLASFHNEAK

QAYTSGKILFEHLPSLAQVRVASAVGPSDGERFGLSHQQTQRLLTLREGKLEALLRDLRKIGFHEGVIM

GDMGDSDSAHGLVSTTSTPTFRLAELWRRQHSRVDKALSSAGLSRSEDIPPDLNLSINALAGGAALNAD

RMSEREAELLSVLCEVSEKMMRAGVRLPADDGSVDSAHSQAPYGLRTAGLIAGLVDYDALLSSTDAQAL

EMAERLQQDARLAALCKLGLSSWGQLAAFDDVVTTFREQISLPGSARRTQLLKNLGLPPDAAPDEMAAR

MSDLLLDLFNRSTFFSTQSRGLELRGSLGSADWKHLNAFSVGVTGEALQVLGVERIGDGKDGDAGLVAF

FVRHAKASVSATSGIGIDFKPGPGTGGRVIDSRPGRSMNSTWGGSTNLGISGAYQHGQGAAVIIAPSTI

SDFVRLLFDVNHPDTTQILRTGVNGGSIGLDLFETNVNASVGANVSVSPFSLSQKYGPQKPTADAAVSG

PDNRRSTASGSLSVGGTAQAGAHWGQMELHLDHAWADIIGLEFQGRTDPNLEFNSGLNLGGALSSALGD

NPQKLINASTGNGNLQLAGIRVASSDVQLPTDAVVDDKRRGPFLSTASYKRTFDTEVAKPVTAGEWSQM

RQRLAKAFPDNIAELGALDYPTRPGERIATIKQVIDRIQGAKARSVEAVGAMDGKALHRQRFDAAREMS

NAGNSVWRASSEIERASIVEMLHQLRQQEQSAVQNHARAIPGARVEFNLFGRESLETVVFHAIGHLGLG

SKLNDLAELRRKVPGLDQVMLSFQSLPKVNQVRYVFEMRPQARFAINDALLAREQQASARALGLQGPSG

SELNWRGVLDKIKTTPDLYRLAAIAVHNTDENPVTSRIGLPLLNVSATGATSHQLFEAEIQFRYGLYDG

LQGVELLEAGNRALQSPLRALQQSGIQALGQRTQAGEVAYGPPSPRKESPLRTAVDAAALTTSDIARQL

EVKVQRMNTAHEREANAISSFQQAYGIASAHLDRLLLRIPELPLPEIDDRDVDGGRVRGTFASLQRHHQ

ALDDAISAMHQASEKVYTIPGKQATQEQDPALAQLLSVEKRRRSLGHALETLAGRGVEAGTATGLELNR

VSSQVNDLVARRDALLRQRESGVQEGGLDSEELEMELQLTTSVLQRLRADLLGERQAMEATAKRLDQAS

RAALEGERSFSDAVRDRAWGELDNV
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixty-first nucleic acid molecule encodes a HrpA-related protein and has a nucleotide sequence according to SEQ ID NO: 121 as follows:

```
atgaacattacgccgctcacgtcagccgcgggcaagggctcgtccgcacaaggcacagacaaaatttcc attcccaactccacgcgcatgatcaatgccgcttcaatcaagtggttgaataaggtgcgtagcgccatc agtgaccacatccgcaccagcatcgagaaagggaaactgttcgagctcgcctccttgggcagcaacatg ttcggtgtcccggctctttcagcgcgcccctcgacgctccaacctgtgttggcgtttgaggctgacccc aatcacgacctgaaccttgtcagggtctatatgcaggacagcgccggcaagctcactccctgggacccg acgcccaacgcggtcacgacgacgtcgaatccatcagagcctgatgcgcagagcgatacggcttcgtca tcattacctcggcggcctcccgcaggctcggtgctgagtttgctgggcattgcgctggatcacgcgcaa cgccacagtcctcgcgcggacaggtctgccaagggacgacctggccgagaggagaggaacggggcaagg ttcaatgccaagcaaacaaagccgacagaggctgaagcctacggtgatcatcagacacccaatcctgat
```

-continued
```
ttgcacaggcaaaagagacagctcaacgcgttgctgaaagcatcaacagcatgcgagagcagcaaaat ggaatgcaacgcgccgaagggcttctcagagccaaagaagcgttgcaagctcgggaagccgcgcgcaag cagcttctggacgtgctcgaggccatccaggctggccgtgaagactccaccgacaagaagatcagcgcc actgaaaagaacgccacgggcatcaactaccagtga
```

The Hrp-A related protein has an amino acid sequence according to SEQ ID NO: 122 as follows:

```
MNITPLTSAAGKGSSAQGTDKISIPNSTRMINAASIKWLNKVRSAISDHIRTSIEKGKLFELASLGSNM

FGVPALSARPSTLQPVLAFEADPNHDLNLVRVYMQDSAGKLTPWDPTPNAVTTTSNPSEPDAQSDTASS

SLPRRPPAGSVLSLLGIALDHAQRHSPRADRSAKGRPGREERNGARFNAKQTKPTEAEAYGDHQTPNPD

LHRQKETAQRVAESINSMREQQNGMQRAEGLLRAKEALQAREAARKQLLDVLEAIQAGREDSTDKKISA

TEKNATGINYQ
```

The HrpA-related protein, has significant homology, as detected by BLAST analysis (5e-07), to the C-terminal 43 amino acids of HrpA (GenBank Accession AF232004; Alfano et al., *Proc. Natl. Acad. Sci. USA* 97:4856–4861 (2000), each of which is hereby incorporated by reference in its entirety). Expression of the hrpA-related gene is activated by HrpL, as indicated by miniTn5gus mutagenesis. This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. HrpA is the Hrp pilus subunit protein (Roine et al., *Proc. Natl. Acad. Sci. USA* 94:3459–3464 (1997), which is hereby incorporated by reference in its entirety).

A sixty-second nucleic acid encodes ORF01152 and has a nucleotide sequence according to SEQ ID NO: 123 as follows:

```
atgaccttaagaatcaatactcgttctgctaccccggttgtacctctggaaacaggctctacatcgcag ccgacaccaccgccggtcacggcaagagcgactgagcctcccccgtcgccaatcctgcggcgcctaaa tcagcgccaggtgttcagcaagcacacgggctgaagacgcgcatcgctggcaagctttccgaacgtcag accaatttcagtctcgggattcccggcactggtcgtactctcaaccggcccttgcgcagcgggattccg gaggaaggtgagcaggtatcgaacgaggagagtcatgatccgttgctcaaggaagcgcatgaactgcag cgtatggtggagtcggcgctgacccatctgaaggcggcaccgacgtctctctgggagcgtcccgcccct tcaacggtaaggcgtattaccaccaagattttccgtggctaaagcctgcccgctgcgcgaagtcgca agcaatggcagcaacgccaagaccaagatcaagatcaactcacagcaaagccctgaaccatcgcagcg gcggtgaaagagctgagcacccggctcgatcaccagagcaaggtgctcgccacagccacccacgcactg gtcgctgcgcgtgagcatcttgaatcgctcgaacaggccacccgccctcgtcgaccgaaccactggac catgccagggctcgcgttcaacaagccgactccaccacccgcctggccagtcagcaacttcgtgagctg attcagggtacagacgtgttgcaactgggcgcgctgagtgaagggcaggatcaggttgaacagaaagcc gagttttct
```

The protein encoded by the nucleic acid molecule has an amino acid sequence according to SEQ ID NO: 124 as follows:

```
MTLRINTRSATPVVPLETGSTSQPTPPPVTARATEPPPVANPAAPKSAPGVQQAHGLKTRIAGKLSERQ

TNFSLGIPGTGRTLNRPLRSGIPEEGEQVSNEESHDPLLKEAHELQRMVESALTHLKAAPTSLWERPAP

STVRRITTKIFPWLKPAPLREVASNGSNAKTKIKINSQQSPETIAAAVKELSTRLDHQSKVLATATHAL
```

-continued

VAAREHLESLEQATPPSSTEPLDHARARVQQADSTTRLASQQLRELIQGTDVLQLGALSEGQDQVEQKA

EFS

Expression of ORF01152 is activated by HrpL, as indicated by miniTn5gus mutagenesis (Fouts et al., *Proc. Natl. Acad. Sci. USA* 99(4):2275–2280 (2001), which is hereby incorporated by reference in its entirety). This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixty-third nucleic acid molecule encodes HopPtoF (formerly AvrPphF$_{Pto}$ ORF2) and has a nucleotide sequence according to SEQ ID NO: 125 as follows:

```
ataggtaatatttgcggcacctcgggctcacgtcatgtgtatagcccatcccatacacaacgaataact
tcagctccctctacatccactcatgttggtggagatacactgacatccattcatcagctttcgcatagt
cagagagagcagtttctgaacatgcatgatccaatgagagtaatgggacttgaccatgataccgagctt
ttcagaacgacggatagtcgctatataaaaaacgataaactcgcgggcaatccacaatccatggcgagt
atccttatgcatgaagaactgcgccccaatcgttttgccagccatacaggtgcccaaccacacgaagca
agggcgtacgttccgaaaagaataaaagccaccgatctaggagttccatcactgaacgtaatgactggc
tcgctagcgcgagacggaattagagcttatgatcacatgagtgataatcaggtctctgtcaaaatgcga
ctgggagattttctcgaaaggggtggcaaggtctatgccgacgcttcgtctgtagctgacgatgggaa
acatcacaagctctgattgtcacattgcccaaaggacagaaagtgccggtcgaaagggtctga
```

HopPtoF has an amino acid sequence according to SEQ ID NO: 126 as follows:

MGNICGTSGSRHVYSPSHTQRITSAPSTSTHVGGDTLTSIHQLSHSQREQ

FLNMHDPMRVMGLDHDTELFRTTDSRYIKNDKLAGNPQSMASILMHEELR

PNRFASHTGAQPHEARAYVPKRIKATDLGVPSLNVMTGSLARDGIRAYDH

MSDNQVSVKMRLGDFLERGGKVYADASSVADDGETSQALIVTLPKGQKVP

VERV

Contrary to the previously identified sequence of hopPtoF (see U.S. patent application Ser. No. 10/114,828 to Collmer et al., filed Apr. 2, 2002, which is hereby incorporated by reference in its entirety), hopPtoF possesses a rare ATA start codon, which is believed to be involved in regulating protein synthesis in DC3000. HopPtoF has been shown to be expressed by DC3000 and it has been shown to be translocated in planta, where it is localized to the plant plasma membrane and has a role in virulence. HopPtoF has also been shown to cause a hypersensitive response in *Arabidopsis* Col-0. The homologous *Pseudomonas syringae* pv. *phaseolicola* AvrPpbF effector protein has been shown to play a role in both development of the hypersensitive response and virulence in several plants (Tsiamis et al., "Cultivar-specific avirulence and virulence functions assigned to avrPphF in *Pseudomonas syringae* pv. *phaseolicola*, the cause of bean halo-blight disease," *EMBO J.* 19(13):3204–3214 (2000), which is hereby incorporated by reference in its entirety). Finally, HopPtoF has since been shown to be cytotoxic to eukaryotic cells, specifically cultured mammalian CHO and HEK293 cell lines.

A sixty-fourth nucleic acid molecule encodes IaaL$_{Pto}$ and has a nucleic acid sequence according to SEQ ID NO: 208 as follows:

```
atgactgcctacgatgtagaaaaggaatggagcagaatttccaatactgccgctaaaactcaccagaac
aacgattttgaaggtttcacctaccaggacttcagaacccacgtaccgatcatggacaaggaaggcttc
gcggcacaaaccgaacgctgccttgagcgcaacgagcgcaactgcctgatcggctttaccagtggcacc
agcggcaacctcaaacgctgttattactactacgactgtgaagtcgatgaagacagttcccgctccaac
gtcttccgcagcaatggtttcattcaacccggtgatcgctgcgccaacctgttcaccatcaacctgttt
tctgccctgaacaacatcaccaccatgatggccggtaactgcggtgcgcatgtggtgtccgtaggcgat
```

-continued
```
atcaccctgctgaccaagagtcacttcgaggcgctcaactcgatcaagctcaacgtactgctcggcgta ccctcgaccatcctgcagttcatcgatgccatgcagcagcacggtgtgcacatcgatatcgaaaaggtc gtcttcaatggcgagggcctgaaaacctttcagaagaaaatcatcagggaagcctttggcgaacaggtc tccatcgtcggcgtatatggcagttccgagggcggcattctgggtttcaccaacagcccttgccacacc gaatacgagtttctttccgacaaatacttcatcgagaagaaggcgacagcatcctcatcacctcgttg acccgcgagaacttcacaccgctgctccggtatcgcctgggagacaccgcaacgctttcgctgaaaggc gacaagctctatttgactgacatccagcgggaggacatgagcttcaacttcatgggcaacctcattggt ctgggcatcattcaacaagcgatcaaacagacactgggccgcacgctggaaatccaggttcacctgtca gtgactgatgcgcgcaaagaactggtgaccgttttcgttcaggcctcggaagtcaacgaagatgaacgc gccagaatcgaaacagccatcgccgatattccggacatcaacgaggcctatcagaaagaccagggcagc gtgctggttgtgcgcaaggatgccagagactacgccgtctcggagcgaggcaaaatgctctacatcatt gaccgcaggaat
```

IaaL$_{Pto}$ has an amino acid sequence according to SEQ ID NO: 209 as follows:

```
MTAYDVEKEWSRISNTAAKTHQNNDFEGFTYQDFRTHVPIMDKEGFAAQTERCLERNERNCLIGFTSGT

SGNLKRCYYYYDCEVDEDSSRSNVFRSNGFIQPGDRCANLFTINLFSALNNITTMMAGNCGAHVVSVGD

ITLLTKSHFEALNSIKLNVLLGVPSTILQFIDAMQQHGVHIDIEKVVFNGEGLKTFQKKIIREAFGEQV

SIVGVYGSSEGGILGFTNSPCHTEYEFLSDKYFIEKEGDSILITSLTRENFTPLLRYRLGDTATLSLKG

DKLYLTDIQREDMSFNFMGNLIGLGIIQQAIKQTLGRTLEIQVHLSVTDARKELVTVFVQASEVNEDER

ARIETAIADIPDINEAYQKDQGSVLVVRKDARDYAVSERGKMLYIIDRRN
```

IaaL$_{Pto}$ has significant homology, as detected by BLAST analysis (0), to IAA-lysine synthetase (GenBank accession M35373; Roberto et al., *Proc. Natl. Acad. Sci. USA* 87: 5797–5801 (1990), each of which is hereby incorporated by reference in its entirety).

Fragments of the above-identified proteins or polypeptides as well as fragments of full length proteins can also be used according to the present invention.

Suitable fragments can be produced by several means. Subclones of the gene encoding a known protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for activity, e.g., as a product required for pathogen virulence.

In another approach, based on knowledge of the primary structure of the protein, fragments of the protein-coding gene may be synthesized using the PCR technique together with specific sets of primers chosen to represent particular portions of the protein. Erlich, H. A., et al., "Recent Advances in the Polymerase Chain Reaction," *Science* 252: 1643–51 (1991), which is hereby incorporated by reference. These can then be cloned into an appropriate vector for expression of a truncated protein or polypeptide from bacterial cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active virulence proteins or polypeptides.

Chemical synthesis can also be used to make suitable fragments. Such a synthesis is carried out using known amino acid sequences for the polyppetide being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The proteins or polypeptides used in accordance with the present invention are preferably produced in purified form (preferably at least about 80%, more preferably 90%, pure)

by conventional techniques. Typically, the protein or polypeptide of the present invention is secreted into the growth medium of recombinant host cells (discussed infra). Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest is subjected to gel filtration in an appropriately sized dextran or polyacrylamide column to separate the proteins. If necessary, the protein fraction may be further purified by HPLC.

Other DNA molecules encoding other effector proteins or polypeptides can also be identified by determining whether such DNA molecules hybridize under stringent conditions to a nucleic acid molecule as identified above. An example of suitable stringency conditions is when hybridization is carried out for about 8 to about 20 hours at a temperature of about 37° C. using a hybridization medium that includes 0.9× sodium citrate ("SSC") buffer, followed by washing for about 5 minutes to about 1 hour with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. up to and including about 65° C. (inclusive of all temperature in such range) for about 8 up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 µg/ml *E. coli* DNA, followed by washing for about 5 minutes to about 1 hour, at about 42° C. up to and including about 65° C. (inclusive of all temperatures in such range) in a 0.2×SSC buffer. Such hybridizing nucleic acid molecules preferably hybridize over substantially over their entire length. Moreover, such hybridizing nucleic acid molecules does not include previously reported nucleic acid molecules that encode effector proteins.

The delivery of effector proteins or polypeptides can be achieved in several ways: (1) as a stable transgene; (2) transiently expressed via *Agrobacterium* or viral vectors; (3) delivered by the type III secretion systems of disarmed pathogens or recombinant nonpathogenic bacteria which express a functional, heterologous type III secretion system; or (4) delivered via topical application followed by TAT protein transduction domain-mediated spontaneous uptake into cells. Each of these is discussed infra.

The DNA molecule encoding the protein or polypeptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Because it is desirable for recombinant host cells to secrete the encoded protein or polypeptide, it is preferable that the host cell also possess a functional type III secretion system. The type III secretion system can be heterologous to host cell (Ham et al., "A Cloned *Erwinia chrysanthemi* Hrp (Type III Protein Secretion) System Functions in *Escherichia coli* to Deliver *Pseudomonas syringae* Avr Signals to Plant Cells and Secrete Avr Proteins in Culture," *Microbiol.* 95:10206–10211 (1998), which is hereby incorporated by reference in its entirety) or the host cell can naturally possess a type III secretion system. Host cells which naturally contain a type III secretion system include many pathogenic Gram-negative bacterium, such as numerous *Erwinia* species, *Pseudomonas* species, *Xanthomonas* species, etc. Other type III secretion systems are known and still others are continually being identified. Pathogenic bacteria that can be utilized to deliver effector proteins or polypeptides are preferably disarmed according to known techniques, i.e., as described above. Alternatively, isolation of the effector protein or polypeptide from the host cell or growth medium can be carried out as described above.

Another aspect of the present invention relates to a transgenic plant which express a protein or polypeptide of the present invention and methods of making the same.

In order to express the DNA molecule in isolated plant cells or tissue or whole plants, a plant expressible promoter is needed. Any plant-expressible promoter can be utilized regardless of its origin, i.e., viral, bacterial, plant, etc. Without limitation, two suitable promoters include the nopaline synthase promoter (Fraley et al., *Proc. Natl. Acad. Sci. USA* 80:4803–4807 (1983), which is hereby incorporated by reference in its entirety) and the cauliflower mosaic virus 35S promoter (O'Dell et al., "Identification of DNA Sequences Required for Activity of the Cauliflower Mosaic Virus 35S Promoter," *Nature*, 313(6005):810–812 (1985), which is hereby incorporated by reference in its entirety). Both of these promoters yield constitutive expression of coding sequences under their regulatory control.

While constitutive expression is generally suitable for expression of the DNA molecule, it should be apparent to those of skill in the art that temporally or tissue regulated expression may also be desirable, in which case any regulated promoter can be selected to achieve the desired expression. Typically, the temporally or tissue regulated promoters will be used in connection with the DNA molecule that are expressed at only certain stages of development or only in certain tissues.

In some plants, it may also be desirable to use promoters which are responsive to pathogen infiltration or stress. For example, it may be desirable to limit expression of the protein or polypeptide in response to infection by a particular pathogen of the plant. One example of a pathogen-inducible promoter is the gst1 promoter from potato, which is described in U.S. Pat. Nos. 5,750,874 and 5,723,760 to Strittmayer et al., each of which is hereby incorporated by reference in its entirety.

Expression of the DNA molecule in isolated plant cells or tissue or whole plants also requires appropriate transcription termination and polyadenylation of mRNA. Any 3' regulatory region suitable for use in plant cells or tissue can be operably linked to the first and second DNA molecules. A number of 3' regulatory regions are known to be operable in plants. Exemplary 3' regulatory regions include, without limitation, the nopaline synthase 3' regulatory region (Fraley et al., *Proc. Nat'l. Acad. Sci. USA*, 80:4803–4807 (1983), which is hereby incorporated by reference in its entirety) and the cauliflower mosaic virus 3' regulatory region (Odell, et al., *Nature*, 313(6005):810–812 (1985), which is hereby incorporated by reference in its entirety).

The promoter and a 3' regulatory region can readily be ligated to the DNA molecule using well known molecular cloning techniques described in Sambrook et al., *Molecular Cloning: A Laboratory Manual*, Second Edition, Cold Spring Harbor Press, NY (1989), which is hereby incorporated by reference in its entirety.

One approach to transforming plant cells with a DNA molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., each of which is hereby incorporated by reference in its entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the DNA molecule into plant cells is fusion of protoplasts with other entities, either minicells, cells, lysosomes, or other fusible lipid-surfaced bodies that contain the DNA molecule. Fraley et al., *Proc. Natl. Acad. Sci. USA*, 79:1859–63 (1982), which is hereby incorporated by reference in its entirety.

The DNA molecule may also be introduced into the plant cells by electroporation. Fromm, et al., *Proc. Natl. Acad. Sci. USA*, 82:5824 (1985), which is hereby incorporated by reference in its entirety. In this technique, plant protoplasts are electroporated in the presence of plasmids containing the DNA molecule. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *Agrobacterium rhizogenes* previously transformed with the DNA molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA molecule of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, *Science*, 237:1176–83 (1987), which is hereby incorporated by reference in its entirety.

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the DNA molecule of the present invention. Suitable selection markers include, without limitation, markers coding for antibiotic resistance, such as kanamycin resistance (Fraley et al., *Proc. Natl. Acad. Sci. USA*, 80:4803–4807 (1983), which is hereby incorporated by reference in its entirety). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that includes a DNA molecule of the present invention, wherein the promoter induces transcription of the first DNA molecule in response to infection of the plant by an oomycete. Preferably, the DNA molecule is stably inserted into the genome of the transgenic plant of the present invention.

Plant regeneration from cultured protoplasts is described in Evans, et al., *Handbook of Plant Cell Cultures, Vol. 1:* (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), each of which is hereby incorporated by reference in their entirety.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA molecule is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Diseases caused by the vast majority of bacterial pathogens result in limited lesions. That is, even when everything is working in the pathogen's favor (e.g., no triggering of the hypersensitive response because of R-gene detection of one of the effectors), the parasitic process still triggers defenses after a couple of days, which then stops the infection from spreading. Thus, the very same effectors that enable parasitism to proceed must also eventually trigger defenses. Therefore, premature expression of these effectors is believed to "turn on" plant defenses earlier (i.e., prior to infection) and make the plant resistant to either the specific bacteria from which the effector protein was obtained or many pathogens. An advantage of this approach is that it involves natural products and plants seem highly sensitive to pathogen effector proteins.

According to one embodiment, a transgenic plant is provided that contains a heterologous DNA molecule of the present invention. When the heterologous DNA molecule is expressed in the transgenic plant, plant defenses are activated, imparting disease resistance to the transgenic plant. The transgenic plant can also contain an R-gene whose product is activated by the protein or polypeptide product of the heterologous DNA molecule. The R gene can be naturally occurring in the plant or heterologously inserted therein. By disease resistance, it is believed that the effector proteins of the present invention can impart to plants resistance against bacterial, viral, and/or fungal diseases.

In addition to imparting disease resistance, it is believed that stimulation of plant defenses in transgenic plants of the present invention will also result in a simultaneous enhancement in growth and resistance to insects.

Alternative to transgenic expression is topical application of the effector proteins to plants. The embodiments of the present invention where the effector polypeptide or protein is applied to the plant can be carried out in a number of ways, including: 1) application of an isolated protein (or composition containing the same) or 2) application of bacteria which do not cause disease and are transformed with a gene encoding the effector protein of the present invention. In the latter embodiment, the effector protein can be applied to plants by applying bacteria containing the DNA molecule encoding the effector protein. Such bacteria are preferably capable of secreting or exporting the protein so that the protein can contact plant cells. In these embodiments, the protein is produced by the bacteria in planta.

Such topical application can be carried out using an effector-TAT protein, which will afford transduction domain-mediated spontaneous uptake of the effector protein into cells. Basically, this is carried out by fusing an 11-amino acid peptide (YGRKKRRQRRR, SEQ ID No: 127) by standard rDNA techniques to the N-terminus of the effector protein, and the resulting tagged protein is taken up into animal cells by a poorly understood process. This peptide is the protein transduction domain (PTD) of the human immunodeficiency virus (HIV) TAT protein (Schwarze et al., "Protein transduction: unrestricted delivery into all cells?" *Trends Cell Biol.* 10:290–295 (2000), which is hereby incorporated by reference in its entirety). Other PTDs are known and can be used for this purpose (Prochiantz, "Messenger proteins: homeoproteins, TAT and others," *Curr. Opin. Cell Biol.* 12:400–406 (2000), which is hereby incorporated by reference in its entirety). See PCT Application Publication No. WO 01/19393 to Collmer et al., which is hereby incorporated by reference in its entirety.

When the effector protein is topically applied to plants, it can be applied as a composition, which includes a carrier in the form, e.g., of water, aqueous solutions, slurries, or dry powders. In this embodiment, the composition contains greater than about 5 nM of the protein of the present invention.

Although not required, this composition may contain additional additives including fertilizer, insecticide, fungicide, nematicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and, in some instances, abrading agents. These materials can be used to facilitate the process of the present invention.

According to one embodiment, a transgenic plant including a heterologous DNA molecule of the present invention expresses one or more effector proteins, wherein the transgenic plant is capable of supporting growth of compatible nonpathogenic bacteria. The compatible nonpathogenic bacteria can be naturally occurring or it can be recombinant. Preferably, the nonpathogenic bacteria is recombinant and expresses one or more useful products. Thus, the transgenic plant becomes a green factory for producing desirable products. Desirable products include, without limitation, products that can enhance the nutritional quality of the plant or products that are desirable in isolated form. If desired in isolated form, the product can be isolated from plant tissues. To prevent competition between the non-pathogenic bacteria which express the desired product and those that do not, it is possible to tailor the needs of recombinant, non-pathogenic bacteria so that only they are capable if living in plant tissues expressing a particular effector protein or polypeptide of the present invention.

The effector proteins or polypeptides of the present invention are believed to alter the plant physiology by shifting metabolic pathways to benefit the parasite and by activating or suppressing cell death pathways. Thus, they may also provide useful tools for efficiently altering the nutrient content of plants and delaying or triggering senescence. There are agricultural applications for all of these possible effects.

Thus, a further aspect of the present invention relates more generally to a method of modifying a metabolic pathway in a cell by introducing into the cell an effector protein or polypeptide of the present invention which interacts with a native cellular protein involved in a metabolic pathway of the cell. As a result of introducing the protein or polypeptide into the cell, the protein or polypeptide modifies the metabolic pathway through its interaction with the native cellular protein. By way of example, it is believed that HopPtoD2 is a tyrosine phosphatase that interacts with MAPK.

Yet another aspect of the present invention relates to a method of causing eukaryotic cell death which is carried out by introducing into a eukaryotic cell a protein which is cytotoxic and causes cell death. The eukaryotic cell which is treated can be either in vitro or in vivo. When treating eukaryotic cells in vivo, a number of different protein- or DNA-delivery systems can be employed to introduce the effector protein into the target eukaryotic cell.

Another aspect of the present invention relates to a method of inhibiting programmed cell death which is carried out by introducing into a eukaryotic cell susceptible to programmed cell death, a protein that is a hypersensitive response suppressor, where the introduction thereof is performed under conditions effective to inhibit programmed cell death of the eukaryotic cell. By inhibiting programmed cell death, it is intended that such inhibition includes both delaying the occurrence of programmed cell death as well as preventing programmed cell death. The eukaryotic cell which is treated can be either in vitro or in vivo. When treating eukaryotic cells in vivo, a number of different protein- or DNA-delivery systems can be employed to introduce the effector protein into the target eukaryotic cell. By way of example, hypersensitive response suppressor proteins include, without limitation, AvrPphE$_{Pto}$, AvrPpiB1$_{Pto}$, AvrPtoB, HopPtoD1, HopPtoE, HopPtoF (previously designated AvrPphF$_{Pto}$ ORF2), and HopPtoK.

Because programmed cell death (including apoptosis) is involved in the pathogenesis of a variety of diseases, the HR suppressor proteins of the present invention can be used in the regulation thereof and, thus, as therapeutic agents in the intervention of a wide array of disease processes or maladies (see Rudin & Thompson, *Ann. Rev. Med.* 48:267–81 (1997), which is hereby incorporated by reference in its entirety).

The protein- or DNA-delivery systems can be provided in the form of pharmaceutical compositions which include the delivery system in a pharmaceutically acceptable carrier, which may include suitable excipients or stabilizers. The dosage can be in solid or liquid form, such as powders, solutions, suspensions, or emulsions. Typically, the composition will contain from about 0.01 to 99 percent, preferably from about 20 to 75 percent of active compound(s), together with the carrier, excipient, stabilizer, etc.

The compositions of the present invention are preferably administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Alternatively, the effector proteins can also be delivered via solution or suspension packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art.

One approach for delivering an effector protein into cells involves the use of liposomes. Basically, this involves providing a liposome which includes that effector protein to be delivered, and then contacting the target cell with the liposome under conditions effective for delivery of the effector protein into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), each of which is hereby incorporated by reference in their entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238–252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in their entirety.

An alternative approach for delivery of effector proteins involves the conjugation of the desired effector protein to a polymer that is stabilized to avoid enzymatic degradation of the conjugated effector protein. Conjugated proteins or polypeptides of this type are described in U.S. Pat. No. 5,681,811 to Ekwuribe, which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a ligand domain and, e.g., an effector protein of the present invention. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein, which allows the effector protein to destabilize the cell checkpoint control mechanism, affording its cytotoxic effects.

When it is desirable to achieve heterologous expression of an effector protein of the present invention in a target cell, DNA molecules encoding the desired effector protein can be delivered into the cell. Basically, this includes providing a nucleic acid molecule encoding the effector protein and then introducing the nucleic acid molecule into the cell under conditions effective to express the effector protein in the cell. Preferably, this is achieved by inserting the nucleic acid molecule into an expression vector before it is introduced into the cell.

When transforming mammalian cells for heterologous expression of an effector protein, an adenovirus vector can be employed. Adenovirus gene delivery vehicles can be readily prepared and utilized given the disclosure provided in Berkner, Biotechniques 6:616–627 (1988) and Rosenfeld et al., Science 252:431–434 (1991), WO 93/07283, WO 93/06223, and WO 93/07282, each of which is hereby incorporated by reference in their entirety. Adeno-associated viral gene delivery vehicles can be constructed and used to deliver a gene to cells. The use of adeno-associated viral gene delivery vehicles in vitro is described in Chatterjee et al., Science 258:1485–1488 (1992); Walsh et al., Proc. Nat'l. Acad. Sci. 89:7257–7261 (1992); Walsh et al., J. Clin Invest. 94:1440–1448 (1994); Flotte et al., J. Biol. Chem. 268: 3781–3790 (1993); Ponnazhagan et al., J. Exp. Med. 179: 733–738 (1994); Miller et al., Proc. Nat'l Acad. Sci. 91:10183–10187 (1994); Einerhand et al., Gene Ther. 2:336–343 (1995); Luo et al., Exp. Hematol. 23:1261–1267 (1995); and Zhou et al., Gene Ther. 3:223–229 (1996), each of which is hereby incorporated by reference in their entirety. In vivo use of these vehicles is described in Flotte et al., Proc. Nat'l Acad. Sci. 90:10613–10617 (1993); and Kaplitt et al., Nature Genet. 8:148–153 (1994), each of which is hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; and U.S. Pat. No. 5,885,808 to Spooner et al.; and U.S. Pat. No. 5,871,727 to Curiel, each of which is hereby incorporated by reference in their entirety).

Retroviral vectors which have been modified to form infective transformation systems can also be used to deliver nucleic acid encoding a desired effector protein into a target cell. One such type of retroviral vector is disclosed in U.S. Pat. No. 5,849,586 to Kriegler et al., which is hereby incorporated by reference in its entirety.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired effector protein, thereby causing cytotoxic effects.

Particularly preferred is use of the effector proteins of the present invention to treat a cancerous condition (i.e., the eukaryotic cell which is affected is a cancer cell). This can be carried out by introducing or administering to a patient, a cytotoxic Pseudomonas protein under conditions effective to inhibit cancer cell division, thereby treating the cancer condition.

By introducing, it is intended that the effector protein is administered to the patient, preferably in the form of a composition which will target delivery to the cancer cells. Alternatively, when using DNA-based therapies, it is intended that the introducing be carried out by administering a targeted DNA delivery system to the patient such that the cancer cells are targeted and the effector protein is expressed therein. A number of targeted delivery systems are known in the art and can be employed herewith.

EXAMPLES

The following Examples are intended to be illustrative and in no way are intended to limit the scope of the present invention.

Materials & Methods for Example 1–2

Strains and Media: Escherichia coli strain DH5α was used for cloning experiments, and P. s. tomato DC3000 or derivatives and P. s. phaseolicola 3121 were used for secretion or translocation assays, respectively. Routine culture conditions for bacteria are similar to those described (van Dijk et al., J. Bacteriol. 181:4790–4797 (1999), which is hereby incorporated by reference in its entirety). Antibiotics were used at the following concentrations: 100 μg/ml ampicillin, 20 μg/ml chloramphenicol, 10 μg/ml gentamicin, 100 μg/ml rifampicin, 10 μg/ml kanamycin, and 20 μg/ml tetracycline.

Secretion Assays: All of the secretion assays used P. s. tomato DC3000 strains carrying a pML123 derivative containing a PCR-cloned ORF (encoding a candidate Hrp-secreted protein) fused to nucleotide sequences that encoded either the hemagglutinin or FLAG epitopes along with their native ribosome binding sites (Labes et al., Gene 89:37–46 (1990), which is hereby incorporated by reference in its entirety). Details about the primers and the constructs are provided below.

HopPtoE: The hopPtoE gene was cloned using forward primer
(agtaggatccatagaaaaataccataggggtgca, SEQ ID No: 128) containing a BamHI site and reverse primer
(agtatctagatcacttgtcatcgtcgtccttgtagtcgtcaatcacatgcgcttg, SEQ ID No: 129) containing an XbaI site and FLAG epitope codons. The hopPtoC gene was cloned into plasmid vector pLN162.

HopPtoG: The hopPtoG gene was cloned using forward primer
(atgcggatcccgtatgaccttgtaaaat, SEQ ID No: 130) containing a BamHI site and reverse primer
(atgctctagatcaagcgtaatctggaa-catcgtatgggtagccgttgtaaaactgctt, SEQ ID No: 131) containing an XbaI site and HA epitope codons. The hopPtoG gene was cloned into plasmid vector pLN131.

HopPtoH: The hopPtoH gene was cloned using forward primer
(agtcggatccgataatcctggatgatccattg, SEQ ID No: 132) containing a BamHI site and reverse primer
(agtcctcgagtcacttgtcatcgtcgtccttgtagtcttgatgtgccctgtactt, SEQ ID No: 133) containing an XhoI site and FLAG epitope codons. The hopPtoH gene was cloned into plasmid vector pLN150.

HopPtoI: The hopPtoI gene was cloned using forward primer
(agtaaagcttacgggcaggtattgcaag, SEQ ID No: 134) containing a BamHI site and reverse primer
(agtatctagatcacttgtcatcgtcgtccttgtagtcttttttgggcagccagcg, SEQ ID No: 135) containing an XbaI site and FLAG epitope codons. The hopPtoC gene was cloned into plasmid vector pLN165.

HopPtoL: The hopPtoL gene was cloned using forward primer
(agtaggatcctgcctccaactattggct, SEQ ID No: 136) containing a BamHI site and reverse primer (agtatctagatcacttgtcatcgtcgtccttgtagtctctcgctttgaacgcctg, SEQ ID No: 137) containing an XbaI site and FLAG epitope codons. The hopPtoL gene was cloned into plasmid vector pLN224.

HopPtoS1: The hopPtoS1 gene was cloned using forward primer (ataggatcccgagaacggcgcggacgtg, SEQ ID No: 138) containing a BamHI site and reverse primer (atatctagatcatttatcatcatcatctttataatcctcgtcagagctctctgc, SEQ ID No: 139) containing an XbaI site and FLAG epitope codons. The hopPtoC gene was cloned into plasmid vector pLN142.

HopPtoS2: The hopPtoS2 gene was cloned using forward primer (gatggatccacgcacataacaacggtg, SEQ ID No: 140) containing a BamHI site and reverse primer (atatctagatcatttatcatcatcatctttataatcaatctgacttaatac, SEQ ID No: 141) containing an XbaI site and FLAG epitope codons. The hopPtoC gene was cloned into plasmid vector pLN223.

Constructs carrying different epitope-tagged ORFs were electroporated into DC3000 and a DC3000 hrcC mutant and grown in Hrp-inducing conditions (Yuan & He, *J. Bacteriol.* 178:6399–6402 (1996), which is hereby incorporated by reference in its entirety). Additionally, all of the DC3000 strains also carried pCPP2318, a construct that contains blaM lacking signal peptide sequences (Charkowski et al., *J. Bacteriol.* 179:3866–3874 (1997), which is hereby incorporated by reference in its entirety). DC3000 cultures were separated into cell-bound and supernatant fractions as described (van Dijk et al., *J. Bacteriol.* 181:4790–4797 (1999), which is hereby incorporated by reference in its entirety). Proteins were separated with SDS/PAGE by standard procedures (Sambrook et al., *Molecular Cloning: A Laboratory Manual*, Cold Spring Harbor Lab Press, Plainview, N.Y. (1989), which is hereby incorporated by reference in its entirety), transferred to polyvinylidene difluoride membranes, and immunoblotted by using anti-FLAG (Sigma), anti-hemagglutinin (Roche Molecular Biochemicals), or anti-β-lactamase (5 Prime→3 Prime) as primary antibodies. Primary antibodies were recognized by goat anti-rabbit IgG-alkaline phosphatase conjugate (Sigma), which were visualized by chemiluminescence by using a Western-Light chemiluminescence detection system (Tropix, Bedford, Mass.) and X-Omat x-ray film.

Plant Materials and Translocation Assays: *Arabidopsis thaliana* accession Columbia (Col-0) and rps2-201 (Kunkel et al., *Plant Cell* 5:865–875 (1993), which is hereby incorporated by reference in its entirety) mutant plants were grown in a growth chamber with 12 h of light at 24° C. (22° C. at night) and 70% relative humidity. Details about the primers and constructs described below.

AvrRpt2: The avrRpt2 gene was cloned using forward primer (attggtacctctagaggatccaaccttcaatctgaa, SEQ ID No: 142) containing KpnI, XbaI, and BamHI sites and reverse primer (atgtcgacttagcggtagagcattgcg, SEQ ID No: 143) containing an SalI site. The avrRpt2 gene was cloned into plasmid vector pÑavrRpt2.

HopPtoG-AvrRpt2: The chimeric gene was cloned using forward primer (gcgaattcgttagttgattttgtctagcg, SEQ ID NO: 144) containing an EcoRI site, and reverse primer (gaggatccgccgttgtaaaactgcttaga, SEQ ID NO: 145) containing a BamHI site. The chimeric gene was cloned into plasmid vector phopPtoGÑavrRpt2.

The partial avrRpt2 gene with the N-terminal 40 codons deleted was amplified by using standard PCR procedures and cloned into pMOD (Epicentre Technologies, Madison, Wis.). After confirmation by sequence analysis, it was cloned into the KpnI and SalI sites of the broad-host-plasmid pLK, resulting in pΔavrRpt2. DNA fragments spanning 200 bp upstream of the Hrp boxes and the complete ORF for hopPtoG was cloned into pΔavrRpt2 to produce phopPtoG-ΔavrRpt2. The construct was introduced in *P. s. phaseolicola* 3121 by electroporation. Bacterial strains in 10 mM $MgCl_2$ at a cell density of $10^8$ colony-forming units/ml were infiltrated into *A. thaliana* Col-0 and Col-0 rps2-201 plants with a needleless syringe.

Identification of Putative Effector Protein ORFs: Several approaches were employed for the identification of putative effector proteins, including the use of a Hidden Markov Model to analyze regions upstream of ORFs for hrp-related promoters (Fouts et al., *Proc. Natl. Acad. Sci. USA* 99(4): 2275–2280 (2001), which is hereby incorporated by reference in its entirety), a miniTn5gus transposon-based assay which identifies HrpL-activated insertions, via insertions downstream of Hrp boxes (Fouts et al., *Proc. Natl. Acad. Sci. USA* 99(4):2275–2280 (2001), which is hereby incorporated by reference in its entirety), and computer search for candidate Hrp-secreted proteins based on an algorithm that identifies compliance or non-compliance with export signal rules of known effector proteins (N-terminal 50 amino acids) (Petnicki-Ocwieja et al., *Proc. Natl. Acad. Sci. USA* 99:7652–7657 (2002); U.S. patent application Ser. No. 10/341,180 to Collmer et al., filed Jan. 13, 2003, each of which is hereby incorporated by reference in its entirety).

Materials & Methods for Example 3–8

Bacterial strains, plasmids, and media: *Escherichia coli* strains DH5α and DB3.1. (Invitrogen) were used for general cloning and Gateway technology manipulations, respectively. *P. s.* pv. *tomato* DC3000 and *P. fluorescens* strains were grown in King's B (KB) broth at 30° C. (King et al., *J. Lab. Med.* 22:301–307 (1954), which is hereby incorporated by reference in its entirety). *E. coli* and *Agrobacterium tumefaciens* C58C1 were grown in LB broth at 37° C. or 30° C., respectively. Unless otherwise noted, constructs used were made by PCR and Table 1 below includes a list of nucleotide primer sequences that were used. The pHIR11 derivative, pLN18, which lacks shcA and hopPsyA was generated as described previously (van Dijk et al., *Mol. Microbiol.* 44:1469–1481 (2002), which is hereby incorporated by reference in its entirety). Briefly, 2 kb regions upstream and downstream of shcA and hopPsyA were PCR cloned into pBluescript-II KS on either side of an nptII antibiotic marker. When transformed into the *E. coli* strain C2110 (Kahn and Hanawalt, *J. Mol. Biol.* 128:501–525 (1979), which is hereby incorporated by reference in its entirety) containing pHIR11, this construct recombined into pHIR11 because ColE1 plasmids, such as pBluescript-II KS, cannot replicate in this polA mutant at 42° C. When this strain was grown at 30° C., the ColE1 replicon replicated, forcing it to recombine out of pHIR11. pHIR11 derivatives that lacked shcA and hopPsyA were identified with PCR. Antibiotics were used at the following concentrations (μg/ml): rifampicin, 100; ampicillin, 100; gentamicin, 10; kanamycin, 50; tetracycline, 20; nalidixic acid, 20; and spectinomycin 50.

TABLE 1

Additional information on plasmid constructions

| Gene Name | Primer Nucleotide Sequences (5'→3') and Other Relevant Features | SEQ ID NO: | Parent Plasmid | Plasmid Construct |
|---|---|---|---|---|
| shcA and hopPsyA | P21: gtaaaacgacggccagt | 146 | pHIR11 | pLN18 |
|  | P23: atgagaattcgcatctccatgcatctt (Eco RI) | 147 |  |  |
|  | P227: cggactcgagctcagggcgcgaaactga (Xho I) | 148 |  |  |
|  | P228: gtatggtaccccgacctggcaaccgcag (Kpn I) | 149 |  |  |
| avrPto | P792: agtcctcgagactaaagagggtatacgaatgggaaatata (Xho I) | 150 | pBBR1 MCS2 | pLN526 |
|  | P793: agtcgatatctcattgccagttacggtacgggc (Eco RV) | 151 |  |  |
| hopPtoT | P582: gatggatccaagtaaccggtctgcaca (Bam HI) | 152 | pML123 | pLN256 |
|  | P583: atatctagatcatttatcatcatcatctttatatgactttgagccgcc tg (Xba I) | 153 |  |  |
| mouse α-Bax | P0942: ggcctcgagatggacgggtccggggagcagctt (Xho I) | 154 | pTA7002 | pLN555 |
|  | P0943: ggcactagttcagcccatcttcttccagatggtg (Spe I) | 155 |  |  |
| avrPphE$_{Pto}$ | P683: cacctatttaattcgttgagaaacaatgaaaata | 156 | Gateway entry | pCPP5057 |
|  | P684: gacatctcgtctcgccaagcc | 157 |  |  |
| avrPpiB1$_{Pto}$ | P685: caccaagcaacgtctgaggcaacaatgca | 158 | Gateway entry | pCPP5052 |
|  | P686: gtcgcctaggaaattatttagttcccatga | 159 |  |  |
| avrPtoB | P693: caccaagatcggagaggatcagaatatggcg | 160 | Gateway entry | pLN323 |
|  | P694: ggggactattctaaaagcatacttggc | 161 |  |  |
| hopPsyA | P787: caccttagcgtaaggagctaacaatgaaccc | 162 | Gateway entry | pLN458 |
|  | P788: gtttcgcgccctgagcgc | 163 |  |  |
| hopPtoE | P695: caccccataggggtgcaataacaatgaataga | 164 | Gateway entry | pLN324 |
|  | P696: gtcaatcacatgcgcttggcc | 165 |  |  |
| hopPtoF | P900: aaaaagcaggcttcgaaggagatagaaccatgtatagcccatcc | 166 | Gateway entry | pCPP5070 |
|  | P901: agaaagctgggtaacagacccttcgac | 167 |  |  |
| hopPtoG | P0904: caccccacataggatatgtaaacaatgcaaataaagaac | 168 | Gateway entry | pLN520 |
|  | P0905: gccgttgtaaaactgcttagaggc | 169 |  |  |
| hopPtoK | P940: caccacaaagaggttttcaaacaatgaatc | 170 | Gateway entry | pCPP5100 |
|  | P941: gcagtagagcgtgtcgcgac | 171 |  |  |
| avrPphE$_{Pto}$ | Gateway recombination |  | pML123 pPZP212 | pCPP5068 pLN535 |
| avrPpiB1$_{Pto}$ | Gateway recombination |  | pML123 pPZP212 | pCPP5063 pLN503 |
| avrPtoB | Gateway recombination |  | pML123 pPZP212 | pLN347 pLN502 |
| hopPsyA | Gateway recombination |  | pPZP212 | pLN474 |
| hopPtoE | Gateway recombination |  | pPZP212 | pLN524 |
| hopPtoF | Gateway recombination |  | pML123 pPZP212 | pCPP5070 pLN525 |
| hopPtoG | Gateway recombination |  | pPZP212 | pLN530 |
| hopPtoK | Gateway recombination |  | pML123 | pCPP5100 |
| avrPPhE$_{Pto}$ | P166: atacataacgctggccta | 172 | pKnockout- | pLN15 |
|  | P167: cggatccatgacaatcgt | 173 |  |  |
| avrPpiB1$_{Pto}$ | P168: gcaaatcctttaagctct | 174 | pKnockout- | pLN16 |
|  | P169: tgtttcgctaagccactg | 175 |  |  |
| avrPtoB | P304: tcgcgccaaaccagggag | 176 | pKnockout- | pLN42 |
|  | P305: tcccacattctgcaacgc | 177 |  |  |
| hopPsyA$_{Pto}$ | P188: aaccccattcagtcacgc | 178 | pKnockout- | pLN23 |
|  | P189: tttgccatgcgtgattgc | 179 |  |  |
| hopPtoD1 | P160: cctctacgatctattcaa | 180 | pKnockout- | pLN4 |
|  | P161: ggcaatgctcgcggcctg | 181 |  |  |
| hopPtoE | P913: tccggtagctcgtcagcg | 182 | pKnockout- | pLN543 |
|  | P914: gtggatgaccacatagttatg | 183 |  |  |
| hopPtoF | P179: agcccatcccatacacaa | 184 | pKnockout- | pLN7 |
|  | P180: cactttctgtccttggg | 185 |  |  |
| hopPtoG | P256: tattcagcttcaagaatg | 186 | pKnockout- | pLN29 |
|  | P257: acccgcatagacctgtctg | 187 |  |  |
| hopPtoH | P194: atcactccgtctcgatatc | 188 | pKnockout- | pLN27 |
|  | P195: tgccctgtacttcatgcg | 189 |  |  |
| hopPtoJ | P173: ctatgtatttcaaaacac | 190 | pKnockout- | pLN8 |
|  | P174: atcaccctctgtaattccc | 191 |  |  |
| hopPtoK | P171: cgcatttcaaccagctca | 192 | pKnockout- | pLN9 |
|  | P172: cagcaccggaagcccttc | 193 |  |  |
| hopPtoS1 | P190: ggtaatatttgtggtacttc | 194 | pKnockout- | pLN41 |
|  | P191: cagatgtaacgtgacatc | 195 |  |  |
| hopPtoT | P192: acagtcagcaatcactcg | 196 | pKnockout- | pLN25 |
|  | P193: tacactccatcacactgctg | 197 |  |  |
| avrPphE$_{Pto}$ | P854: ttgaattcatgaaaatacataacgctgg (Eco RI) | 198 | pGilda | pLN508 |
|  | P855: ttctcgagtcagacatctcgtctcgc (Xho I) | 199 |  |  |

TABLE 1-continued

Additional information on plasmid constructions

| Gene Name | Primer Nucleotide Sequences (5'→3') and Other Relevant Features | SEQ ID NO: | Parent Plasmid | Plasmid Construct |
|---|---|---|---|---|
| avrPpiB1$_{Pto}$ | P860: ttggatccgtatgcacgcaaatcctttaagctc (Bam HI) | 200 | pGilda | pLN507 |
| | P861: ttctcgagtcagtcgcctaggaaattatttagttcc (Xho I) | 201 | | |
| hopPtoE | P858: ttgaattcatgaatagagtttccggtagctc (Eco RI) | 202 | pGilda | pLN504 |
| | P859: ttctcgagtcagtcaatcacatgcgcttgg (Xho I) | 203 | | |
| hopPtoF | P856: ttgaattcatgggtaatatttgcggcacctc (Eco RI) | 204 | pGilda | pLN505 |
| | P857: ttctcgagtcagaccctttcgaccgg (Xho I) | 205 | | |
| hopPtoG | P862: ttgaattcatgcaaataaagaacagtcatctc (Eco RI) | 206 | pGilda | pLN506 |
| | P863: ttctcgagtcagccgttgtaaaactgcttagag (Xho I) | 207 | | |

Hypersensitive Response Assays: The broad-host-range vector pML123 was used to express effector genes in Pseudomonas strains (Labes et al., Gene 89:37–46 (1990), which is hereby incorporated by reference in its entirety). The pML123 constructs containing hopPtoC, hopPtoD1, hopPtoD2, and hopPtoJ are described in U.S. patent application Ser. No. 10/114,828 to Collmer et al., filed Apr. 2, 2002, which is hereby incorporated by reference in its entirety; and pML123 constructs containing hopPtoE, hopPtoG, hopPtoH, hopPtoI, hopPtoL, hopPtoS1, and hopPtoS2 are described above. A pML123 construct containing hopPtoB was similarly prepared. pML123 constructs containing hopPtoF, hopPtoK, hopPtoT, avrPtoB, avrPphEPto, avrPpiB1Pto, and avrPto are detailed in Table 1. P. fluorescens(pHIR11) carrying pML123 constructs with effector genes or vector controls with an OD600 of 0.2 (ca. $10^8$ cells/ml) in 5 mM MES (pH 5.6) and infiltrated into Nicotiana tabacum cv. Xanthi, N. benthamiana, or A. thaliana Ws-0 leaves. For bacterial mixing experiments involving two different P. fluorescens strains, P. fluorescens(pLN18) and a pML123 effector construct were infiltrated 2 h before P. fluorescens(pHIR11). The plants were scored for the production of an HR after 24 h. DC3000 strains were tested for their ability to elicit an HR on Nicotiana tabacum cv. xanthi by infiltrating strains with an OD600 of 0.2 along with 10-fold serially diluted samples with a needleless syringe.

Type III secretion assays, SDS-PAGE, and immunoblot analysis: DC3000 and DC3000 hrcC mutant (Yuan and He, J. Bacteriol. 178:6399–6402 (1996), which is hereby incorporated by reference in its entirety) carrying the plasmids pLN162, pLN526, pCPP2318, which encode for HopPtoE-FLAG, AvrPto, and β-lactamase, respectively, were grown in type III-inducing minimal medium (Huynh et al., Science 245:1374–1377 (1989), which is hereby incorporated by reference in its entirety). Cells were adjusted to an initial OD600 of 0.3 and grown for 6 h and separated into cell-bound and supernatant fractions by centrifugation at 4° C. Protein samples from bacterial cultures were prepared similarly as described (van Dijk et al., J. Bacteriol. 181:4790–4797 (1999), which is hereby incorporated by reference in its entirety). Cell and supernatant fractions were analyzed by SDS-PAGE (Sambrook and Russell, Molecular Cloning: A Laboratory Manual, Cold Spring Harbor Laboratory Press, Cold Spring Harbor, N.Y. (2001), which is hereby incorporated by reference in its entirety), transferred to polyvinylidene difluoride membranes, and immunobloted using anti-AvrPto, -β-lactamase, or -FLAG as primary antibodies. Generation of anti-AvrPto antibodies has been described (van Dijk et al., J. Bacteriol. 181:4790–4797 (1999), which is hereby incorporated by reference in its entirety). The anti-β-lactamase antibodies were purchased from Chemicon International and the anti-FLAG antibodies were purchased from Sigma Chemical Co. Primary antibodies were recognized by goat anti-immunoglobulin G-alkaline phosphatase conjugate (Sigma Chemical Co.), and visualized by chemiluminescence using a chemiluminescence detection system and X-Omat X-ray film.

Agrobacterium-mediated transient assays: The avr gene hopPsyA was recombined into a derivative of pPZP212 (Hajdukiewicz et al., Plant Mol. Biol. 25:989–994 (1994), which is hereby incorporated by reference in its entirety), pLN462, which was modified to be a Gateway Destination vector, resulting in pLN474. The bax gene was PCR-cloned into pTA7002, creating pLN531, and expression of bax was induced with dexamethasome as previously described (Aoyama and Chua, Plant Journal 11:605–612 (1997), which is hereby incorporated by reference in its entirety). The effector genes carried on Gateway entry vectors avrPphEPto, avrPpiB1Pto, avrPtoB, hopPtoE, hopPtoF, and hopPtoG were recombined into pLN462 (which fused each gene to a hemagglutinin epitope) creating constructs pLN535, pLN503, pLN502, pLN524, pLN525, and pLN530, respectively. Agrobacterium-mediated transient expression experiments were done by infiltrating A. tumefaciens C58C1 (van Larebeke et al., Nature 252:169–170 (1974), which is hereby incorporated by reference in its entirety) harboring the disabled Ti plasmid pMP90 (Koncz and Schell, Mol. Gen. Genet. 204:383–396 (1986), which is hereby incorporated by reference in its entirety) at an OD600 of 0.4 into N. benthamiana and N. tabacum cv. xanthi plants using a needleless syringe as described (van den Ackerveken et al., Cell 87:1307–1316 (1996), which is hereby incorporated by reference in its entirety). For co-expression experiments, Agrobacterium strains carrying pPZP212 binary plasmids with different effector genes were infiltrated 4 h prior to infiltration of strains expressing either Bax or HopPsyA. Evidence of production of effectors from transient assays was acquired by harvesting 1 cm diameter leaf disks from infiltrated zones, grinding leaf tissue with a mortar and pestle in the presence of liquid nitrogen, and resuspending plant material in 50 μl of 1× SDS-PAGE tracking buffer. SDS-PAGE and immunoblot analysis were performed as described above using high affinity anti-hemagglutinin antibodies (Roche).

Construction of DC3000 effector mutants: In-frame internal fragments of the effector genes were PCR cloned into XcmI digested pKnockout-. (Windgassen et al., FEMS Microbiol. Lett. 193:201–205 (2000), which is hereby incorporated by reference in its entirety) using the primer sets listed in Table 1 above. The resulting constructs were conjugated separately into DC3000 by triparental mating using spectinomycin as selection for the plasmid marker. The following effector mutants were confirmed with primers that flanked each coding region: hopPtoD1, UNL104; hopPtoC, UNL106; hopPtoE, UNL139; hopPtoK, UNL107; hopPtoJ, UNL108; hopPtoF, UNL109; avrPhEPto, UNL113; avrPpiB1Pto, UNL114; hopPtoH, UNL118; hopPtoT, UNL122; hopPtoG, UNL124; hopPtoS1, UNL126; and avrPtoB, UNL127.

Yeast viability assays: To determine whether type III effector-encoding plasmids rescued yeast from Bax-induced lethality, the effector genes avrPphEPto, avrPpiB1Pto, hopPtoG, hopPtoF, and hopPtoE were PCR-cloned into the yeast expression vector pGilda (Clontech, Palo Alto, Calif.) resulting in constructs pLN508, pLN507, pLN506, pLN505, and pLN504, respectively. Table 1 above contains information for the nucleotide primers used to make these constructs. *S. cerevisiae* EGY48 strain containing pJG4-5-Bax (kindly provided by J. C. Reed, Burnham Institute, La Jolla, Calif.) and various pGilda plasmids containing effector genes were grown in SC-U-L/glucose media overnight. The chicken Bcl-xL cloned in pGilda was kindly provided by C. Thompson (University of Chicago, Chicago, Ill.), which acted as a positive control for PCD suppression in these experiments. The yeast cultures were then serial 10-fold diluted into SC medium, and 5 µl of each dilution was dropped onto SC-U-L/Galactose or SC-UL/Glucose plates. Cells were incubated at 30° C. for 5 days, and photographed. For oxidative stress experiments, EGY48 strains containing pGilda effector constructs were grown in SC-U media overnight and treated as described in Abramovitch et al. (Abramovitch et al., *EMBO* 22:60–69 (2003), which is hereby incorporated by reference in its entirety).

Example 1

**Demonstration of *Pseudomonas syringae* pv. *tomato* DC3000 Protein Secretion**

From the hidden Markov model analysis, 28 candidate effector ORFs were identified that were not homologs of known Avr proteins/Hops or of any proteins unlikely to be secreted, and whose low G+C % content and association with mobile genetic elements suggested horizontal acquisition. Several of the predicted proteins shared amino acid identity with proteins likely to be effectors. For example, HopPtoS1 (ORF5) yields several ADP-ribosyltransferases in BLASTP searches (highest BLAST E value 1e-5), including a type III-secreted ADP-ribosyltransferase from *Pseudomonas aeruginosa* (Yahr et al., *Mol. Microbiol.* 22:991–1003 (1996)), and HopPtoH (ORF2) is homologous to an ORF adjacent to the avrPpiC2 avr gene of *P. s. pisi* (Arnold et al., *Microbiology* 147:1171–1182 (2001), which is hereby incorporated by reference in its entirety) (see Table 2 below).

To test whether these proteins travel the Hrp pathway, the ORFs were cloned into a broad-host-range vector fused to either the hemagglutinin or FLAG epitope. DC3000 wild-type and Hrp mutant cultures carrying these constructs were separated into supernatant and cell fractions and analyzed with SDS/PAGE and immunoblots. Five of the eight proteins tested were secreted via the DC3000 Hrp system (FIG. 1A) and consequently were designated as HopPtoE, HopPtoG, HopPtoH, HopPtoI, and HopPtoS1, respectively. Although three ORFs (ORF6, ORF 7, and ORF8) were not detectably secreted in culture, they may still be effectors because AvrB similarly is not secreted in culture although translocated in planta (van Dijk et al., *J. Bacteriol.* 181: 4790–4797 (1999); Gopalan et al., *Plant Cell* 8:1095–1105 (1996), each of which is hereby incorporated by reference in its entirety).

TABLE 2

ORFs with 5' Hrp Promoter Sequences and Encoding Proteins Demonstrated to be Secreted by the *P. syringae* Hrp System

| Initial designation | New designation | Size (bp) | % G + C | Homolog (BLASTP E value) | GenBank Accession[‡] |
|---|---|---|---|---|---|
| ORF1 | HopPtoI | 1,899 | 48.9 | None | NA |
| ORF2[†] | HopPtoH | 657 | 47.2 | ORF3 from P. s. pisi avrPpiC2 locus (1e-114) | CAC 16702 |
| ORF3 | HopPtoE | 636 | 50.7 | None | NA |
| ORF4 | HopPtoG | 1,482 | 43.7 | Hypothetical protein from R. solanacearum (1e-137) | NP_521884 |
| ORF5[‡] | HopPtoS1 | 852 | 46.5 | Chicken ADP-ribosyltransferase (1e-5) | P55807 |

[‡]Each of the listed Genbank Accessions is hereby incorporated by reference in its entirety.
[†]ORF2: homolog described in Arnold et al., *Microbiology* 147:1171-1182 (2001), which is hereby incorporated by reference in its entirety.
[‡]ORF5: homolog described in Tsuchiya et al., *J.Biol.Chem.* 269:27451-27457 (1994), which is hereby incorporated by reference in its entirety. Determined to possess an ART domain (pfam1129), further confirming its similarity to ADP-ribosyltransferases.

To determine whether the export signal-based search had identified any novel Hrp-secreted proteins, secretion assays were also performed on ORF29 and ORF30, both of which seemed to be particularly promising candidates. The products encoded by ORF29 and ORF30 share similarity with a putative type III effector from *S. enterica*, SrfC, and ADP-ribosyltransferases, respectively. Both ORFs were PCR-cloned into a broad-host-range vector fused to the FLAG epitope, and each construct was introduced into DC3000 wild-type and Hrp mutant strains. The epitope-tagged ORF29 and ORF30 proteins were secreted by DC3000 in a Hrp-dependent manner without leakage of a cytoplasmic marker protein (FIG. 1B), and consequently they were designated as HopPtoL and HopPtoS2, respectively (see Table 3 below).

TABLE 3

Selected ORFs Encoding Candidate Effector Proteins That Were
Identified by the Genomewide Search Based on Export-Signal Patterns

| Designation | New Designation | Size (bp) | % G + C' | Hrp promoter[‡] | Mobile DNA[†] | Homolog (BLASTP E value) | GenBank Accession[‡] |
|---|---|---|---|---|---|---|---|
| ORF29[§] | HopPtoL | 2700 | 61.0 | n | n | SPI-2 regulated SrfC (1e-21) | AAF74575 |
| ORF30[Ø,¶] | HopPtoS2 | 795 | 46.5 | y | n | Clostridium exoenzyme C3 ADP ribosyl-Tansferase (1e-5) | NP_346979 |
| ORF31[₤,¶] | NA | 897 | 49.8 | y | y | Chicken ADP ribosyl-transferase (5e-3) | P55807 |
| ORF32[₤,¶] | NA | 507 | 54.2 | y | y | Chicken ADP ribosyl-transferase (5e-3) | P55807 |
| ORF33[Θ] | NA | 2823 | 55.2 | n | y | SepC insecticidal toxin (1e-128) | NP_065279 |
| ORF34* | NA | 534 | 63.5 | y | n | Lytic enzyme (3e-36) | BAA83137 |

[‡]Indicates that the ORF is within 10 kb of a HrpL-responsive Hrp promoter identified in Fouts
[†]Indicates that a transposon, plasmid, or a phage-related sequence is within 10 kb.
[‡]Each of the listed Genbank Accessions is hereby incorporated by reference in its entirety.
[¶]ORF was determined to possess an ART domain (pfam1129), further confirming its similarity to ADP-ribosyltransferases.
[§]Homolog identified in Worley et al., Mol. Microbiol. 36:749-761 (2000), which is hereby incorporated by reference in its entirety.
[Ø]Homolog identified in Nolling et al., J. Bacteriol. 183:4823-4838 (2001), which is hereby incorporated by reference in its entirety.
[₤]Homolog identified in Tsuchiya et al., J. Biol. Chem. 269:27451-27457 (1994), which is hereby incorporated by reference in its entirety.
[Θ]Homolog identified in Hurst et al., J. Bacteriol. 182:5127-5138 (2000), which is hereby incorporated by reference in its entirety.
*Homolog identified in Nakayama et al., Mol. Microbiol. 38:213-231 (2000), which is hereby incorporated by reference in its entirety.

Interestingly, the export signal-based search found a putative effector, SrfC, that is predicted to travel the type III pathway encoded by SPI2 of *S. enterica* (Worley et al., *Mol. Microbiol.* 36:749–761 (2000), which is hereby incorporated by reference in its entirety). A further indicator of the efficacy of the search was the finding of three additional ADP-ribosyltransferases, ORF 30, 31, and 32, all with significant amino acid sequence identity to HopPtoS 1 (Table 3).

Example 2

AvrRpt2 Translocation Assay Indicates that at Least One of the Additional Hops Is Translocated into Plant Cells.

HopPtoG was selected to test for translocation into plant cells because it shared no similarities with any sequences in the databases and was shown to be secreted (FIG. 1B). *P. s. phaseolicola* carrying a plasmid expressing hopPtoG-Δ avr-Rpt2 elicited an RPS2-dependent hypersensitive response in *A. thaliana* Col-0 (FIG. 1C), indicating that targeting information in HopPtoG directed translocation of the AvrRpt2 fusion protein into plant cells. Thus, HopPtoG appears to be a Hrp-injected effector protein.

Discussion of Examples 1–2

One demonstration of the selectivity of the export signal rules is that only the chicken ADP-ribosyltransferase NRT2$_{CHK}$ shows major violations of the rules even though this protein is more similar to HopPtoS1 and S2 than either of the type III-secreted ADP-ribosyltransferases from *P. aeruginosa*, ExoS and ExoT (see Petnicki-Ocwieja et al., *Proc. Natl. Acad. Sci. USA* 99:7652–7657 (2002); U.S. patent application Ser. No. 10/341,180 to Collmer et al., filed Jan. 13, 2003, each of which is hereby incorporated by reference in its entirety).

HopPtoS1 and HopPtoS2 share sequence similarity with ADP-ribosyltransferases, proteins that have long been implicated in bacterial pathogenesis in animals through the modification of host signal transduction pathways (Finlay & Falkow, *Microbiol. Mol. Biol. Rev.* 61:136–169 (1997), which is hereby incorporated by reference in its entirety), but until now have not been implicated in the bacterial pathogenesis of plants. The DC3000 genomic studies described in Fouts et al. (*Proc. Natl. Acad. Sci. USA* 99:2275–2280 (2002), which is hereby incorporated by reference in its entirety) clearly show that several of the effectors in DC3000 are redundant. By using the pattern-based export prediction, three ADP-ribosyltransferase genes (in addition to hopPtoS1) that have N-termini putative export signals were identified in the genome of DC3000. One of these, ORF32, appears to be truncated. The other two, HopPtoS2 and ORF31, are full-length genes based on sequence alignments. HopPtoS2 is secreted by the Hrp system (FIG. 1B) and ORF31 shares high amino acid sequence identity with the Hrp-secreted HopPtoS1. Interestingly, HopPtoS1 contains putative myristoylation and palmitoylation sites at its N terminus, whereas the other two do not, indicating that HopPtoS1 may be localized to the plasma membrane. Thus, there appear to be at least three Hrp-secreted ADP-ribosyltransferases and these may localize to different regions of the plant cell. The existence of these proteins in *Pseudomonas syringae* is particularly noteworthy given that ADP-ribosyltransferase genes have not been identified in the bacterial plant pathogen genomes that have been published thus far (Simpson et al., *Nature* 406: 151–159 (2000); Wood et al., *Science* 294:2317–2323 (2001); Goodner et al., *Science* 294:2323–2328 (2001); Salanoubat et al., *Nature* 415:497–502 (2002), each of which is hereby incorporated by reference in its entirety). Significantly, the genomewide search for export signals yielded a homolog of the *S. enterica* candidate effector SrfC, further adding to the growing list of effectors shared between plant and animal pathogens. It is also noteworthy that one of the ORFs found by the genomewide search (ORF48) is a homolog of a bacterial catalase (BLASTP 1e-126), and another (ORF49) is a glucokinase homolog (BLASTP 3e-42). These putative effectors likely have a role in oxidative stress and regulation of sugar metabolism, respectively.

Example 3

Figure 2B:
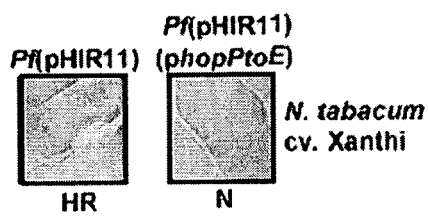
Figure 2C:
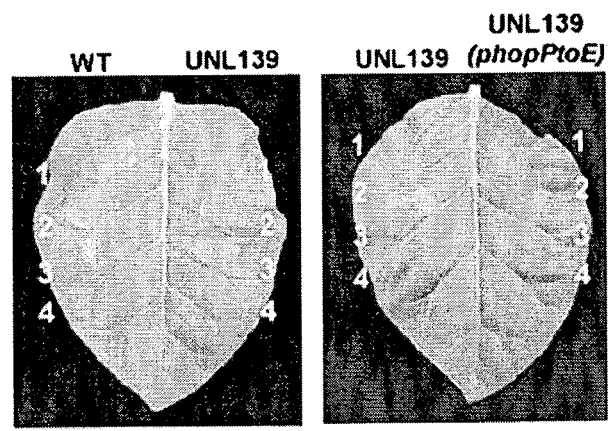

HopPtoE Suppresses the Hypersensitive Response in Tobacco and a DC3000 hopPtoE Mutant Possesses an Enhanced Hypersensitive Response Phenotype In the course of experiments with confirmed DC3000 type III effectors, the effector HopPtoD2 was observed capable of suppressing the HR elicited by *P. s. phaseolicola* on *Nicotiana benthamiana* plants. These results prompted the screening other effector proteins for HR suppressor activity (Collmer et al., *Trends Microbiol.* 10:462–470 (2002)). To do this, the pHIR11 system was used, allowing nonpathogens such as *E. coli* and *P. fluorescens* to elicit the HR and secrete effectors in culture via the TTSS. This tool allowed for testing whether individual effectors were capable of suppressing the HopPsyA-dependent HR as depicted in FIG. 2A. *P. fluorescens*(pHIR11) strains carrying a number of different effector constructs were infiltrated into tobacco (*N. tabacum* cv. *xanthi*). Interestingly, HopPtoD2, the effector that suppressed an HR elicited by *P. phaseolicola*, did not suppress the HopPsyA-dependent HR (FIG. 4A). The first identified effector to suppress or block the HR elicited by *P. fluorescens*(pHIR11) was HopPtoE (FIG. 2B). To detect a potential phenotype consistent with HopPtoE acting as an HR suppressor, a DC3000 mutant defective in HopPtoE was constructed. Both DC3000 and the hopPtoE mutant, UNL139, elicited an HR in tobacco when infiltrated into leaf panels at high inoculum (FIG. 2C).

Based on this result, it is likely that effectors have functionally redundant roles, which may partially mask a phenotype. Therefore, a more sensitive HR assay was performed, where 10-fold serially diluted bacterial strains were infiltrated into tobacco leaf panels to detect any subtle difference in the 5 ability of different strains of bacteria to elicit an HR. When UNL139 was tested in this assay, it was more effective than DC3000 at HR elicitation at lower cell density (FIG. 2C). Interestingly, when hopPtoE was provided in trans to UNL139, the mutant strain was less effective at HR elicitation than DC3000 (FIG. 2C). Thus, the enhanced HR phenotype of the hopPtoE mutant was complemented by hopPtoE. These observations are consistent with HopPtoE acting as an HR suppressor and suggest that HopPtoE contributes incrementally to the ability of the pathogen to suppress the HR.

Example 4

HopPtoE Does Not Block the DC3000 Type III Secretion System

Figure 3A:
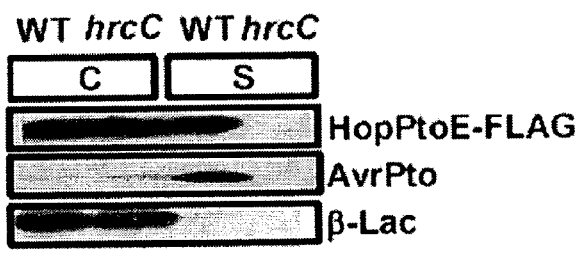
FIGS. 3A–C illustrate that HR suppression is not due to blocking TTSS, and the TTSS is functional.
Figure 3B:
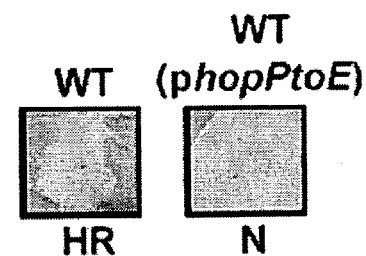

One possible explanation for the observed phenotypes was that HopPtoE was blocking the type III secretion of other type III substrates, including Avr proteins. There is actually a precedent for type III substrates, such as HrpZ and HrpW, to block the type III secretion of proteins from *P. syringae* (Alfano et al., *Mol. Microbiol.* 19:715–728 (1996); Charkowski et al., *J. Bacteriol.* 180:5211–5217 (1998), each of which is hereby incorporated by reference in its entirety) and it was crucial to consider this alternative. To test this, DC3000 and a DC3000 hrcC mutant defective in the TTSS, both carrying plasmids that contained avrPto and hopPtoE, were grown in a medium that induced type III secretion. These cultures were separated into supernatant and cell fractions, and analyzed them by SDS-PAGE and immunoblots with either anti-FLAG or -AvrPto antibodies. Both AvrPto and HopPtoE were secreted in culture via the TTSS (FIG. 3B), indicating that, at least in culture, over-expression of hopPtoE did not block type III secretion. It was next determined whether expression of hopPtoE in DC3000 altered its HR-eliciting ability. Because DC3000 contains a native copy of hopPtoE in its genome, these experiments actually tested whether over-expression of HopPtoE altered the HR phenotype. DC3000 strains, with and without plasmid-encoded hopPtoE, were infiltrated into tobacco at high inoculum levels ($10^8$ cells/ml). After 24 hours, DC3000 elicited an HR on tobacco, whereas DC3000 with a plasmid containing hopPtoE did not (FIG. 3B), indicating that over-expression of HopPtoE suppressed the HR. However, after approximately 3 h, DC3000 with hopPtoE in trans also elicited an HR. Thus, hopPtoE in trans in DC3000 only delayed the ability of this pathogen to elicit an HR. When these experiments were repeated in *N. benthamiana*, the HR delay was greater than 24 h, indicating that the suppression ability of HopPtoE depended to a certain extent on the test plant. To eliminate the possibility that HopPtoE affected the ability of *P. fluorescens*(pHIR11) to deliver the Avr protein HopPsyA into plant cells, a different bacterial strain was used to deliver HopPsyA (as compared to the strain used to deliver HopPtoE) into plant cells. To accomplish this, a pHIR11 derivative, pLN18, was constructed so as to lack hopPsyA and shcA, a gene that encodes a chaperone for HopPsyA (van Dijk et al., *Mol. Microbiol.* 44:1469–148 (2002), which is hereby incorporated by reference in its entirety). *P. fluorescens*(pLN18) does not elicit an HR on tobacco because it lacks HopPsyA (FIG. 3C), while maintaining the ability to secrete proteins via its functional TTSS.

Figure 3C:
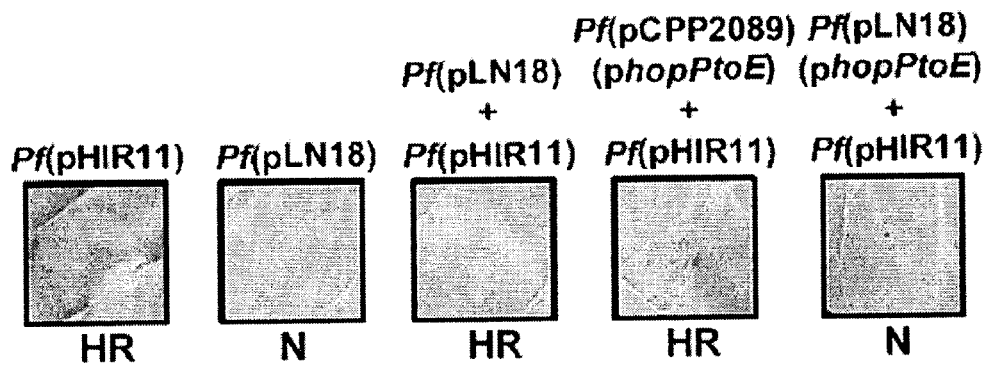

In planta mixed-inoculum experiments were performed by first infiltrating into tobacco *P. fluorescens*(pLN18) with hopPtoE contained in a broad-host-range plasmid and, after 2 h, *P. fluorescens*(pHIR11). *P. fluorescens*(pHIR11) was infiltrated at an OD600 sufficient to cause HR elicitation. FIG. 3C shows that *P. fluorescens*(pLN18) retained the ability to suppress the pHIR11-dependent HR. This indicates that the HR suppression activity does not occur in the bacterial cell.

Example 5 pHIR11 Assays Identify Seven Effectors Capable of Suppressing the HopPsyA-Dependent Hypersensitive Response Nineteen confirmed effector genes were cloned into a broad-host-range plasmid and tested to determine whether the encoded effectors were able to suppress the HR elicited by *P. fluorescens*(pHIR11) (see FIG. 4A for a list of the effectors tested). Each candidate suppressor gene was expressed in *P. fluorescens*(pHIR11) and these strains were infiltrated into tobacco and *Arabidopsis thaliana* ecotype Ws-0, two plants that produce an HR in response to pHIR11-containing bacteria.

Surprisingly, seven of the nineteen effectors tested were able to suppress the pHIR11-dependent HR on both *A.*

*thaliana* and tobacco (FIGS. 4B–C). In planta mixed-inoculum experiments similar to those describe in FIG. 3C demonstrated that all of the identified suppressors were able to inhibit the pHIR11-dependent HR. These results indicate that the site of suppressor activity was outside of the bacteria. Two of the identified suppressors, HopPtoF and AvrPtoB, were homologs of AvrPphF and VirPphA, respectively, two Avr proteins able to "block" the HR produced by *P. s. phaseolicola* (Jackson et al., *Proc. Natl. Acad. Sci. USA* 96:10875–10880 (1999); Tsiamis et al., *EMBO J.* 19:3204–3214 (2000), each of which is hereby incorporated by reference in its entirety). The VirPphA homolog, AvrPtoB, was recently reported to suppress the HR elicited by AvrPto (Abramovitch et al., *EMBO J.* 22:60–69 (2003), which is hereby incorporated by reference in its entirety). Thus, these findings demonstrate that AvrPtoB and HopPtoF are HR suppressors. The other HR suppressors identified were AvrPphE$_{Pto}$, AvrPpiB1$_{Pto}$, HopPtoD1, and HopPtoK. The HR suppression observed for HopPtoD1 and HopPtoK was not complete (i.e., the HR was present, although much reduced).

Example 6

Figure 5A:
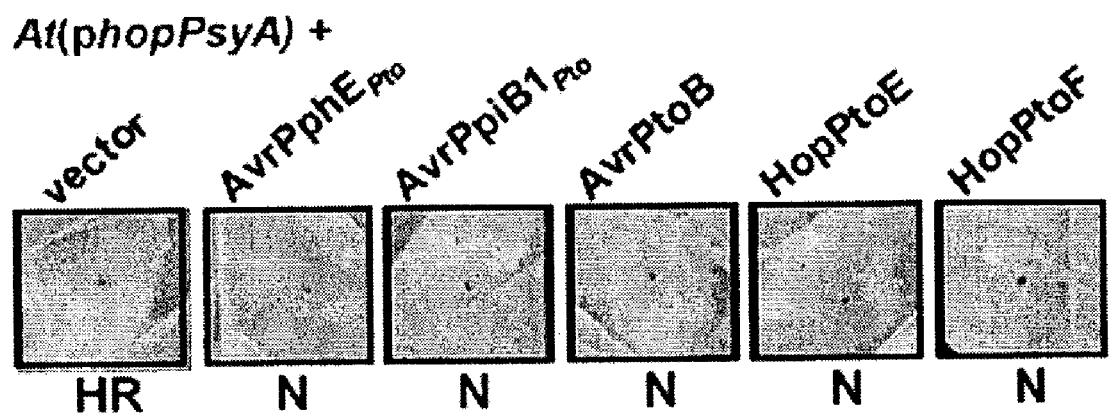
FIGS. 5A–B illustrate that the HR elicited by HopPsyA can be suppressed via *Agrobacterium* transient expression of effectors.
Figure 5B:
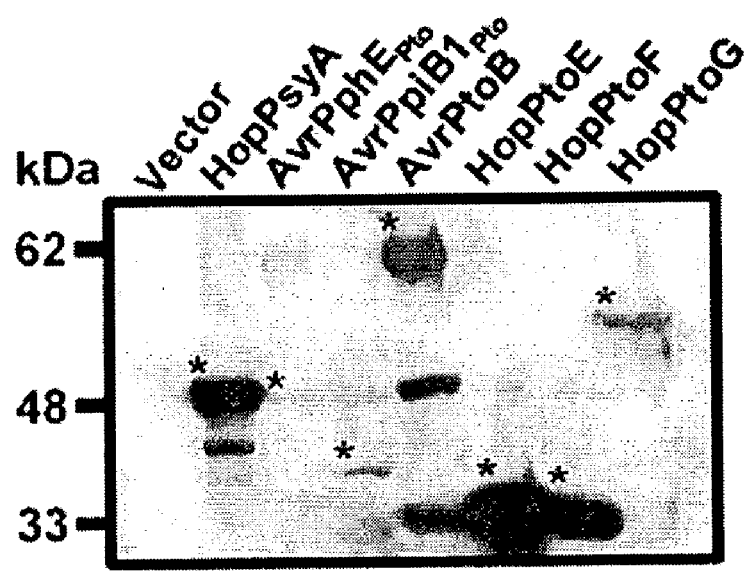

Agrobacterium Transient Assays that Co-Deliver HopPsyA and Individual Hypersensitive Response Suppressors Confirm that Each Effector Alone Suppresses the HopPsyA-Dependent Hypersensitive Response Inside Plant Cells To determine if the HR suppression is due solely to the suppressor proteins, both HopPsyA and individual HR suppressor effectors were transiently co-delivered using *Agrobacterium*-mediated transient assays (agroinfitrations) (van den Ackerveken et al., *Cell* 87:1307–1316 (1996), which is hereby incorporated by reference in its entirety). In each case, the effector suppressed the HopPsyA-dependent HR (FIG. 5A). Protein expression was confirmed with immunoblots that showed the agroinfiltrations produced both HopPsyA and the specific suppressor tested (FIG. 5B). These data complement the bacteria-delivered suppressor data shown above, because agroinfiltrations demonstrate that the suppressor activity is dependent only on the suppressor and that the suppressor acts within plant cells, whereas the experiments where *P. fluorescens*(pHIR11) deliver each suppressor resemble what happens in nature and protein levels are closer to the levels that the pathogen "inject" into plant cells.

Example 7

Figure 6:
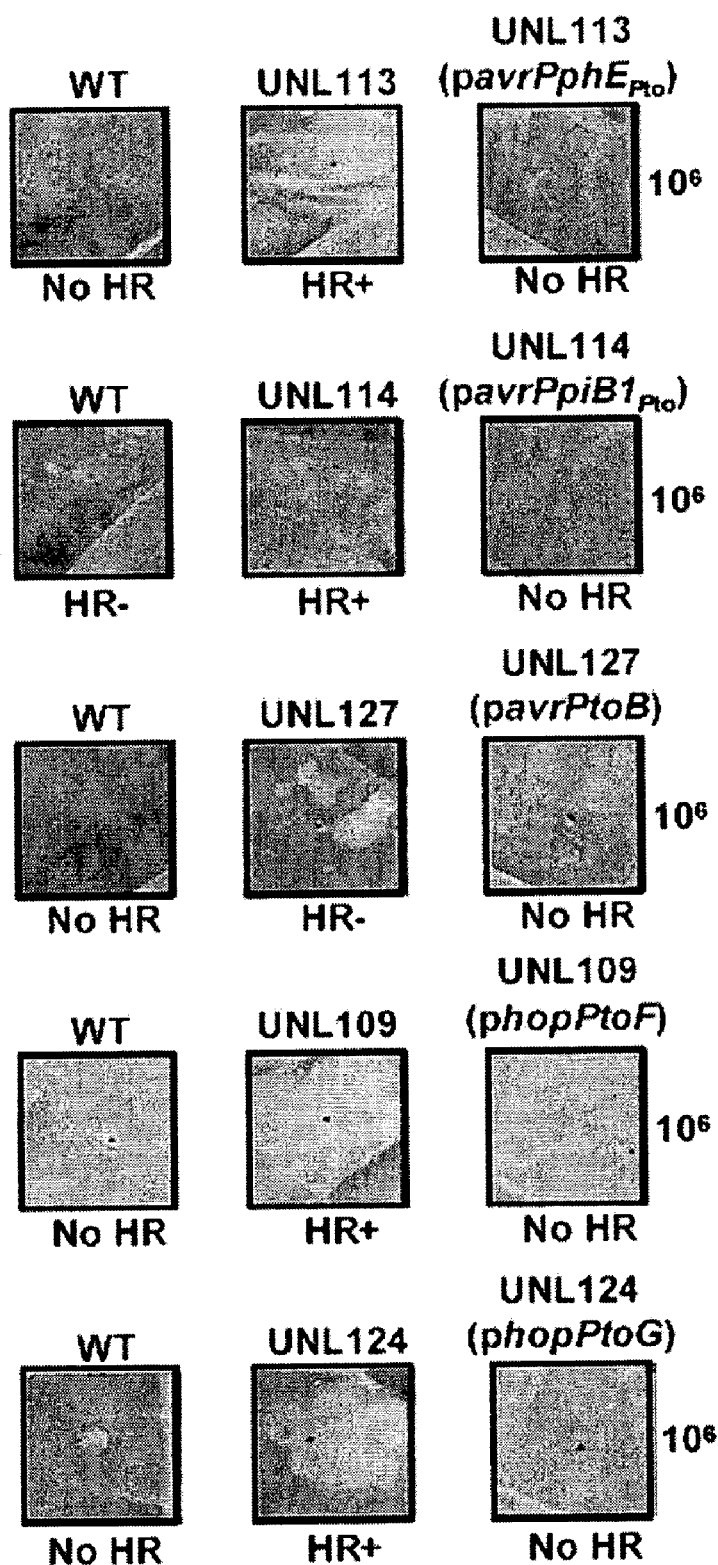
FIG. 6 is an image showing that *Pseudomonas syringae* pv. *tomato* DC3000 suppressor mutants display an enhanced ability to elicit the HR. *N. tabacum* cv. *xanthi* leaves were infiltrated with *P. syringae* strains that were 10-fold serially diluted from $10^8$ cells/ml. The last dilution ($10^6$ cells/ml) that resulted in an HR is shown. In all cases, the mutants exhibit more HR at this dilution than the wild type, and this phenotype was complemented when the suppressors were provided in trans. The following strains were infiltrated: DC3000 wild type, WT; avrPphEPto mutant, UNL113; avrPpiB1Pto mutant, UNL114; avrPtoB mutant, UNL127; hopPtoF mutant, UNL109; hopPtoG mutant, UNL124. HR was scored for each sample: spotty HR (HR−); strong HR (HR+); or no HR.

DC3000 Suppressor Mutants Display an Enhanced Ability to Elicit a Hypersensitive Response on Nonhost Plants, Consistent with Loss of Hypersensitive Response Suppression Activity in the Pathogen Based on the above findings, it was recognized that a pathogen may encode multiple HR suppressors, each contributing, perhaps incrementally, to the suppression of the HR and/or plant defenses. To analyze these proteins in more detail, mutants defective in each gene corresponding to the effectors listed in FIG. 4A were made. The ability of DC3000 and the suppressor mutants to induce defense responses on non-host plants were tested, similar to the experiments described in FIG. 2C. Tobacco leaves were infiltrated with different dilutions of DC3000 or each mutant, and then their ability to elicit an HR was analyzed. Interestingly, all the mutants were more effective at eliciting an HR at lower concentrations, generally producing an HR at 10-fold higher dilution than wild type DC3000 (FIG. 6). As an example, UNL105 caused a confluent HR at a titer of $10^6$ cells/ml, whereas DC3000 only produced a spotty HR or no HR at this titer. It is important to note that DC3000 produced a typical HR at dilutions of $10^6$ cells/ml or higher. This enhanced HR phenotype produced by each suppressor mutant resulted from the absence of the effector, because when each was supplied in trans the HR-eliciting ability returned to a DC3000-like HR (FIG. 6).

Although HopPtoG was not identified as an HR suppressor in the assays with *P. fluorescens*(pHIR11), the hopPtoG mutant UNL124 caused an enhanced HR phenotype. Moreover, additional assays shown below suggest that HopPtoG does function as a suppressor. Thus, these findings demonstrate that the phenotype of potential suppressor mutants on non-host plants is consistent with and complements HR suppression data. Therefore, the HR titration assays should be useful in the identification of other HR suppressors in bacterial plant pathogens.

Example 8

Figure 7A:
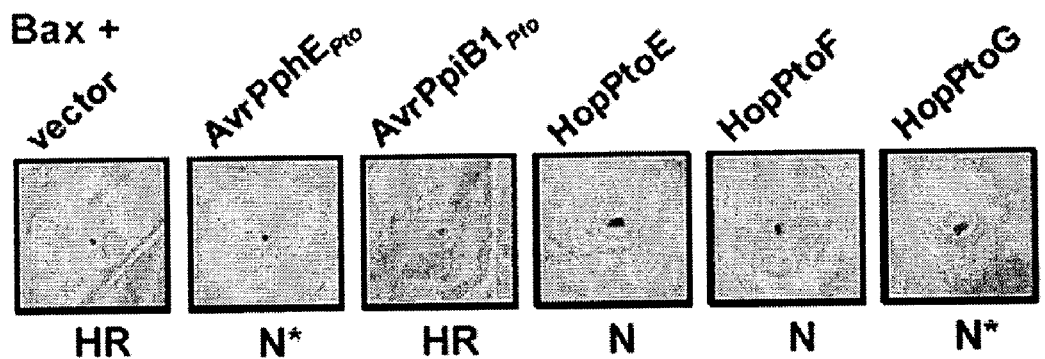
FIGS. 7A–B illustrate that *Pseudomonas syringae* pv. *tomato* DC3000 HR suppressors inhibit the PCD initiated by Bax in plants and yeast.
Figure 7B:
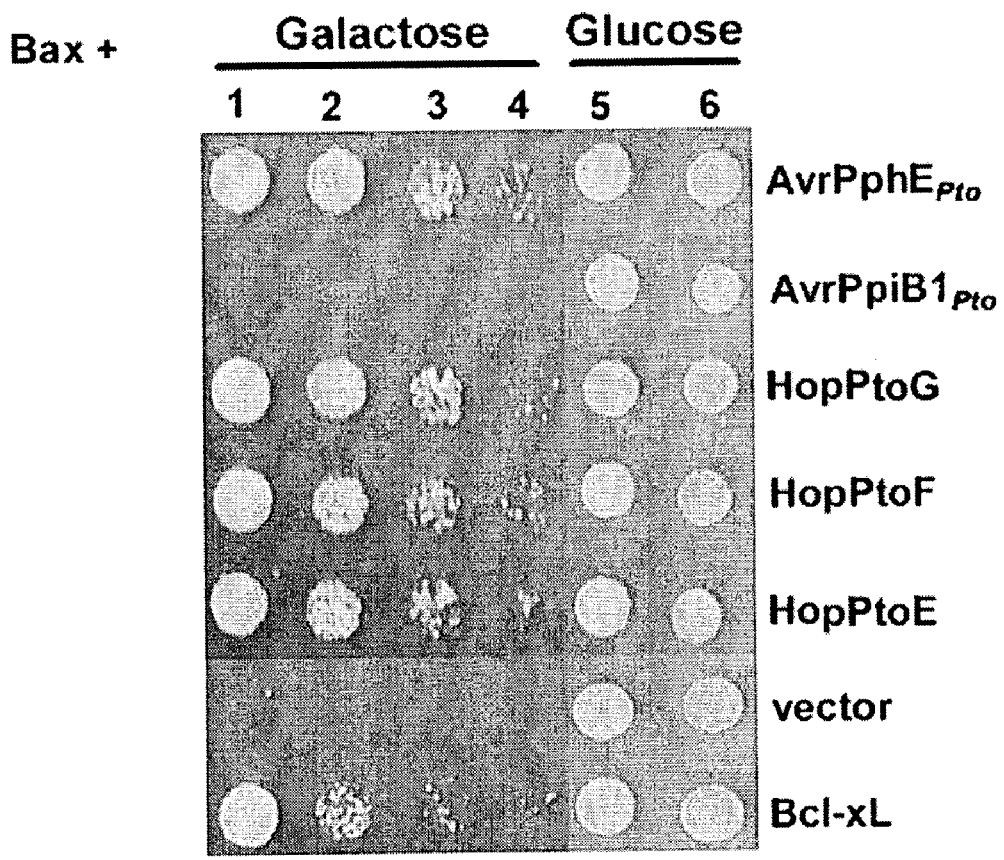

*Pseudomonas syringae* Hypersensitive Response Suppressors Inhibit Programmed Cell Death Induced by the Pro-apoptotic Protein Bax in both Plants and Yeast The pro-apoptotic mouse protein Bax has been shown to induce PCD in plants that resembles the HR (Kawai-Yamada et al., *Proc. Natl. Acad. Sci. USA* 98:12295–12300 (2001); Lacomme and Santa Cruz, *Proc. Natl. Acad. Sci. USA* 96:7956–7961 (1999), each of which is hereby incorporated by reference in its entirety). Bax is a member of the Bcl-2 family of pro-apoptotic proteins and is thought to initiate programmed cell death ("PCD") by localizing to the mitochondria and causing the release of pro-apoptotic factors, including cytochrome c (Jurgensmeier et al., *Proc. Natl. Acad. Sci. USA* 95:4997–5002 (1998), which is hereby incorporated by reference in its entirety). Recently, Abramovitch et al. (*EMBO J.* 22:60–69 (2003), which is hereby incorporated by reference in its entirety) reported that AvrPtoB suppresses Bax-induced PCD in plants. The suppressors identified in Examples 3–7 were tested in their ability to suppress Bax-induced PCD in plants. With the exception of AvrPpiB1$_{Pto}$, all of them suppressed Bax-induced cell death in plants (FIG. 7A). Interestingly, AvrPphE, HopPtoG, HopPtoF, and HopPtoE also suppressed Bax-induced PCD in yeast (FIG. 7B). The fact that AvrPtoB was unable to suppress Bax-induced PCD in yeast highlights a difference between the activity of these suppressors. Moreover, AvrPphE, HopPtoG, HopPtoF, and HopPtoE were unable to suppress the PCD initiated in yeast by $H_2O_2$, while AvrPtoB did suppress PCD in this assay (Abramovitch et al., *EMBO J.* 22:60–69 (2003), which is hereby incorporated by reference in its entirety). This further demonstrates that the PCD suppressors display different PCD suppressing characteristics.

Discussion of Examples 3–8

Effectors delivered by the Hrp TTSS appear central to *P. syringae* pathogenesis, but the anti-host functions of these proteins remain obscure. The above Examples identify a founding inventory of Hrp effectors from *P. s. tomato* DC3000 using several novel bioassays and provide evidence that many of these proteins appear to suppress one or more broadly conserved eukaryote PCD pathways. To understand these results, it is useful to consider the collection of effectors that were assayed, the utility and limitations of the bioassays, and the role of plant cell death in disease and defense. The nineteen effectors considered here were recently identified in DC3000 on the basis of their homology with known effectors and/or their ability to be secreted and/or translocated by the Hrp TTSS. In general, P. syringae TTSS effectors identified on the basis of avirulence phenotypes are designated Avrs, whereas those identified through secretion assays are designated Hops. However, the working assumption is that all of the "Avrs" are injected into plant cells by the Hrp system and many of the "Hops" will confer avirulence phenotypes to bacteria if tested in hosts that happen to carry a corresponding R gene; that is, effectors, Avrs, and Hops are synonymous terms.

It must be noted that the effector described herein do not represent the entire inventory of DC3000 effectors. Effectors encoded within the Hrp pathogenicity island are described elswhere (Alfano et al., Proc. Natl. Acad. Sci. USA 97:4856–4861 (2000), which is hereby incorporated by reference in its entirety. Additional candidate effectors in DC3000 have also been identified (Collmer et al., Trends Microbiol. 10:462–470 (2002), which is hereby incorporated by reference in its entirety).

However, the set of effectors analyzed here suggests that many DC3000 effectors have HR suppression activity. The bioassays used herein were designed to efficiently detect HR suppressor activity, determine whether suppressor action occurs in plant cells rather than in bacteria, and determine if the test effectors could also suppress PCD in other plants and the model eukaryote, yeast. The primary screen, based on suppression of the HR elicited by P. fluorescens(pHIR11) in tobacco, proved to be simple and effective (FIG. 2). Although there is the formal possibility that suppressors identified with this bioassay could be merely interfering with the delivery of HopPsyA, multiple lines of evidence indicate that they act after delivery into plant cells. For example, HopPtoE overexpression had no effect on the secretion of AvrPto (FIG. 3A), a representative type III substrate, and HopPtoE suppressed HopPsyA-dependent HR elicitation when delivered by a functional TTSS in a different strain (FIG. 3C) or when transiently expressed in plant cells following inoculation with A. tumefaciens (FIG. 5A). It is also noteworthy that the suppressors identified herein functioned when delivered via the TTSS, a natural route that is thought to yield relatively low levels of effectors within plant cells. Agrobacterium-mediated transient expression, in contrast, can produce far higher levels of effectors within plant cells potentially leading to artifactual responses. It should also be noted that HopPtoD1 and HopPtoK appear to exhibit limited suppressor activity.

In an attempt to identify plant targets or sites of action of the suppressors in plants, HopPtoE, AvrPphE$_{Pto}$, AvrPiB1$_{Pto}$, AvrPtoB, HopPtoF, and HopPtoG were subjected to cursory bioinformatic analyses. BLASTP and PSI-BLAST searches (Altschul et al., Nucleic Acids Res. 25: 3389–3402 (1997), which is hereby incorporated by reference in its entirety) did not identify any proteins (other than clear Avr homologs) that shared significant similarity with any of the suppressors. However, 3D-PSSM analyses, a method that uses protein fold recognition to identify proteins with similar folding patterns (Kelley et al., J. Mol. Biol. 299:499–520 (2000), which is hereby incorporated by reference in its entirety), indicated that AvrPtoB had similarity to heme-dependent peroxidases (above 90% certainty; PSSM E value 0.0895). Moreover, when AvrPtoB was aligned with a lignin peroxidase, a representative heme-dependent peroxidase (Welinder, Eur. J. Biochem. 151: 497–504 (1985), which is hereby incorporated by reference in its entirety), the amino acids within the peroxidase active site were present similarly spaced in AvrPtoB. This result is intriguing because of the clear involvement of reactive oxygen species (ROS) in plant defense (Mittler, Trends Plant Sci. 7:405–410 (2002), which is hereby incorporated by reference in its entirety) and the potential of peroxidases to modulate ROS. Moreover, there have been reports of peroxidases rescuing Bax-induced cell death in yeasts (Kampranis et al., J. Biol. Chem. 275:29207–29216 (2000); Moon et al., Biochem. Biophys. Res. Commun. 290:457–462 (2002), each of which is hereby incorporated by reference in its entirety) and transgenic antisense tobacco plants with reduced amounts of ascorbate peroxidase were "hyperresponsive" to P. syringae (Mittler et al., Proc. Natl. Acad. Sci. USA 96:14165–14170 (1999), which is hereby incorporated by reference in its entirety), producing a phenotype reminiscent of the enhanced HR phenotypes produced by the suppressor mutants reported here. However, Abramovitch et al. (EMBO J. 22:60–69 (2003), which is hereby incorporated by reference in its entirety) reported that AvrPtoB possessed predicted structural features similar to domains within Bcl-2 family members, an equally intriguing finding due to the involvement of these proteins in PCD regulation. Yeast has emerged as model for studying PCD and has proven particularly useful for the analysis of cell death inducers and suppressors obtained from multicellular eukaryotes with more complex PCD pathways (Madeo et al., Curr. Genet. 41:208–216 (2002), which is hereby incorporated by reference in its entirety). An example of the utility of the yeast system to plant PCD research is found in the induction of yeast PCD by the plant defense protein osmotin (Narasimhan et al., Mol. Cell 8:921–930 (2001), which is hereby incorporated by reference in its entirety). A particularly fruitful use of the yeast system involves heterologous expression of the mammalian Bax protein, which induces PCD in yeast. Yeast expressing Bax can be screened, as done here, for heterologously expressed genes that block Bax-induced PCD. This system has been used to identify the Arabidopsis ethylene-responsive element binding protein (AtEBP) as a suppressor of PCD (Pan et al., FEBS Lett. 508:375–378 (2001), which is hereby incorporated by reference in its entirety) and its relevance to plant biology is further indicated by observations that Bax expression in tobacco can induce an apparent HR and that Bcl-2 (an anti-aptototic gene of the Bax/Bcl-2 family) expression in tobacco strongly alters plant-pathogen interactions (Dickman et al., Proc. Natl. Acad. Sci. USA 98:6957–6962 (2001); Lacomme and Santa Cruz, Proc. Natl. Acad. Sci. USA 96:7956–7961 (1999), each of which is hereby incorporated by reference in its entirety).

Four of the five effectors tested (AvrPphE$_{Pto}$, HopPtoG, HopPtoF, and HopPtoE) suppress Bax-induced yeast PCD, indicating that the targets are likely to be broadly conserved and not unique to plants. Interestingly, AvrPpiB1$_{Pto}$ and AvrPtoB failed to do so, even though both suppressed the HR elicited by P. fluorescens(pHIR11) in both tobacco and Arabidopsis, and DC3000 avrPtoB and avrPpiB1Pto mutants produced enhanced HRs. It is also puzzling that HopPtoG failed to suppress the HR elicited by P. fluorescens (pHIR11) although a DC3000 hopPtoG mutant had enhanced HR activity and HopPtoG suppressed Bax-induced yeast PCD. Moreover, it is also noteworthy that HopPtoD2, an effector that was recently identified to suppresses an HR elicited by avirulent P. syrinage strains did not suppress the HR elicited by P. fluorescens(pHIR11).

These exceptions suggest that multiple bioassays will be required to identify all of the DC3000 effectors with some ability to suppress PCD.

While the suppressors described here were identified due to their ability to suppress PCD, it is possible they suppress other more general plant defenses as well. Indeed, HopPtoD2 has been found to be an active protein tyrosine phosphatase that appears to modulate a mitogen-activated protein kinase (MAPK) pathway in tobacco. An analogous MAPK pathway in *Arabidopsis* is part of the plant innate immune system activated in response to bacterial flagellin (Asal et al., *Nature* 415:977–983 (2002); Felix et al., *Plant J.* 18:265–276 (1999), each of which is hereby incorporated by reference in its entirety). The innate immune systems of mammals, insects, and plants have the capacity to recognize common markings on microorganisms, such as flagellin or LPS (Boller, *Annu. Rev. Plant Physiol. Plant Mol. Biol.* 46:189–214 (1995); Medzhitov and Janeway, *Trends Microbiol.* 8:452–456 (2000), each of which is hereby incorporated by reference in its entirety). These common components have been referred to as pathogen-associated molecular patterns (PAMPs) and they are not known to elicit the HR in plants. Thus, the assays used herein would not detect the activity of suppressors that specifically targeted PAMP-induced defense pathways unless the target was at convergence points of PCD pathways and PAMP-induced innate immunity pathways. Future research will determine whether these PCD suppressors specifically target Avr-induced PCD pathways or also suppress other plant defenses generally grouped into a broad category of defenses typically referred to as non-host resistance (Heath, *Curr. Opin. Plant Biol.* 3:315–319 (2000), which is hereby incorporated by reference in its entirety).

A general model of suppressor function must also reconcile several behaviors of bacterium-plant interactions that involve multiple effectors. Expression in *P. syringae* of a heterologous effector typically results in HR elicitation in test plants that carry a corresponding R gene despite the presence of resident suppressor effectors. For example, DC3000 heterologously expressing avrRpt2 or avrRps4 elicits the HR in *Arabidopsis* plants carrying the corresponding R genes (Hinsch and Staskawicz, *Mol. Plant—Microbe Interact.* 9:55–61 (1996); Kunkel et al., *Plant Cell* 5:865–875 (1993), which is hereby incorporated by reference in its entirety). On the other hand, suppressors can block HR elicitation by resident effectors, as revealed by the original discovery of suppressors like VirPphA and effectors with masked avirulence activity in *P. s. phaseolicola* (Jackson et al., *Proc. Natl. Acad. Sci. USA* 96:10875–10880 (1999), which is hereby incorporated by reference in its entirety) and by the observations presented here that several effectors can block HR elicitation by HopPsyA in the heterologous *P. fluorescens*(pHIR11) system. Perhaps the simplest explanation is that there is a hierarchy in the delivery of effectors by wild-type strains. Such a hierarchy in delivery has been proposed to explain the deployment of effectors with conflicting activities, such as the *Salmonella* SopE and SptP proteins, in animal pathogens (Cornelis and van Gujsegem, *Annu. Rev. Microbiol.* 54:734–774 (2000); Galán and Zhou, *Proc. Natl. Acad. Sci. USA* 97:8754–8761 (2000), each of which is hereby incorporated by reference in its entirety). The global identification of a set of suppressors in *P. s. tomato* DC3000 should facilitate systematic investigation of the underlying functions of TTSS effectors in *P. syringae* pathogenesis.

A final aspect of PCD and pathogenesis is that the ability to elicit host cell death appears to be a general characteristic of TTSS-dependent pathogens like *P. syringae* despite the fact that these bacteria typically rely upon living host cells as sites of multiplication (Alfano and Collmer, *J. Bacteriol.* 179:5655–5662 (1997); Knodler and Finlay, *Microbes Infect.* 3:1321–1326 (2001), each of which is hereby incorporated by reference in its entirety). This is particularly puzzling with *P. syringae* because late-stage infections with most strains produce necrotic lesions, but the symptomless growth of *P. s. syringae* gacS mutants suggests that such cell killing maybe gratuitous (Willis et al., *Mol. Plant—Microbe Interact.* 3:149–156 (1990), which is hereby incorporated by reference in its entirety). Similarly puzzling are recent observations suggesting that plants compromised in PCD pathways are unexpectedly more resistant to *P. syringae* (Lincoln et al., *Proc. Natl. Acad. Sci. USA* 99:15217–15221 (2002); Stone et al., *Plant Cell* 12:1811–1822 (2000); Richael et al., *Physiol. Mol. Plant Pathol.* 59:213–221 (2001), each of which is hereby incorporated by reference in its entirety). Thus, rapid and delayed host cell death are associated with defense and disease, respectively, and pathogen manipulation of cell death pathways may be a central process in pathogenesis.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of modifying a cell death pathway in a cell comprising:

introducing into a cell (i) a protein or polypeptide comprising the amino acid sequence of SEQ ID NO: 58 or (ii) a protein or polypeptide encoded by a nucleic acid molecule that hybridizes to the complement of SEQ ID NO: 57 under hybridization conditions comprising 1M Na$^+$ at 65° C. followed by wash conditions comprising 0.2× sodium citrate at 65° C. wherein the protein or polypeptide has ADP-ribosyl transferase activity.

2. The method according to claim 1, wherein said introducing is carried out with the protein or polypeptide comprising the amino acid sequence of SEQ ID NO: 58.

3. The method according to claim 1, wherein said introducing is carried out by transformation of the cell with a transgene encoding the protein or polypeptide.

4. The method according to claim 1, wherein said introducing is carried out by delivery of the protein or polypeptide into the cell.

5. The method according to claim 1, wherein the cell death pathway is suppressed.

* * * * *